(12) United States Patent
Von Nussbaum et al.

(10) Patent No.: US 7,718,611 B2
(45) Date of Patent: May 18, 2010

(54) CYCLIC NONAPEPTIDE AMIDES

(75) Inventors: Franz Von Nussbaum, Duesseldorf (DE); Nina Brunner, Essen (DE); Chantal Fuerstner, Muelheim an der Ruhr (DE); Rainer Endermann, Wuppertal (DE); Jacques Ragot, Duesseldorf (DE); Joachim Telser, Wuppertal (DE); Werner Schroeder, Wuppertal (DE); Sonja Anlauf, Wuppertal (DE); Joachim Schuhmacher, Wuppertal (DE); Elke Hartmann, Wuppertal (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 0 days.

(21) Appl. No.: 11/800,495

(22) Filed: May 4, 2007

(65) Prior Publication Data

US 2008/0070884 A1    Mar. 20, 2008

Related U.S. Application Data

(63) Continuation of application No. PCT/EP2005/011451, filed on Oct. 26, 2005.

(30) Foreign Application Priority Data

Nov. 5, 2004    (DE) ..................... 10 2004 053 410

(51) Int. Cl.
*A61K 38/12* (2006.01)
*C07K 7/54* (2006.01)
(52) U.S. Cl. .......................... 514/11; 530/317
(58) Field of Classification Search .................. None
See application file for complete search history.

(56) References Cited

U.S. PATENT DOCUMENTS

| | | | |
|---|---|---|---|
| 4,754,018 | A | 6/1988 | Tymiak et al. |
| 6,380,156 | B1 | 4/2002 | Rinehart et al. |
| 7,056,942 | B2 | 6/2006 | Hildesheim et al. |
| 7,368,424 | B2 | 5/2008 | Von Nussbaum et al. |
| 7,531,507 | B2 | 5/2009 | Von Nussbaum et al. |
| 2005/0075281 | A1 | 4/2005 | Von Nussbaum et al. |
| 2005/0272646 | A1 | 12/2005 | Koteva et al. |
| 2006/0264358 | A1 | 11/2006 | Von Nussbaum et al. |
| 2008/0051424 | A1 | 2/2008 | Von Nussbaum et al. |
| 2008/0058251 | A1 | 3/2008 | Von Nussbaum et al. |
| 2008/0058253 | A1 | 3/2008 | Von Nussbaum et al. |
| 2008/0070884 | A1 | 3/2008 | Von Nussbaum et al. |
| 2009/0105119 | A1 | 4/2009 | Von Nussbaum et al. |

FOREIGN PATENT DOCUMENTS

| | | |
|---|---|---|
| DE | 10 2004 053410 | 5/2006 |
| EP | 196042 | 10/1986 |
| JP | 01132600 | 5/1989 |
| WO | WO-01/05814 | 1/2001 |
| WO | WO-2004/099239 | 11/2004 |
| WO | WO-2006/048156 | 5/2006 |

OTHER PUBLICATIONS

.R. Vippagunta, et al. Adv. Drug Delivery Rev. (2001) 48, pp. 3-26.*
C.W. Thornber. Chem. Soc. Rev. (1979) 8(4), pp. 563-580.*
Translation of the International Preliminary Report on Patentability for PCT/EP2005/011451, mailed Jul. 12, 2007, 8 pages.
Baquero, J. Antimicrob. Chemother. (1997 Suppl. A) 39:1-6.
Bonner et al., J. Antibiot. (1988) 41:1745-1751.
Goldrick, Am. J. Nurs. (2002) 102:17.
Green, Expert Opin. Ther. Targets (2002) 6:1-19.
International Search Report for PCT/EP2005/011451, Mailed on Feb. 27, 2006, 4 pages.
Johnson et al., J. Hosp. Infect. (2001 Suppl. A) 49:3-11.
Lee et al., Tetrahedron (2001) 57:2139-2145.
Merino et al., Tetrahedron: Asymmetry (1998) 9:629-646.
O'Sullivan et al., J. Antibiot. (1988) 41:1740-1744.
Shoji et al., J. Antibiot. (1988) 41:713-718.
Tymiak et al., J. Org. Chem. (1989) 54:1149-1157.
Alker et al., Tetrahedron (1998) 54:6089-6098.
Anderson and McGregor, J Am Chem Soc (1957) 79:6180-6183.
Bacterial Urinary Tract Infections from the Merck Manual, 8 pages.
Barret et al., Tetrahedron Lett (2001) 42(4):703-705.
Belokon et al., Tetrahedron: Asymmetry (2001) 12:481-485.
Blackburn et al., Drug Metabolism and Disposition (1993) 21(4):573-579.
Bull et al., J Chem Soc Perkin Trans (2001) 1:3281-3287.
Cardillo et al., Synlett (1999) 1727-1730.
Cellulitis from the Merck Manual, 3 pages.
Cohen et al., J Am Chem Soc (2004) 124:2534-2543.
Cystic Fibrosis from the Merck Manual, 7 pages.
Dikler et al., J Mass Spectrometry (1997) 32:1337-1349.
Echner et al., Liebigs Ann Chem (1988) 1095-1098.
Egner et al., Tetrahedron (1997) 53(41):14021-14030.
English Translation of the International Preliminary Report on Patentability for PCT/EP2005/010856, issued Apr. 24, 2007, 10 pages.
Harada et al., J of Chrom (2001) 932:75-81.
Hingley, retrieved at http://fda.gov/FDAC/features/1998/398_alz.html on Jan. 7, 2009, 6 pages.
International Search Report for PCT/EP2005/010857, mailed on Mar. 27, 2006, 4 pages.
International Search Report for PCT/EP2007/000645, mailed on May 7, 2007, 4 pages.
International Search Report and Written Opinion for PCT/EP2007/003303, dated Jul. 19, 2007, 16 pages.
International Search Report and Written Opinion for PCT/EP2007/003313, dated Jul. 20, 2007, 10 pages.
IUPAC, Nomenclature and Symbolism for Amino Acids and Peptides, Names and Symbols for Derivatives of Named Peptides, Section 3AA-22 (Recommendations 1983-1992).

(Continued)

*Primary Examiner*—Andrew D Kosar
(74) *Attorney, Agent, or Firm*—Morrison & Foerster LLP

(57) ABSTRACT

The invention relates to cyclic nonapeptide amides and to methods for their preparation and to their use for the production of medicaments for the treatment and/or prophylaxis of diseases, especially bacterial infectious diseases.

8 Claims, 2 Drawing Sheets

OTHER PUBLICATIONS

Jetten et al., Tetrahedron Lett (1991) 32:6025-6028.
Jiang et al., J Am Chem Soc (2003) 125:1877-1887.
Kalvin et al., J Org Chem (1985) 50(13):2259-2263.
Kato et al., J Antibiot (1988) 41:719-725.
Maki et al., Antimicrob Agents and Chemotherapy (2001) 45(6):1823-1827.
Mattingly et al., J Org Chem (1983) 48:3556-3559.
Merget et al., Organomet Chem (2001) 628:183-194.
Murakami et al., Tetrahedron (2000) 56(46):9121-9128.
Neises et al., Org Synth (1985) 63:183-187.
Nomenclature and Symbolism for Amino Acids and Peptides (Recommendations 1983) Biochemical Journal (1984) 219:345-373.
Norman et al., J Org Chem (1998) 63(15):5288-5294.
Oliyai et al., Pharm Res (1995) 12(3):323-328.
Palomo et al., Tetrahedron Lett (2001) 42:8955-8957.
Panico et al., eds., A Guide to IUPAC Nomenclature of Organic Compounds, Blackwell Science LTD., 1993, pp. 1-190 (Recommendations 1993).
Rane et al., Tetrahedron Lett (1993) 34(20):3201-3204.
Rao et al., Tetrahedron Lett (1991) 32:4393-4396.
Schuhmacher et al., J Pharm Sci (2004) 93:816-830.
Seebach et al., Helv Chim Acta (1996) 79:913-941.
Shemyakin et al., Esperienta (1966) 22(8):535-536.
Tenover, Am J Infect Control (2006) 34:S3-S10.
Translation of the International Preliminary Report on Patentability for PCT/EP2005/010857, Apr. 24, 2007, 11 pages.
Translation of the International Preliminary Report on Patentability for PCT/EP2005/010858, issued Apr. 24, 2007, 5 pages.
Translation of the International Preliminary Report on Patentability for PCT/EP2007/000645, issued Sep. 9, 2008, 9 pages.
Ulhaq et al., Bioorg Med Chem (1999) 7(9):1787-1796.
Van Hof et al., Biol Chem (2001) 382:597-619.
U.S. Appl. No. 10/840,749, filed May 6, 2004 [Von Nussbaum et al.].
Preliminary Amendment for U.S. Appl. No. 10/840,749, filed Dec. 17, 2004, 15 pages.
Restriction Requirement for U.S. Appl. No. 10/840,749, mailed Dec. 5, 2005, 7 pages.
Request for Extension of Time and Response to Restriction Requirement for U.S. Appl. No. 10/840,749, filed May 8, 2005, 2 pages.
Non-Final Office Action for U.S. Appl. No. 10/840,749, mailed on Aug. 8, 2006, 7 pages.
Amendment in Response to Non-Final Office Action for U.S. Appl. No. 10/840,749, filed Nov. 8, 2006, 14 pages.
Non-Final Office Action for U.S. Appl. No. 10/840,749, mailed on Feb. 22, 2007, 11 pages.
Terminal Disclaimer for U.S. Appl. No. 10/840,749, filed Jun. 22, 2007, 1 page.
Amendment in Response to Non-Final Office Action for U.S. Appl. No. 10/840,749, filed Jun. 22, 2007, 16 pages.
Supplemental Amendment in Response to Non-Final Office Action for U.S. Appl. No. 10/840,749, filed Nov. 20, 2007, 15 pages.
Notice of Allowance for U.S. Appl. No. 10/840,749, mailed on Dec. 3, 2007, 6 pages.
U.S. Appl. No. 11/267,063, filed Nov. 4, 2005 [Von Nussbaum et al.].
Preliminary Amendment for U.S. Appl. No. 11/267,063, filed Jul. 13, 2006, 7 pages.
Restriction Requirement for U.S. Appl. No. 11/267,063, mailed on Apr. 12, 2007, 8 pages.
Amendment in Response to Non-Final Office Action for U.S. Appl. No. 11/267,063, filed Jul. 11, 2007, 8 pages.
Non-Final Office Action for U.S. Appl. No. 11/267,063, mailed on Aug. 17, 2007, 18 pages.
Amendment in Response to Non-Final Office Action for U.S. Appl. No. 11/267,063, filed Jan. 15, 2008, 9 pages.
Non-Final Office Action for U.S. Appl. No. 11/267,063, mailed on Apr. 14, 2008, 8 pages.
Interview Summary for U.S. Appl. No. 11/267,063, mailed on Aug. 6, 2008, 4 pages.
Amendment in Response to Non-Final Office Action for U.S. Appl. No. 11/267,063, filed Sep. 8, 2008, 8 pages.
Notice of Allowance for U.S. Appl. No. 11/267,063, mailed on Dec. 30, 2008, 7 pages.
U.S. Appl. No. 11/788,590, filed Apr. 19, 2007 [Von Nussbaum et al.].
Restriction Requirement for U.S. Appl. No. 11/788,590, mailed on Oct. 30, 2008, 10 pages.
Response to Restriction Requirement for U.S. Appl. No. 11/788,590, filed Dec. 29, 2008, 5 pages.
Non-Final Office Action for U.S. Appl. No. 11/788,590, mailed on Mar. 30, 2009, 19 pages.
Amendment in Response to Non-Final Office Action for U.S. Appl. No. 11/788,590, filed Jun. 23, 2009, 17 pages.
U.S. Appl. No. 11/788,649, filed Apr. 20, 2007 [Von Nussbaum et al.].
Restriction Requirement for U.S. Appl. No. 11/788,649, mailed on Jul. 24, 2008, 10 pages.
Response to Restriction Requirement for U.S. Appl. No. 11/788,649, filed Sep. 19, 2008, 5 pages.
Non-Final Office Action for U.S. Appl. No. 11/788,649, mailed on Jan. 26, 2009, 15 pages.
Amendment for U.S. Appl. No. 11/788,649, filed Jun. 26, 2009, 19 pages.
U.S. Appl. No. 11/788,690, filed Apr. 19, 2007 [Von Nussbaum et al.].
Restriction Requirement for U.S. Appl. No. 11/788,690, mailed on Mar. 23, 2009, 12 pages.
Response to Restriction Requirement for U.S. Appl. No. 11/788,690, filed Apr. 16, 2009, 6 pages.
U.S. Appl. No. 12/180,507, filed Jul. 25, 2008 [Von Nussbaum et al.].
U.S. Appl. No. 12/249,880, filed Oct. 10, 2008 [Von Nussbaum et al.].
U.S. Appl. No. 12/249,888, filed Oct. 10, 2008 [Von Nussbaum et al.].

* cited by examiner

CYCLIC NONAPEPTIDE AMIDES

CROSS-REFERENCE TO RELATED APPLICATIONS

This application is a continuation of pending international application PCT/EP2005/011451, filed Oct. 26, 2005, designating US, which claims priority from German patent application DE 10 2004 053 410.1, filed Nov. 5, 2004. The contents of the above-referenced applications are incorporated herein by this reference in their entirety.

BACKGROUND OF THE INVENTION

The invention relates to cyclic nonapeptide amides and methods for their preparation as well as to their use for the production of medicaments for the treatment and/or prophylaxis of diseases, especially bacterial infectious diseases.

The bacterial cell wall is synthesized by a number of enzymes (cell wall biosynthesis) and is essential for the survival and reproduction of microorganisms. The structure of this macromolecule, as well as the proteins involved in its synthesis, are highly conserved within the bacteria. Owing to its essential nature and uniformity, cell wall biosynthesis is an ideal point of attack for new antibiotics (D. W. Green, The bacterial cell wall as a source of antibacterial targets, *Expert Opin. Ther. Targets* (2002) 6:1-19).

Vancomycin and penicillins are inhibitors of bacterial cell wall biosynthesis and represent successful examples of the antibiotic potency of this principle of action. They have been employed for several decades clinically for the treatment of bacterial infections, in particular with Gram-positive pathogens. Owing to the growing occurrence of resistant microorganisms, for example methicillin-resistant Staphylococci, penicillin-resistant pneumococci and vancomycin-resistant enterococci (F. Baquero, Gram-positive resistance: challenge for the development of new antibiotics, *J. Antimicrob. Chemother.* (1997) (39), Suppl A:1-6; A. P. Johnson, D. M. Livermore, G. S. Tillotson, Antimicrobial susceptibility of Gram-positive bacteria: what's current, what's anticipated?, *J. Hosp. Infect.* (2001) (49), Suppl A:3-11), and also recently, for the first time, vancomycin-resistant Staphylococci (B. Goldrick, First reported case of VRSA in the United States, *Am. J. Nurs.* (2002) 102:17), these substances are increasingly losing their therapeutic efficacy.

The present invention describes a novel class of cell wall biosynthesis inhibitors without cross-resistances to known classes of antibiotics.

The natural product lysobactin and some derivatives are described as having antibacterial activity in U.S. Pat. No. 4,754,018. The isolation and antibacterial activity of lysobactin is also described in EP-A-196 042 and JP 01132600. WO04/099239 describes derivatives of lysobactin having antibacterial activity.

The antibacterial activity of lysobactin and katanosin A is furthermore described in O'Sullivan, J. et al., *J. Antibiot.* (1988) 41: 1740-1744, Bonner, D. P. et al., *J. Antibiot.* (1988) 41:1745-1751, Shoji, J. et al., *J. Antibiot.* (1988) 41:713-718 and Tymiak, A. A. et al., *J. Org. Chem.* (1989) 54:1149-1157.

The stability of an active compound is an important parameter for its suitability as a medicament. Among other factors, the stability plays a role in the storage and the administration of medicaments. Many natural products exhibit a stability insufficient for medicaments.

The antibacterially active depsipeptide lysobactin hydrolyzes in an aqueous neutral to basic medium (pH>7) within days. This forms the antibacterially inactive "open-lysobactin" which has been opened at the lactone. Active analogs of lysobactin with a higher ring stability are therefore desirable.

SUMMARY OF THE INVENTION

It is one object of the present invention to provide alternative compounds to lysobactin with comparable or improved antibacterial activity, better tolerability, e.g. lower nephrotoxicity, and improved stability in an aqueous neutral to basic medium, for the treatment of bacterial diseases in humans and animals.

In the context of this invention, it has surprisingly been found that, lysobactin amides (cyclic nonapeptide amides) have analogous antibacterial activity to lysobactin and are hydrolysis-stable in an aqueous neutral to basic medium. Lysobactin amides are aza analogs of lysobactin which have not been described to date and in which the central lactone functionality has been replaced by a lactam functionality.

The invention relates to compounds of formula

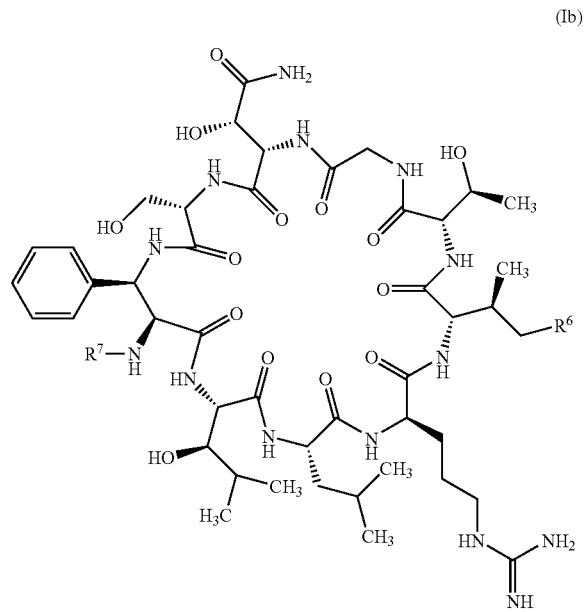

(Ib)

in which
R$^6$ represents hydrogen or methyl,
R$^7$ represents a group of formula

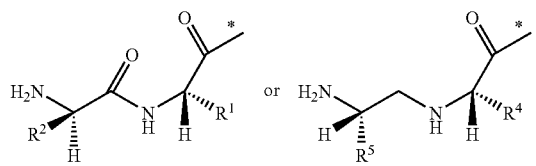

whereby
* is the linkage site to the amine,
R$^1$ represents C$_1$-C$_6$-alkyl, C$_2$-C$_6$-alkenyl, C$_3$-C$_6$-cycloalkyl or C$_6$-C$_{10}$-aryl,
whereby alkyl, alkenyl, cycloalkyl and aryl can be substituted with 0, 1, 2 or 3 substituents selected independently of one another from the group consisting of halogen, hydroxy, amino, cyano, trimethylsilyl, C$_1$-C$_6$-alkyl, C$_1$-C$_6$-alkoxy, benzyloxy, C$_3$-C$_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-aryl-carbonyl and benzyloxycarbonylamino, wherein cycloalkyl, aryl, heterocyclyl and heteroaryl for their part can be substituted with 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, $R^2$ represents $C_1$-$C_6$-alkyl, $C_2$-$C_6$-alkenyl, $C_3$-$C_6$-cycloalkyl or $C_6$-$C_{10}$-aryl, whereby alkyl, alkenyl, cycloalkyl and aryl can be substituted with 0, 1, 2 or 3 substituents selected independently of one another from the group consisting of halogen, hydroxy, amino, cyano, trimethylsilyl, $C_1$-$C_6$-alkyl, $C_1$-$C_6$-alkoxy, benzyloxy, $C_3$-$C_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-arylcarbonyl and benzyloxycarbonylamino, wherein cycloalkyl, aryl, heterocyclyl and heteroaryl for their part can be substituted with 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, $R^4$ represents $C_1$-$C_6$-alkyl, $C_2$-$C_6$-alkenyl, $C_3$-$C_6$-cycloalkyl or $C_6$-$C_{10}$-aryl, whereby alkyl, alkenyl, cycloalkyl and aryl can be substituted with 0, 1, 2 or 3 substituents selected independently of one another from the group consisting of halogen, hydroxy, amino, cyano, trimethylsilyl, $C_1$-$C_6$-alkyl, $C_1$-$C_6$-alkoxy, benzyloxy, $C_3$-$C_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-arylcarbonyl and benzyloxycarbonylamino, wherein cycloalkyl, aryl, heterocyclyl and heteroaryl for their part can be substituted with 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, $R^5$ represents $C_1$-$C_6$-alkyl, $C_2$-$C_6$-alkenyl, $C_3$-$C_6$-cycloalkyl or $C_6$-$C_{10}$-aryl, whereby alkyl, alkenyl, cycloalkyl and aryl can be substituted with 0, 1, 2 or 3 substituents selected independently of one another from the group consisting of halogen, hydroxy, amino, cyano, trimethylsilyl, $C_1$-$C_6$-alkyl, $C_1$-$C_6$-alkoxy, benzyloxy, $C_3$-$C_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-aryl-carbonyl and benzyloxycarbonylamino, wherein cycloalkyl, aryl, heterocyclyl and heteroaryl for their part can be substituted with 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, and their salts, their solvates and the solvates of their salts.

Compounds of the invention are the compounds of formula (I), (Ia) and (Ib) and their salts, solvates, solvates of the salts and prodrugs, the compounds of the formulae specified below encompassed by formula (I), (Ia) and (Ib) and their salts, solvates, solvates of the salts and prodrugs, and the compounds which are specified below as exemplary embodiments and are encompassed by formula (I), (Ia) and (Ib) and their salts, solvates, solvates of the salts and prodrugs, in so far as the compounds subsequently mentioned, encompassed by formula (I), (Ia) and (Ib) are not already salts, solvates, solvates of the salts and prodrugs.

Depending on their structure, the compounds of the invention can exist in stereoisomeric forms (enantiomers, diastereomers). The invention therefore relates to the enantiomers or diastereomers and their respective mixtures. The stereoisomerically uniform constituents can be isolated in a known manner from such mixtures of enantiomers and/or diastereomers.

Where the compounds of the invention can occur in tautomeric forms, the present invention comprises all tautomeric forms.

Salts preferred for the purpose of the present invention are physiologically acceptable salts of the compounds of the invention. However, mixed salts or salts which are not suitable for pharmaceutical applications themselves but can be used, for example, for the isolation or purification of the compounds of the invention are also included. A mixed salt means for the purpose of the present invention an addition salt which contains two or more different acids or bases, for example a trifluoroacetate mesylate salt.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases, such as, by way of example and preferably, alkali metal salts (e.g. sodium and potassium salts), alkaline earth metal salts (e.g. calcium and magnesium salts) and ammonium salts, derived from ammonia or organic amines having 1 to 16 carbon atoms, such as, by way of example and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates for the purpose of the invention refer to those forms of the compounds of the invention which form a complex in the solid or liquid state by coordination with solvent molecules. Hydrates are a special form of solvates in which coordination takes place with water.

For the purpose of the present invention, the substituents have the following meaning, unless specified otherwise:

Alkyl per se and "alk" and "alkyl" in alkoxy, alkylamino, alkylcarbonyl, alkoxycarbonyl and alkylcarbonylamino represents a linear or branched alkyl radical normally having 1 to 6, preferably 1 to 4, particularly preferably 1 to 3 carbon atoms, by way of example and preferably methyl, ethyl, n-propyl, isopropyl, tert-butyl, 2,2-dimethylprop-1-yl, 2,2-dimethylbut-1-yl, n-pentyl and n-hexyl.

Alkoxy by way of example and preferably represents methoxy, ethoxy, n-propoxy, isopropoxy, tert-butoxy, n-pentoxy and n-hexoxy.

Alkenyl represents a straight-chain or branched alkenyl radical having 2 to 6 carbon atoms. A straight-chain or branched alkenyl radical having 2 to 4, particularly preferably having 2 to 3 carbon atoms, is preferred. For example and preferably, the following may be mentioned: vinyl, allyl, n-prop-1-en-1-yl, n-but-2-en-1-yl, 2-methylprop-1-en-1-yl and 2-methylprop-2-en-1-yl.

Alkylamino represents an alkylamino radical having one or two (chosen independently of one another) alkyl substituents, by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino. $C_1$-$C_3$-Alkylamino, for example, represents a monoalkylamino radical having 1 to 3 carbon atoms or a dialkylamino radical having 1 to 3 carbon atoms each per alkyl substituent.

Arylamino represents an aryl substituent bonded via an amino group, with a further substituent optionally being bonded to the amino group, such as, for example, aryl or alkyl, by way of example and preferably phenylamino, naphthylamino, phenylmethylamino or diphenyl-amino.

Alkylcarbonyl represents, by way of example and preferably, methylcarbonyl, ethyl-carbonyl, n-propylcarbonyl, isopropylcarbonyl, tert-butylcarbonyl, n-pentylcarbonyl and n-hexylcarbonyl.

Alkoxycarbonyl represents, by way of example and preferably, methoxycarbonyl, ethoxycarbonyl, n-propoxycarbonyl, isopropoxycarbonyl, tert-butoxycarbonyl, n-pentoxycarbonyl and n-hexoxycarbonyl.

Arylcarbonyl represents an aryl substituent bonded via a carbonyl group, by way of example and preferably phenylcarbonyl, naphthylcarbonyl and phenanthrenylcarbonyl.

Alkylcarbonylamino represents, by way of example and preferably, methylcarbonylamino, ethylcarbonylamino, n-propylcarbonylamino, isopropylcarbonylamino, tert-butylcarbonylamino, n-pentylcarbonylamino and n-hexylcarbonylamino.

Arylcarbonylamino represents, by way of example and preferably, phenylcarbonylamino, naphthylcarbonylamino and phenanthrenylcarbonylamino.

Cycloalkyl represents a cycloalkyl group normally having 3 to 6 carbon atoms, by way of example and preferably cyclopropyl, cyclobutyl, cyclopentyl and cyclohexyl.

Aryl represents a mono- to tricyclic aromatic, carbocyclic radical normally having 6 to 10 carbon atoms; by way of example and preferably phenyl and naphthyl.

Heterocyclyl represents a mono- or polycyclic, preferably mono- or bicyclic, heterocyclic radical normally having 5 to 7 ring atoms and up to 3, preferably up to 2, hetero-atoms and/or hetero groups from the series N, O, S, SO, $SO_2$. The heterocyclyl radicals can be saturated or partly unsaturated. 5- to 7-membered, monocyclic saturated heterocyclyl radicals having up to two heteroatoms from the series O, N and S are preferred, such as, by way of example and preferably, tetrahydrofuranyl, pyrrolidinyl, pyrrolinyl, piperidinyl, tetrahydropyranyl, piperazinyl, morpholinyl and perhydroazepinyl.

Heteroaryl represents an aromatic, mono- or bicyclic radical normally having 5 to 10, preferably 5 to 6 ring atoms and up to 5, preferably up to 4 heteroatoms from the series S, O and N, by way of example and preferably thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl and isoquinolinyl.

Halogen represents fluorine, chlorine, bromine and iodine, preferably fluorine and chlorine.

BRIEF DESCRIPTION OF THE DRAWINGS

Description of the Figures

Figure 1:
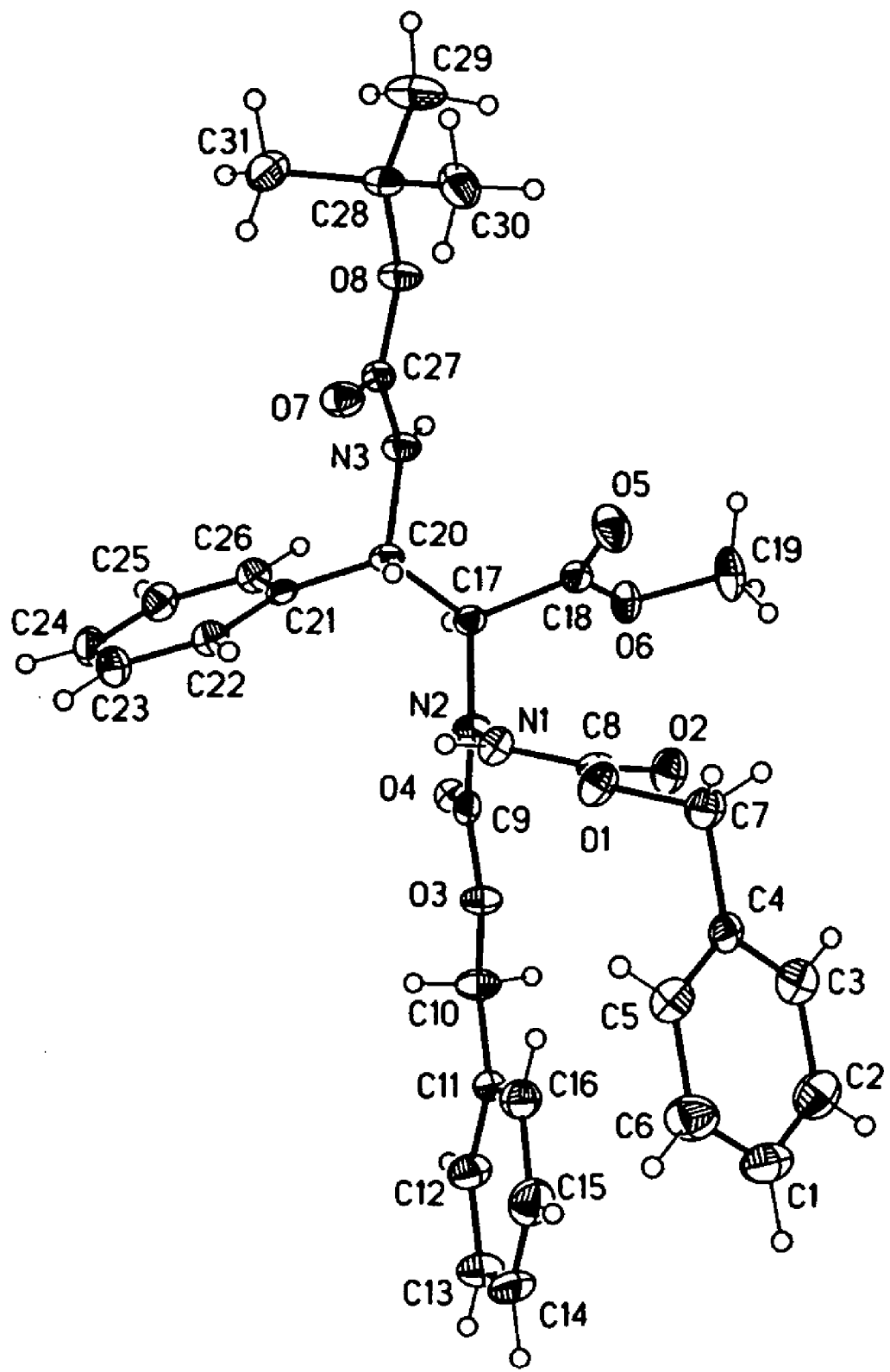

FIG. 1: Single-crystal X-ray structure of Example 12A, Ortep plot (50%).

Figure 2:
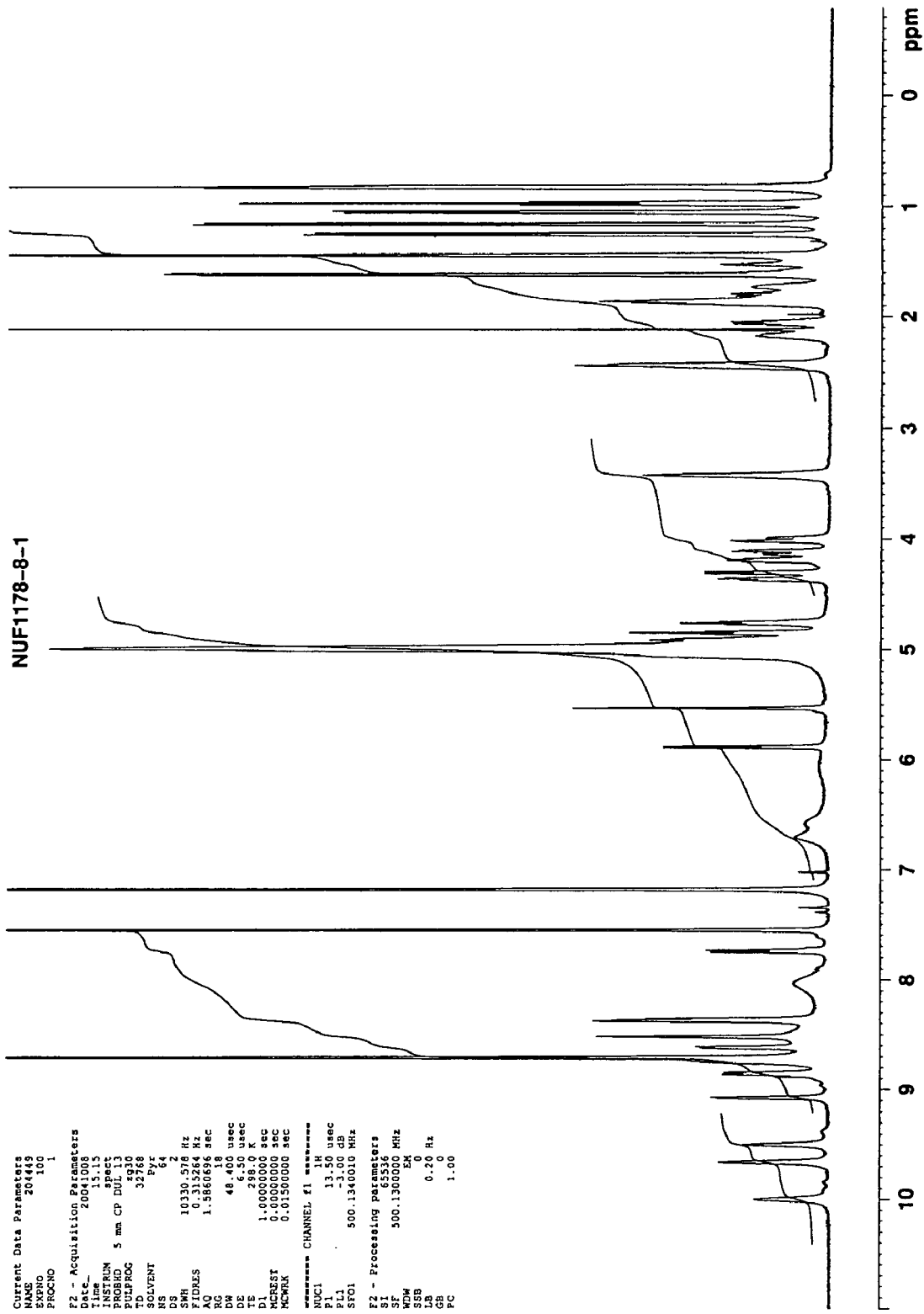

FIG. 2: $^1$H NMR (500 MHz, $d_5$-pyridine) of Example 21A

Preference is given to compounds of formula (Ib) in which $R^6$ represents methyl, $R^7$ represents a group of formula

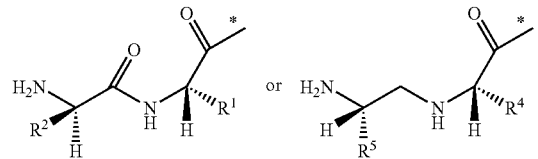

whereby

\* is the linkage site to the amine, $R^1$ represents 2-methylprop-1-yl, 2,2-dimethylprop-1-yl, 2,2-dimethylbut-1-yl, trimethylsilylmethyl, 1-hydroxy-2-methylprop-1-yl, 1-hydroxy-2,2-dimethylprop-1-yl, 1-hydroxy-2,2-dimethylbut-1-yl, 1-hydroxy-2-ethyl-2-methylbut-1-yl, 1-hydroxy-2,2-diethylbut-1-yl, phenylmethyl, 1-hydroxy-1-phenylmethyl, 2-pyridylmethyl or 3-pyridylmethyl, whereby 2-pyridylmethyl or 3-pyridylmethyl can be substituted with 0, 1, 2 or 3 substituents selected independently of one another from the group consisting of hydroxy, amino, trifluoromethyl, methyl, methoxy and morpholinyl, $R^2$ represents 2-methylprop-1-yl, 2,2-dimethylprop-1-yl, 2,2-dimethylbut-1-yl, trimethylsilylmethyl, 1-hydroxy-2-methylprop-1-yl, 1-hydroxy-2,2-dimethylprop-1-yl, 1-hydroxy-2,2-dimethylbut-1-yl, 1-hydroxy-2-ethyl-2-methylbut-1-yl, 1-hydroxy-2,2-diethylbut-1-yl, phenylmethyl, 1-hydroxy-1-phenylmethyl, 2-pyridylmethyl or 3-pyridylmethyl, whereby 2-pyridylmethyl or 3-pyridylmethyl can be substituted with 0, 1, 2 or 3 substituents selected independently of one another from the group consisting of hydroxy, amino, trifluoromethyl, methyl, methoxy and morpholinyl, $R^4$ represents 2-methylprop-1-yl, 2,2-dimethylprop-1-yl, 2,2-dimethylbut-1-yl, trimethylsilylmethyl, 1-hydroxy-2-methylprop-1-yl, 1-hydroxy-2,2-dimethylprop-1-yl, 1-hydroxy-2,2-dimethylbut-1-yl, 1-hydroxy-2-ethyl-2-methylbut-1-yl, 1-hydroxy-2,2-diethylbut-1-yl, phenylmethyl, 1-hydroxy-1-phenylmethyl, 2-pyridylmethyl or 3-pyridylmethyl, whereby 2-pyridylmethyl or 3-pyridylmethyl can be substituted with 0, 1, 2 or 3 substituents selected independently of one another from the group consisting of hydroxy, amino, trifluoromethyl, methyl, methoxy and morpholinyl, $R^5$ represents 2-methylprop-1-yl, 2,2-dimethylprop-1-yl, 2,2-dimethylbut-1-yl, trimethylsilylmethyl, 1-hydroxy-2-methylprop-1-yl, 1-hydroxy-2,2-dimethylprop-1-yl, 1-hydroxy-2,2-dimethylbut-1-yl, 1-hydroxy-2-ethyl-2-methylbut-1-yl, 1-hydroxy-2,2-diethylbut-1-yl, phenylmethyl, 1-hydroxy-1-phenylmethyl, 2-pyridylmethyl or 3-pyridylmethyl, whereby 2-pyridylmethyl or 3-pyridylmethyl can be substituted with 0, 1, 2 or 3 substituents selected independently of one another from the group consisting of hydroxy, amino, trifluoromethyl, methyl, methoxy and morpholinyl, and their salts, their solvates or the solvates of their salts.

Preference is also given to compounds of formula (Ib) in which $R^6$ represents methyl, $R^7$ represents a group of formula

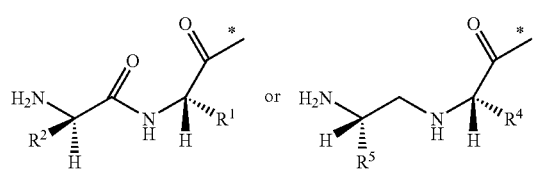

whereby
* is the linkage site to the amine,
$R^1$ represents 2-methylprop-1-yl, 2,2-dimethylprop-1-yl, trimethylsilylmethyl or 3-pyridylmethyl, whereby 3-pyridylmethyl can be substituted with 0, 1 or 2 substituents selected independently of one another from the group consisting of hydroxy, amino, trifluoromethyl, methyl, methoxy and morpholinyl, $R^2$ represents 2-methylprop-1-yl, 2,2-dimethylprop-1-yl, trimethylsilylmethyl or 3-pyridylmethyl, whereby 3-pyridylmethyl can be substituted with 0, 1 or 2 substituents selected independently of one another from the group consisting of hydroxy, amino, trifluoromethyl, methyl, methoxy and morpholinyl, $R^4$ represents 2-methylprop-1-yl, 2,2-dimethylprop-1-yl, trimethylsilylmethyl or 3-pyridylmethyl, whereby 3-pyridylmethyl can be substituted with 0, 1 or 2 substituents selected independently of one another from the group consisting of hydroxy, amino, trifluoromethyl, methyl, methoxy and morpholinyl, $R^5$ represents 2-methylprop-1-yl, 2,2-dimethylprop-1-yl, trimethylsilylmethyl or 3-pyridylmethyl, whereby 3-pyridylmethyl can be substituted with 0, 1 or 2 substituents selected independently of one another from the group consisting of hydroxy, amino, trifluoromethyl, methyl, methoxy and morpholinyl, and their salts, their solvates or the solvates of their salts.

Preference is also given to compounds of formula (Ib) in which $R^6$ represents methyl,
$R^7$ represents a group of formula

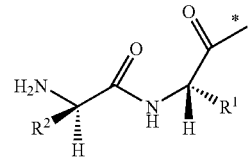

whereby
* is the linkage site to the amine,
and $R^1$ and $R^2$ have the meaning indicated above.

Preference is also given to compounds of formula (Ib) in which $R^6$ represents methyl,
$R^7$ represents a group of formula

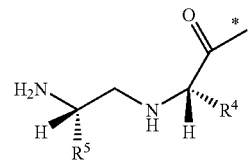

whereby
* is the linkage site to the amine,
and $R^4$ and $R^5$ have the meaning indicated above.

The invention also relates to compounds of formula

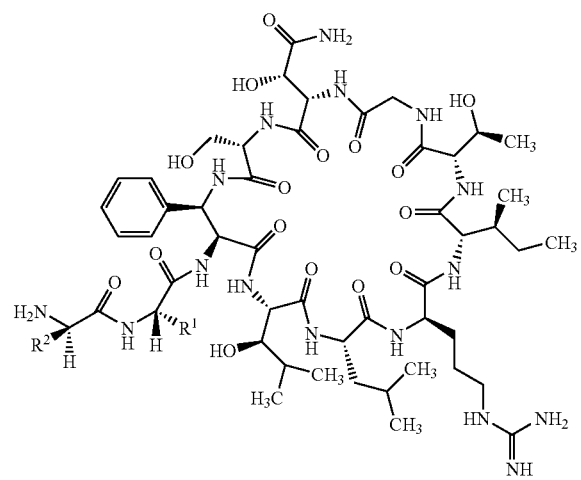

(I)

in which
$R^1$ represents $C_1$-$C_6$-alkyl, $C_2$-$C_6$-alkenyl, $C_3$-$C_6$-cycloalkyl or $C_6$-$C_{10}$-aryl, whereby alkyl, alkenyl, cycloalkyl and aryl can be substituted with 0, 1, 2 or 3 substituents selected independently of one another from the group consisting of halogen, hydroxy, amino, cyano, trimethylsilyl, $C_1$-$C_6$-alkyl, $C_1$-$C_6$-alkoxy, benzyloxy, $C_3$-$C_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-arylcarbonyl and benzyloxycarbonylamino, wherein cycloalkyl, aryl, heterocyclyl and heteroaryl for their part can be substituted with 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, $R^2$ represents $C_1$-$C_6$-alkyl, $C_2$-$C_6$-alkenyl, $C_3$-$C_6$-cycloalkyl or $C_6$-$C_{10}$-aryl, whereby alkyl, alkenyl, cycloalkyl and aryl can be substituted with 0, 1, 2 or 3 substituents selected independently of one another from the group consisting of halogen, hydroxy, amino, cyano, trimethylsilyl, $C_1$-$C_6$-alkyl, $C_1$-$C_6$-alkoxy, benzyloxy, $C_3$-$C_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-arylcarbonyl and benzyloxycarbonylamino, wherein cycloalkyl, aryl, heterocyclyl and heteroaryl for their part can be substituted with 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, and their salts, their solvates and the solvates of their salts.

Preference is also given to compounds of formula (I) in which $R^1$ represents 2-methylprop-1-yl, 2,2-dimethylprop-1-yl, 2,2-dimethylbut-1-yl, trimethylsilylmethyl, 1-hydroxy-2-methylprop-1-yl, 1-hydroxy-2,2-dimethylprop-1-yl, 1-hydroxy-2,2-dimethyl-but-1-yl, 1-hydroxy-2-ethyl-2-methyl-but-1-yl, 1-hydroxy-2,2-diethylbut-1-yl, phenylmethyl, 1-hydroxy-1-phenylmethyl, 2-pyridylmethyl or 3-pyridylmethyl, whereby 2-pyridylmethyl or 3-pyridylmethyl can be substituted with 0, 1, 2 or 3 substituents selected independently of one another from the group consisting of hydroxy, amino, trifluoromethyl, methyl, methoxy and morpholinyl, $R^2$ represents 2-methylprop-1-yl, 2,2-dimethylprop-1-yl, 2,2-dimethylbut-1-yl, trimethylsilylmethyl, 1-hydroxy-2-methylprop-1-yl, 1-hydroxy-2,2-dimethylprop-1-yl, 1-hydroxy-2,2-dimethyl-but-1-yl, 1-hydroxy-2-ethyl-2-methyl-but-1-yl, 1-hydroxy-2,2-diethylbut-1-yl, phenylmethyl, 1-hydroxy-1-phenylmethyl, 2-pyridylmethyl or 3-pyridylmethyl, whereby 2-pyridylmethyl or 3-pyridylmethyl can be substituted with 0, 1, 2 or 3 substituents selected independently of one another from the group consisting of hydroxy, amino, trifluoromethyl, methyl, methoxy and morpholinyl, and their salts, their solvates and the solvates of their salts.

Preference is also given to compounds of formula (I) in which $R^1$ represents 2-methylprop-1-yl, 2,2-dimethylprop-1-yl, trimethylsilylmethyl or 3-pyridylmethyl, whereby 3-pyridylmethyl can be substituted with 0, 1 or 2 substituents selected independently of one another from the group consisting of hydroxy, amino, trifluoromethyl, methyl, methoxy and morpholinyl, $R^2$ represents 2-methylprop-1-yl, 2,2-dimethylprop-1-yl, trimethylsilylmethyl or 3-pyridylmethyl, whereby 3-pyridylmethyl can be substituted with 0, 1 or 2 substituents selected independently of one another from the group consisting of hydroxy, amino, trifluoromethyl, methyl, methoxy and morpholinyl, and their salts, their solvates and the solvates of their salts.

The invention also relates to compounds of formula

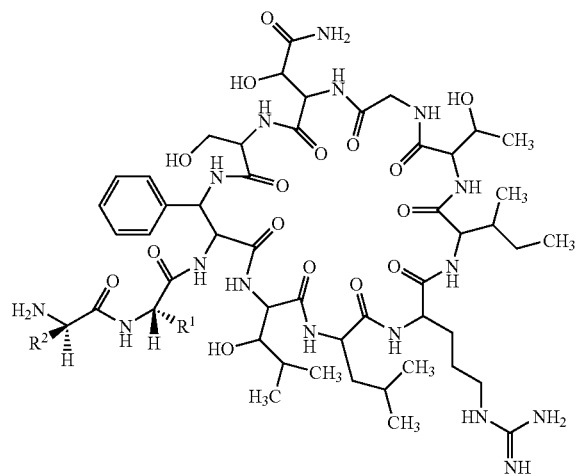

(Ia)

in which $R^1$ represents $C_1$-$C_6$-alkyl, $C_2$-$C_6$-alkenyl, $C_3$-$C_6$-cycloalkyl or $C_6$-$C_{10}$-aryl, whereby alkyl, alkenyl, cycloalkyl and aryl can be substituted with 0, 1, 2 or 3 substituents selected independently of one another from the group consisting of halogen, hydroxy, amino, cyano, trimethylsilyl, $C_1$-$C_6$-alkyl, $C_1$-$C_6$-alkoxy, benzyloxy, $C_3$-$C_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-arylcarbonyl and benzyloxycarbonylamino, wherein cycloalkyl, aryl, heterocyclyl and heteroaryl for their part can be substituted with 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, $R^2$ represents $C_1$-$C_6$-alkyl, $C_2$-$C_6$-alkenyl, $C_3$-$C_6$-cycloalkyl or $C_6$-$C_{10}$-aryl, whereby alkyl, alkenyl, cycloalkyl and aryl can be substituted with 0, 1, 2 or 3 substituents selected independently of one another from the group consisting of halogen, hydroxy, amino, cyano, trimethylsilyl, $C_1$-$C_6$-alkyl, $C_1$-$C_6$-alkoxy, benzyloxy, $C_3$-$C_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-arylcarbonyl and benzyloxycarbonylamino, wherein cycloalkyl, aryl, heterocyclyl and heteroaryl for their part can be substituted with 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, and their salts, their solvates and the solvates of their salts.

The invention further relates to a method for preparing the compounds of formula (Ib), whereby

[A] the compounds of formula

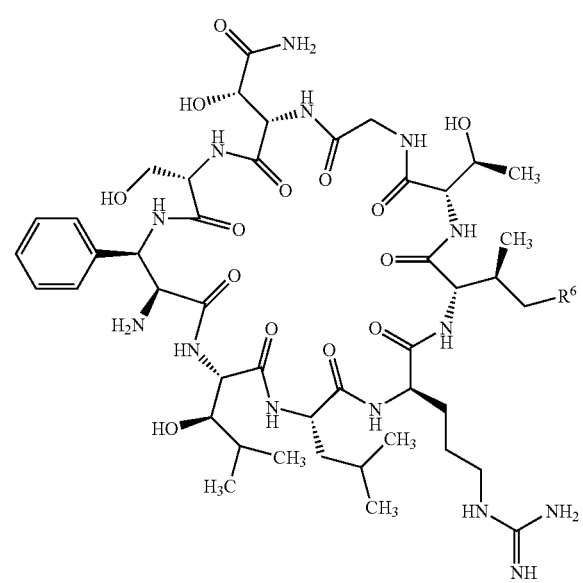

(II)

in which $R^6$ has the meaning indicated above are reacted first with compounds of formula

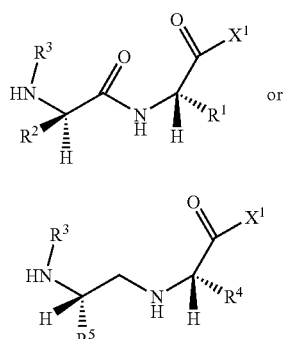

(III)

or (VI)

in which $R^1$, $R^2$, $R^4$ and $R^5$ have the meaning indicated above, $R^3$ represents tert-butoxycarbonyl or benzyloxycarbonyl, and $X^1$ represents halogen, preferably bromine, chlorine or fluorine, or hydroxy, and then with an acid and/or by hydrogenolysis, or

[B] the compounds of formula

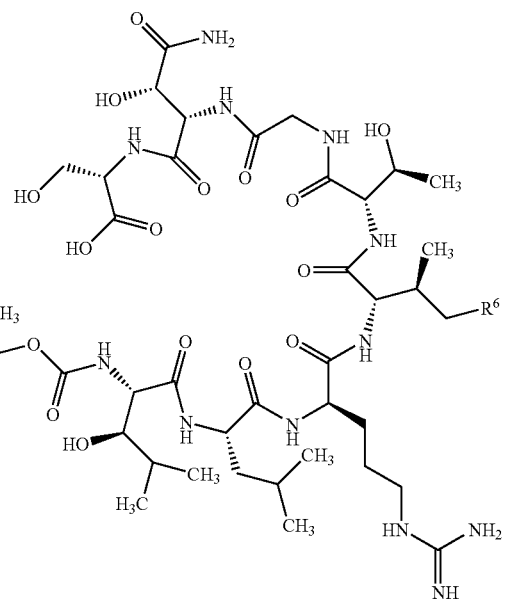

(IV)

in which $R^6$ has the meaning indicated above are reacted first with compounds of formula

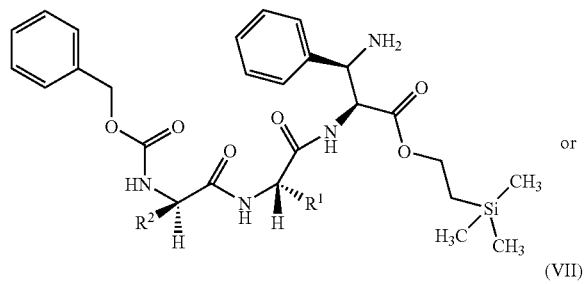

(V)

or (VII)

in which $R^1$, $R^2$, $R^4$ and $R^5$ have the meaning indicated above, and then, in a 4-stage synthesis, a) with a fluoride reagent, such as tetrabutylammonium fluoride, b) with an acid, c) with a dehydrating reagent, where appropriate in the presence of a base, and d) by hydrogenolysis.

Method [A]:

If $X^1$ is halogen, the reaction of the first stage generally takes place in inert solvents, where appropriate in the presence of a base, preferably in a temperature range from −30° C. to 50° C. under atmospheric pressure.

Inert solvents are, for example, tetrahydrofuran, methylene chloride, pyridine, dioxane, dimethylacetamide, N-methylpyrrolidine or dimethylformamide; pyridine or dimethylformamide are preferred.

Bases are, for example, triethylamine, diisopropylethylamine or N-methylmorpholine; diisopropylethylamine is preferred.

If $X^1$ is hydroxy, the reaction of the first stage generally takes place in inert solvents, in the presence of a dehydrating reagent, where appropriate in the presence of a base, preferably in a temperature range from −30° C. to 50° C. under atmospheric pressure.

Inert solvents are, for example, halohydrocarbons such as dichloromethane or trichloromethane, hydrocarbons such as benzene, nitromethane, dioxane, dimethylformamide or acetonitrile. It is likewise possible to employ mixtures of the solvents. Dichloromethane or dimethylformamide are particularly preferred.

Suitable dehydrating reagents are, for example, carbodiimides, for example N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or benzotriazol-1-yloxytris(pyrrolidino)phosphonium hexafluorophosphate (PyBOP), or N-hydroxysuccinimide, or mixtures of these with bases.

Bases are, for example, alkali metal carbonates, for example sodium or potassium carbonate, or hydrogencarbonate, or organic bases such as trialkylamines, for example triethylamine, N-methylmorpholine, N-methylpiperidine, 4-dimethylaminopyridine or diisopropylethylamine.

Preferably the condensation is carried out using HATU or using EDC in the presence of HOBt.

The reaction with an acid in the second stage of the process preferably takes place in a temperature range from 0° C. to 40° C. under atmospheric pressure.

Suitable acids hereby are hydrogen chloride in dioxane, hydrogen bromide in acetic acid or trifluoroacetic acid in methylene chloride.

The hydrogenolysis in the second stage of the process generally takes place in a solvent in the presence of hydrogen and palladium on activated carbon, preferably in a temperature range from 0° C. to 40° C. under atmospheric pressure.

Solvents are, for example, alcohols such as methanol, ethanol, n-propanol or isopropanol, in a mixture with water and acetic acid or aqueous hydrochloric acid; a mixture of ethanol, water and acetic acid, or a mixture of isopropanol and aqueous hydrochloric acid is preferred.

Method [B]:

The reaction of the compounds of formula (IV) with compounds of formula (V) or (VII) generally takes place in inert solvents, in the presence of a dehydrating reagent, where appropriate in the presence of a base, preferably in a temperature range from −30° C. to 50° C. under atmospheric pressure.

Inert solvents are, for example, halohydrocarbons such as dichloromethane or trichloromethane, hydrocarbons such as benzene, nitromethane, dioxane, dimethylformamide or acetonitrile. It is likewise possible to employ mixtures of the solvents. Dichloromethane or dimethylformamide are particularly preferred.

Suitable dehydrating reagents hereby are, for example, carbodiimides, for example N,N'-diethyl-, N,N'-dipropyl-, N,N-diisopropyl-, N,N'-dicyclohexyldicarbodiimide, N-(3-dimethylaminoisopropyl)-N'-ethylcarbodiimide hydrochloride (EDC), N-cyclohexyl-carbodiimide-N'-propyloxymethylpolystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or benzotriazol-1-yloxytris(pyrrolidino)phosphonium hexafluorophosphate (PyBOP), or N-hydroxysuccinimide, or mixtures of these with bases.

Bases are, for example, alkali metal carbonates, for example sodium or potassium carbonate, or hydrogencarbonate, or organic bases such as trialkylamines, for example triethylamine, N-methylmorpholine, N-methylpiperidine, 4-dimethylaminopyridine or diisopropylethylamine.

Preferably the condensation is carried out using HATU or using EDC in the presence of HOBt.

The reaction with tetrabutylammonium fluoride in the first stage (a) of the further method generally takes place in inert solvents, preferably in a temperature range from 0° C. to 40° C. under atmospheric pressure.

Inert solvents are, for example, halohydrocarbons such as dichloromethane or trichloromethane, or ethers such as tetrahydrofuran or dioxane. Tetrahydrofuran is particularly preferred.

The reaction with an acid in the second stage (b) of the method preferably takes place in a temperature range from 0° C. to 40° C. under atmospheric pressure.

Acids suitable hereby are hydrogen chloride in dioxane, hydrogen bromide in acetic acid or trifluoroacetic acid in methylene chloride.

The reaction in the third stage (c) of the method takes place in analogy to the reaction of the compounds of formula (IV) with compounds of formula (V) or (VII).

The hydrogenolysis in the fourth stage (d) of the method generally takes place in a solvent in the presence of hydrogen and palladium on activated carbon, preferably in a temperature range from 0° C. to 40° C. under atmospheric pressure.

Solvents are, for example, alcohols such as methanol, ethanol, n-propanol or isopropanol, in a mixture with water and acetic acid or aqueous hydrochloric acid; a mixture of ethanol, water and acetic acid or a mixture of isopropanol and aqueous hydrochloric acid is preferred.

The compound of formula (II) can be synthesized by hydrogenation, enzymatic cleavage and recyclization from lysobactin (Example 1A) or katanosin A, as described in the experimental part under Example 2A, 3A and 20A to 26A. The compound of formula (IV) is an intermediate in this synthesis sequence.

The compounds of formulae (III), (V), (VI) and (VII) are known or can be synthesized from the corresponding starting materials by known methods or by the methods described below.

The preparation of the compounds of the invention can be illustrated by the following synthesis schemes.

Synthesis scheme 1:

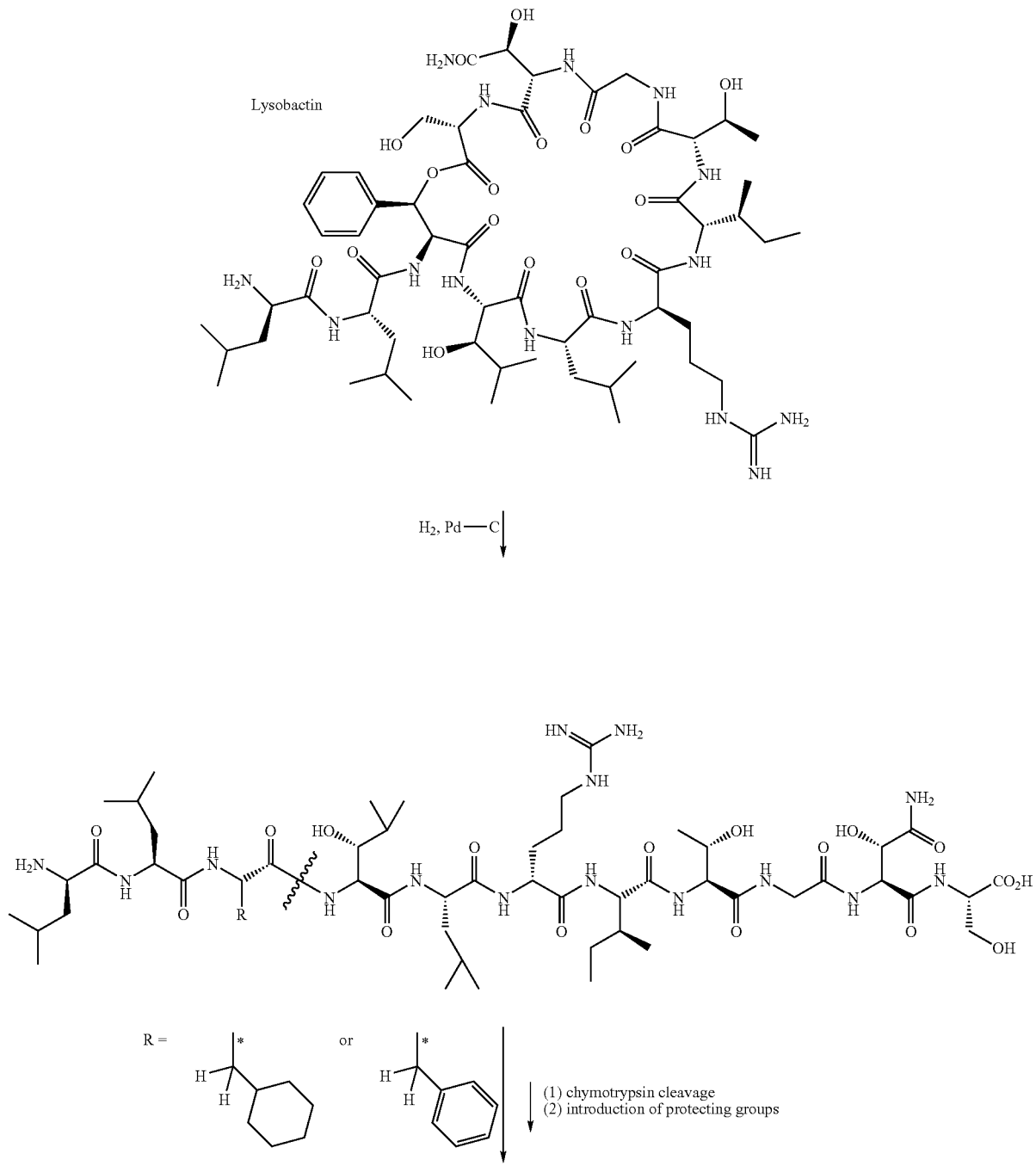

-continued
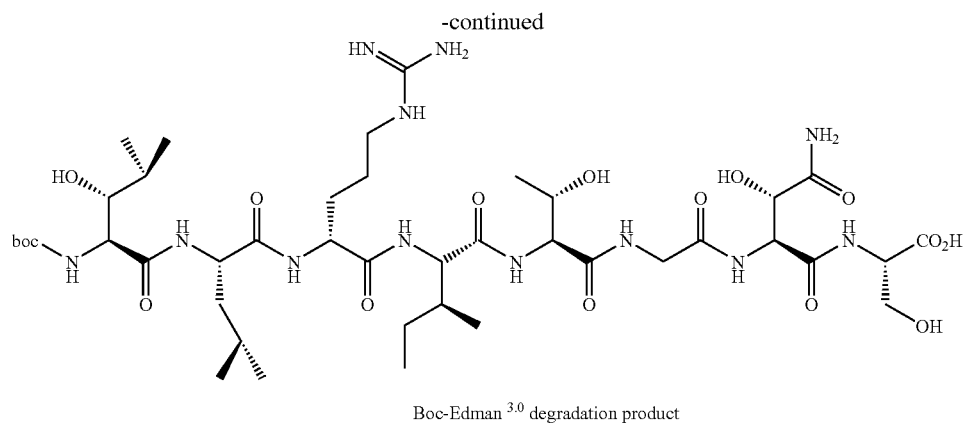
Boc-Edman[3.0] degradation product
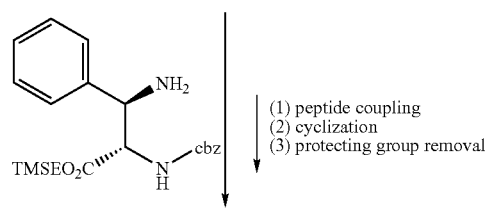
(1) peptide coupling
(2) cyclization
(3) protecting group removal
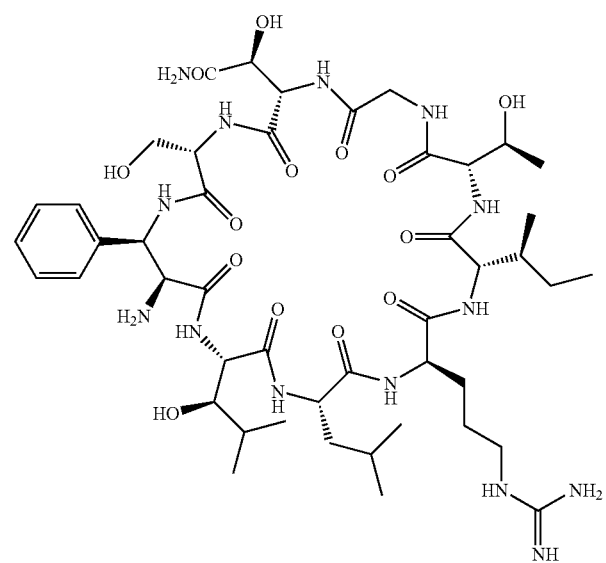
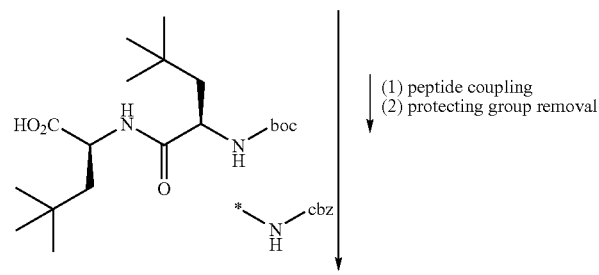
(1) peptide coupling
(2) protecting group removal

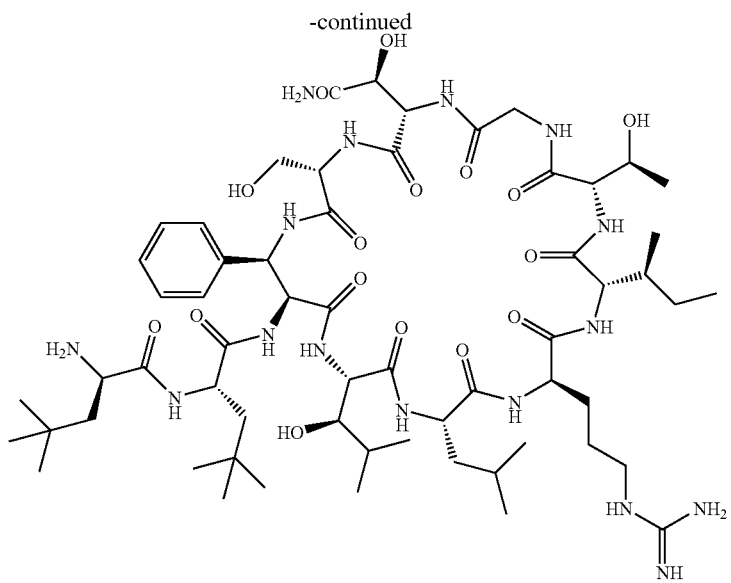
Synthesis scheme 2:
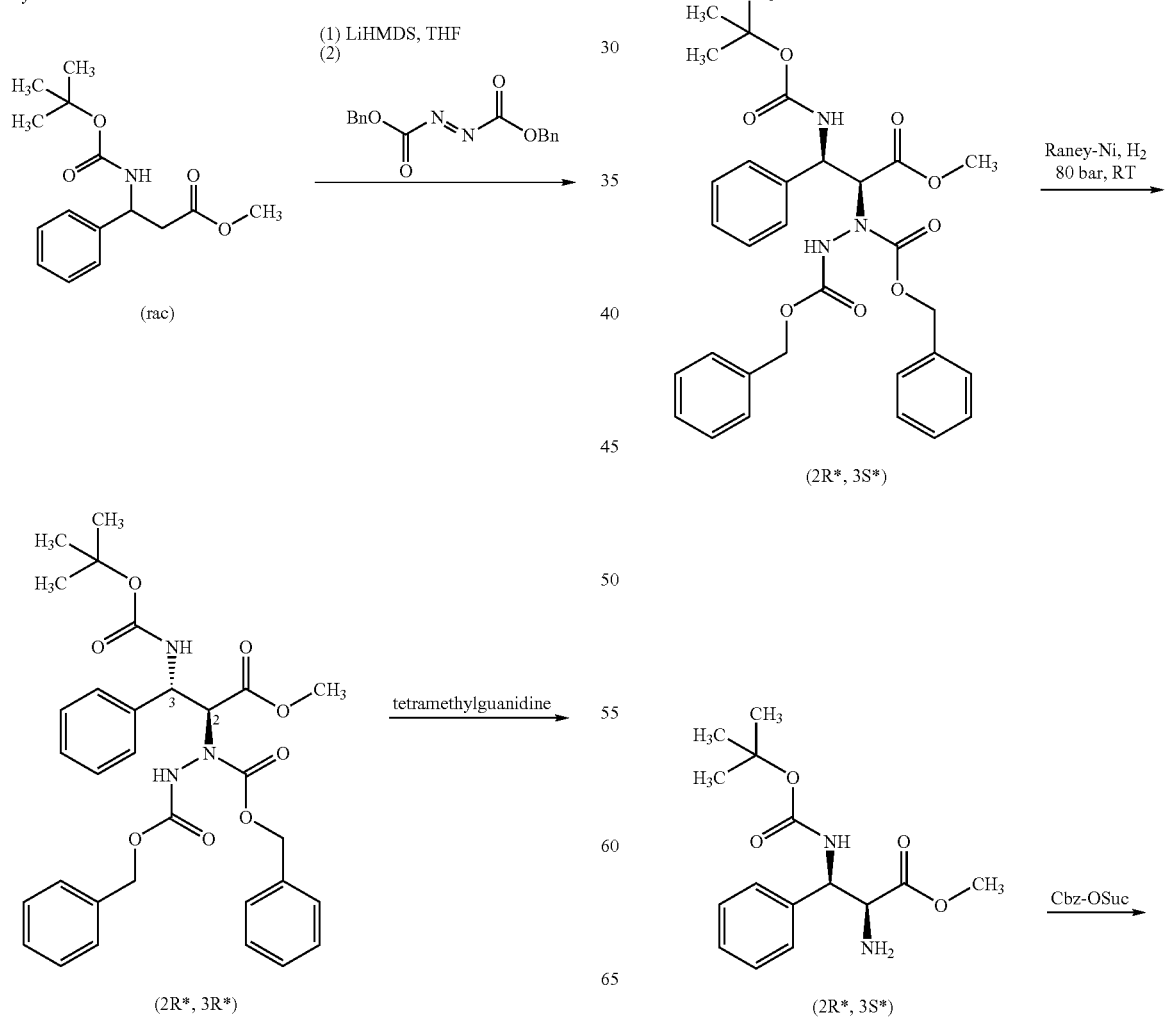

-continued

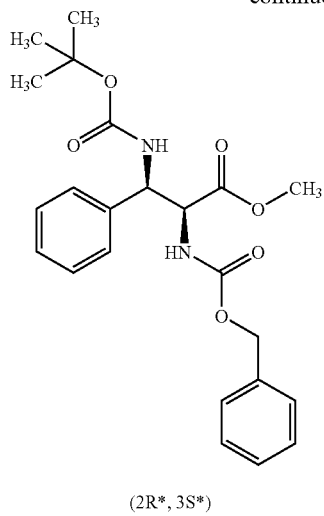

(2R*, 3S*)

(1) LiOH, THF water
(2) chiral chromatography →

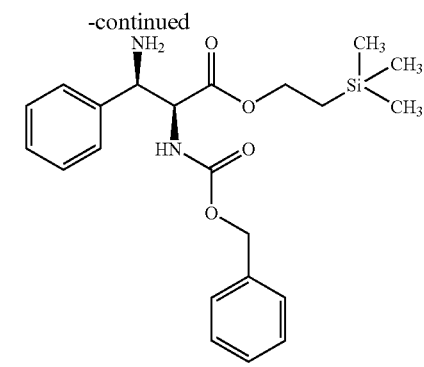

The present invention further relates to a process for preparing the compound of the formula 2-(trimethylsilyl)ethyl-(3R)-3-amino-$N^2$-[(benzyloxy)carbonyl]-L-phenylalaninate trifluoroacetate (Example 19A)

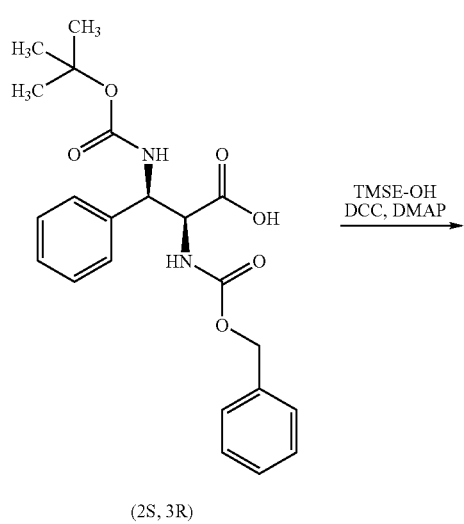

(2S, 3R)

TMSE-OH
DCC, DMAP →

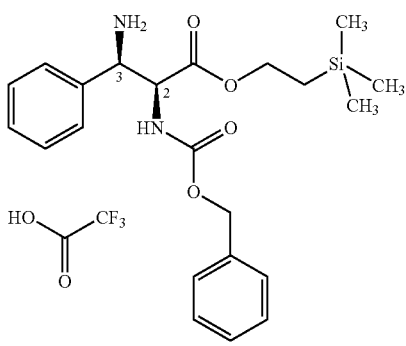

characterized in that, in a 6-stage synthesis, the compound of the formula methyl (rac)-3-[(tert-butoxycarbonyl)amino]-3-phenylpropanoate

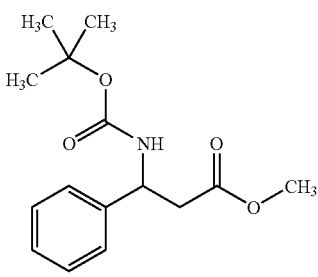

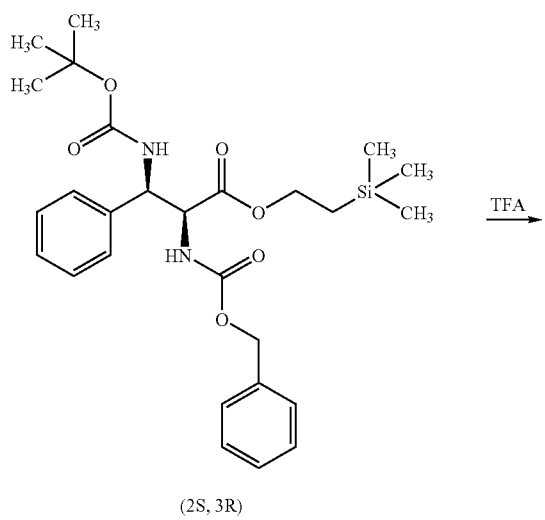

(2S, 3R)

TFA → is reacted a) in the presence of a base, preferably lithium hexamethyldisilazide, with dibenzyl azadicarboxylate, b) with N,N,N,N-tetramethylguanidine, c) with hydrogen in the presence of Raney nickel, d) with N-benzyloxycarbonyloxysuccinimide ester in the presence of a base, preferably N-methylmorpholine, e) with a base, preferably lithium hydroxide, and subsequent chromatographic separation of the enantiomers and f) with trifluoroacetic acid in dichloromethane or hydrogen chloride in dioxane.

The detailed synthesis is described in the experimental part under Example 12A to Example 19A.

The present invention further relates to the compound of the formula
(3R)—N²-[(Benzyloxy)carbonyl]-3-[(tert-butoxycarbonyl)amino]-L-phenylalanine (Example 17A and Example 35A)

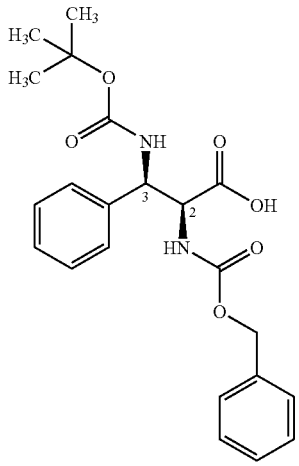

or
2-(trimethylsilyl)ethyl(3R)—N-[(benzyloxy)carbonyl]-3-[(tert-butoxycarbonyl)amino]-L-phenylalaninate (Example 18A)

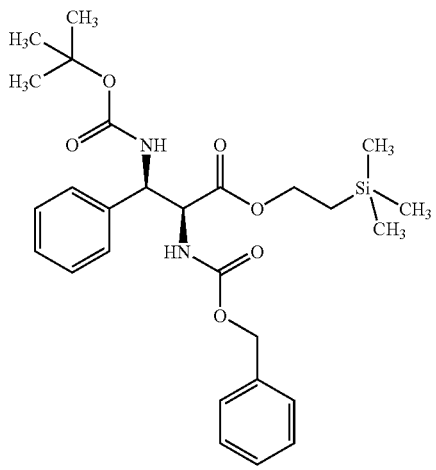

or
2-(trimethylsilyl)ethyl(3R)-3-amino-N²-[(benzyloxy)carbonyl]-L-phenylalaninate trifluoroacetate (Example 19A)

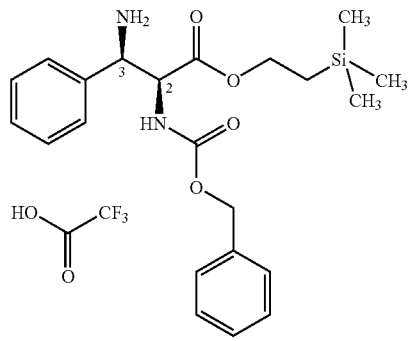

or
methyl(2S,3R)-3-[(tert-butoxycarbonyl)amino]phenylalaninate (Example 33A)

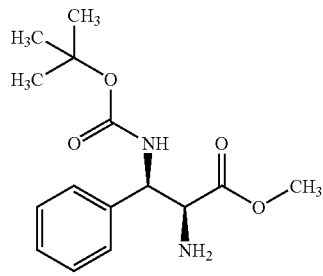

or
methyl(2S,3R)—N-[(benzyloxy)carbonyl]-3-[(tert-butoxycarbonyl)amino]phenylalaninate (Example 34A)

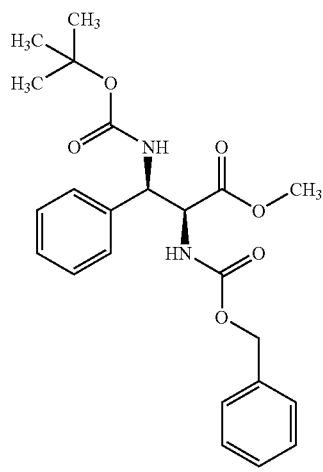

or
(3S)—N²-[(benzyloxy)carbonyl]-3-[(tert-butoxycarbonyl)amino]-D-phenylalanine (Example 36A)

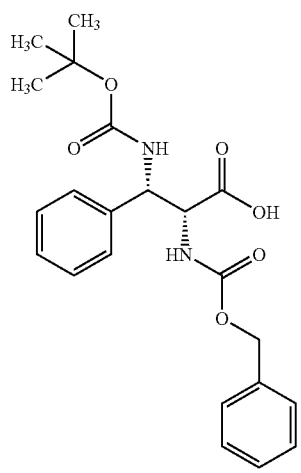

or
2-(trimethylsilyl)ethyl(3S)—N-[(benzyloxy)carbonyl]-3-[(tert-butoxycarbonyl)amino]-D-phenylalaninate (Example 37A)

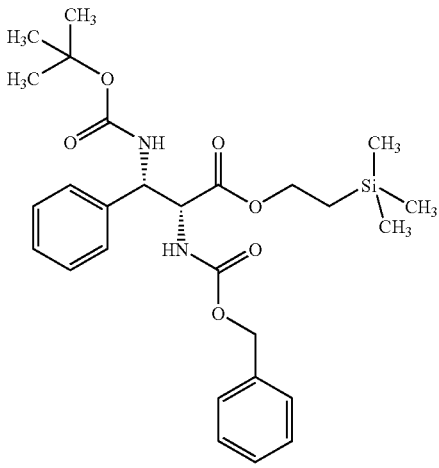

or
2-(trimethylsilyl)ethyl(3S)-3-amino-N²-[(benzyloxy)carbonyl]-D-phenylalaninate trifluoroacetate (Example 38A)

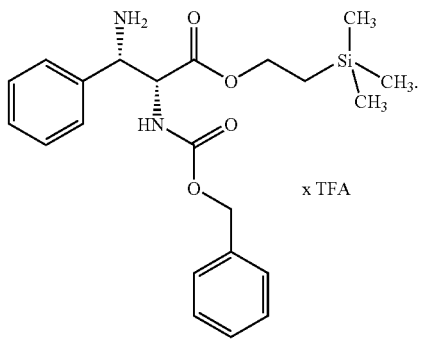

The compounds of the invention show a valuable spectrum of pharmacological activity. They show antibacterial activity.

They are therefore suitable for use as medicaments for the treatment and/or prophylaxis of diseases in humans and animals.

The compounds of the invention are distinguished by a lower nephrotoxicity compared to lysobactin.

The compounds of the invention are distinguished by an improved stability in an aqueous neutral to basic medium. This property improves the storage of the compounds of the invention and the administration as medicaments.

The nonadepsipeptides described act as inhibitors of the bacterial cell wall biosynthesis.

The preparations of the invention are particularly effective against bacteria and bacteria-like microorganisms. They are therefore particularly suitable for the prophylaxis and chemotherapy of local and systemic infections caused by these pathogens in human and veterinary medicine.

In principle, the preparations of the invention can be used against all bacteria and bacteria-like microorganisms which possess a bacterial cell wall (Murein sacculus) or the corresponding enzyme systems, for example by the following pathogens or by mixtures of the following pathogens:

Gram-negative cocci (*Neisseria gonorrhoeae*) as well as Gram-negative rods such as Enterobacteriaceae, e.g. *Escherichia coli, Haemophilus influenzae, Pseudomonas, Klebsiella, Citrobacter* (*C. freundii, C. divernis*), *Salmonella* and *Shigella*; furthermore *Enterobacter* (*E. aerogenes, E. agglomerans*), *Hafnia, Serratia* (*S. marcescens*), *Providencia, Yersinia*, as well as the genus *Acinetobacter, Branhamella* and *Chlamydia*. Moreover, the antibacterial spectrum includes strictly anaerobic bacteria such as, for example, *Bacteroides fragilis*, representatives of the genus *Peptococcus, Peptostreptococcus* as well as the genus *Clostridium*; furthermore *Mycobacteria*, e.g. *M. tuberculosus*. The compounds of the invention show a particularly pronounced effect on Gram-positive cocci, e.g. staphylococci (*S. aureus, S. epidermidis, S. haemolyticus, S. carnosus*), enterococci (*E. faecalis, E. faecium*) and streptococci (*S. agalactiae, S. pneumoniae, S. pyogenes*).

The above list of pathogens is to be interpreted only by way of example and in no way as restrictive. Diseases which may be caused by the pathogens mentioned or mixed infections and can be prevented, ameliorated or cured by the preparations according to the invention include, for example:

infectious diseases in humans such as, for example, uncomplicated and complicated urinary tract infections, uncomplicated skin and superficial infections, complicated skin and soft tissue infections, pneumonia acquired in hospital and as an outpatient, nosocomial pneumonia, acute exacerbations and secondary bacterial infections of chronic bronchitis, acute otitis media, acute sinusitis, streptococcal pharyngitis, bacterial meningitis, uncomplicated gonococcal and non-gonococcal urethritis/cervicitis, acute prostatitis, endocarditis, uncomplicated and complicated intra-abdominal infections, gynaecological infections, pelvic inflammatory disease, bacterial vaginosis, acute and chronic osteomyelitis, acute bacterial arthritis, empirical therapy in febrile neutropenic patients, furthermore bacteremias, MRSA infections, acute infectious diarrhea, *Helicobacter pylori* infections, postoperative infections, odontogenic infections, ophthalmological infections, postoperative infections (incl. periproctal abscess, wound infections, biliary infections, mastitis and acute appendicitis), cystic fibrosis and bronchiectasis.

Apart from in humans, bacterial infections can also be treated in other species. Examples which may be mentioned are:

Pigs: diarrhea, enterotoxemia, sepsis, dysentery, salmonellosis, metritis-mastitis-agalactiae syndrome, mastitis;

Ruminants (cattle, sheep, goats): diarrhea, sepsis, bronchopneumonia, salmonellosis, pasteurellosis, genital infections;

Horses: bronchopneumonia, joint-ill, puerperal and post-puerperal infections, salmonellosis;

Dogs and cats: bronchopneumonia, diarrhea, dermatitis, otitis, urinary tract infections, prostatitis;

Poultry (chickens, turkeys, quails, pigeons, ornamental birds and others): *E. coli* infections, chronic respiratory diseases, salmonellosis, pasteurellosis, psittacosis.

It is likewise possible to treat bacterial diseases in the raising and keeping of productive and ornamental fish, the antibacterial spectrum thereby extending beyond the previously mentioned pathogens to further pathogens such as, for example, *Pasteurella, Brucella, Campylobacter, Listeria, Erysipelothris, Corynebacteria, Borellia, Treponema, Nocardia, Rikettsia, Yersinia*.

The present invention further relates to the use of the compounds of the invention for the treatment and/or prophylaxis of diseases, in particular of bacterial infectious diseases.

The present invention further relates to the use of the compounds of the invention for the treatment and/or prophylaxis of diseases, in particular the aforementioned diseases.

The present invention further relates to the use of the compounds of the invention for the production of a medicament for the treatment and/or prophylaxis of diseases, in particular the aforementioned diseases.

The compounds of the invention are preferably used for the production of medicaments which are suitable for the prophylaxis and/or treatment of bacterial diseases.

The present invention further relates to a process for the treatment and/or prophylaxis of diseases, in particular the aforementioned diseases, using an antibacterially active amount of the compounds of the invention.

The present invention further relates to medicaments, comprising at least one compound of the invention and at least one or more further active compounds, in particular for the treatment and/or prophylaxis of the aforementioned diseases. Preferred active compounds for combination are antibacterially active compounds which have a different spectrum of activity, in particular a supplementary spectrum of action, and/or are synergistic to the compounds of the invention.

The compounds of the invention can act systemically and/or locally. For this purpose, they can be administered in a suitable way, such as, for example, orally, parenterally, pulmonarily, nasally, sublingually, lingually, buccally, rectally, dermally, transdermally, conjunctivally, otically or as an implant or stent.

The compounds of the invention can be administered in administration forms suitable for these routes of administration.

Suitable for oral administration, are administration forms which function according to the prior art and deliver the compounds of the invention rapidly and/or in a modified fashion and which contain the compounds of the invention in crystalline and/or amorphized and/or dissolved form, such as, for example, tablets (uncoated or coated tablets, for example having enteric coatings or coatings which are insoluble or dissolve with a delay and control the release of the compound of the invention), tablets or films/wafers, which disintegrate rapidly in the oral cavity, films/lyophilizates, capsules (for example hard or soft gelatine capsules), sugar-coated tablets, granules, pellets, powders, emulsions, suspensions, aerosols or solutions.

Parenteral administration can take place with avoidance of an absorption step (e.g. intravenous, intraarterial, intracardial, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates, or sterile powders.

Suitable for the other administration routes are, for example, pharmaceutical forms for inhalation (inter alia powder inhalers, nebulizers), nasal drops, solutions, sprays; tablets, films/wafers or capsules for lingual, sublingual or buccal administration, suppositories, preparations for ears or eyes, vaginal capsules, aqueous suspensions (lotions, shaking mixtures), lipophilic suspensions, ointments, creams, transdermal therapeutic systems (such as, for example, patches), milk, pastes, foams, dusting powder, implants or stents.

The compounds of the invention can be converted into the stated administration forms. This can take place in a manner known per se by mixing with inert, non-toxic, pharmaceutically acceptable excipients. These excipients include, inter alia, carriers (for example microcrystalline cellulose, lactose, mannitol), solvents (e.g. liquid polyethylene glycols), emulsifiers and dispersants or wetting agents (for example sodium dodecylsulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and taste and/or odor corrigents.

The present invention furthermore relates to medicaments which comprise at least one compound of the invention, usually together with one or more inert, non-toxic, pharmaceutically suitable excipients, and their use for the aforementioned purposes.

In general, it has proved advantageous on intravenous administration to administer amounts of about 0.001 to 100 mg/kg, preferably about 0.1 to 10 mg/kg of body weight to achieve effective results, and on oral administration the dosage is about 0.01 to 50 mg/kg, preferably 0.5 to 10 mg/kg, of body weight.

It may nevertheless be necessary where appropriate to deviate from the stated amounts, in particular as a function of body weight, route of administration, individual behaviour towards the active compound, type of preparation and time or interval over which administration takes place. Thus, in some cases it may be sufficient to make do with less than the aforementioned minimum amount, while in other cases the stated upper limit must be exceeded. In the case of the administration of larger amounts, it can be advisable to divide these into a number of individual doses over the course of the day.

The percentages in the following Tests and Examples are, unless stated otherwise, percentages by weight; parts are parts by weight. Solvent ratios, dilution ratios and concentrations of liquid/liquid solutions are in each case based volume.

DETAILED DESCRIPTION OF PREFERRED EMBODIMENTS

A. Examples

Abbreviations aq. aqueous
Area (Peak) area
BHI Brain heart infusion
Boc tert-butyloxycarbonyl
br. broad signal (in NMR spectra)
calc. calculated
conc. concentrated
d doublet (in NMR spectra)
DCC dicyclohexylcarbodiimide
DCI direct chemical ionization (in MS)
DCM dichloromethane
DIEA N,N-diisopropylethylamine
DMAP 4-N,N-dimethylaminopyridine
DMF N,N-dimethylformamide
DMSO dimethylsulfoxide
EA ethyl acetate (acetic acid ethyl ester)
EDC 1-ethyl-3-(3-dimethylaminopropyl)carbodiimide (also EDCI)
EDCxHCl 1-ethyl-3-(3-dimethylaminopropyl)carbodiimide hydrochloride
EDTA ethylenediaminetetraacetic acid
EI electron impact ionization (in MS)
ESI electrospray ionization (in MS)

Ex. Example
h hour
HATU O-(7-azabenzotriazol-1-yl)-N,N,N',N'-tetramethyluronium hexafluorophosphate
HOBt 1-hydroxybenzotriazole
HPLC high-pressure or high-performance liquid chromatography
HR high resolution
i. V. in vacuo
LC-MS liquid chromatography-coupled mass spectroscopy
LDA lithium diisopropylamide
LLA (3-cyclo-hexyl) D-Leu-Leu-(3-cyclohexyl)Ala
LLF D-Leu-Leu-Phe
m middle (in UV and IR spectra)
m multiplet (in NMR spectra)
MALDI matrix-assisted laser desorption/ionization
MIC minimum inhibitory concentration
min minute/minutes
Mp. melting point
MRSA methicillin-resistant *Staphylococcus aureus*
MS mass spectroscopy
NCCLS National Committee for Clinical Laboratory Standards
neg. negative
NMM N-methylmorpholine
NMR nuclear magnetic resonance spectroscopy
p.a. pro analysi
Pd palladium
Pd—C palladium on carbon
pos. positive
PTFE poly tetrafluoroethylene
quant. quantitative
RP-HPLC reverse phase HPLC
RT room temperature
$R_t$ retention time (in HPLC)
s strong (in UV and IR spectra)
s singlet (in NMR spectra)
sat. saturated
TBAF tetrabutylammonium fluoride
TBTU O-(benzotriazol-1-yl)-N,N,N',N'-tetramethyluronium tetrafluoroborate
TCTU O-(1H-6-chlorobenzotriazol-1-yl)-1,1,3,3-tetramethyluronium tetrafluoroborate
TFA trifluoroacetic acid
TFE 2,2,2-trifluoroethanol
THF tetrahydrofuran
TLC thin-layer chromatography
TMG N,N,N,N-tetramethylguanidine
TMSE 2-(trimethylsilyl)ethyl
TOF time of flight
UV ultraviolet
Vis visible
VRSA vancomycin-resistant *Staphylococcus aureus*
W weak (in UV and IR spectra)
Z, Cbz benzyloxycarbonyl

LITERATURE

For the nomenclature of the peptides and cyclodepsipeptides, c.f.:
1. A Guide to IUPAC Nomenclature of Organic Compounds (Recommendations 1993), 1993, Blackwell Scientific publications.
2. Nomenclature and symbolism for amino acids and peptides. Recommendations 1983. IUPAC-IUB Joint Commission on Biochemical Nomenclature, UK. *Biochemical Journal* (1984) 219:345-373. And cited literature.

General Methods GC-MS, LC-MS, HR-MS, HPLC and Gel Chromatography

Method 1 (TOF-HR-MS): TOF-HR-MS-ESI+ spectra are recorded with a Micromass LCT instrument (capillary voltage: 3.2 KV, cone voltage: 42 V, source temperature: 120° C., desolvation temperature: 280° C.). To this end, a syringe pump (from Harvard Apparatus) is used for the sample supply. Leucine encephalin is used as standard (Tyr-Gly-Gly-Phe-Leu).

Method 2 (analytical HPLC; Synergi): instrument type HPLC: HP 1100 Series; UV DAD; column: Phenomenex Synergi 2µ Hydro-RP Mercury 20 mm×4 mm; eluent A: 1 l of water+1.0 ml of 50% formic acid, eluent B: 1 l of acetonitrile; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 3 (analytical HPLC; Synergi): instrument type HPLC: HP 1050 Series; UV DAD; column: Phenomenex Synergi 2µ Max-RP Mercury 20 mm×4 mm; eluent A: 1 l of water+0.05% trifluoroacetic acid, eluent B: 1 l of acetonitrile; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 4 (analytical HPLC): instrument type HPLC: HP 1050 Series; UV DAD 1100 Series; column: Kromasil $C_{18}$, 60×2 mm, 3.5 µm; eluent A: water/0.5% perchloric acid, eluent B: acetonitrile; gradient: 0-0.5 min 2% B, 0.5-4.5 min 2-90% B, 4.5-6.5 min 90% B, 6.5-6.7 min 90-2% B, 6.7-7.5 min 2% B; flow rate: 0.75 ml/min, oven: 30° C., UV detection 210 nm.

Method 5 (LC-MS): instrument type MS: Micromass LCT (ESI pos./neg.); instrument type HPLC: HP 1100 Series; UV DAD 1100 Series; column SymmetryPrep™$C_{18}$, Waters, 50×2.1 mm, 3.5 µm; eluent A: water/0.1% formic acid, eluent B: acetonitrile/0.1% formic acid; gradient: 0-1 min 0% B, 1-6 min 0-90% B, 6-8 min 90-100% B, 8-10 min 100% B, 10-10.1 min 100-0% B, 10.1-12 min 0% B, then regeneration of the chromatography column. Oven: 40° C., flow rate: 0.5 ml/min (at 10.1 min briefly to 1 ml/min), UV detection: 210 nm.

Method 6 (preparative HPLC; Xterra, $C_{18}$, 0.1% TFA): instrument: Gilson Abimed HPLC; binary pump system; column: Xterra, Waters, 5 µm; 150×10 mm; eluent A: water/0.1% trifluoroacetic acid, eluent B: acetonitrile; gradient: 0-7 min 5% B, 7-9 min 5-40% B, 9-11 min 40% B, 11-18 min 40-90% B, then regeneration of the chromatography column; flow rate: 8 m/min; UV detector 210 nm.

Method 7 (LC-MS): instrument type MS: Micromass ZQ; instrument type HPLC: Waters Alliance 2795; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 8 (LC-MS): Instrument: Micromass Quattro LCZ with HPLC Agilent Series 1100; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 9 (amino acid analysis): The amino acid analyses are performed with an LC3000 Amino Acid Analyzer from Eppendorf/Biotronik. A slightly modified standard separation program from Eppendorf/Biotronik is used. The separation programs and the function of the analyzer are described in detail in the handbook of the instrument (Handbuch des Aminosäureanalysators LC 3000 [Handbook of the LC 3000 Amino Acid Analyzer], Wissenschaftliche Geräte GmbH Biotronik, Maintal, 1996).

Method 10 (preparative HPLC, Nucleodur, TFA): instrument: Gilson Abimed HPLC; binary pump system; column: Nucleodur $C_{18}$ Gravity, Macherey-Nagel, 5 µm; 250×21 mm; eluent A: water/0.1% trifluoroacetic acid, eluent B: acetonitrile; gradient: 0-8 min 5% B, 8-40 min 5-60% B, 40-60 min 60% B, 60-75 min 60-100% B, 75-80 min 100% B, then regeneration of the chromatography column; flow rate: 7-15 ml/min; UV detector 210 nm.

Method 11 (preparative HPLC, Nucleodur, acetic acid): instrument: Gilson Abimed HPLC; binary pump system; column: Nucleodur $C_{18}$ Gravity, Macherey-Nagel, 5 µm; 250×40 mm; eluent A: water/0.2% acetic acid, eluent B: acetonitrile/0.2% acetic acid; gradient: 0-10 min 10% B, 10-24 min 10-30% B, 24-28 min 30-50% B, 28-35 min 50% B, 35-45 min 50-60% B, 45-53 min 60-70% B, 53-60 min 60-90% B, 60-70 min 100% B, then regeneration of the chromatography column; flow rate: 15-45 ml/min; UV detector 210 nm.

Method 12 (preparative HPLC, Symmetry, acetic acid): instrument: Gilson Abimed HPLC; binary pump system; column: SymmetryPrep™$C_{18}$, Waters, 7 µm; 300×19 mm; eluent A: water/0.5-0.25% acetic acid, eluent B: acetonitrile; gradient: 0-2 min 5% B, 2-60 min 5-90% B, 60-80 min 100% B, then regeneration of the chromatography column; flow rate: 7 ml/min; UV detector 210 nm.

Method 13 (preparative HPLC; Kromasil, acetic acid): instrument: Gilson Abimed HPLC; binary pump system; column: Kromasil-100A $C_{18}$, 5 µm; 250×30 mm; eluent A: water/0.25% acetic acid, eluent B: acetonitrile; gradient: 0-3 min 5% B, 3-30 min 5-100% B, 30-38 min 100% B, then regeneration of the chromatography column; flow rate: 25 ml/min; UV detector 210 nm.

Method 14 (gel chromatography on Sephadex LH-20): Gel chromatography is performed without pressure on Sephadex LH-20 (from Pharmacia). Fractionation (ISCO Foxy 200 fraction collector) is carried out according to UV activity (UV detector for 254 nm, Knauer). Column dimensions: 32×7 cm (1000-100 µmol scale); 30×4 cm (100-10 µmol scale); 25×2 cm (10-1 µmol scale). Methanol or methanol/0.2% acetic acid is used as eluent.

Method 15 (chiral preparative HPLC): column (steel column, dimensions 250×30 mm); stationary phase (chiral silica/polyamide composite KBD 5326, based on the selector poly(N-methacryloyl-L-leucine-dicyclopropylmethyla-mide); eluent: ethyl acetate, isocratic; flow rate: 25 ml/min; temperature: 24° C.; UV detection: 225 nm; sample: repetitive injection of 2000 µl.

Method 16 (determination of the enantiomeric purity): column (steel column, dimensions 250×4.6 mm); stationary phase (chiral silica/polyamide composite KBD 5326, based on the selector poly(N-methacryloyl-L-leucine-dicyclopropylmethyl-amide); eluent: ethyl acetate, isocratic; flow rate: 1 ml/min; temperature: 25° C.; UV detection: 220 nm; sample: injection of 10 µl.

Method 17 (analytical HPLC): instrument type HPLC: HP 1100 Series; UV DAD column: Zorbax Eclipse XBD-C8 (Agilent), 150 mm×4.6 mm, 5 µm; eluent A: 5 ml of $HClO_4$/l of water, eluent B: acetonitrile; gradient: 0-1 min 10% B, 1-4 min 10-90% B, 4-5 min 90% B; flow rate: 2.0 ml/min; oven: 30° C.; UV detection: 210 and 254 nm.

Method 18 (analytical HPLC): column: Kromasil RP-18, 60 mm×2 mm, 3.5 µm; eluent A: 5 ml of $HClO_4$/l of water, eluent B: acetonitrile; gradient: 0 min 2% B, 0.5 min 2% B, 4.5 min 90% B, 9 min 90% B; flow rate: 0.75 ml/min; oven: 30° C.; UV detection: 210 nm.

Method 19 (analytical HPLC): column: Kromasil RP-18, 250 mm×4 mm, 5 µm; eluent A: 5 ml of $HClO_4$/l of water, eluent B: acetonitrile; gradient: 0 min 5% B, 10 min 95% B; flow rate: 1 ml/min; oven: 40° C.; UV detection: 210 nm.

Method 20 (analytical HPLC): column: Kromasil RP-18, 250 mm×4 mm, 5 µm; eluent A: 2 ml of $HClO_4$/l of water, eluent B: acetonitrile; isocratic: 45% B, 55% A; flow rate: 1 ml/min; oven: 40° C.; UV detection: 210 nm.

Method 21 (preparative HPLC; Nucleodur, 0.05-0.1% TFA): instrument: Gilson Abimed HPLC; binary pump system; column: Nucleodur $C_{18}$ Gravity, Macherey-Nagel, 5 µm, 250×21 mm; eluent A: water/0.05-0.1% TFA, eluent B: acetonitrile; gradient: 0-8 min 5% B, 8-40 min 5-60% B, 40-60 min 60% B, 60-75 min 60-100% B, 75-80 min 100% B, then regeneration of the chromatography column; flow rate: 7-15 ml/min; UV detection: 210 nm.

Method 22 (analytical HPLC): instrument type HPLC: HP 1050 Series; UV DAD 1100 Series; column: Kromasil $C_{18}$, 60 mm×2 mm, 3.5 µm; eluent A: water/0.5% perchloric acid, eluent B: acetonitrile; gradient: 0-0.5 min 2% B, 0.5-4.5 min 2-90% B, 4.5-9.0 min 90% B, 9.0-9.2 min 90-2% B, 9.2-10.0 min 2% B; flow rate: 0.75 ml/min, oven: 30° C., UV detection 210 nm.

Method 23 (analytical HPLC): Agilent 1100 with DAD (G1315B), binary pump (G1312A), autosampler (G1313A), Degasser (G1379A) and column thermostat (G1316A); column: Synergi 4µ Hydro-RP 80A, 4.6×150×5 mm; eluent A: water+0.05% 70% perchloric acid; eluent B: acetonitrile; gradient: 0-1 min 10% B, ramp, 4-5 min 90% B, ramp, 5.5 min 10% B; flow rate: 2.00 ml/min; oven temperature: 30° C.

Method 24 (analytical HPLC): instrument: Agilent 1100 with DAD (G1315B), binary pump (G1312A), autosampler (G1313A), solvent degasser (G1379A) and column thermostat (G1316A); column: Agilent Eclipse XDB-C8 4.6×150×5 mm; eluent A: 0.05% 70% perchloric acid in water; eluent B: methanol; isocratic: 0-7 min 55% B; flow rate: 2.00 ml/min; column temperature: 40° C.

Method 25 (analytical HPLC): instrument type HPLC: HP 1050 Series; UV DAD; column: Zorbax 300 mSB-C18 3.5µ, 4.6 mm×150 mm; eluent A: 1 l of water+0.1% trifluoroacetic acid, eluent B: 400 ml of acetonitrile/600 ml of water+0.1% trifluoroacetic acid; gradient: 0.0 min 100% A, 1.3 min 10% B, 18.0 min 80% B, 20.0 min 80% B, 21.0 min 100% B, 25.0 min 100% B, 26.0 min 0% B, 30.0 min 0% B. flow rate: 1 ml/min; oven: 40° C.; UV detection: 210 nm.

Method 26 (chiral HPLC): Gilson Abimed HPLC; column: Daicel Chiralpak AD-H 5 µm; 250 mm×20 mm; eluent A: isohexane, eluent B: 0.2% acetic acid/1% water/2-propanol; isocratic; flow rate: 15 ml/min; UV detector 212 nm.

Method 27 (determination of the enantiomeric purity): steel column: dimensions 250 mm×4.6 mm; stationary phase: Daicel Chiralpak AD-H, 5 µm; eluent: ethanol/water/acetic acid 1000:10:2, isocratic; flow rate: 0.7 ml/min; temperature: 45° C.; UV detection: 215 nm; sample: injection of 5 µl.

Method 28 (determination of the enantiomeric purity): column (steel column: dimensions 250 mm×4.6 mm); stationary phase (Chiralpak IA); eluent: isohexane/isopropanol 4:1, isocratic; flow rate: 1 ml/min; temperature: 25° C.; UV detection: 254 nm; sample: injection of 10 µl.

Method 29 (LC-MS): UV detection: 210 nm. instrument type MS: Micromass ZQ; instrument type HPLC: Waters Alliance 2795; column: Phenomenex Synergi 2, Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 m/min, 2.5 min/3.0 min/4.5 min 2 ml/min; oven: 50° C.; UV detection: 210 nm.

Method 30 (LC-MS): Instrument: Micromass Platform LCZ with HPLC Agilent Series 1100; column: Phenomenex Synergi 2µ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 m/min, 2.5 min/3.0 min/4.5 min 2 ml/min; oven: 50° C.; UV detection: 210 nm.

Method 31 (MALDI-MS): The MALDI-MS/MS investigations are carried out using a 4700 Proteomics Analyzer (Applied Biosystems, Framingham, Mass., USA), which is equipped with TOF/TOF ion optics and a 200 Hz Nd:YAG Laser (355 nm). The quasimolecular ions are accelerated in the ion source at 8 kV, selected using an electrical deflector (MS1) and impacted with argon atoms in an impact cell arranged between MS1 and MS2. The resulting fragment ions are reaccelerated using 15 kV and characterized using the second time-of-flight mass analyzer (MS2).

Method 32 (chiral preparative HPLC): steel column: dimensions 420 mm×75 mm; stationary phase: silica gel phase with the selector poly(N-methacryloyl-D-leucine-dicyclopropylmethylamide); eluent A: tert-butyl methyl ether, eluent B: methanol; gradient: 0-22.17 min 100% A, 22.18-27.24 min 100% B, 27.25-40.30 min 100% A; flow rate: 100 ml/min; temperature: 24° C.; UV detection: 260 nm; sample: repetitive injection of 50000 µl.

Method 33 (preparative HPLC, Nucleodur, 0.05-0.1% TFA): instrument: Gilson Abimed HPLC; binary pump system; column: Nucleodur $C_{18}$ Gravity, Macherey-Nagel, 5 µm; 250 mm×40 mm; eluent A: water/0.05-0.1% trifluoroacetic acid, eluent B: acetonitrile; gradient: 0-10 min 10% B, 10-24 min 10-30% B, 24-28 min 30-50% B, 28-35 min 50% B, 35-45 min 50-60% B, 45-53 min 60-70% B, 53-60 min 60-90% B, 60-70 min 100% B, then regeneration of the chromatography column; flow rate: 15-45 ml/min; UV detector 210 nm.

Method 34 (preparative HPLC Kromasil 0.05% TFA): instrument: Gilson Abimed HPLC; UV-detector 210 nm; binary pump system; column: Kromasil $C_{18}$, 5 µm, 100 Å, 250 mm×20 mm; eluent A: 0.05% trifluoroacetic acid in water, eluent B: 0.05% trifluoroacetic acid in acetonitrile: flow rate: 20 ml/min; 0-3 min 10% B, ramp, 30-38 min 90% B, 38-45 min 10% B.

Method 35 (preparative HPLC, Nucleodur $C_{18}$ Gravity, 0.05-0.1% TFA): instrument: Gilson Abimed HPLC; binary pump system; column: Nucleodur $C_{18}$ Gravity, 5 µm; 250 mm×40 mm; eluent A: water/0.05-0.1% trifluoroacetic acid, eluent B: acetonitrile; 0-10 min 10% B, ramp, 10.01-55 min 100% B; flow rate: 10-60 ml/min; UV detector 210 nm.

Method 36 (preparative HPLC, Kromasil, 0.05% TFA): instrument: Gilson Abimed HPLC; binary pump system; column: Kromasil-100A $C_{18}$, 5 µm; 250 mm×30 mm; eluent A: water/0.05% trifluoroacetic acid, eluent B: acetonitrile; 0-10 min 10% B, ramp, 10.01-55 min 100% B; flow rate: 30 ml/min; UV detector 210 nm.

Method 37 (preparative HPLC, Kromasil, 0.05% TFA): instrument: Gilson Abimed HPLC; binary pump system; column: Kromasil-100A $C_{18}$, 5 µm; 250 mm×21 mm; eluent A: water/0.05% trifluoroacetic acid, eluent B: acetonitrile; 0-10 min 10% B, ramp, 10.01-55 min 100% B; flow rate: 20 ml/min; UV detector 210 nm.

Method 38 (preparative HPLC, Kromasil, 0.05% TFA): instrument: Gilson Abimed HPLC; binary pump system; column: Kromasil-100A $C_{18}$, 5 µm; 250 mm×21 mm; eluent A: water/0.05% trifluoroacetic acid, eluent B: acetonitrile/water 50/50; 0-10 min 10% B, ramp, 10.01-55 min 100% B; flow rate: 20 ml/min; UV detector 210 nm.

Method 39 (preparative HPLC, Kromasil, 0.05% TFA): instrument: Gilson Abimed HPLC; binary pump system; column: Kromasil-100A $C_{18}$, 5 µm; 250 mm×30 mm; eluent A: water/0.05% trifluoroacetic acid, eluent B: acetonitrile; 0-10 min 10% B, ramp, 10.01-55 min 100% B; flow rate: 10-60 ml/min; UV detector 210 nm.

Method 40 (preparative HPLC): instrument: Gilson Abimed HPLC; UV-detector 210 nm; binary pump system; column: Waters Symmetry-Prep™ $C_{18}$, 7 µm, 300 mm×19 mm; eluent A: 0.05% trifluoroacetic acid in water, eluent B: 0.05% trifluoroacetic acid in acetonitrile: flow rate: 20 ml/min; 0-3 min 10% B, ramp, 30-38 min 90% B, 38-45 min 10% B.

Method 41 (preparative HPLC, Grom-Sil, 0.1% TFA): instrument: Gilson Abimed HPLC; UV-detector 210 nm; binary pump system; column: Grom-Sil SNr.4051 120 ODS-4HE, 10 µm, 250 mm×40 mm; eluent A: 0.1% trifluoroacetic acid in water, eluent B: 0.1% trifluoroacetic acid in acetonitrile; flow rate: 50 ml/min; 0-3 min 10% B, 3-27 min gradient ramp, 27-35 min 95% B, 35-40 min 10% B.

Method 42 (chiral preparative HPLC): column (steel column, dimensions 500 mm×50 mm); stationary phase (Chiralpak AD, 20 µm); eluent A: isohexane, eluent B: isopropanol; gradient: 0-11.74 min 15% B, 11.74-11.75 min 100% B, 15.74 min 100% B, 15.75 min 15% B, 21.25 min 15% B; sample preparation: dissolve in 50 ml isopropanol/200 ml isohexane; injection volume: 30 ml, temperature: 24° C.; UV detection: 220 nm.

Method 43 (preparative HPLC): instrument: Gilson Abimed HPLC; UV detector 254 nm; binary pump system; column: Nucleosil RP-18, 7 µm; 250×50 mm; flow rate: 30 ml/min; eluent A: water/0.1% trifluoroacetic acid, eluent B: acetonitrile/0.1% trifluoroacetic acid; gradient: 0-40 min 20-25% B, 40-60 min 25% B, 60-110 min 25-50% B, 110-120 min 50% B, 120-130 min 50-100% B, 130-160 min 100% B, then regeneration of the chromatography column.

Method 44 (preparative HPLC): instrument: Gilson Abimed HPLC; UV detector 254 nm; binary pump system; column: Nucleosil RP-18, 7 µm; 250×50 mm; flow rate: 40 ml/min; eluent A: water/0.05% trifluoroacetic acid, eluent B: acetonitrile/0.05% trifluoroacetic acid; gradient: 0-105 min 20-25% B, 105-111 min 25% B, 111-131 min 25-27% B, 131-157 min 27-35% B, 157-192 min 35-40% B, 192-207 min 40-45% B, then regeneration of the chromatography column.

General Working Procedures

Working Procedure 1 (Removal of Boc Protecting Groups with TFA)

The Boc-protected compound is suspended in dichloromethane (⅕-1/10 of the reaction solution) and then trifluoroacetic acid in dichloromethane (30%; about 1 ml/10 mg of starting material on the 100-1 millimole scale, about 1 ml/1 mg on the 100-1 micromole scale) is added under an argon protective gas atmosphere and the mixture is stirred at room temperature until the HPLC chromatogram shows complete conversion (Method 2). The solvent is then distilled off in vacuo, whereby the bath temperature should not exceed 30°

C. The crude product is suspended in toluene, concentrated again on a rotary evaporator and dried under high vacuum. This procedure is repeated several times with toluene or with dichloromethane (two to five times).

Working Procedure 2 (Removal of the N-Tert-Butoxycarbonyl Protecting Group, Dioxane, 4 N Hydrogen Chloride)

The N-(tert-butoxycarbonyl)-protected compound (1 mmol) is provided in dioxane (2-3 ml) under an argon protective gas atmosphere. At RT and with vigorous stirring, 4 N hydrochloric acid in dioxane (30 ml) is added dropwise. The mixture is stirred until analytical HPLC (Method 2) indicates complete conversion (about 2 h). The reaction mixture is evaporated at RT in vacuo. The Crude product is taken up in a little dichloromethane and again freed of solvent in vacuo. This operation is repeated several times with toluene (twice) and with dichloromethane (twice). Finally, the crude product is lyophilized or reacted further directly after high-vacuum drying.

Working Procedure 3 (Hydrogenolytic Ester Cleavage, Removal of the Cbz Protecting Group)

The peptidic benzyl ester or the peptidic N-Cbz-protected amine (1.2 mmol) is dissolved in methanol (60 ml) and ten percent palladium-carbon (100 mg) is added under an argon protective gas atmosphere. The mixture is hydrogenated at RT and under atmospheric pressure until analytical HPLC (Method 2) indicates complete conversion. The reaction mixture is filtered (for example through kieselguhr, Celite®), concentrated in vacuo and dried under high vacuum.

Working Procedure 4 (Hydrolytic Ester Cleavage, Hydrolysis)

The carboxylic ester (3 mmol) is provided in THF/water/DMF 200/100/2.5 (20 ml) under an argon protective gas atmosphere. At 0° C. with strict temperature control, powdered lithium hydroxide (3.6 mmol, 1.2 equivalents) is added in portions to the vigorously stirred solution. When no complete conversion is observed by means of analytical HPLC after 2 h, solid lithium hydroxide is added again (3.3 mmol, 1.1 equivalents). This operation is repeated up to complete conversion, whereupon the reaction mixture is then adjusted at 0° C. to pH 3-4 with 0.1 N hydrochloric acid and then freeze-dried. The crude product can then be gel-chromatographed (Method 14) and/or fine-purified by means of preparative HPLC (Method 13).

Working Procedure 5 (Amide Coupling)

HATU (1.5-1.8 equivalents) is added first at −20° C. under an argon protective gas atmosphere to a solution of the aminic cyclopeptide (1.0 equivalent), the dipeptide acid (1.5-1.8 equivalents) and NMM (1.0-2.0 equivalents) in dry DMF. The reaction mixture is stirred (about 15 min) and NMM (2.5-3.0 equivalents) is again added. The reaction mixture is warmed slowly from −10° C. to RT and the mixture is stirred further at this temperature until complete conversion of the amine component is found. Solid potassium dihydrogen phosphate (10 equivalents, 500 µmol) is added and the reaction mixture is then evaporated under high vacuum and purified by chromatography.

Alternatively, water and methanol can, on completion of conversion, be added to the reaction and the product is then obtained after purification via preparative RP-HPLC or gel chromatography.

Starting Compounds

Example 1A

D-Leucyl-$N^1$-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoroacetate (lysobactin)

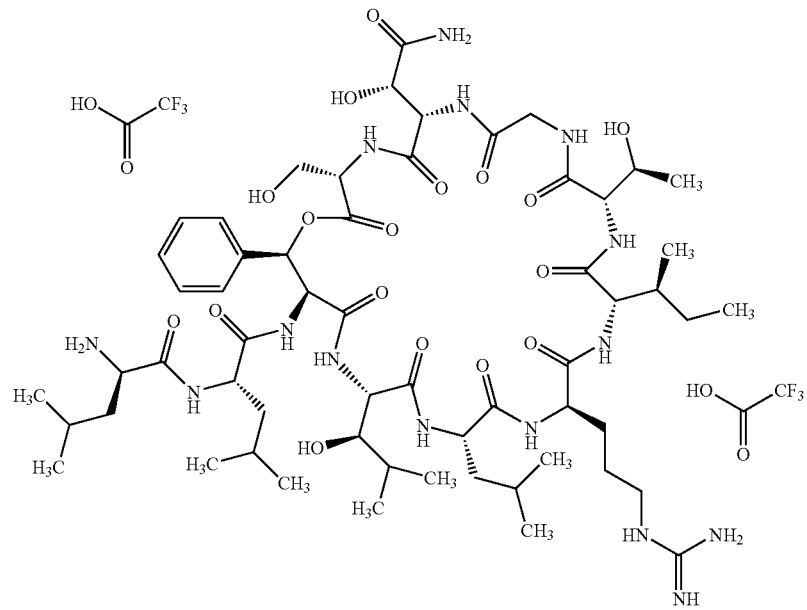

Fermentation:
Culture Medium:
YM: yeast-malt agar: D-glucose (4 g/l), yeast extract (4 g/l), malt extract (10 g/l), 1 liter of Lewatit water. Before sterilization (20 minutes at 121° C.), the pH is adjusted to 7.2. HPM: mannitol (5.4 g/l), yeast extract (5 g/l), meat peptone (3 g/l).

Working preserve: The lyophilized strain (ATCC 53042) is grown in 50 ml of YM medium.

Flask fermentation: 150 ml of YM medium or 100 ml of HPM medium in a 1 l Erlenmeyer flask are inoculated with 2 ml of the working preserve and allowed to grow on a shaker for 30-48 hours at 28° C. and 240 rpm.

30 l fermentation: 300 ml of the flask fermentation (HPM medium) are used to inoculate a sterile 30 l nutrient medium solution (1 ml of SAG 5693/l antifoam). This culture is allowed to grow for 21 hours at 28° C., 300 rpm and aeration with sterile air of 0.3 vvm. The pH is kept constant at pH=7.2 with 1 M hydrochloric acid. In total, 880 ml of 1 M hydrochloric acid are added during the culturing period.

Main culture (200 l): 15×150 ml of YM medium in 1 l Erlenmeyer flasks are inoculated with 2 ml of the working preserve and allowed to grow on the shaker for 48 hours at 28° C. and 240 rpm. 2250 ml of this culture are used to inoculate a sterile 200 l nutrient medium solution (YM) (1 ml of antifoam SAG 5693/l) and it is allowed to grow for 18.5 hours at 28° C., 150 rpm and aeration with sterile air of 0.3 vvm.

Hourly samples (50 ml) are taken to check the course of the fermentation. 1 ml of methanol (0.5% trifluoroacetic acid) are added 2 ml of this culture broth and the mixture is filtered through a 0.45 µm filter. 30 µl of this suspension are analyzed by means of HPLC (Method 17 and Method 18).

After 18.5 hours, the culture broth of the main culture is separated into supernatant and sediment at 17 000 rpm.

Isolation:

The supernatant (183 l) is adjusted to pH 6.5-7 using concentrated trifluoroacetic acid or a sodium hydroxide solution and loaded onto a Lewapol column (OC 1064, contents 60 l). Elution is subsequently carried out with pure water, water/methanol 1:1 and subsequently with pure methanol (containing 0.1% trifluoroacetic acid). This organic phase is concentrated in vacuo to a residual aqueous residue of 11.5 l.

The residual aqueous phase is bound to silica gel $C_{18}$ and separated (MPLC, Biotage Flash 75, 75×30 cm, KP-C18-WP, 15-20 µm, flow rate: 30 ml; eluent: acetonitrile/water containing 0.1% trifluoroacetic acid; gradient: 10%, 15% and 40% acetonitrile). The 40% acetonitrile phase, which contains the main amount of Example 1A, is concentrated in vacuo and subsequently lyophilized (about 13 g). This mixture of solids is separated in 1.2 g portions, first on a preparative HPLC (Method 43), subsequently by gel filtration on Sephadex LH-20 (5×70 cm, acetonitrile/water 1:1, in each case containing 0.05% trifluoroacetic acid) and a further preparative HPLC (Method 44).

This process yields 2250 mg of Example 1A.

The sediment is taken up in 4 l of acetone/water 4:1, 2 kg of Celite are added, the mixture is adjusted to pH=6 using trifluoroacetic acid, stirred and centrifuged. The solvent is concentrated in vacuo and the residue is freeze-dried. The lyophilizate obtained (89.9 g) is taken up in methanol, filtered, concentrated and separated on silica gel (Method 20). Example 1A is then purified by gel filtration (Sephadex LH-20, 5×68 cm, water/acetonitrile 9:1 (containing 0.05% trifluoroacetic acid), flow rate: 2.7 ml/min, fraction size 13.5 ml) to give the pure substance.

This process yields 447 mg of Example 1A.

HPLC (Method 17): $R_t$=6.19 min

MS (ESIpos): m/z=1277 (M+H)$^+$ $^1$H NMR (500.13 MHz, $d_6$-DMSO): δ=0.75 (d, 3H), 0.78 (d, 6H), 0.80 (t, 3H), 0.82 (d, 3H), 0.90 (d, 3H), 0.91 (d, 3H), 0.92 (d, 3H), 0.95 (d, 3H), 0.96 (d, 3H), 1.05 (m, 1H), 1.19 (d, 3H), 1.25 (m, 2H), 1.50 (m, 4H), 1.51 (m, 2H), 1.55 (m, 1H), 1.61 (m, 1H), 1.65 (m, 1H), 1.84 (m, 1H), 1.85 (m, 1H), 1.86 (m, 1H), 1.89 (m, 1H), 1.95 (m, 1H), 2.75 (m, 2H), 3.40 (m, 1H), 3.52 (m, 2H), 3.53 (dd, 1H), 3.64 (m, 2H), 3.66 (m, 1H), 3.68 (dd, 1H), 3.73 (m, 2H), 4.00 (dd, 1H), 4.02 (br., 1H), 4.13 (br., 1H), 4.32 (dd, 1H), 4.39 (t, 1H), 4.55 (m, 1H), 4.75 (dd, 1H), 5.19 (t, 1H), 5.29 (d, 1H), 5.30 (br., 1H), 5.58 (m, 2H), 6.68 (m, 3H), 6.89 (d, 1H), 6.93 (m, 3H), 6.94 (br., 1H), 6.98 (d, 1H), 7.12 (br., 1H), 7.20 (br., 2H), 7.23 (m, 2H), 7.42 (m, 2H), 7.54 (d, 1H), 7.58 (d, 1H), 8.32 (br., 1H), 9.18 (br., 1H), 9.20 (m, 2H), 9.50 (br., 1H).

$^{13}$C NMR (125.77 MHz, $d_6$-DMSO): δ=10.3, 15.3, 19.0, 19.2, 19.6, 20.0, 20.9, 22.0, 22.4, 23.0, 23.2, 24.3, 24.4, 25.0, 25.4, 26.0, 27.8, 30.9, 35.4, 39.5, 40.8, 40.9, 41.6, 44.1, 51.5, 52.7, 55.9, 56.2, 56.4, 57.9, 58.8, 60.2, 61.1, 62.6, 70.1, 71.6, 71.7, 75.5, 128.1, 128.6, 136.7, 156.8, 168.2, 170.1, 170.4, 171.2, 171.5, 171.9, 172.2, 172.4, 173.7.

The assignment of the signals was carried out according to the assignment described in the literature (T. Kato, H. Hinoo, Y. Terui, *J. Antibiot.*, 1988, 61, 719-725).

Example 2A

Mixture of dihydrolysobactin trifluoroacetate {D-Leu-Leu-Phe-[(3R)-Leu(3-OH)]-Leu-D-Arg-Ile-aThr-Gly-[(3S)-3-Asn(3-OH)]-Ser trifluoroacetate} and octahydrolysobactin trifluoroacetate {D-Leu-Leu-Ala(3-cyclohexyl)-[(3R)-Leu(3-OH)]-Leu-D-Arg-Ile-aThr-Gly-[(3S)-3-Asn(3-OH)]-Ser trifluoroacetate}

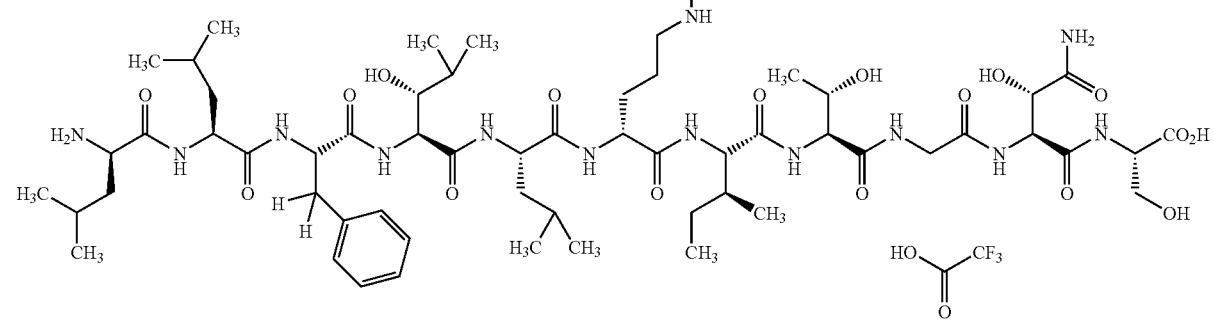

-continued

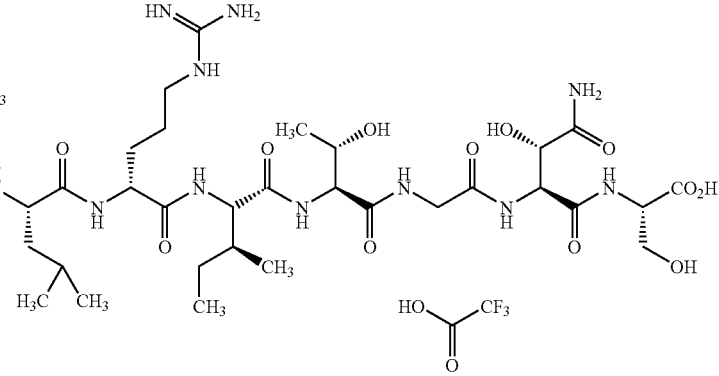

Lysobactin bistrifluoroacetate (Example 1A, 500 mg, 0.33 mmol) is dissolved in isopropanol/water 2:1 (30 ml). Under an argon protective gas atmosphere, palladium on carbon (10%; 100 mg) is added. The reaction mixture is (after degassing) stirred in a pressure autoclave under 80-70 bar hydrogen pressure and at RT for 48 h. For the reaction, palladium on carbon (10%; 100 mg) is again added. The reaction mixture is (after degassing) stirred again in a pressure autoclave under 80-70 bar hydrogen pressure and at RT for 48 h. Now, no lysobactin is detectable any more by means of HPLC (Method 2). The reaction mixture is filtered through a glass frit (pore size 4) or through kieselguhr, concentrated in vacuo, taken up again in methanol/0.2% acetic acid, filtered through a syringe filter (from Biotage, PTFE), concentrated in vacuo and dried under high vacuum. 496 mg (quant.) of product (80% dihydrolysobactin, 20% octahydrolysobactin) are obtained.

Example 3A

[(3R)-3-Hydroxy-L-leucyl]-L-leucyl-D-arginyl-L-isoleucyl-L-allothreonyl-glycyl-[(3S)-3-hydroxy-L-asparaginyl]-L-serine trifluoroacetate {Edman[3.0] degradation product trifluoroacetate}

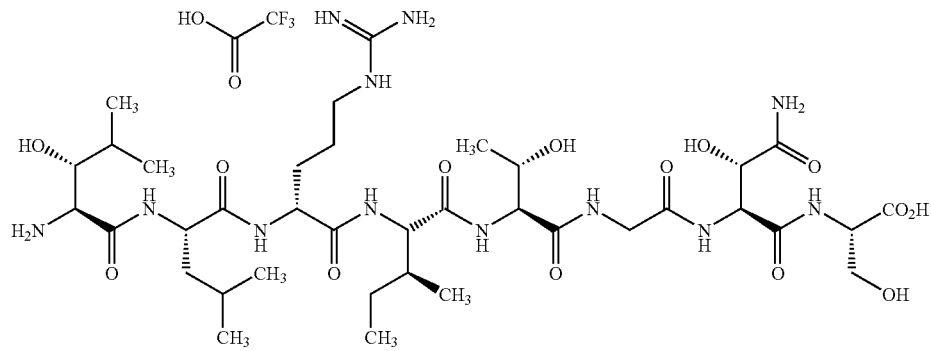

775 mg of dihydrolysobactin and octahydrolysobactin are dissolved in 77.5 ml of methanol and then 667 ml of cleavage buffer (0.1 M ammonium hydrogen carbonate solution/0.5 M urea, pH 8) are added. Before the addition of enzyme, the solution is heated to 37° C. in a drying cabinet. 31 mg of chymotrypsin (31 ml of chymotrypsin solution in 1:1 water/ethylene glycol, 1 mg/ml; 1:25; preheated to 37° C.) are added and the reaction is performed at 37° C. After 60 min, the enzyme reaction is stopped with 30 ml of acetonitrile and about 6 ml of TFA. The pH of the solution is between 1-2. The solution can be stored at −20° C. until the preparative separation.

Preparative Separation of the Fragments 1-3 and 4-11

About 800 ml of the cleavage solution are filtered through a filter (0.2 μm) and chromatographed in two portions of about 400 ml each on a Source 15RPC column (40 ml) with an acetonitrile/TFA gradient. Conditions: eluent A: 0.1% TFA, eluent B: 0.1% TFA/acetonitrile; gradient: 0% B to 45% B within 40 min; flow rate: 2 ml/min; UV detection 210 nm; fraction size 1.5 ml.

Fragments 4-11 ($R_t$=approx 15 min) and 1-3 (LLF) ($R_t$=about 25 min) and 1-3 (LLA(3-cyclohexyl)) ($R_t$=about 30 min) are combined and lyophilized. In this way, the title compound is obtained as fragment 4-11.

HPLC/UV-Vis (Method 3): $R_t$=1.2 min.

LC-MS (Method 7): $R_t$=1.0 min;

MS (ESIpos.): m/z (%)=453.5 (100) $[M+2H]^{2+}$, 906 (10) $[M+H]^+$.

MS (ESIneg.): m/z (%)=904 (100) $[M-H]^-$.

LC-MS (Method 5): $R_t$=3.6 min;

MS (ESIpos.): m/z (%)=453.5 (100) $[M+2H]^{2+}$.

MS (ESIneg.): m/z (%)=904 (100) $[M-H]^-$.

Example 4A

Methyl (Z)-2-[(tert-butoxycarbonyl)amino]-4,4-dimethylpent-2-enoate

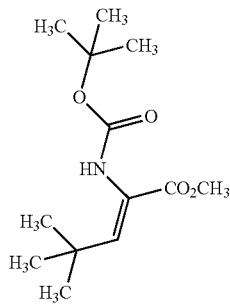

Pivalaldehyde (303.2 g, 3.41 mol, 10 equivalents) and methyl {[tert-butoxycarbonyl]amino}-(dimethoxyphosphoryl)acetate (101.5 g, 0.341 mol, 1.0 equivalent) are dissolved in tetrahydrofuran (800 ml) and cooled to −70° C. At −70° C., N,N,N,N-tetramethylguanidine (78.7 g, 0.683 mmol, 6.95 ml, 2.0 equivalents) is slowly added dropwise and the mixture is then stirred at −70° C. for 4 h, subsequently, the mixture is stirred at RT for 4 days. The reaction mixture is concentrated, then extracted with ethyl acetate (2×500 ml) against water, and the combined organic phases are washed with a saturated sodium chloride solution (100 ml) and dried over sodium sulfate. After concentration, the crude product is chromatographed (1.5 kg of silica gel, eluent: cyclohexane/ethyl acetate 5:1). 67 g (76% of theory) of the title compound are obtained.

Alternatively, the crude product can, after the aqueous workup, be purified by crystallization from cyclohexane/ethyl acetate.

$R_f$ (silica gel, 4:1 cyclohexane/ethyl acetate)=0.5

LC-MS (Method 7): $R_t$=2.5 min;

MS (ESIpos.): m/z (%)=158 (100) $[M-Boc+H]^+$, 280 (5) $[M+Na]^+$.

$^1$H NMR (400 MHz, $d_6$-DMSO): δ=1.08 (s, 9H, C(CH$_3$)$_3$), 1.38 (s, 9H, OC(CH$_3$)$_3$), 3.61 (s, 3H, CO$_2$CH$_3$), 6.40 (s, 1H, C$^\beta$H), 8.14 (s, 1H, NH).

HR-TOF-MS (Method 1): $C_{13}H_{23}NO_4$ $[M+H]^+$ found 258.1696, calc. 258.1700.

Example 5A

N-tert-Butoxycarbonyl-3-tert-butyl-D-alanine methyl ester

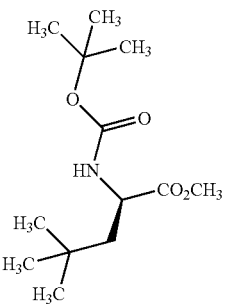

Methyl (2Z)-2-[(tert-butoxycarbonyl)amino]-4,4-dimethylpent-2-enoate (Example 4A, 60 g, 233.2 mmol) is dissolved in ethanol p.a./dioxane 3:1 (1000 ml). Argon is passed through for about 10 min using a cannula. The solution is placed into an ultrasound bath (about 5 min), and (+)-1,2-bis[(2R,5R)diethylphospholano]benzene(cyclooctadiene) rhodium(I) triflate (600 mg, 1% by weight) is added. The mixture is hydrogenated under 3.5 bar hydrogen pressure and at RT for 3 days. The reaction mixture is filtered through kieselguhr and the eluate is concentrated. The crude product is chromatographed (silica gel, eluent: cyclohexane/ethyl acetate 4:1). 60 g (99% of theory) of the title compound are obtained.

$[\alpha]^{20}_{Na}$=+5° (c=0.33 in CHCl$_3$).

DCI-MS (NH$_3$): m/z (%)=221 (100), 260 (40) $[M+H]^+$, 277 (100) $[M+NH_4]^+$.

$^1$H NMR (400 MHz, CDCl$_3$): δ=0.93 (s, 9H), 1.40 (m, 10H), 1.68 (dd, J=3.7, 14.5 Hz, 1H), 3.68 (s, 3H), 4.30 (t, J=7.9 Hz, 1H), 4.81 (d, br, J=7.7 Hz, 1H).

$^{13}$C NMR (126 MHz, CDCl$_3$): δ=28.30 (3C), 29.52 (3C), 30.61, 46.27, 51.19, 52.17, 79.79, 155.11, 174.39.

HR-TOF-MS (Method 1): $C_{26}H_{51}N_2O_8$ calc. 519.3640, found 519.3634 $[M+H]^+$.

Example 6A

N-tert-Butoxycarbonyl-3-tert-butyl-D-alanine

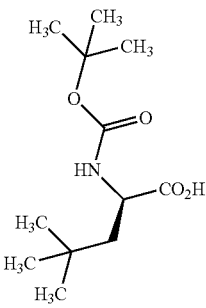

N-tert-Butoxycarbonyl-3-tert-butyl-D-alanine methyl ester (Example 5A, 60 g, 231 mmol) is dissolved in tetrahydrofuran p.a. (463 ml). At RT, a solution of lithium hydroxide monohydrate (19.4 g, 462.7 mmol) in water (463 ml) is slowly added dropwise. When the HPLC chromatogram (Method 2) shows complete conversion (about 20 h), the reaction mixture is cautiously adjusted to pH 3-4 with 1 N aqueous hydrochloric acid with ice cooling. Sodium chloride (150 g) is added to the reaction mixture in order subsequently to extract it with ethyl acetate (2×500 ml). The combined organic phases are dried with a saturated sodium chloride solution and then with sodium sulfate and filtered. The filtrate is concentrated on a rotary evaporator and dried under high vacuum. 55.4 g (98% of theory) of the title compound are obtained.

HPLC/UV-Vis (Method 4): $R_t$=4.2 min.

DCI-MS (NH$_3$): m/z (%)=263 (100) [M+NH$_4$]$^+$, 280 (5) [M+N$_2$H$_7$]$^+$.

$^1$H NMR (400 MHz, CDCl$_3$): δ=0.96 (s, 9H, C(CH$_3$)$_3$), 1.42 (m, 10H, OC(CH$_3$)$_3$, H$^\beta$), 1.79 ("d", J=14.4 Hz, 1H, H$^\beta$), 4.31 (t, J=8.0 Hz, 1H, H$^\alpha$), 4.82 (d, J=8.4 Hz, 1H, NH).

$^{13}$C NMR (126 MHz, CDCl$_3$): δ=28.32 (3C), 29.54 (3C), 30.74, 45.92, 51.24, 80.19, 155.41, 178.93.

HR-TOF-MS (Method 1): C$_{24}$H$_{47}$N$_2$O$_8$ calc. 491.3327, found 491.3328 [2M+H]$^+$.

Example 7A 3-tert-Butyl-L-alanine methyl ester hydrochloride

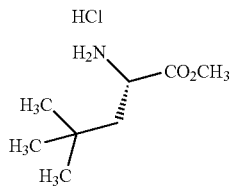

For the preparation of the title compound, see S. D. Bull, S. G. Davies, A. C. Garner, M. D. O'Shea, *J. Chem. Soc. Perkin Trans.* 1 (2001) 3281-3287.

The title compound is obtained according to working procedure 2 from N-tert-butoxycarbonyl-3-tert-butyl-L-alanine methyl ester (28.0 g, 108 mmol) and 4 N hydrochloric acid in dioxane (280 ml). Yield 22 g (quantitative). The product is reacted further without purification.

$^1$H NMR (400 MHz, d$_6$-DMSO): δ=0.95 (s, br, 9H, tBu), 1.65 (dd, 1H), 1.80 (dd, 1H), 3.75 (s, 3H, OCH$_3$), 3.90 (dd, 1H), 8.60 (s, br, 3H).

Example 8A

N-(tert-Butoxycarbonyl)-3-tert-butyl-D-alanyl-3-tert-butyl-L-alanine methyl ester

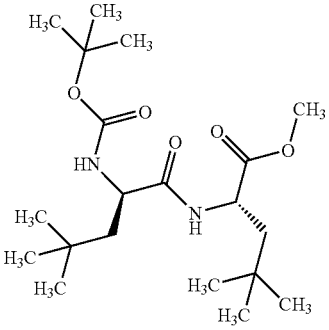

HOBt (3 equivalents, 39.4 g, 292 mmol), N-methylmorpholine (3 equivalents, 32.1 ml, 291.8 mmol), N-tert-butoxycarbonyl-3-tert-butyl-D-alanine (Example 6A, 1.0 equivalent, 97.3 mmol), EDC (2 equivalents, 37.3 g, 194.6 mmol) and again N-methylmorpholine (2 equivalents, 21.4 ml, 194.5 mmol) are added successively at −20° C. to a solution of 3-tert-butyl-L-alanine methyl ester hydrochloride (1.1 equivalents, 21 g, 107 mmol) in dichloromethane p.a. (1.4 l). The reaction mixture warms slowly (about 12 h) to RT, whereby complete conversion of the amine component is observed by means of HPLC. The reaction mixture is then washed with a saturated aqueous sodium hydrogen carbonate solution (300 ml), 5% aqueous citric acid (2×500 ml), a saturated aqueous sodium hydrogen carbonate solution (500 ml) and a saturated sodium chloride solution. The reaction mixture is dried over sodium sulfate and filtered. The mixture is concentrated to dryness in vacuo and then dried further under high vacuum. 36 g (96% of theory) of the title compound are obtained, which is reacted without further purification.

DCI-MS (NH$_3$): m/z (%)=387 (40) [M+H]$^+$, 404 (100) [M+NH$_4$]$^+$.

$^1$H NMR (400 MHz, d$_6$-DMSO): δ=0.95 (s, br, 18H, tBu), 1.35 (dd, 1H), 1.45 (s, 9H, OtBu), 1.50 (dd, 1H), 1.65 (dd, 1H), 1.95 (dd, br, 1H), 3.70 (s, 3H, OCH$_3$), 4.15 ("t", br, 1H), 4.55 ("t", br, 1H), 4.80 (d, 1H), 6.65 (d, br, 1H).

Example 9A

N-(tert-Butoxycarbonyl)-D-leucyl-L-leucine benzyl ester

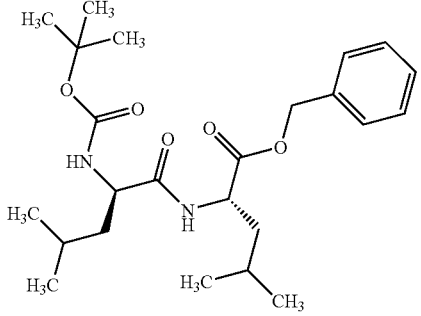

HOBt (4 equivalents, 540 mg, 4 mmol), N-methylmorpholine (3 equivalents, 3 mmol), N-tert-butoxycarbonyl-D-leucine (1.0 equivalent, 230 mg, 1 mmol; Bachem), EDC (2 equivalents, 380 mg, 2 mmol) and again N-methylmorpholine (2 equivalents, 2 mmol) are added successively at −10° C. to a solution of L-leucine benzyl ester hydrochloride (1.1 equivalents, 300 mg, 1.1 mmol; cf. T. Wakamiya, M. Kamata, S. Kusumoto, H. Kobayashi, Y. Sai, et al., *Bull. Chem. Soc. Jpn.*, 1998, 71, 699-710) in dichloromethane p.a. (30 ml). The reaction mixture warms slowly (about 12 h) to RT, whereby complete conversion of the amine component is observed by means of HPLC. The reaction mixture is concentrated in vacuo, taken up in acetonitrile and purified by means of preparative HPLC (Method 13). 362 mg (80% of theory) of the title compound are obtained.

HPLC/UV-Vis (Method 4): $R_t$=5.3 min.

$[\alpha]^{20}_{Na}$=+19° (c=0.10 in methylene chloride).

Example 10A

N-(tert-Butoxycarbonyl)-3-tert-butyl-D-alanyl-3-tert-butyl-L-alanine

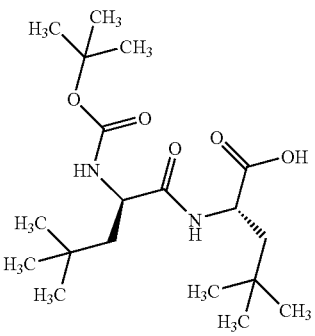

N-(tert-Butoxycarbonyl)-3-tert-butyl-D-alanyl-3-tert-butyl-L-alanine methyl ester (Example 8A, 36 g, 93.1 mmol) is dissolved in tetrahydrofuran p.a. (279 ml). At about 10° C., a solution of lithium hydroxide monohydrate (7.82 g, 186.3 mmol, 2 equivalents) in water (187 ml) is slowly added dropwise. When the HPLC chromatogram (Method 2) shows complete conversion (about 20 h), the reaction mixture is freed of the THF at 200 mbar and then extracted with methyl tert-butyl ether (200 ml). The organic phase is diluted with ethyl acetate (500 ml) and then water is added and the mixture is subsequently adjusted cautiously to pH 3-4 with 1 N aqueous hydrochloric acid. The combined organic phases are washed with a saturated aqueous sodium chloride solution, dried over sodium sulfate, filtered, evaporated in vacuo and dried under high vacuum. 97.4 g (97% of theory) of the title compound are added.

LC-MS (Method 7): $R_t$=2.26 min;

MS (ESIpos.): m/z (%)=373 (100) [M+H]⁺.

HR-TOF-MS (Method 1): $C_{19}H_{37}N_2O_5$ calc. 373.2702, found 373.2717 [M+H]⁺.

¹H NMR (400 MHz, $d_6$-DMSO): δ=0.83 (s, br, 18H, tBu), 1.31 (s, 9H, OtBu), 1.40 (d, J=6.1 Hz, 2H, ββ-CH₂), 1.48 (dd, J=14.1, 9.4 Hz, 1H, ββ-CH), 1.59 (dd, J=14.1, 2.7 Hz, 1H, β-CH'), 3.98 (m, 1H, α-CH), 4.12 (m, 1H, α-CH), 6.73 (d, J=9.1 Hz, 1H, NH), 7.72 (d, J=7.9 Hz, 1H, NH), 12.42 (s, br, 1H, CO₂H).

¹³C NMR (125 MHz, $d_6$-DMSO): δ=28.49 (3C), 29.66 (3C), 29.78 (3C), 30.52, 30.58, 44.63 (β-CH₂), 45.24 (β-CH₂), 49.67 (α-CH), 52.40 (α-CH), 78.29, 155.05, 172.97, 174.61.

Example 11A

N-(tert-Butoxycarbonyl)-D-leucyl-L-leucine

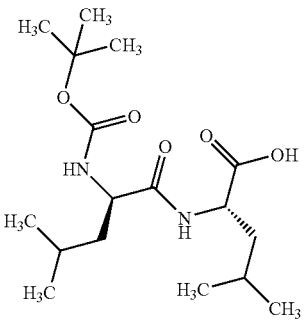

N-(Butoxycarbonyl)-D-leucyl-L-leucine benzyl ester (Example 9A, 308 mg, 0.69 mmol) is reacted according to working procedure 3. 244.6 mg (99% of theory) of the title compound are obtained.

HPLC/UV-Vis (Method 4): $R_t$=4.5 min.

HR-TOF-MS (Method 1): $C_{18}H_{35}N_2O_5$ [M+H]⁺ found 359.2535, calc. 359.2546.

¹H NMR (400 MHz, $d_6$-DMSO): δ=0.85 (m, 14H, 4×CH₃, 2×γ-CH), 1.35 (m, 10H, OtBu, β-CH), 1.50-1.65 (m, 3×β-CH), 4.00 (dd, 1H, α-CH), 4.20 ("t", 1H, α-CH), 6.70 (d, 1H, NH), 7.90 (d, 1H, NH), 12.50 (s, br, 1H, CO₂H).

Example 12A

Methyl (2R*,3R*)—N²-[(benzyloxy)carbonyl]-N²-[(benzyloxy)carbonylamino]-3-[(tert-butoxy-carbonyl)amino]phenylalaninate

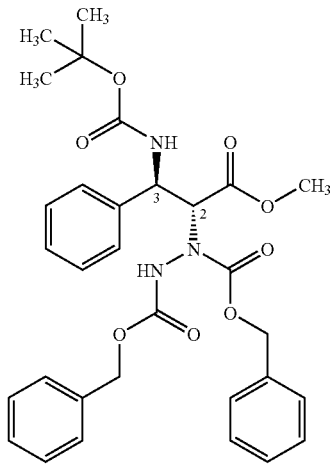

-continued

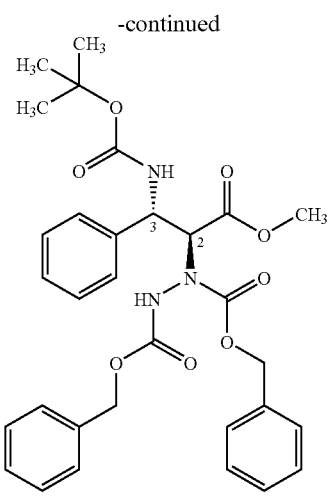

Under an argon protective gas atmosphere, a 1 N solution of lithium hexamethyldisilazide (157.5 mmol, 157.5 ml, 2.2 equivalents) in THF is provided in the reaction solvent THF (300 ml). At −78° C., a solution of methyl (rac)-3-[(tert-butoxycarbonyl)amino]-3-phenylpropanoate (A. V. Rao Rama, A. K. Singh, Ch. V. N. S. Varaprasad, *Tetrahedron Lett.*, 32, 1991, 4393-4396) (20 g, 71.2 mmol) is slowly added dropwise. The mixture is stirred at −25° C. for 10 min and then again cooled down to −78° C. Dibenzyl azadicarboxylate (34.2 g, 114.6 mmol, 1.6 equivalents) is added to the reaction mixture in one portion. The mixture is stirred at −60 to −45° C. for 3 h. In order to stop the reaction, the mixture is again cooled down to −78° C. and acetic acid (20.5 ml, 358 mmol, 5 equivalents) is added, and then warmed to 0° C. and finally RT. The reaction mixture is evaporated in vacuo and taken up in ethyl acetate (1000 ml). The suspension is washed with a saturated aqueous sodium hydrogen carbonate solution (twice), water (once), 5% aqueous citric acid (twice) and a saturated aqueous sodium chloride solution (once). All aqueous phases are reextracted individually with ethyl acetate. All organic phases are evaporated in vacuo and taken up again in dichloromethane (2000 ml), filtered, dried over sodium sulfate, filtered again, evaporated in vacuo and dried under high vacuum. 7.2 g (18% of theory) of the title compound are obtained as a solid. The filtrate of the dichloromethane phase (vide supra) is concentrated and is then recrystallized again from methanol to obtain 13.2 g (26% of theory) of the title compound.

Alternative synthesis method: Under an argon protective gas atmosphere, a 1 N solution of lithium hexamethyldisilazide (590.7 mmol, 590.7 ml, 2.2 equivalents) in THF is provided in the reaction solvent THF (2500 ml). At −78° C., a solution of methyl (rac)-3-[(tert-butoxycarbonyl)amino]-3-phenylpropanoate (75 g, 268.5 mmol) is slowly added dropwise (internal temperature about −70° C.). The mixture is stirred at −25° C. for 10 min and then again cooled down to −70° C. Dry dibenzyl azadicarboxylate (128.2 g, 429.6 mmol, 1.6 equivalents) is added to the reaction mixture as a solid in four portions. The mixture is stirred at −60 to −50° C. for 2 h. In order to stop the reaction, the mixture is again cooled down to −78° C. and acetic acid (76.9 ml, 1342 mmol, 5 equivalents) is added, and the mixture is then warmed to 0° C. and finally RT. Thereby, the title compound precipitates as a solid, which is dried in a vacuum drying cabinet (4.1 g, 2.2% of theory, crystals 1). The reaction mixture is evaporated in vacuo and the residue is recrystallized in ethyl acetate, whereby the title compound is obtained as a solid (38.8 g, 24.3% of theory, crystals 2). The mother liquor is diluted with ethyl acetate and then washed with water (twice) and a saturated aqueous sodium chloride solution (twice). The organic phase is dried over sodium sulfate, filtered, evaporated in vacuo and dried under high vacuum. The crude product is recrystallized from ethyl acetate-diethyl ether. The title compound is obtained as a solid (50.4 g, 28% of theory, crystals 3). The mother liquor is evaporated and purified by means of flash chromatography (1.5 kg of silica gel, toluene/ethyl acetate 4:1). 4.7 g (1.7% of theory) of the title compound are obtained. Total yield 98.0 g of the title compound (56.2% of theory).

LC-MS (Method 5): $R_t$=6.8 min;

MS (ESIpos.): m/z (%)=578 (40) $[M+H]^+$, 1156 (100) $[2M+H]^+$.

MS (ESIneg.): m/z (%)=576 (100) $[M-H]^-$.

HR-TOF-MS (Method 1): $C_{31}H_{36}N_3O_8$ $[M+H]^+$ found 578.2490, calc. 578.2497.

The relative stereochemistry of the title compound is confirmed by an X-ray structure (FIG. 1).

Example 13A

Methyl (2S*,3R*)-N-[(benzyloxy)carbonyl]-N-[(benzyloxy)carbonylamino]-3-[(tert-butoxy-carbonyl)amino]phenylalaninate

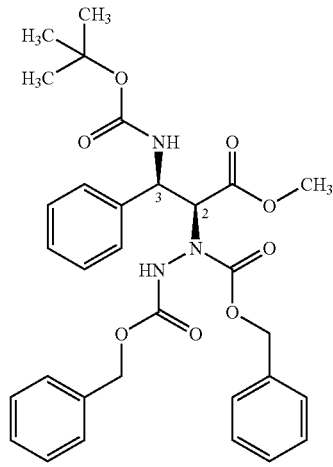

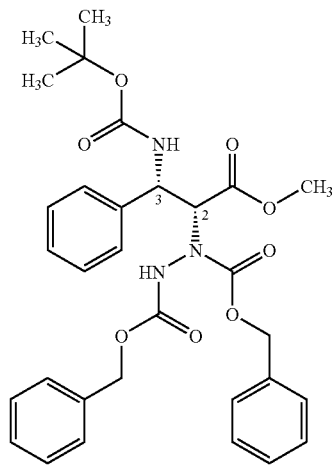

Under an argon protective gas atmosphere, N,N,N,N-tetramethylguanidine (50 ml, 399 mmol) is added to a solution of methyl (2R*,3R*)—N²-[(benzyloxy)carbonyl]-N²-[(benzyloxy)carbonylamino]-3-[(tert-butoxycarbonyl)amino] phenylalaninate (Example 12A, 20.5 g, 35.5 mmol) in dry DMF p.a. (750 ml) at 0° C. The reaction mixture is allowed to thaw and stirred until the HPLC chromatogram (Method 2) indicates complete conversion (about 60% product) (about 12 h), in order to stop the reaction by the addition of acetic acid (pH 4-6). The reaction mixture is evaporated at RT in vacuo and taken up in ethyl acetate. The organic phase is washed with water (twice), 5% citric acid (twice), water (once), a saturated aqueous sodium hydrogen carbonate solution (twice), a saturated aqueous sodium chloride solution (once), dried over sodium sulfate, filtered, evaporated and dried under high vacuum. The crude product is purified by means of preparative HPLC (Method 11) or flash chromatography (silica gel, cyclohexane/ethyl acetate 3:1). 7.7 g (37% of theory) of the title compound and 5 g of the starting compound (25% of theory) are obtained.

Alternative synthesis method: Under an argon protective gas atmosphere, N,N,N,N-tetramethylguanidine (50 ml, 399 mmol) are added to a solution of methyl (2R*,3R*)—N²-[(benzyloxy)carbonyl]-N²-[(benzyloxy)carbonylamino]-3-[(tert-butoxycarbonyl)-amino]phenylalaninate (Example 13A, 22.0 g, 38.1 mmol) in dry dichloromethane p.a. (540 ml) at 0° C. The reaction mixture is allowed to thaw and stirred until the HPLC chromatogram indicates complete conversion (about 65% product) (about 12 h), in order to stop the reaction by the addition of acetic acid (23 ml, pH 4-6). The organic phase is washed with water (twice), a saturated aqueous sodium hydrogen carbonate solution (twice) and a saturated aqueous sodium chloride solution (once). The aqueous phases are reextracted with dichloromethane. The combined organic phases are dried over sodium sulfate, filtered, evaporated in vacuo and dried under high vacuum. The crude product is purified by means of flash chromatography (6 l of silica gel, cyclohexane/ethyl acetate 3:1). 13.7 g (62% of theory, based on recovered starting material 69%) of the title compound and 3.1 g of the starting compound (10% of theory) are obtained.

HPLC/UV-Vis (Method 2): $R_t$=3.0 min.

LC-MS (Method 8): $R_t$=3.0 min;

MS (ESIpos.): m/z (%)=478 (100) [M−Boc+H]⁺, 578 (30) [M+H]⁺.

LC-MS (Method 5): $R_t$=7.0 min;

MS (ESIpos.): m/z (%)=578 (40) [M+H]⁺, 1156 (100) [2M+H]⁺.

MS (ESIneg.): m/z (%)=576 (100) [M−H]⁻.

HR-TOF-MS (Method 1): $C_{31}H_{36}N_3O_8$ [M+H]⁺ found 578.2483, calc. 578.2497.

Example 14A

Methyl (2S*,3R*)-3-[(tert-butoxycarbonyl)amino] phenylalaninate

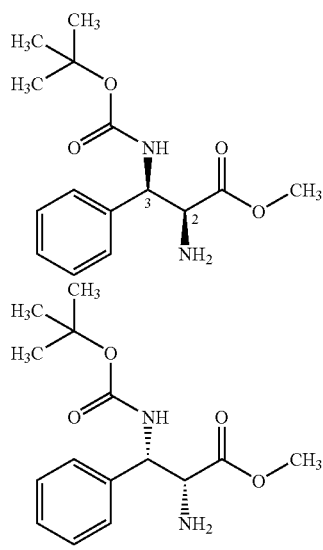

Under an argon protective gas atmosphere, Raney nickel (61 mg, about 10 mol %) is added to a solution of methyl (2S*,3R*)-N-[(benzyloxy)carbonyl]-N-[(benzyloxy)-carbonylamino]-3-[(tert-butoxycarbonyl)amino]phenylalaninate (Example 13A, 705 mg, 1.22 mmol) in methanol/dichloromethane 1:1 (42 ml). The reaction mixture is hydrogenated in a pressure autoclave under 80 bar hydrogen pressure and at RT (40 h). The HPLC chromatogram shows complete conversion. The reaction mixture is filtered through a glass frit under an argon protective gas atmosphere; the glass frit is washed several times with methanol/water/0.2% acetic acid. The filtrate is evaporated in vacuo and dried under high vacuum. A solid (about 3 g) is obtained which is then suspended in ethyl acetate in an ultrasound bath. A solution of EDTA (400 mg) in a 7% aqueous sodium hydrogen carbonate solution (400 ml) is added to the suspension. The aqueous phase is extracted with ethyl acetate (100 ml, three times). The combined organic phases are then washed with a saturated sodium hydrogen carbonate solution (once) and with a saturated aqueous sodium chloride solution (twice). All aqueous phases are reextracted individually with ethyl acetate. The combined organic phases are then dried over sodium sulfate, filtered and dried under high vacuum. The product obtained is a solid (1.26 g, quant.), which is reacted further without fine-purification.

HPLC/UV-Vis (Method 3): $R_t$=1.7 min.

LC-MS (Method 5): $R_t$=4.1 min;

MS (ESIpos.): m/z (%)=239 (100), 295 (80) [M+H]⁺.

¹H NMR (400 MHz, $d_6$-DMSO): δ=1.36 (s, 9H), 3.34 (s, 3H), 3.60 (d, J=5.3 Hz, 1H), 4.89 (dd, J=9.6, 4.9 Hz, 1H), 7.20-7.34 (m, 5H), 7.41 (d, J=9.4 Hz, 1H).

¹³C NMR (125 MHz, $d_6$-DMSO): δ=28.24 (3C), 52.84, 54.91, 56.86, 79.23, 127.14 (2C), 128.44, 128.88 (2C), 137.28, 154.86, 168.16.

HR-TOF-MS (Method 1): $C_{15}H_{22}N_2O_4$ [M+H]$^+$ found 295.1658, calc. 295.1653.

Example 15A
Methyl (2S*,3R*)-N-[(benzyloxy)carbonyl]-3-[(tert-butoxycarbonyl)amino]phenylalaninate

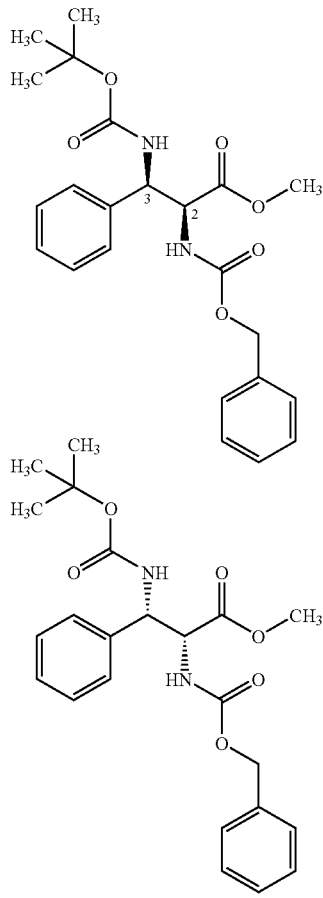

Under an argon protective gas atmosphere, N-methylmorpholine (260 mg, 2.6 mmol, 2.1 equivalents) is added at 0° C. to a solution of methyl (2S*,3R*)-3-[(tert-butoxy-carbonyl)amino]phenylalaninate (Example 14A, 360 mg, 1.2 mmol) and N-benzyl-oxycarbonyloxysuccinimide ester (610 mg, 2.44 mmol, 2 equivalents) in THF (25 ml). The reaction mixture warms up slowly (12 h), whereby complete conversion is observed by means of HPLC (Method 2). Subsequently, acetic acid (0.7 ml) is added, and the mixture is concentrated in vacuo and purified by means of preparative HPLC (Method 13). 396 mg (76% of theory) of the title compound are obtained.

HPLC/UV-Vis (Method 3): $R_t$=2.7 min.
LC-MS (Method 5): $R_t$=6.4 min;
MS (ESIpos.): m/z (%)=329 (100) [M−Boc+H]$^+$, 429 (80) [M+H]$^+$, 858 (60) [2M+H]$^+$.
$^1$H NMR (500 MHz, $d_6$-DMSO): δ=1.35 (s, 9H), 3.63 (s, 3H), 4.57 (dd, J=9.5, 4.0 Hz, 1H), 4.93 (m, 2H), 5.27 (dd, J=10.1, 4.1 Hz, 1H), 7.19-7.34 (m, 10H), 7.50 (d, J=10.2 Hz, 1H), 7.59 (d, J=10.2 Hz, 1H).
$^{13}$C NMR (126 MHz, $d_6$-DMSO): δ=28.26 (3C), 52.33, 54.67, 59.06, 65.73, 78.73, 126.66 (2C), 127.42, 127.65 (2C), 128.00, 128.44 (2C), 128.53 (2C), 136.91, 139.26, 154.98, 156.25, 170.91.
HR-TOF-MS (Method 1): $C_{23}H_{28}N_2O_6Na$ [M+Na]$^+$ found 451.1823, calc. 451.1845.

Example 16A
(2S*,3R*)—N$^2$-[(Benzyloxy)carbonyl]-3-[(tert-butoxycarbonyl)amino]phenylalanine

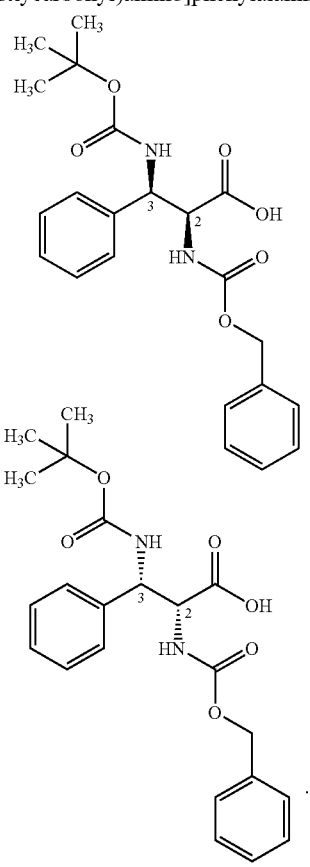

Under an argon protective gas atmosphere, a solution of methyl (2S*,3R*)-N-[(benzyloxy)carbonyl]-3-[(tert-butoxycarbonyl)amino]phenylalaninate (Example 15A, 755 mg, 1.76 mmol) is provided in THF/water 2:1 (30 ml). At 0° C. with vigorous stirring, a degassed 1% aqueous solution of lithium hydroxide monohydrate (86.5 mg, 3.6 mmol, 2 equivalents) is slowly added dropwise. The mixture is stirred at RT until the HPLC chromatogram (Method 2) indicates complete conversion (about 1 h). Subsequently, acetic acid (0.5 ml) is added to the reaction mixture, the reaction mixture is concentrated in vacuo and layered with ethyl acetate (100 ml). The aqueous phase is now acidified with 5% citric acid (pH 2-3) and then extracted with ethyl acetate (50 ml, three times). The combined organic phases are washed with a saturated aqueous sodium chloride solution (20 ml, twice), dried over sodium sulfate, filtered, concentrated in vacuo and dried under high vacuum. 750 mg (quant.) of crude product of the title compound are obtained, which is fine-purified by means of preparative HPLC (Method 13).

HPLC/UV-Vis (Method 2): $R_t$=2.4 min.
LC-MS (Method 5): $R_t$=6.1 min;
MS (ESIpos.): m/z (%)=359 (100), 415 (60) [M+H]$^+$, 829 (60) [2M+H]$^+$.
MS (ESIneg.): m/z (%)=413 (100) [M−H]$^-$.
$^1$H NMR (500 MHz, $d_6$-DMSO): δ=1.31 (s, 9H), 4.42 (dd, J=10.0, 3.9 Hz, 1H), 4.87 (s, 2H), 5.22 (dd, J=10.0, 3.7 Hz, 1H), 7.14-7.28 (m, 10H), 7.43-7.46 (m, 2H), 12.91 (s, br, 1H).
$^{13}$C NMR (126 MHz, $d_6$-DMSO): δ=28.33 (3C), 54.84 (C$^α$), 58.94 (C$^β$), 65.54, 78.56, 126.52 (2C), 127.22, 127.53 (2C), 127.92, 128.37 (2C), 128.49 (2C), 137.03, 140.14, 155.08, 156.29, 171.60.
HR-TOF-MS (Method 1): $C_{22}H_{26}N_2O_6$ [M+H]$^+$ found 415.1860, calc. 415.1864.

Example 17A (3R)—N²-[(Benzyloxy)carbonyl]-3-[(tert-butoxycarbonyl)amino]-L-phenylalanine

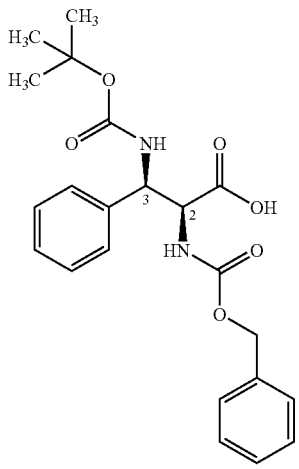

The enantiomer mixture of (2S*,3R*)-N-[(benzyloxy)carbonyl]-3-[(tert-butoxycarbonyl)amino]phenylalanine (Example 16A, 750 mg, 1.8 mmol) is separated by means of preparative HPLC (Method 15). 334 mg (98% ee, 45% of theory) of (2S,3R)—N-[(benzyloxy)carbonyl]-3-[(tert-butoxycarbonyl)amino]phenylalanine (title compound) and 275 mg (98% ee, 37% of theory) of (2R,3S)—N-[(benzyloxy)carbonyl]-3-[(tert-butoxycarbonyl)amino]phenylalanine (further enantiomer) are obtained.

Enantiomer determination by Method 16.

$[\alpha]^{20}_{Na}$=+22° (c=0.50 in chloroform) (title compound).

$[\alpha]^{20}_{Na}$=−20° (c=0.49 in chloroform) (further enantiomer).

$^1$H NMR (500 MHz, d$_6$-DMSO): δ=1.35 (s, 9H), 4.46 (dd, J=9.6, 3.6 Hz, 1H), 4.91 (s, 2H), 5.26 (dd, J=9.9, 3.6 Hz, 1H), 7.18-7.32 (m, 10H), 7.48-7.51 (m, 2H), 12.95 (s, br, 1H).

$^{13}$C NMR (126 MHz, d$_6$-DMSO): δ=28.34 (3C), 54.84, 58.96, 65.55, 78.56, 126.53 (2C), 127.23, 127.55 (2C), 127.93, 128.39 (2C), 128.51 (2C), 137.05, 140.16, 155.09, 156.30, 171.62.

HR-TOF-MS (Method 1): C$_{22}$H$_{26}$N$_2$O$_6$ [M+H]$^+$ found 415.1864, calc. 415.1864.

Example 18A 2-(Trimethylsilyl)ethyl-(3R)—N-[(benzyloxy)carbonyl]-3-[(tert-butoxycarbonyl)amino]-L-phenylalaninate

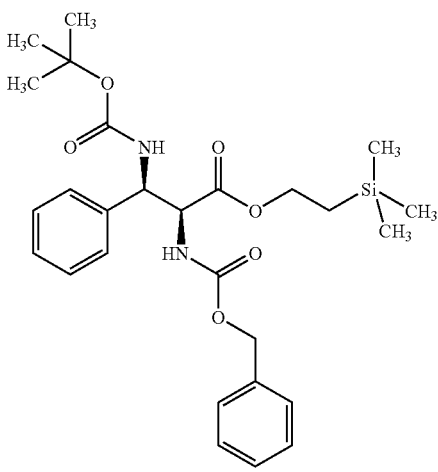

A mixture of (3R)—N²-[(benzyloxy)carbonyl]-3-[(tert-butoxycarbonyl)amino]-L-phenylalanine (Example 17A, 151 mg, 0.36 mmol), 2-(trimethylsilyl)ethanol (431 mg, 3.64 mmol, 10 equivalents) and 4 Å molecular sieve (about 10 mg) in dry dichloromethane p.a. (2.7 ml) is stirred under an argon protective gas atmosphere at RT for 30 min. Subsequently, DCC (150 mg, 0.73 mmol, 2 equivalents) and DMAP (44.5 mg, 0.36 mmol, 1 equivalent) are added at −30° C. The reaction mixture is allowed to thaw (about 12 h) and stirred at RT until the HPLC chromatogram indicates complete conversion (12-72 h). The reaction mixture is evaporated in vacuo at RT and purified by means of preparative HPLC (Method 13). 145 mg (77% of theory) of the title compound are obtained.

$[\alpha]^{20}_{Na}$=+7.8° (c=0.45 in chloroform)

HPLC/UV-Vis (Method 3): R$_t$=3.3 min.

LC-MS (Method 5): R$_t$=7.3 min;

MS (ESIpos.): m/z (%)=515 (100) [M+H]$^+$, 1030 (60) [2M+H]$^+$.

$^1$H NMR (500 MHz, d$_6$-DMSO): δ=−0.02 (s, 9H), 0.88 (t, J=8.6 Hz, 2H), 1.31 (s, 9H), 4.01-4.15 (m, 2H), 4.48 (dd, J=9.5, 4.0 Hz, 1H), 4.86 (d, J=13.1 Hz, 1H), 4.90 (d, J=12.6 Hz, 1H), 5.25 (dd, J=10.0, 4.0 Hz, 1H), 7.14-7.29 (m, 10H), 7.48 (d, 1H, J=10.2 Hz), 7.51 (d, 1H, J=9.5 Hz).

$^{13}$C NMR (126 MHz, d$_6$-DMSO): δ=−1.67 (3C), 16.78, 27.96 (3C), 54.38, 58.83, 62.95, 65.34, 78.30, 126.29 (2C), 127.06, 127.30 (2C), 127.66, 128.13 (2C), 128.20 (2C), 136.63, 139.17, 154.58, 155.95, 170.02.

HR-TOF-MS (Method 1): C$_{27}$H$_{38}$N$_2$O$_6$Si [M+H]$^+$ found 515.2564, calc. 515.2572.

Example 19A 2-(Trimethylsilyl)ethyl (3R)-3-amino-N²-[(benzyloxy)carbonyl]-L-phenylalaninate trifluoroacetate

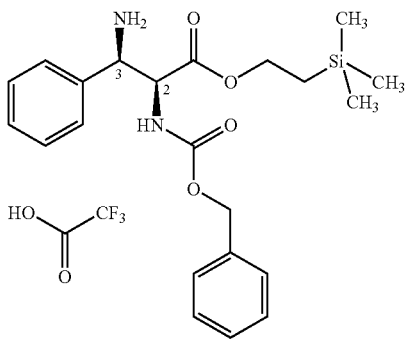

2-(Trimethylsilyl)ethyl (3R)—N-[(benzyloxy)carbonyl]-3-[(tert-butoxycarbonyl)amino]-L-phenylalaninate (Example 18A, 550 mg, 1.7 mmol) is reacted according to working procedure 1 (reaction time: 10 min). The crude product is purified by means of preparative HPLC (Method 21). 424 mg (75% of theory) of the title compound are obtained.

$[\alpha]^{20}_{Na}$=−11.2° (c=0.47 in chloroform)

HPLC/UV-Vis (Method 2): R$_t$=1.9 min.

LC-MS (Method 7): R$_t$=2.0 min;

MS (ESIpos.): m/z (%)=387.2 (60), 415 (100) [M+H]$^+$.

$^1$H NMR (500 MHz, d$_6$-DMSO): δ=−0.07 (s, 9H), 0.52 (m, 2H), 3.77 (m, 1H), 3.88 (m, 1H), 4.50 (d, J=9.0 Hz, 1H), 4.58 ("t", J=about 8.2 Hz, 1H), 5.08 (s, 2H), 7.34-7.43 (m, 10H), 8.12 (d, 1H, J=8.5 Hz, 1H), 8.67 (s, br, 2H).

$^{13}$C NMR (126 MHz, d$_6$-DMSO): δ=−1.46 (3C), 16.51, 55.14, 57.92, 63.36, 66.28, 128.02 (2C), 128.18, 128.22 (2C), 128.56 (2C), 128.95 (2C), 129.54, 134.00, 136.70, 156.14, 169.06.

HR-TOF-MS (Method 1): C$_{22}$H$_{30}$N$_2$O$_4$Si [M+H]$^+$ found 415.2036, calc. 415.2048.

Example 20A

N²·¹-tert-Butoxycarbonyl[(3R)-3-hydroxy-L-leucyl]-L-leucyl-D-arginyl-L-isoleucyl-L-allothreonyl-glycyl-[(3S)-3-hydroxy-L-asparaginyl]-L-serine trifluoroacetate

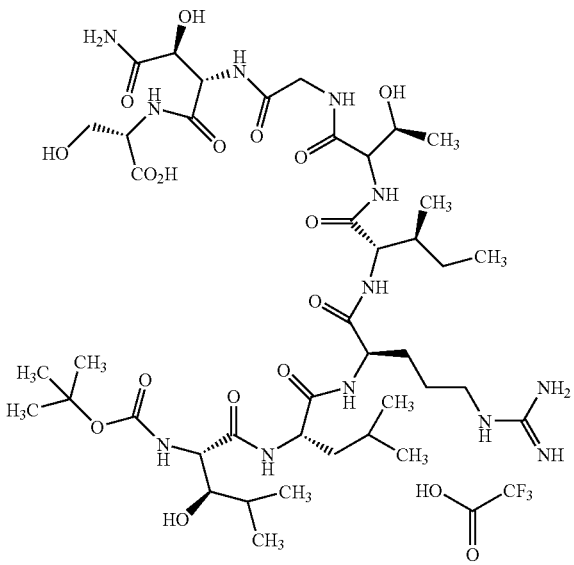

Under an argon protective gas atmosphere, di-tert-butyl dicarbonate (369 mg, 1.69 mmol, 2.5 equivalents) and N-methylmorpholine (68 mg, 680 µmol, 1 equivalent) are added to a solution of the Edman$^{3.0}$ precursor (Example 3A, 690 mg, 680 µmol, 1 equivalent) in water/dioxane 1:2 (30 ml). The reaction mixture is stirred until the HPLC chromatogram shows complete conversion (about 48 h). Potassium dihydrogen phosphate (5 equivalents) is added to the reaction mixture, the mixture is concentrated in vacuo and purified by means of preparative HPLC (Method 21 or Method 11 followed by subsequent salt exchange of the chromatography product by the addition of TFA (2000 µmol, as a 0.05% solution in acetonitrile-water 1:1)). 531 mg (70% of theory) of the title compound are obtained.

HPLC/UV-Vis (Method 3): $R_t$=1.7 min.

LC-MS (Method 5): $R_t$=4.6 min;

MS (ESIpos.): m/z (%)=453.5 (60) [M−Boc+2H]$^{2+}$, 1006 (100) [M+H]$^+$.

MS (ESIneg.): m/z (%)=1004 (100) [M−H]$^-$.

HR-TOF-MS (Method 1): $C_{42}H_{77}N_{12}O_{16}$ [M+H]$^+$ found 1005.5560, calc. 1005.5576.

Example 21A

N²-(Benzyloxycarbonyl)-N³-{N²·¹-tert-butoxycarbonyl[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-1-phenylalanine 2-(trimethylsilyl)ethyl ester trifluoroacetate

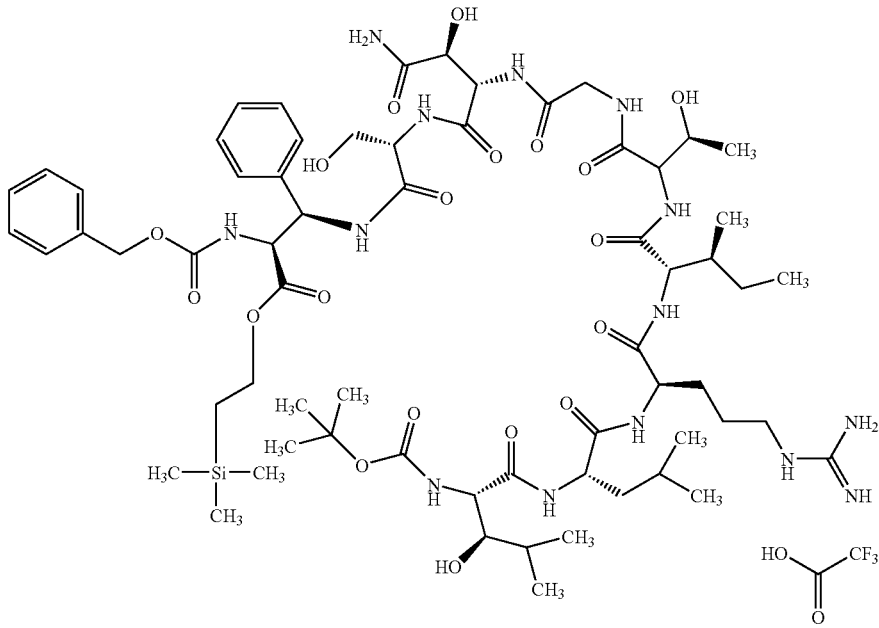

Under an argon protective gas atmosphere, HATU (1.5 equivalents, 38.2 mg, 100 μmol) is first added at 0° C. to a solution of the diamino acid (Example 19A, 1.2 equivalents, 42.5 mg, 80 μmol), the octapeptide acid (Example 20A, 1.0 equivalent, 75.0 mg, 70 μmol) and N-methylmorpholine (1.0 equivalent, 70 μmol) in dry dimethylformamide (2 ml). The reaction mixture is stirred (about 15 min) and N-methylmorpholine (2.5 equivalents, 175 μmol) is again added. The reaction mixture warms slowly (about 12 h) to room temperature and then shows complete conversion of the amine component (HPLC monitoring). Solid potassium dihydrogen phosphate (5 equivalents, 350 μmol) is added to the reaction mixture and the mixture is then evaporated under high vacuum and purified by chromatography (Method 21 or Method 13 followed by subsequent salt exchange of the chromatography product by the addition of TFA (200 μmol, as a 0.05% solution in acetonitrile-water 1:1)). 73.5 mg (72% of theory) of product are obtained.

HPLC/UV-Vis (Method 2): $R_t$=2.3 min.

LC-MS (Method 5): $R_t$=5.5 min;

MS (ESIpos.): m/z (%)=637.6 (60), 1402 (100) [M+H]$^+$.

MS (ESIneg.): m/z (%)=1400 (100) [M−H]$^-$, 1447 (20) [M−HCO$_2$H−H]$^-$.

Example 22A

N$^2$-(Benzyloxycarbonyl)-N$^3$-{N$^{2.1}$-tert-butoxycarbonyl[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-L-phenylalanine trifluoroacetate

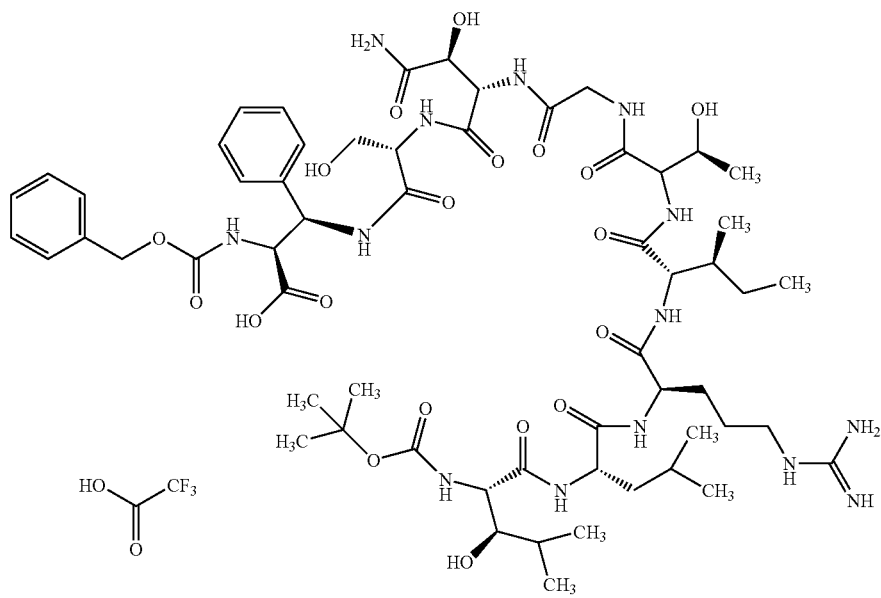

The nonapeptide trimethylsilyl ester (Example 21A, 70 mg, 46 µmol) and 4 Å molecular sieve (about 10 mg) are provided in dry THF (3 ml) under an argon protective gas atmosphere. At RT, a 1 N TBAF-THF solution (320 µl, 7 equivalents) is added dropwise with vigorous stirring and the mixture is stirred until the HPLC chromatogram (Method 2) shows complete conversion (about 1 h). The reaction mixture is now neutralized with acetic acid (50 µl, about 20 equivalents). The reaction mixture is evaporated in vacuo and purified by means of preparative HPLC (Method 21 or Method 13 followed by subsequent salt exchange of the chromatography product by adding TFA (200 µmol, as a 0.05% solution in acetonitrile-water 1:1)). 50.2 mg (77% of theory) of the title compound are obtained.

HPLC/UV-Vis (Method 2): $R_t$=2.1 min.

LC-MS (Method 5): $R_t$=5.2 min;

MS (ESIpos.): m/z (%)=601.6 (60) $[M-Boc+2H]^{2+}$, 1302 (100) $[M+H]^+$.

MS (ESIneg.): m/z (%)=1300 (100) $[M-H]^-$.

Example 23A $N^2$-(Benzyloxycarbonyl)-$N^3$-{$N^{2.1}$-tert-butoxycarbonyl[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-L-phenylalanine pentafluorophenyl ester trifluoroacetate

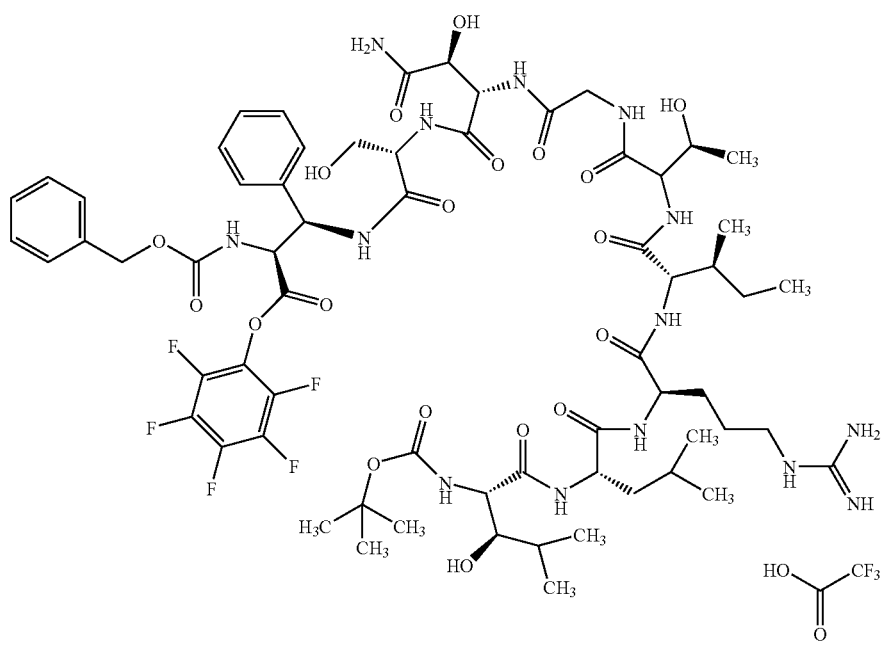

The nonapeptide acid (Example 22A, 54.4 mg, 38 µmol) is provided in dichloromethane (1 ml) under an argon protective gas atmosphere. At −20° C., pentafluorophenol (71 mg, 380 µmol, 10 equivalents), EDC (17 mg, 192 µmol, 2.3 equivalents) and DMAP (1 mg, 8 µmol, 0.2 equivalent) are added successively. The mixture is allowed to thaw slowly (about 3 h) and stirred at RT (about 12 h) until the HPLC chromatogram indicates complete conversion (Method 2). The crude product is reacted further without purification.

LC-MS (Method 8): $R_t$=2.3 min;

MS (ESIpos.): m/z (%)=685 (100) [M−Boc+2H]$^{2+}$, 1468 (10) [M+H]$^+$.

MS (ESIneg.): m/z (%)=1282 (100), 1465 (40) [M−H]$^-$.

Example 24A

N$^2$-(Benzyloxycarbonyl)-N$^3$-{[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-L-phenylalanine pentafluorophenyl ester bishydrochloride

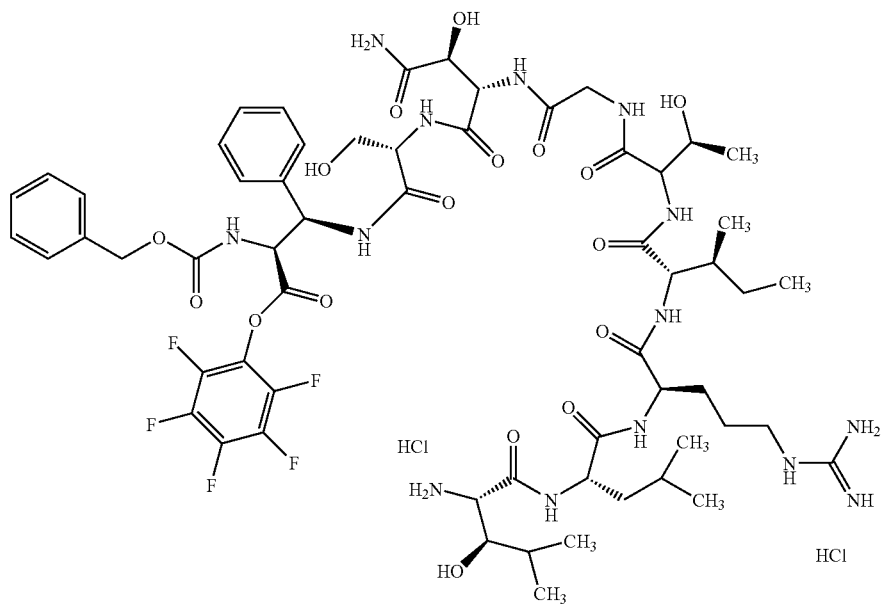

According to working procedure 2, the N-(tert-butoxycarbonyl) cyclopeptide (Example 23A, 60 mg, 40 μmol) is reacted under an argon protective gas atmosphere. After freeze-drying, 50 mg (96% of theory) of product are obtained which is reacted directly without further purification.

HPLC/UV-Vis (Method 2): $R_t$=1.9 min, $\lambda_{max}$ (qualitative)=210 nm (s), 255-270 (w).

LC-MS (Method 5): $R_t$=4.7 min;

MS (ESIpos.): m/z (%)=684.3 (100) [M+2H]$^{2+}$, 1368 (50) [M+H]$^+$.

MS (ESIneg.): m/z (%)=1366 (100) [M−H]$^-$.

Example 25A $N^{2.1}$-(Benzyloxycarbonyl)-[(3R-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.9}$—$N^{3.1}$-lactam trifluoroacetate

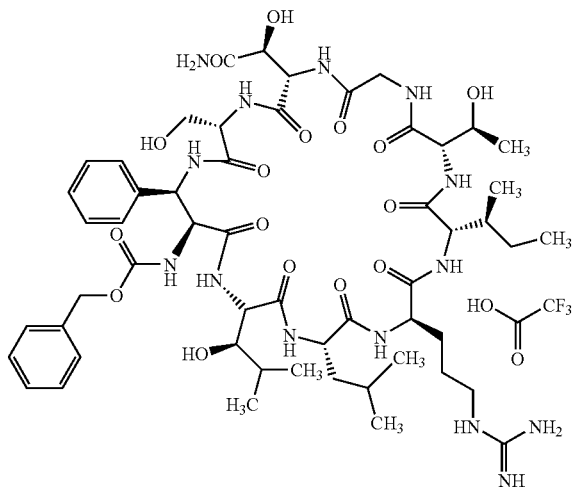

A solution of the pentafluorophenol ester (Example 24A, 15.8 mg, 11 μmol) in DMF (1 ml) is diluted with dioxane (20 ml) and then added dropwise (as a suspension) with vigorous stirring under an argon protective gas atmosphere into pyridine p.a. (80 ml) preheated to 80° C. The reaction mixture is stirred at 85° C. until the HPLC chromatogram (Method 2) shows complete conversion (about 1 h). The mixture is then concentrated in vacuo. The crude product is first gel-chromatographed (Method 14) and then fine-purified by means of preparative HPLC (Method 10). 4.3 mg (33% of theory) of the title compound are obtained.

Alternative synthesis method (direct cyclization of the free nonapeptidic amino acid): HATU (245 mg, 0.65 mmol, 3 equivalents) is added to a solution of the free nonapeptide ($N^2$-(benzyloxycarbonyl)-$N^3$-{[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-L-phenylalanine trifluoroacetate, 280 mg, 0.22 mmol) in DMF (70 ml) and NMM (142 μl, 6 equivalents) at 0° C. The reaction mixture is stirred until complete conversion (1.5 h, HPLC monitoring). Subsequently, the reaction mixture is quenched with methanol (10 ml), concentrated in vacuo and purified directly by means of preparative HPLC (Method 35). Product is obtained as a solid (201.5 mg, 70% of theory).

LC-MS (Method 5): $R_t$=4.8 min;

MS (ESIpos.): m/z (%)=592.6 (20) [M+2H]$^{2+}$, 1184 (100) [M+H]$^+$.

MS (ESIneg.): m/z (%)=1182 (100) [M−H]$^-$.

LC-MS (Method 7): $R_t$=1.8 min;

MS (ESIpos.): m/z (%)=592.7 (50) [M+2H]$^{2+}$, 1184 (100) [M+H]$^+$.

MS (ESIneg.): m/z (%)=536.6 (100), 1182 (50) [M−H]$^-$, 1229 [M−H+HCO$_2$H]$^-$.

HR-TOF-MS (Method 1): $C_{54}H_{83}N_{14}O_{16}$ [M+H]$^+$ found 1183.6122, calc. 1183.6106.

Example 26A

[(3R)-3-Amino-L-phenylalanyl])-[(3R)-3-hydroxy-L-leucyl]-L-leucyl-D-arginyl-L-isoleucyl-L-allothreonyl-glycyl-[(3S)-3-hydroxy-L-asparaginyl]-L-serine-$C^{1.9}$—$N^{3.1}$-lactam bishydrochloride

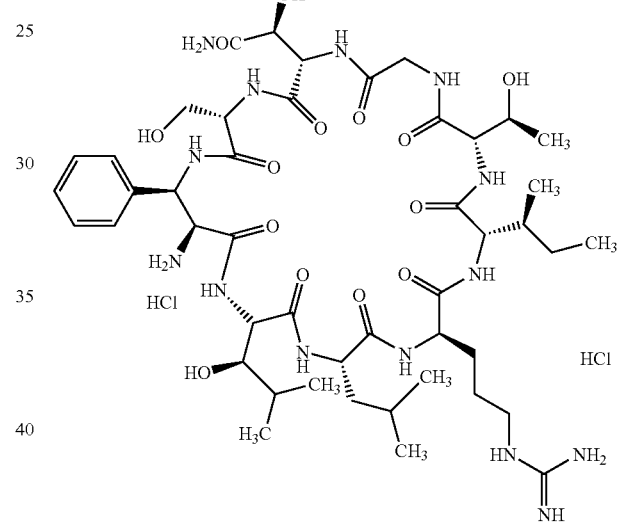

The Cbz-protected cyclopeptide (Example 25A, 4.3 mg, 3.3 μmol) is dissolved in methanol (4 ml) and ten percent palladium-carbon (100 mg) and aqueous 1 N hydrochloric acid (200 μl) are added under an argon protective gas atmosphere. The mixture is hydrogenated at RT and atmospheric pressure (about 1 h) until analytic HPLC (Method 2) indicates complete conversion. The reaction mixture is filtered (through kieselguhr, Celite® or a syringe filter, Biotage, PTFE), concentrated in vacuo and dried under high vacuum. 4 mg (quant.) of the title compound are obtained.

Alternative preparation method (title compound as the trifluoroacetate): The Cbz-protected cyclopeptide (Example 25A, 330 mg, 254 μmol) is dissolved in methanol (200 ml) and 10% palladium-carbon (127 mg) and hydrochloric acid (1526 μl, 6 equivalents) are added under an argon protective gas atmosphere. The mixture is hydrogenated for about 1 h, and catalyst (100 mg) and hydrochloric acid (3 equivalents, 760 μl) are added again. The hydrogenation is continued at RT and atmospheric pressure until (about 1 h) analytical HPLC (Method 2) indicates complete conversion. The reaction mixture is filtered (through kieselguhr, Celite), concentrated in vacuo and dried under high vacuum. The crude product is purified by means of preparative HPLC (Method 33). 250 mg (77% of theory) of the title compound are obtained as the trifluoroacetate.

HPLC/UV-Vis (Method 3): $R_t$=1.4 min,
$\lambda_{max}$ (qualitative)=210 nm (s), 255-270 (w).
LC-MS (Method 7): $R_t$=1.1 min;
MS (ESIpos.): m/z (%)=525.6 (100) [M+2H]$^{2+}$.
MS (ESIneg.): m/z (%)=1048 (100) [M−H]$^-$, 1095 [M−H+HCO$_2$H]$^-$.
HR-TOF-MS (Method 1): $C_{46}H_{77}N_{14}O_{14}$ [M+H]$^+$ found 1049.5728, calc. 1049.5739.

Example 27A

N$^{2.1}$-(tert-Butoxycarbonyl)-[3-tert-butyl-D-alanyl]-[3-tert-butyl-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine C$^{1.11}$—N$^{3.3}$-lactam trifluoroacetate Under an argon protective gas atmosphere, HATU (4.1 equivalents, 14.6 mg, 40 µmol) is first added at 0° C. to a solution of the cyclopeptide (Example 26A, 1.0 equivalent, 11.0 mg, 10 µmol), the dipeptide acid N-(tert-butoxycarbonyl)-3-tert-butyl-D-alanyl-3-tert-butyl-L-alanine (4.0 equivalents, 14.6 mg, 40 µmol) and N-methylmorpholine (2.0 equivalents, 20 µmol) in dry dimethylformamide (270 µl). The reaction mixture is stirred (about 15 min) and N-methylmorpholine (5.0 equivalents, 50 µmol) is again added. The reaction mixture warms slowly (about 12 h) to room temperature and then shows complete conversion of the amine component (HPLC monitoring, Method 3). Solid potassium dihydrogen phosphate (10 equivalents, 500 µmol) is added to the reaction mixture and the mixture is then evaporated under high vacuum and purified by chromatography (Method 21 or Method 13 followed by subsequent salt exchange of the chromatography product by adding TFA (100 µmol as a 0.05% solution in acetonitrile-water 1:1)). 10.5 mg (70% of theory) of product are obtained.

HPLC/UV-Vis (Method 3): $R_t$=2.5 min,
$\lambda_{max}$ (qualitative)=210 nm (s), 255-270 (w).
LC-MS (Method 5): $R_t$=5.5 min;
MS (ESIpos.): m/z (%)=702.6 (30) [M+2H]$^{2+}$, 1404 (20) [M+H]$^+$.
MS (ESIneg.): m/z (%)=700.7 (50) [M−2H]$^{2-}$, 1402 (10) [M−H]$^-$, 1448 [M−H+HCO$_2$H]$^-$.

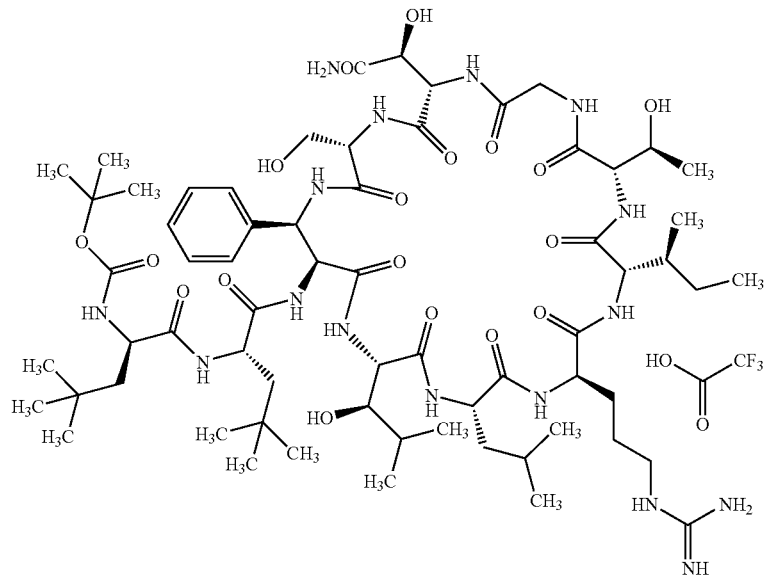

LC-MS (Method 7): $R_t$=2.3 min;
MS (ESIpos.): m/z (%)=653 (100) [M−Boc+2H]$^{2+}$, 1404 (50) [M+H]$^+$.
HR-TOF-MS (Method 1): $C_{65}H_{111}N_{16}O_{18}$ [M+H]$^+$ found 1403.8232, calc. 1403.8257.

Example 28A

N[2.1]-(Benzyloxycarbonyl)-D-leucyl-L-leucyl-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine C[1.11]—N[3.3]-lactam trifluoroacetate

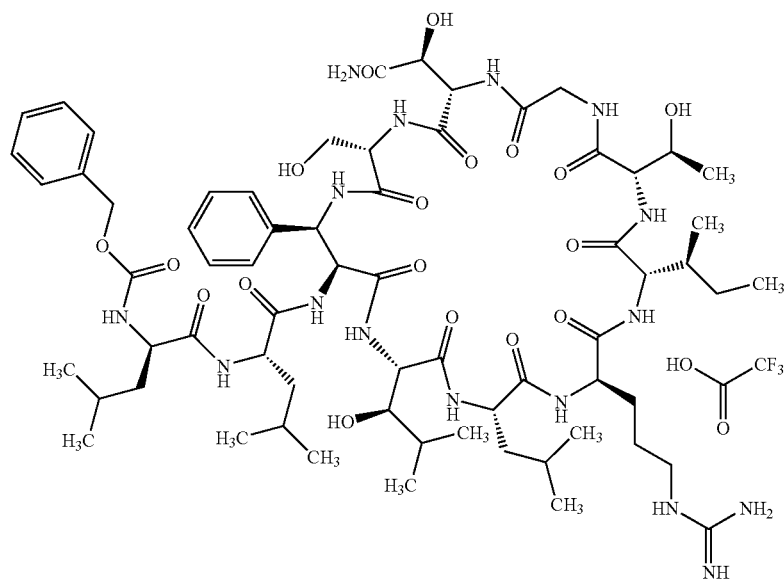

Preparation in analogy to Example 27A from the compound from Example 26A (900 µg, 0.8 µmol) and N-(benzyloxycarbonyl)-D-leucyl-L-leucine (Example 30A, 1200 µg, 3.2 µmol, 4 equivalents). The crude product is purified by means of gel chromatography (Method 14), whereby 500 µg (41% of theory) of product are obtained as a solid after freeze-drying.

HPLC/UV-Vis (Method 3): $R_t$=2.3 min,

LC-MS (Method 5): $R_t$=5.2 min;

MS (ESIpos.): m/z (%)=706.2 (100) [M+2H]$^{2+}$, 1410 (20) [M+H]$^+$.

MS (ESIneg.): m/z (%)=1408 (100) [M−H]$^-$.

Example 29A

N-(Benzyloxycarbonyl)-D-leucyl-L-leucine methyl ester

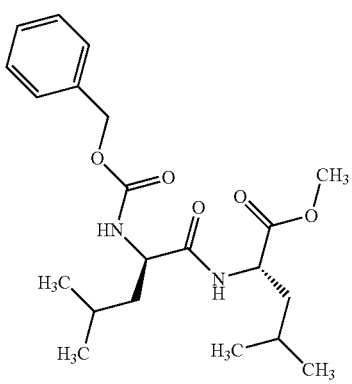

HOBt (4 equivalents, 2038 mg, 15.08 mmol), N-methylmorpholine (3 equivalents, 11.3 mmol), N-benzyloxycarbonyl-D-leucine (1.0 equivalent, 1000 mg, 3.8 mmol), EDC (2 equivalents, 1441 mg, 7.5 mmol) and again N-methylmorpholine (2 equivalents, 7.5 mmol) are added successively at −10° C. to a solution of L-leucine methyl ester hydrochloride (1.1 equivalents, 753.2 mg, 4.15 mmol) in dichloromethane p.a. (20 ml). The reaction mixture warms slowly (about 12 h) to RT, whereby complete conversion of the amine component is observed by means of HPLC. The reaction mixture is concentrated, taken up in ethyl acetate (about 200 ml) and then washed with a saturated aqueous sodium hydrogen carbonate solution (once), 5% aqueous citric acid (twice), a saturated aqueous sodium hydrogen carbonate solution (once) and a saturated sodium chloride solution. The mixture is dried over sodium sulfate and filtered. The mixture is evaporated to dryness in vacuo and then dried further under high vacuum. 1483 mg (93% of theory) of the title compound are obtained, which is reacted without further purification.

LC-MS (Method 7): $R_t$=2.59 min;

MS (ESIpos.): m/z (%)=393 (100) [M+H]$^+$.

Example 30

N-(Benzyloxycarbonyl)-D-leucyl-L-leucine

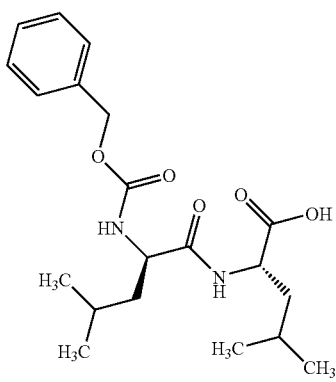

N-(Benzyloxycarbonyl)-D-leucyl-L-leucine methyl ester (Example 29A, 1.12 g, 2.85 mmol) is provided at 0° C. in THF/water 2:1 (15 ml) and then lithium hydroxide monohydrate (140 mg, 5.71 mmol, 2 equivalents) is added. When the HPLC chromatogram (Method 2) shows complete conversion (about 1 h), the reaction mixture is adjusted to pH 3-4 with acetic acid, concentrated in vacuo under cold conditions and then freed of solvent by freeze-drying overnight. The crude product is purified by means of preparative HPLC (Method 13) whereby 958 mg (88.7% of theory) of the title compound are obtained.

LC-MS (Method 7): $R_t$=2.33 min;

MS (ESIpos.): m/z (%)=379 (100) [M+H]$^+$.

HR-TOF-MS (Method 1): $C_{20}H_{31}N_2O_5$ [M+H]$^+$ found 379.2227, calc. 379.2233.

Example 31A

Methyl (2R,3R)—N$^2$-[(benzyloxy)carbonyl]-N$^2$-[(benzyloxy)carbonylamino]-3-[(tert-butoxy-carbonyl)amino]phenylalaninate

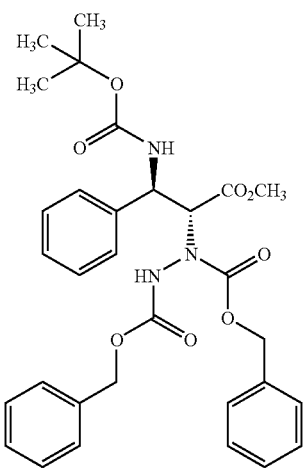

Method A (5 g scale): Under an argon protective gas atmosphere, a 1 N solution of lithium hexamethyldisilazide (39.4 mmol, 39.4 ml, 2.2 equivalents) in THF is provided in the reaction solvent THF (200 ml). At −78° C., a solution of methyl (S)-3-[(tert-butoxycarbonyl)amino]-3-phenylpropanoate (5.0 g, 17.9 mmol) is slowly added dropwise. The mixture is stirred at −25° C. for 10 min and then again cooled down to −78° C. Dibenzyl azadicarboxylate (8.54 g, 28.6 mmol, 1.6 equivalents) is added to the reaction mixture in one portion. The mixture is stirred at −50 to −60° C. for 3 h. In order to stop the reaction, the mixture is again cooled down to −78° C. and acetic acid (5.1 ml, 89.5 mmol, 5 equivalents) is added, and the mixture is then warmed to 0° C. and finally RT. Workup in analogy to Example 12A (Method B). 4.8 g (44% of theory) of the title compound are obtained as a solid.

Method B (50 g scale): Under an argon protective gas atmosphere, a 1 N solution of lithium hexamethyldisilazide (452.9 mmol, 452.9 ml, 2.2 equivalents) in THF is provided in the reaction solvent THF (1800 ml). At −70° C., a solution of methyl (S)-3-[(tert-butoxycarbonyl)amino]-3-phenylpropanoate (57.5 g, 205.8 mmol) in THF (600 ml) is slowly added dropwise. The mixture is stirred at −25° C. for 10 min and then again cooled down to −70° C. Dibenzyl azadicarboxylate (98.2 g, 329.4 mmol, 1.6 equivalents) is added in 4 portions to the reaction mixture. The mixture is stirred at −50 to −60° C. for 2 h. In order to stop the reaction, the mixture is again cooled down to −70° C. and acetic acid (61.7 ml, 1 mol, 5 equivalents) is added, and the mixture is then warmed to RT overnight. The precipitate in the reaction solution is collected by suction filtration. The filter residue is dried at 50° C. under high vacuum (46.1 g, crude product 1). The filtered mother liquor (reaction mixture) is concentrated in vacuo (crude product 2). The two crude products 1 and 2 are recrystallized from hot ethyl acetate (2×500 ml) (reflux, 1 h; product fractions 1 (31.7 g) and 2 (37.4 g)). The mother liquor is again evaporated and recrystallized from tert-butyl methyl ether (370 ml). Hereby product fraction 3 (14.5 g) is obtained. In total, 83.6 g (70% of theory) of the title compound are obtained as a solid.

[α]$^{20}_{Na}$=−13° (c=0.20 in chloroform).

HPLC/UV-Vis (Method 2): $R_t$=2.88 min.

LC-MS (Method 29): $R_t$=2.8 min;

MS (ESIpos.): m/z (%)=478 (100) [M−Boc+H]$^+$, 578 (70) [M+H]$^+$, 1156 (20) [2M+H]$^+$;

MS (ESIneg.): m/z (%)=576 (100) [M−H]$^−$.

$^1$H NMR (500 MHz, d$_6$-DMSO, 335 K, broad signals): δ=1.35 (s, 9H), 3.15 (s, 3H), 3.30 (s, 3H), 4.90-5.15 (m, 6H), 7.20-7.40 (m, 10H), 8.30, 8.95 (3s, br, 2H).

Example 32A

Methyl (2S,3R)—N-[(benzyloxy)carbonyl]-N-[(benzyloxy)carbonylamino]-3-[(tert-butoxy-carbonyl)amino]phenylalaninate

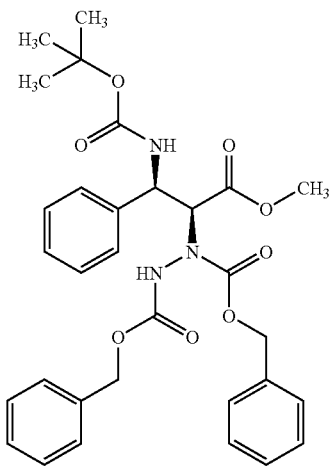

Under an argon protective gas atmosphere, N,N,N,N-tetramethylguanidine (16.6 ml, 132 mmol) is added to a solution of methyl (2R,3R)—N$^2$-[(benzyloxy)carbonyl]-N$^2$-[(benzyloxy)carbonylamino]-3-[(tert-butoxycarbonyl)amino]phenylalaninate (3.95 g, 6.84 mmol) in dry dichloromethane p.a. (170 ml) at 0° C. The reaction mixture is allowed to thaw and stirred until the HPLC chromatogram (Method 2) indicates complete conversion (about 60% product) (about 12 h), in order to stop the reaction by the addition of acetic acid (10.5 ml, pH 4-6). The organic phase is washed with water (twice), a saturated aqueous sodium hydrogen carbonate solution (twice) and a saturated aqueous sodium chloride solution (once). The aqueous phases are reextracted with dichloromethane. The combined organic phases are dried over sodium sulfate, filtered, evaporated in vacuo and dried under high vacuum. The crude product is purified by means of flash chromatography (silica gel, toluene/ethyl acetate 4:1). 2.4 g (61% of theory, based on recovered starting materials 68%) of the title compound and 490 mg of the starting compound (12% of theory) are obtained.

[α]$^{20}_{Na}$=−120.7° (c=0.52 in chloroform).

HPLC/UV-Vis (Method 2): $R_t$=2.99 min.

LC-MS (Method 29): $R_t$=2.9 min;

MS (ESIpos.): m/z (%)=478 (100) [M−Boc+H]$^+$, 578 (50) [M+H]$^+$, 1156 (10) [2M+H]$^+$;

MS (ESIneg.): m/z (%)=502 (100), 576 (40) [M−H]$^−$.

HR-TOF-MS (Method 1): $C_{31}H_{36}N_3O_8$ [M+H]$^+$ found 578.2505, calc. 578.2497.

Example 33A

Methyl (2S,3R)-3-[(tert-butoxycarbonyl)amino]phenylalaninate

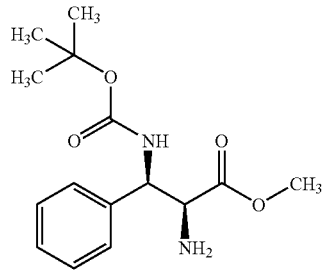

Under an argon protective gas atmosphere, Raney nickel (86 mg) is added to a solution of methyl (2S,3R)—N-[(benzyloxy)carbonyl]-N-[(benzyloxy)carbonylamino]-3-[(tert-butoxycarbonyl)amino]phenylalaninate (600 mg, 1.04 mmol) in methanol/dichloromethane 1:1 (12 ml). The reaction mixture is hydrogenated in a pressure autoclave under 80 bar hydrogen pressure and at RT (72 h). The HPLC chromatogram shows complete conversion. The reaction mixture is filtered under an argon protective gas atmosphere through a (kieselguhr-layered) glass frit. The glass frit is washed repeatedly with methanol/water/0.2% acetic acid. The filtrate is washed with water (twice) and then evaporated in vacuo. The crude product is obtained as a solid (280 mg, 92% of theory) which is reacted further without fine-purification. For analytical purposes, gel chromatographic fine-purification (Method 14, methanol/0.1% TFA) can be undertaken.

[α]$^{20}_{Na}$=+11° (c=0.25 in chloroform) (TFA salt).

HPLC/UV-Vis (Method 2): $R_t$=1.5 min.

LC-MS (Method 29): $R_t$=1.2 min;

MS (ESIpos.): m/z (%)=239 (100), 295 (40) [M+H]$^+$.

$^1$H NMR (500 MHz, d$_6$-DMSO, TFA salt): δ=1.36 (s, 9H), 3.50 (s, 3H), 4.30 (d, J=7.2 Hz, 1H), 5.05 ("t", J=8.0 Hz, 1H), 7.30-7.39 (m, 5H), 7.60 (d, J=9.7 Hz, 1H).

$^{13}$C NMR (125 MHz, d$_6$-DMSO, TFA salt): δ=28.25 (3C), 52.87, 54.88, 56.87, 79.29, 127.12 (2C), 128.45, 128.89 (2C), 137.18, 154.83, 168.14.

HR-TOF-MS (Method 1): $C_{15}H_{22}N_2O_4$ [M+H]$^+$ found 295.1663, calc. 295.1653.

Example 34A

Methyl (2S,3R)—N-[(benzyloxy)carbonyl]-3-[(tert-butoxycarbonyl)amino]phenylalaninate

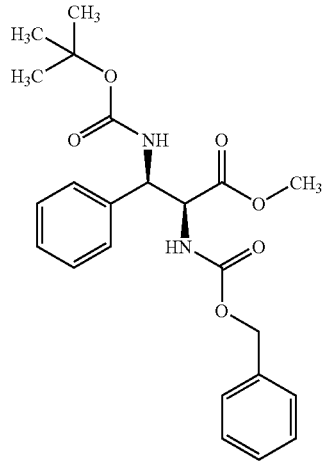

Under an argon protective gas atmosphere, solid sodium hydrogen carbonate (80 mg, 0.93 mmol, 1.5 equivalents) is added at 0° C. to a solution of methyl (2S,3R)-3-[(tert-butoxycarbonyl)amino]phenylalaninate (250 mg, 0.62 mmol) and N-benzyloxycarbonyloxysuccinimide ester (180 mg, 0.71 mmol, 1.15 equivalents) in a mixture of dichloromethane (20 ml) and water (45 ml). The reaction mixture warms up slowly (12 h), whereby complete conversion is observed by means of HPLC (Method 2). The aqueous phase is reextracted with dichloromethane and then washed with 5% aqueous citric acid, a saturated aqueous sodium hydrogen carbonate solution and a saturated sodium chloride solution, dried over sodium sulfate, filtered and concentrated in vacuo. Subsequently, purification is effected by means of flash chromatography (silica gel, toluene/ethyl acetate 4:1). 144 mg (47% of theory) of the title compound are obtained.

$[\alpha]^{20}_{Na}$=+13.3° (c=0.70 in chloroform).

HPLC/UV-Vis (Method 2): $R_t$=2.6 min.

LC-MS (Method 7): $R_t$=2.7 min;

MS (ESIpos.): m/z (%)=329 (100) [M−Boc+H]$^+$, 373 (80), 429 (60) [M+H]$^+$, 858 (10) [2M+H]$^+$.

$^1$H NMR (400 MHz, d$_6$-DMSO): δ=1.37 (s, 9H), 3.62 (s, 3H), 4.58 (dd, J=9.5, 4.2 Hz, 1H), 4.94 (m, 2H), 5.27 (dd, J=10.4, 4.0 Hz, 1H), 7.21-7.35 (m, 10H), 7.50 (d, J=10.5 Hz, 1H), 7.59 (d, J=9.4 Hz, 1H).

$^{13}$C NMR (126 MHz, d$_6$-DMSO): δ=28.25 (3C), 52.31, 54.66, 59.03, 65.71, 78.72, 126.64 (2C), 127.40, 127.63 (2C), 127.99, 128.42 (2C), 128.51 (2C), 136.90, 139.24, 154.97, 156.23, 170.89.

HR-TOF-MS (Method 1): C$_{23}$H$_{29}$N$_2$O$_6$ [M+H]$^+$ found 429.2011, calc. 429.2021.

Example 35A (3R)—N$^2$-[(Benzyloxy)carbonyl]-3-[(tert-butoxycarbonyl)amino]-L-phenylalanine

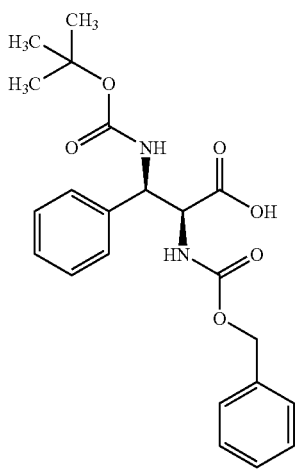

A solution of methyl (2S,3R)—N-[(benzyloxy)carbonyl]-3-[(tert-butoxycarbonyl)amino]phenylalaninate (152 mg, 0.30 mmol) in THF/water 2:1 (22.5 ml) is provided under an argon protective gas atmosphere. At 0° C., a degassed 1% aqueous solution of lithium hydroxide monohydrate (14.8 mg, 0.62 mmol, 2 equivalents) is slowly added dropwise with vigorous stirring. The mixture is stirred at RT until the HPLC chromatogram (Method 2) indicates complete conversion (about 1 h). Subsequently, acetic acid (0.1 ml) is added to the reaction mixture and the reaction mixture is concentrated in vacuo, and the residue is freeze-dried. The crude product is fine-purified by means of preparative HPLC (Method 13). 74 mg (59% of theory) of the title compound are obtained as product.

$[\alpha]^{20}_{Na}$=+22° (c=0.50 in chloroform) (by chiral chromatography);

$[\alpha]^{20}_{Na}$=+21.5° (c=0.51 in chloroform) (by enantioselective synthesis)

LC-MS (Method 7): $R_t$=2.4 min;

MS (ESIpos.): m/z (%)=315 (90), 359 (100), 415 (80) [M+H]$^+$, 729 (30), 829.5 (50) [2M+H]$^+$.

MS (ESIneg.): m/z (%)=413 (100) [M−H]$^-$.

Chiral HPLC/UV-Vis (Method 24): $R_t$=5.4 min (narrow peak).

$^1$H NMR (500 MHz, d$_6$-DMSO): δ=1.35 (s, 9H), 4.46 (dd, J=9.6, 3.6 Hz, 1H), 4.91 (s, 2H), 5.26 (dd, J=9.9, 3.6 Hz, 1H), 7.18-7.32 (m, 10H), 7.48-7.51 (m, 2H), 12.95 (s, br, 1H).

$^{13}$C NMR (126 MHz, d$_6$-DMSO): δ=28.34 (3C), 54.84, 58.96, 65.55, 78.56, 126.53 (2C), 127.23, 127.55 (2C), 127.93, 128.39 (2C), 128.51 (2C), 137.05, 140.16, 155.09, 156.30, 171.62.

HR-TOF-MS (Method 1): C$_{22}$H$_{26}$N$_2$O$_6$ [M+H]$^+$ found 415.1864, calc. 415.1864.

Example 36A (3S)—N$^2$-[(Benzyloxy)carbonyl]-3-[(tert-butoxycarbonyl)amino]-D-phenylalanine

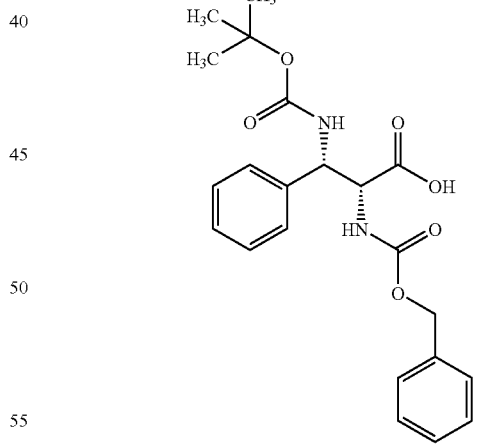

See example 35A for preparation method.

$[\alpha]^{20}_{Na}$=−20° (c=0.49 in chloroform).

Chiral HPLC/UV-Vis (Method 24): $R_t$=11.4 min (broad peak).

LC-MS (Method 7): $R_t$=2.5 min;

MS (ESIpos.): m/z (%)=315 (40), 359 (40), 415 (50) [M+H]$^+$, 729 (20), 829.5 (10) [2M+H]$^+$.

MS (ESIneg.): m/z (%)=413 (100) [M−H]$^-$.

$^1$H NMR (500 MHz, d$_6$-DMSO): δ=1.35 (s, 9H), 4.45 (dd, J=9.6, 3.2 Hz, 1H), 4.91 (s, 2H), 5.26 (dd, J=9.4, 3.6 Hz, 1H), 7.18-7.30 (m, 10H), 7.47-7.52 (m, 2H), 12.95 (s, br, 1H).

HR-TOF-MS (Method 1): C$_{22}$H$_{26}$N$_2$O$_6$ [M+H]$^+$ found 415.1869, calc. 415.1864.

Example 37A 2-(Trimethylsilyl)ethyl(3S)—N-[(benzyloxy)carbonyl]-3-[(tert-butoxycarbonyl)amino]-D-phenylalaninate

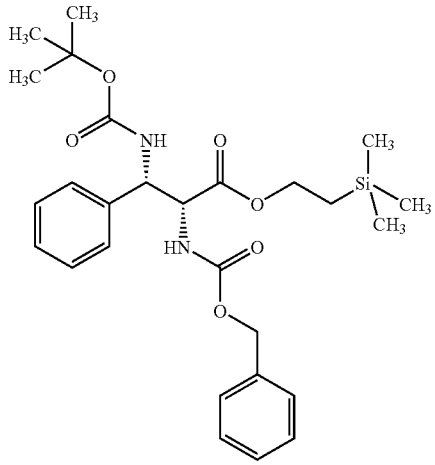

A mixture of (3S)—N$^2$-[(benzyloxy)carbonyl]-3-[(tert-butoxycarbonyl)amino]-D-phenylalanine (3.96 g, 9.55 mmol), 2-(trimethylsilyl)ethanol (11.3 g, 95.6 mmol, 10 equivalents) and 4 Å molecular sieve (about 200 mg, freshly pulverized) in dry dichloromethane p.a. (77 ml) is stirred at RT under an argon protective gas atmosphere for 3 h. Subsequently, DCC (3.94 g, 19.11 mmol, 2 equivalents) and DMAP (1.17 g, 9.55 mmol, 1 equivalent) are added at −30° C. The reaction mixture is allowed to thaw (about 12 h) and stirred at RT until the HPLC chromatogram (Method 2) indicates complete conversion (about 12 h). The reaction mixture is filtered through kieselguhr and then evaporated in vacuo at RT. The crude product is prefractionated on an RP$_{18}$ cartridge (eluent: water, then acetonitrile) and purified by means of preparative flash chromatography (1.5 kg of silica gel, toluene/ethyl acetate 4:1). 3.6 g (73% of theory) of the title compound are obtained.

[α]$^{20}_{Na}$=−8.0° (c=0.52 in chloroform)

HPLC/UV-Vis (Method 3): R$_t$=3.2 min.

LC-MS (Method 7): R$_t$=3.3 min; MS (ESIpos.): m/z (%)=387 (100), 515 (90) [M+H]$^+$.

$^1$H NMR (500 MHz, d$_6$-DMSO): δ=−0.02 (s, 9H), 0.88 (t, J=8.0 Hz, 2H), 1.31 (s, 9H), 4.02-4.15 (m, 2H), 4.48 (dd, J=9.6, 4.3 Hz, 1H), 4.86 (d, J=12.6 Hz, 1H), 4.90 (d, J=12.6 Hz, 1H), 5.25 (dd, J=10.0, 3.8 Hz, 1H), 7.14-7.29 (m, 10H), 7.47 (d, J=10.3 Hz, 1H), 7.50 (d, J=9.7 Hz, 1H).

HR-TOF-MS (Method 1): C$_{27}$H$_{38}$N$_2$O$_6$Si [M+H]$^+$ found 515.2567, calc. 515.2572.

Example 38A 2-(Trimethylsilyl)ethyl(3S)-3-amino-N$^2$-[(benzyloxy)carbonyl]-D-phenylalaninate trifluoroacetate

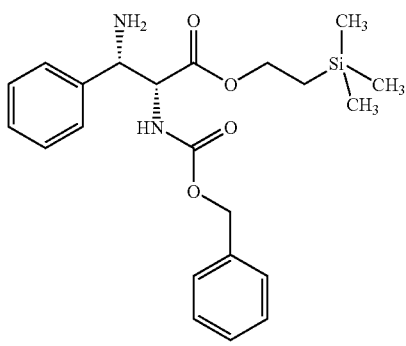

2-(Trimethylsilyl)ethyl(3S)—N-[(benzyloxy)carbonyl]-3-[(tert-butoxycarbonyl)amino]-D-phenylalaninate (3600 mg, 7.0 mmol) is reacted according to working procedure 1 (reaction time: 10 min). The crude product is purified by means of preparative HPLC (Method 13, Method 21). 3060 mg (83% of theory) of the title compound are obtained.

[α]$^{20}_{Na}$=+15.0° (c=0.22 in chloroform)

HPLC/UV-Vis (Method 3): R$_t$=1.9 min.

LC-MS (Method 8): R$_t$=1.8 min;

MS (ESIpos.): m/z (%)=387.2 (60), 415 (100) [M+H]$^+$.

$^1$H NMR (500 MHz, d$_6$-DMSO): δ=−0.06 (s, 9H), 0.52 (m, 2H), 3.76 (m, 1H), 3.88 (m, 1H), 4.49 (d, J=9.3 Hz, 1H), 4.58 ("t", J=9.0 Hz, 1H), 5.08 (s, 2H), 7.34-7.44 (m, 10H), 8.12 (d, J=8.5 Hz, 1H), 8.62 (s, br, 2H).

HR-TOF-MS (Method 1): C$_{22}$H$_{30}$N$_2$O$_4$Si [M+H]$^+$ found 415.2042, calc. 415.2048.

Example 39A (3S)—N-Boc-β-phenylalanine methyl ester

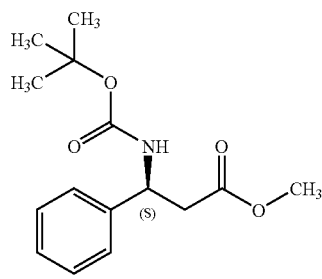

The enantiomer mixture of (rac)-N-Boc-β-phenylalanine methyl ester (62.8 g, 224.8 mmol) is separated into the enantiomers by means of preparative HPLC (Method 32). 29.1 g of (3R)—N-Boc-β-phenylalanine methyl ester (95.7% ee, 46% of theory, example 40, elutes later) and 30.5 g of (3S)—N-Boc-β-phenylalanine methyl ester (>99% ee, 49% of theory, title compound, elutes earlier) are obtained.

[α]$^{20}_{Na}$=−3° (c=0.52 in chloroform).

HPLC/UV-Vis (Method 3): R$_t$=2.5 min.

¹H NMR (500 MHz, d₆-DMSO): δ=1.35 (s, 9H), 2.67 (dd, J=15.4, 6.0 Hz, 1H), 2.75 (dd, J=15.7, 8.6 Hz, 1H), 3.55 (s, 3H), 4.92 (m, 1H), 7.23 (m, 1H), 7.29-7.33 (m, 4H), 7.48 (d, J=8.3 Hz, 1H).

¹³C NMR (126 MHz, d₆-DMSO): δ=28.38 (3C, (C(CH₃)₃)), 41.19 (C$^\beta$H₂), 51.25 (C$^\alpha$H), 51.54 (OCH₃), 78.07 (C(CH₃)₃), 126.47 (2C), 127.17, 128.46 (2C), 142.95, 154.90, 170.86.

HR-TOF-MS (Method 1): $C_{15}H_{22}NO_4$ [M+H]⁺ found 280.1533, calc. 280.1544.

Example 40

(3R)—N-Boc-β-phenylalanine methyl ester

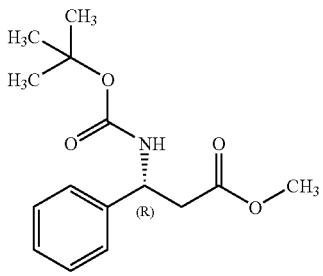

The synthesis takes place according to example 39A.

[α]²⁰$_{Na}$=+30° (c=0.52 in chloroform).

¹H NMR (500 MHz, d₆-DMSO): δ=1.35 (s, 9H), 2.68 (dd, J=15.2, 6.0 Hz, 1H), 2.75 (dd, J=15.6, 8.8 Hz, 1H), 3.55 (s, 3H), 4.92 (m, 1H), 7.23 (m, 1H), 7.30-7.33 (m, 4H), 7.48 (d, J=8.7 Hz, 1H).

HR-TOF-MS (Method 1): $C_{15}H_{21}NO_4$ [M+H]⁺ found 280.1555, calc. 280.1544.

Example 41A

Methyl 3-(6-methylpyridin-2-yl)-L-alaninate

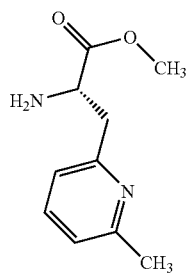

A mixture of methyl N-(benzyloxycarbonyl)-3-(6-methylpyridin-2-yl)-L-alaninate (7.25 g, 22.1 mmol) [S. W. Jones, C. F. Palmer, J. M. Paul, P. D. Tiffin, *Tetrahedron Lett.* 1999, 40, 1211-1214] and 10 percent palladium on carbon (0.690 g) in ethanol (80 ml) is hydrogenated at RT and under atmospheric pressure for 1 h. The reaction mixture is passed through a syringe filter (Millipore, 0.45 μg, hydrophobic PTFE) which is washed with ethanol (2×10 ml). The residue is concentrated on a rotary evaporator (removal of solvent residues by entrainment with toluene, twice) and dried under high vacuum. The product is obtained as an oil (3.89 g, yield 91% of theory).

HPLC/UV-Vis (Method 2): $R_t$=0.3 min.

LC-MS (Method 30): $R_t$=0.70 min, broad peak; MS (ESIpos.): m/z (%)=195 (100) [M+H]⁺.

¹H NMR (400 MHz, d₆-DMSO): δ=1.95 (m, 2H), 2.41 (s, 3H), 2.86 (dd, J=7.4 Hz, 1H), 2.99 (dd, J=5.9 Hz, 1H), 3.59 (s, 3H), 3.73 (dd, J=7.4, 5.7 Hz, 1H), 7.02 (d, J=7.5 Hz, 1H), 7.06 (d, J=7.1 Hz, 1H), 7.56 (t, J=7.5 Hz, 1H).

Example 42A

N-tert-Butoxycarbonyl-3-tert-butyl-D-alanyl-3-(6-methylpyridin-2-yl)-L-alanine methyl ester

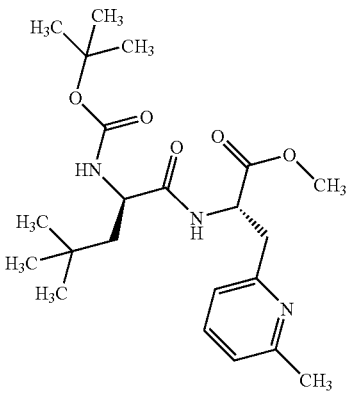

NMM (2 equivalents, 13.1 mmol) and finally HATU (1.3 equivalents, 3.2 g, 8.5 mmol) are added slowly at 0° C. to a solution of N-(tert-butoxycarbonyl)-3-tert-butyl-D-alanine (example 6A, 1.0 equivalent, 1.6 g, 6.6 mmol) and methyl 3-(6-methylpyridin-2-yl)-L-alaninate (example 41A, 1.1 equivalents, 1.4 g, 7.2 mmol) in dry DMF (26 ml). The reaction mixture warms slowly (about 12 h) to RT, whereby complete conversion is observed by means of HPLC (Method 2). For the workup, the reaction mixture is concentrated on a rotary evaporator (waterbath 35° C.), diluted with ethyl acetate (100 ml) and subsequently washed with a saturated sodium hydrogen carbonate solution (2×20 ml), 5 percent citric acid (2×20 ml) and a saturated aqueous sodium chloride solution. The organic phase is dried over sodium sulfate, filtered and concentrated. The product is obtained as a solid (2.88 g, 99% of theory) which can be fine-purified by means of preparative HPLC (Method 13).

HPLC/UV-Vis (Method 2): $R_t$=2.1 min.

LC-MS (Method 29): $R_t$=1.73 min;

MS (ESIpos.): m/z (%)=422 (100) [M+H]⁺;

MS (ESIneg.): m/z (%)=420 (20) [M−H]⁻, 466 (100) [M−H+HCO₂H]⁻.

HR-TOF-MS (Method 1): $C_{21}H_{34}N_3O_5$ [M+H]⁺ calc. 408.2498, found 408.2503.

¹H NMR (400 MHz, d₆-DMSO): δ=0.79 (s, 9H), 1.23-1.43 (m, 11H), 2.42 (s, 3H), 2.99-3.13 (m, 2H), 3.60 (s, 3H), 3.95 (dt, J=8.9, 3.8 Hz, 1H), 4.64 (m, 1H), 6.83 (d, J=8.9 Hz, 1H), 7.02 (d, J=7.8 Hz, 1H), 7.07 (d, J=7.7 Hz, 1H), 7.54 (t, J=7.7 Hz, 1H), 8.18 (d, J=7.9 Hz, 1H).

Example 43A

N-tert-Butoxycarbonyl-3-tert-butyl-D-alanyl-3-(6-methyl-2-pyridyl)-L-alanine

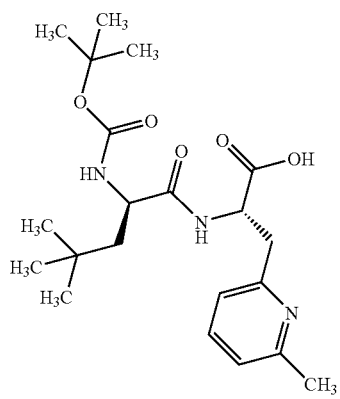

Methyl N-tert-butoxycarbonyl-3-tert-butyl-D-alanyl-3-(6-methyl-2-pyridyl)-L-alaninate (example 42A, 850 mg, 2.02 mmol) is converted according to general working procedure 4. 766 mg (93% of theory) of product are obtained.

HPLC/UV-Vis (Method 2): $R_t$=1.8 min.

LC-MS (Method 8): $R_t$=1.63 min; MS (ESIpos.): m/z (%)=353 (100), 408 (90) [M+H]⁺; MS (ESIneg.): m/z (%)=332 (70), 406 (100) [M−H]⁻.

HR-TOF-MS (Method 1): $C_{21}H_{34}N_3O_5$ [M+H]⁺ calc. 408.2498, found 408.2503.

¹H NMR (400 MHz, d₆-DMSO): δ=0.79 (s, 9H), 1.26-1.37 (m, 11H), 2.43 (s, 3H), 3.01 (dd, J=8.6 Hz, 1H), 3.10 (dd, J=5.3 Hz, 1H), 3.94 (dt, J=9.2 Hz, 3.4 Hz, 1H), 4.57 (m, 1H), 6.81 (d, J=8.9 Hz, 1H), 7.02 (d, J=7.7 Hz, 1H), 7.07 (d, J=7.1 Hz, 1H), 7.54 (t, J=7.7 Hz, 1H), 8.08 (d, J=7.9 Hz, 1H).

Example 44A $N^{2.1}$-(tert-Butoxycarbonyl)-[3-tert-butyl-D-alanyl]-[3-(6-methylpyrid-2-yl)-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam bistrifluoroacetate

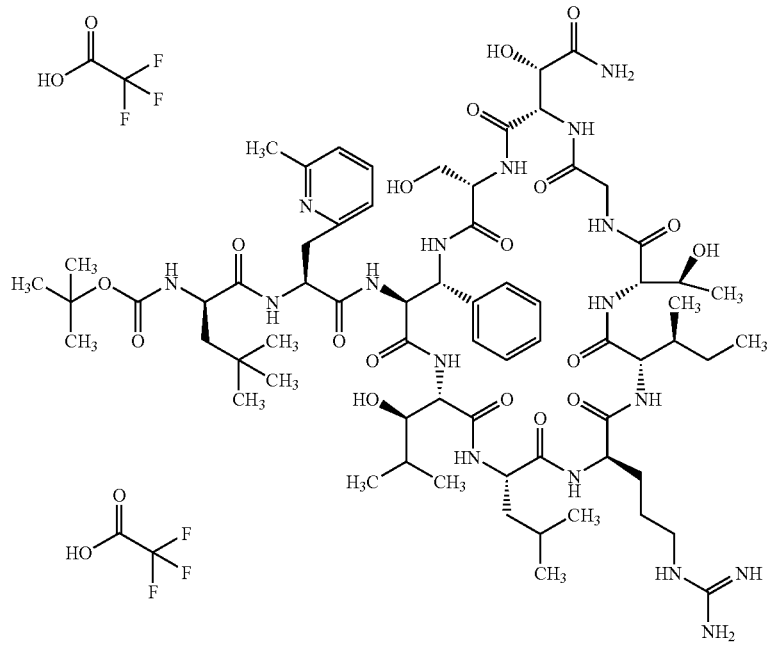

According to working procedure 5, the cyclopeptide (example 26A, 40.0 mg, 31.32 µmol) and the dipeptide acid (example 43A, 22.9 mg, 56.37 µmol, 1.8 equivalents), with the aid of NMM (17.2 µl, 156.58 µmol, 5 equivalents) and HATU (21.43 mg, 56.36 µmol, 1.8 equivalents), are reacted to the amide at −10° C. in DMF (15 ml) within 2.5 h. The title compound is obtained as a solid after chromatographic purification (Method 37) (29.4 mg, 55% of theory).

HPLC/UV-Vis (Method 2): $R_t$=2.25 min.

LC-MS (Method 7): $R_t$=2.05 min;

MS (ESIpos.): m/z (%)=1439 (5) [M+H]$^+$, 720 (100) [M+2H]$^{2+}$;

MS (ESIneg.): m/z (%)=1436 (100) [M−H]$^-$, 718 [M−2H]$^{2-}$.

HR-TOF-MS (Method 1): $C_{67}H_{108}N_{17}O_{18}$ [M+H]$^+$ calc. 1438.8053, found 1438.8060.

Example 45A $N^{2.1}$-(tert-Butoxycarbonyl)-[3-tert-butyl-D-alanyl]-[3-(pyrid-2-yl)-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam bistrifluoroacetate pound is obtained as a solid after chromatographing (Method 35) (111.3 mg, 86% of theory).

HPLC/UV-Vis (Method 25): $R_t$=19.44 min.

LC-MS (Method 7): $R_t$=2.15 min;

MS (ESIpos.): m/z (%)=1424 (25) [M+H]$^+$, 713 (100) [M+2H]$^{2+}$;

MS (ESIneg.): m/z (%)=1422 (100) [M−H]$^-$, 711 [M−2H]$^{2-}$.

HR-TOF-MS (Method 1): $C_{66}H_{106}N_{17}O_{18}$ [M+H]$^+$ calc. 1424.7897, found 1424.7906.

Example 46A

4-Methyl-D-leucine trifluoroacetate

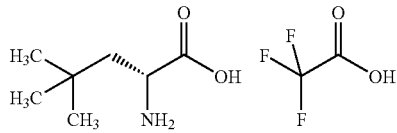

As described in working procedure 1, the title compound is obtained from the Boc-protected amino acid (example 6A, 20.0 g, 81.53 mmol) with a crude yield of 21.7 g (quant.).

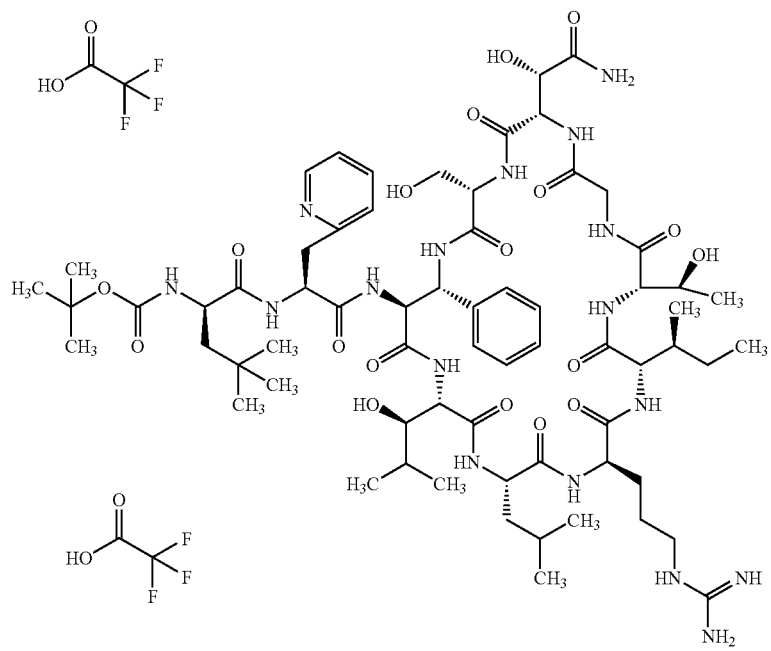

According to working procedure 5, the cyclopeptide (example 26A, 100.0 mg, 78.29 µmol) and N-(tert-butoxycarbonyl)-4-methyl-D-leucyl-3-pyridin-2-yl-L-alanine (55.5 mg, 140.63 µmol, 1.8 equivalents) (see WO2004099239), with the aid of NMM (43.0 µl, 156.58 µmol, 5 equivalents) and HATU (21.43 mg, 391.46 µmol, 1.8 equivalents), are reacted in DMF (8 ml) overnight at RT to the amide. The title compound is obtained as the amide. The title compound is obtained as MS (ESIpos): m/z (%)=146 (100) [M+H]$^+$.

HR-TOF-MS (Method 1): $C_7H_{16}N_2O_2 \cdot C_2H_3N$ [M+CH$_3$CN+H]$^+$ calc. 187.1442, found 187.1450.

$^1$H NMR (500 MHz, d$_6$-DMSO): δ=0.95 (m, 9H), 1.58 (dd, J=14.5 Hz, 5.2 Hz, 1H), 1.81 (dd, J=14.5 Hz, 6.3 Hz, 1H), 3.79 (t, J=5.4 Hz, 1H), 8.32 (s, br, 3H).

$^{13}$C NMR (126 MHz, d$_6$-DMSO): δ=29.27 (3C), 30.26, 44.30, 50.01, 172.23.

Example 47A

N-[(Benzyloxy)carbonyl]-4-methyl-D-leucine

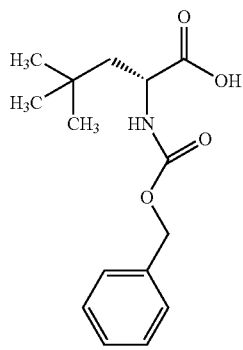

The amino acid (example 46A, 10.0 g, 38.6 mmol) and N-benzyloxycarbonyl-oxysuccinimide ester (11.1 g, 44.4 mmol, 1.15 equivalents) are dissolved in dichloromethane/water 4:1 (250 ml). Solid sodium hydrogen carbonate (4.86 g, 57.9 mmol, 1.5 equivalents) and solid tetra-n-butylammonium bromide (1.2 g. 3.9 mmol, 0.1 equivalent) are added to the reaction mixture at 0° C., in order to stir the reaction mixture at RT overnight. The HPLC chromatogram shows complete conversion. The basic aqueous phase is washed with dichloromethane (six times). Subsequently, the pH is adjusted to 2-3 with 1 N aqueous hydrochloric acid. The aqueous phase is then extracted (three times) with ethyl acetate. The combined organic phases are washed with a conc. aqueous sodium chloride solution, dried over sodium sulfate, filtered and concentrated in vacuo. The resulting crude product is purified by means of preparative HPLC (Method 35). 6.86 g (64% of theory) of the title compound are obtained.

$[\alpha]^{20}_{Na}$=+2° (c=0.17 in CHCl$_3$).
HPLC/UV-Vis (Method 3): R$_t$=2.2 min.
LC-MS (Method 29): R$_t$=2.0 min;
MS (ESIpos.): m/z (%)=236 (100), 280 (50) [M+H]$^+$;
MS (ESIneg): m/z (%)=170 (100), 278 (40) [M−H]$^−$.
$^1$H NMR (400 MHz, d$_6$-DMSO): δ=0.81 (d, J=6.3 Hz, 3H), 0.86 (d, J=6.4 Hz, 3H), 0.89 (s, 9H), 1.48 (m, 3H), 1.57 (m, 2H), 3.61 (s, 3H), 4.14 (m, 1H), 4.23 (m, 1H), 5.03 (s, 2H), 7.27-7.40 (m, 6H), 8.19 (d, J=7.9 Hz, 1H).
$^{13}$C NMR (126 MHz, d$_6$-DMSO): δ=29.53 (3C), 30.50, 44.11, 51.49, 65.47, 127.75 (2C), 127.95, 128.51 (2C), 137.34, 156.03, 174.97.
HR-TOF-MS (Method 1): C$_{15}$H$_{22}$NO$_4$ calc. 280.1544, found 280.1535 [M+H]$^+$.

Example 48A

Methyl N-[(benzyloxy)carbonyl]-4-methyl-D-leucyl-L-leucinate

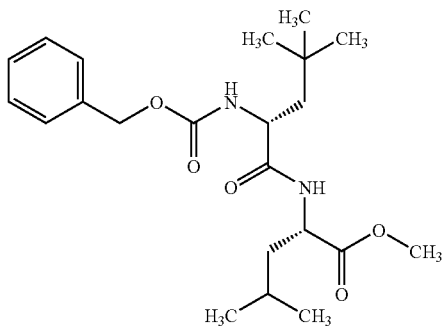

Methyl-L-leucinate hydrochloride (600.9 mg, 3.31 mmol, 1.1 equivalents) is provided under an argon protective gas atmosphere in dichloromethane (250 ml), HOBt (1625.3 mg, 12.03 mmol, 4 equivalents), NMM (992 µl, 9.02 mmol, 3 equivalents), benzyloxycarbonyl-protected amino acid (example 47A, 840.0 mg, 3.0 mmol, 1 equivalent), EDC (1149.7 mg, 6.01 mmol, 2 equivalents) and further NMM (661 µl, 6.02 mmol, 2 equivalents) are added to the solution at −10° C., and the reaction mixture is brought to complete conversion overnight with stirring. For the workup, the reaction solution is concentrated at 30° C. bath temperature on a rotary evaporator, the residue is dissolved in ethyl acetate and a saturated sodium bicarbonate solution, the separated aqueous phase is extracted with ethyl acetate, and the combined organic phases are washed successively with a 5% citric acid solution, with a saturated sodium bicarbonate solution and with a saturated sodium chloride solution and dried over sodium sulfate. After the removal of the drying agent, the solvent is removed completely at 30° C. bath temperature on a rotary evaporator. After lyophilization, the product is obtained with a yield of 1200 mg (98% of theory).

HPLC (Method 2): R$_t$=2.65 min.
LC-MS (Method 7): R$_t$=2.84 min;
MS (ESIpos.): m/z (%)=407 (100), 813 (27) [2M+H]$^+$.
$^1$H NMR (400 MHz, d$_6$-DMSO): δ=0.81 (d, J=6.3 Hz, 3H), 0.86 (d, J=6.3 Hz, 3H), 0.89 (s, 9H), 1.42-1.55 (m, 5H), 3.61 (s, 3H) 4.15 (m, 1H), 4.23 (m, H), 5.03 (s, 2H), 7.28-7.41 (m, 6H), 8.01 (d, J=7.9 Hz, 1H).
HR-TOF-MS (Method 1): C$_{22}$H$_{35}$N$_2$O$_5$ calc. 407.2541, found 407.2534 [M+H]$^+$.

Example 49A

N-[(Benzyloxy)carbonyl]-4-methyl-D-leucyl-L-leucine

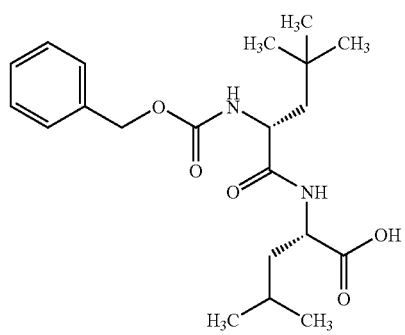

The title compound is prepared from the methyl ester (example 48A, 1.1 g, 2.71 mmol) by hydrolysis according to working procedure 4. After a reaction time of 4 h, the HPLC chromatogram (Method 2) indicates almost complete conversion. For fine-purification, the crude product is chromatographed via preparative RP-HPLC (Method 36), and 980 mg (92% of theory) of product are subsequently obtained.

HPLC (Method 2): $R_t$=2.40 min.

LC-MS (Method 7): $R_t$=2.56 min;

MS (ESIpos.): m/z (%)=393 (100) [M+H]$^+$, 785 (72) [2M+H]$^+$,

MS (ESIneg): m/z (%)=391 (57) [M–H]$^-$, 783 (100) [2M–H]$^-$.

$^1$H NMR (400 MHz, $d_6$-DMSO): δ=0.81 (d, J=6.3 Hz, 3H), 0.86 (d, J=6.3 Hz, 3H), 0.88 (s, 9H), 1.42-1.55 (m, 5H), 4.11-4.23 (m, 2H), 5.03 (s, 2H), 7.27-7.39 (m, 6H), 8.01 (d, J=8.0 Hz, 1H), 12.52 (s, br, 1H).

HR-TOF-MS (Method 1): $C_{21}H_{33}N_2O_5$ calc. 393.2384, found 393.2383 [M+H]$^+$.

Example 50A $N^{2.1}$-(Benzyloxycarbonyl)-[3-tert-butyl-D-alanyl]-L-leucyl-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam trifluoroacetate

Example 51A

Methyl(2Z)-2-{[(benzyloxy)carbonyl]amino}-3-(6-trifluoromethylpyridin-3-yl)acrylate

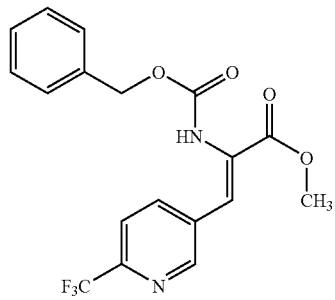

6-Trifluoromethylpyridine-3-carbaldehyde (4.85 g, 27.70 mmol) and methyl {[benzyloxycarbonyl]amino}(dimethoxyphosphoryl)acetate (9.17 g, 27.70 mmol, 1.0

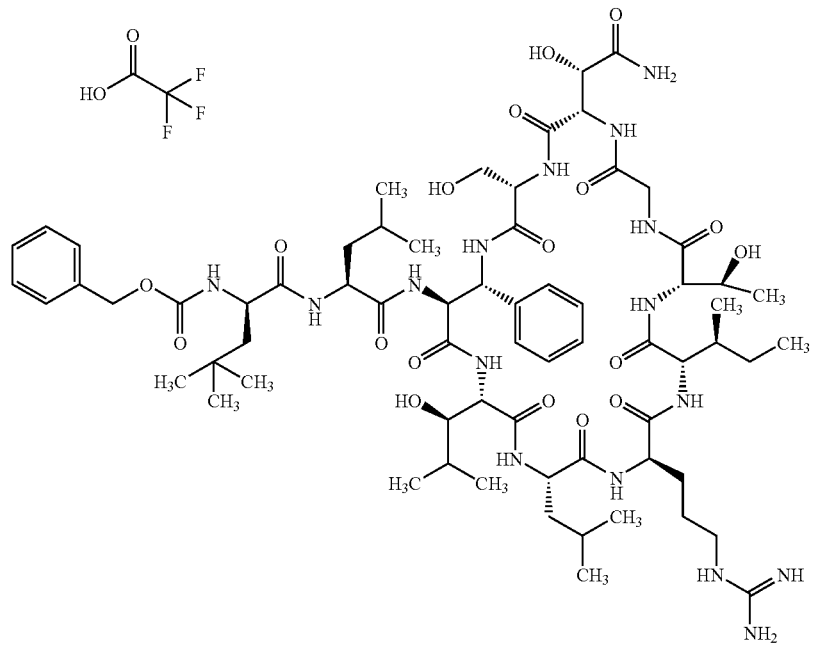

According to working procedure 5, the cyclopeptide (example 26A, 120.0 mg, 93.95 µmol) and the dipeptide acid (example 49A, 63.38 mg, 169.11 µmol, 1.8 equivalents), with the aid of NMM (52 µl, 469.75 µmol, 5 equivalents) and HATU (64.3 mg, 169.11 µmol, 1.8 equivalents), are reacted at RT to the amide overnight in DMF (15 ml). The title compound is obtained after chromatography (Method 35) with a yield of 138 mg (96% of theory).

HPLC (Method 25): $R_t$=21.46 min.

LC-MS (Method 7): $R_t$=2.19 min;

MS (ESIpos.): m/z (%)=1424 (25) [M+H]$^+$, 712 (100) [M+2H]$^{2+}$,

MS (ESIneg): m/z (%)=1422 (22) [M–H]$^-$, 710 (100) [M–2H]$^{2-}$.

HR-TOF-MS (Method 1): $C_{67}H_{107}N_{16}O_{18}$ calc. 1423.7944, found 1423.7964 [M+H]$^+$.

equivalent) are dissolved in THF (70 ml) and cooled to –70° C. At –70° C., N,N,N,N-tetramethylguanidine (6.38 g, 55.39 mmol, 6.95 ml, 2.0 equivalents) is slowly added dropwise and then the mixture is stirred at –70° C. for 4 h, subsequently at RT for 12 h. The reaction mixture is concentrated, and extracted with ethyl acetate (2×100 ml) against water. The combined organic phases are washed with a saturated sodium chloride solution, dried over sodium sulfate and filtered. After concentration, the crude product is chromatographed (silica gel, eluent: toluene, then toluene: ethyl acetate 10:1). 6.93 g (66% of theory) of the title compound are obtained.

HPLC/UV-Vis (Method 22): $R_t$=4.60 min.

HPLC/UV-Vis (Method 17): $R_t$=4.54 min.

LC-MS (Method 29): $R_t$=2.44 min;

MS (ESIpos.): m/z (%)=381 (100) [M+H]$^+$;

MS (ESIneg.): m/z (%)=379 (100) [M–H]$^-$.

¹H NMR (400 MHz, d₆-DMSO): δ=3.74 (s, 3H), 5.10 (s, 2H), 7.27 (s, 1H), 7.33-7.38 (m, 5H), 7.94 (d, J=8.5 Hz, 1H), 8.27 (d, J=8.5 Hz, 1H), 8.93 (s, 1H), 9.51 (s, 1H).

HR-TOF-MS (Method 1): $C_{18}H_{16}N_2O_4F_3$ [M+H]⁺ calc. 381.1062, found 381.1065.

Example 52A

N-[(Benzyloxy)carbonyl]-3-(6-trifluoromethylpyridin-3-yl)-L-alanine methyl ester

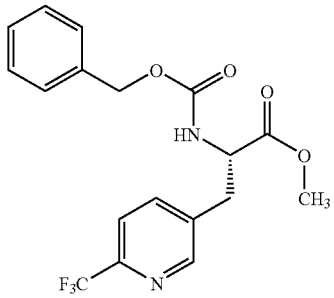

Example compound 51A (10.15 g, 26.69 mmol) is dissolved in methanol p.a. (100 ml). Argon is passed through for about 5 min using a cannula, then (+)-1,2-bis[(2S,5S)diethylphospholano]benzene(cyclooctadiene)rhodium(I) triflate (289 mg, 400 μmol, 0.015 equivalents) is added. The mixture is hydrogenated under 4 bar hydrogen pressure and at RT over 12 h. The mixture is then filtered through kieselguhr (methanol) and the eluate is concentrated. The crude product is chromatographed (silica gel, eluent: toluene: ethyl acetate 5:1). 9.9 g (97% of theory) of the title compound are obtained.

$[\alpha]^{20}_{Na}$=−24° (c=0.093 in methanol).
HPLC/UV-Vis (Method 22): $R_t$=4.5 min.
HPLC/UV-Vis (Method 17): $R_t$=4.49 min.
LC-MS (Method 29): $R_t$=2.40 min;
MS (ESIpos.): m/z (%)=383 (100) [M+H]⁺;
MS (ESIneg.): m/z (%)=273 (100), 381 (50) [M−H]⁻.

¹H NMR (400 MHz, d₆-DMSO): δ=2.99 (dd, J=3.5 and 11.0 Hz, 1H), 3.22 (dd, J=3.5 and 11.0 Hz, 1H), 3.66 (s, 3H), 4.40 (m, 1H), 4.97 (s, 2H), 7.23 (d, J=5.5 Hz, 1H), 7.29-7.33 (m, 3H), 7.83 (d, J=6.5 Hz, 1H), 7.93-7.98 (m, 2H), 8.65 (s, 1H).

HR-TOF-MS (Method 1): $C_{18}H_{18}N_2O_4F_3$ [M+H]⁺ calc. 383.1219, found 383.1223.

Example 53A 3-(6-Trifluoromethylpyridin-3-yl)-L-alanine methyl ester

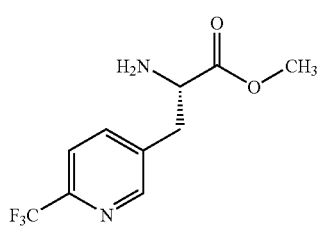

Example compound 52A (9.90 g, 25.89 mmol) is dissolved in methanol (100 ml). Argon is passed through for about 5 min using a cannula, then Pd on C (10%, 990 mg) is added. The mixture is hydrogenated under 4 bar hydrogen pressure and at RT over 12 h. The mixture is then filtered through kieselguhr, concentrated and dried under high vacuum. Yield: 5.8 g (90% of theory) of the title compound.

$[\alpha]^{19.9}_{Na}$=+3° (c=0.186 in methanol).
HPLC/UV-Vis (Method 22): $R_t$=3.34 min.
HPLC/UV-Vis (Method 17): $R_t$=3.22 min.
IR $v_{max}$ (NaCl, cm⁻¹): 3415, 1734, 1339, 1136, 1087.
LC-MS (Method 29): $R_t$=1.74 min;
MS (ESIpos.): m/z (%)=249 (100) [M+H]⁺.

¹H NMR (500 MHz, d₆-DMSO): δ=2.85 (dd, J=5.5 and 13.5 Hz, 1H), 3.01 (dd, J=5.5 and 13.5 Hz, 1H), 3.61 (s, 3H), 3.63-3.69 (m, 1H), 7.82 (d, J=7.5 Hz, 1H), 7.93 (d, J=7.5 Hz, 1H), 8.61 (s, 1H).

HR-TOF-MS (Method 1): $C_{12}H_{15}N_3O_2F_3$ [M+H]⁺ calc. 290.1116, found 290.1122.

Example 54A

N-(tert-Butoxycarbonyl)-3-(tert-butyl-D-alanyl-3-(6-trifluoromethylpyridin-3-yl-L-alanine methyl ester

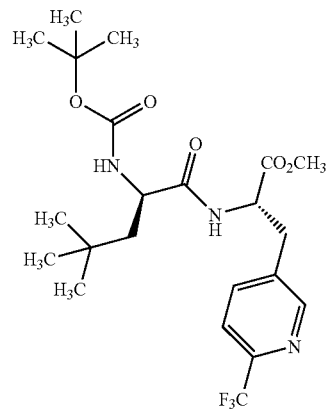

NMM (12.92 g, 127.72 mmol, 14.04 ml, 5 equivalents) and HATU (9.71 g, 25.54 mmol, 1 equivalent) are added slowly at −30° C. to a solution of example compound 53A (6.34 g, 25.54 mmol) and N-(tert-butoxycarbonyl)-3-tert-butyl-D-alanine (6.27 g, 25.54 mmol, 1.0 equivalent) in dry DMF (240 ml). The reaction mixture warms slowly (about 3 h) to RT, whereby complete conversion is observed by means of HPLC (Method 17). Potassium dihydrogen phosphate (34.76 g, 255.44 mmol, 10 equivalents) is added, and the reaction mixture is stirred for 20 min, then filtered, ethyl acetate is added and the mixture is washed with a sat. sodium hydrogen carbonate solution (10 ml). The organic phase is dried by means of sodium sulfate, filtered and concentrated. The crude product is purified by means of flash chromatography (silica gel, eluent: cyclohexane:ethyl acetate gradient 10:1 to 2:1) whereby 9.74 g (73% of theory) of the title compound are obtained.

$[\alpha]^{19.9}_{Na}$=+7.0° (c=0.044 in methanol).

HPLC/UV-Vis (Method 22): $R_t$=4.89 min.

HPLC/UV-Vis (Method 17): $R_t$=4.75 min.

LC-MS (Method 29): $R_t$=2.67 min;

MS (ESIpos.): m/z (%)=476 (100), [M+H]$^+$;

MS (ESIneg.): m/z (%)=400 (80), 474 (40) [M−H]$^-$.

$^1$H NMR (500 MHz, $d_6$-DMSO): δ=0.74 (s, 9H), 0.97-1.00 (m, 1H), 1.20-1.25 (m, 1H), 1.35 (s, 9H), 2.99-3.05 (m, 1H), 3.23-3.26 (m, 1H), 3.66 (s, 3H), 3.94 (m, 1H), 4.60 (m, 1H), 6.82 (d, J=8.5 Hz, 1H), 7.78 (d, J=8.0 Hz, 1H), 7.94 (d, J=8.0 Hz, 1H), 8.34 (d, J=8.5 Hz, 1H), 8.64 (s, 1H).

IR $\nu_{max}$ (NaCl, cm$^{-1}$): 2959, 1742, 1655, 1520, 1336, 1160, 1136, 1087, 1050, 1027.

HR-TOF-MS (Method 1): $C_{22}H_{33}N_3O_5F_3$ [M+H]$^+$ calc. 476.2372, found 476.2364.

Example 55A $N^{2.1}$-(tert-Butoxycarbonyl)-[3-tert-butyl-D-alanyl]-[3-(6-trifluormethylpyrid-3-yl)-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam trifluoroacetate

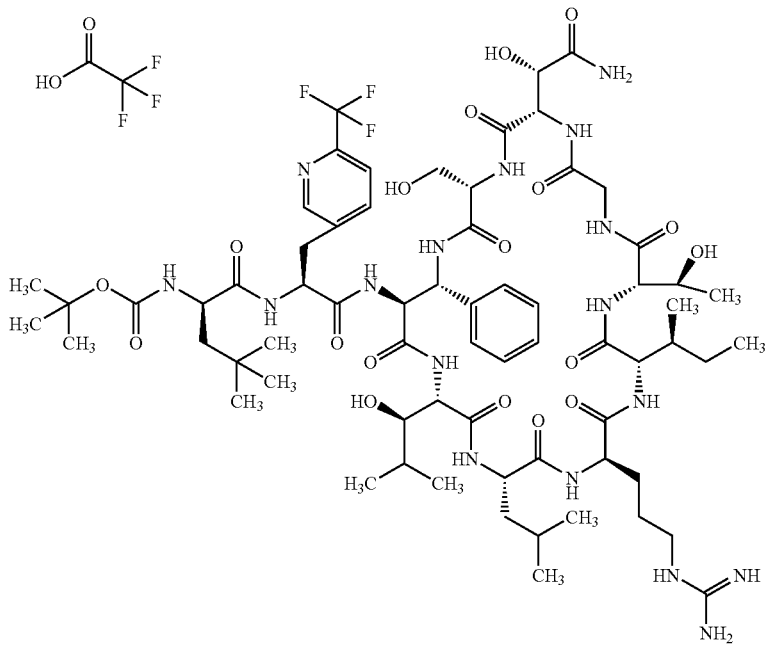

According to working procedure 5, the cyclopeptide (example 26A, 175.0 mg, 0.14 mmol) and the dipeptide acid (example 54A, 113.8 mg, 0.25 μmol, 1.8 equivalents), with the aid of NMM (75 μl, 0.69 mmol, 5 equivalents) and HATU (93.8 mg, 0.25 mmol, 1.8 equivalents), are reacted to the amide at −10° C. in DMF (15 ml) overnight. The title compound is obtained after chromatography (Method 35) with a yield of 190 mg (86% of theory).

HPLC (Method 25): $R_t$=21.51 min.

LC-MS (Method 7): $R_t$=2.27 min;

MS (ESIpos.): m/z (%)=1494 (33) [M+H]$^+$, 747 (100) [M+2H]$^{2+}$,

MS (ESIneg): m/z (%)=1492 (10) [M−H]$^-$, 745 (100) [M−2H]$^{2-}$.

HR-TOF-MS (Method 1): $C_{67}H_{105}N_{17}O_{18}F_3$ calc. 1492.7771, found 1492.7778 [M+H]$^+$.

Example 56A

Methyl(2Z)-2-[(tert-butoxycarbonyl)amino]-3-cyclopentylacrylate

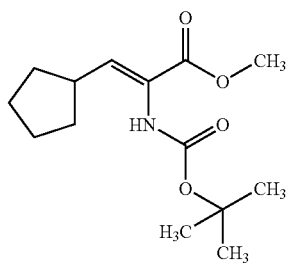

Methyl {[tert-butoxycarbonyl]amino}(dimethoxyphosphoryl)acetate (39.2 g, 132.00 mmol) and cyclopentanecarbaldehyde (38.9 g, 396.00 mmol, 3 equivalents) are provided in THF (320 ml), and N,N,N,N-tetramethylguanidine (24.8 ml, 22.81 g, 198.00 mmol, 1.5 equivalents) is added to the solution at −70° C. While the cold bath thaws, the reaction is brought slowly to RT. Within 2 days, complete conversion is achieved. For the workup, ethyl acetate (1600 ml) and water (800 ml) are added to the reaction, and the separated organic phase is dried over sodium sulfate. The drying agent is separated by filtration and the filtrate is concentrated on a rotary evaporator. The product is isolated from the residue by column chromatography (silica gel 60:1 kg, eluent: cyclohexane/ethyl acetate 4:1) with a yield of 34.8 g (98% of theory).

HPLC/UV-Vis (Method 4): $R_t$=4.76 min.

$^1$H NMR (300 MHz, CDCl$_3$) δ=1.28-1.43 (m, 2H), 1.46 (s, 9H), 1.52-1.78 (m, 4H), 1.83-1.97 (m, 2H), 2.71 (m, 1H), 3.78 (s, 3H), 5.79 (s, br, 1H), 6.50 (d, J=9.9 Hz, 1H).

Example 57A

Methyl N-(tert-butoxycarbonyl)-3-cyclopentyl-L-alaninate

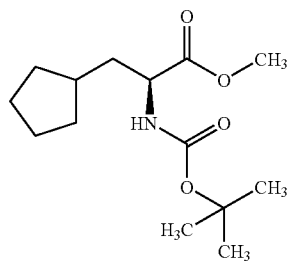

Example compound 56A (13.0 g, 48.27 mmol) is dissolved in ethanol (220 ml), and the solution is flushed with argon for 10 min and placed into an ultrasound bath for 5 min. After the addition of (+)-1,2-bis[(2S,5S)diethylphospholano]benzene (cyclooctadiene)rhodium(I) triflate (100.0 mg, 0.13 mmol), the mixture is flushed once again with argon for 30 min, degassed in an ultrasound bath for 5 min and then hydrogenated at RT under a hydrogen pressure of 3.5 bar for 3 days. For the workup, the solvent is removed completely on a rotary evaporator and the residue is chromatographed on silica gel 60 (300 ml, eluent: cyclohexane/ethyl acetate 2/1). The title compound is obtained with 12.9 g (94% of theory).

HPLC/UV-Vis (Method 4): $R_t$=4.88 min.

DCI-MS (NH$_3$): m/z=289 (100) [M+NH$_4$]$^+$, 560 (15) [2M+NH$_4$]$^+$.

$^1$H NMR (200 MHz, CDCl$_3$) δ=1.00-1.25 (m, 2H), 1.45 (s, 9H), 1.48-1.95 (m, 9H), 3.72 (s, 3H), 4.28 (m, 1H), 4.95 (d, J=8.4 Hz, 1H).

Example 58A

Methyl 3-cyclopentyl-L-alaninate hydrochloride

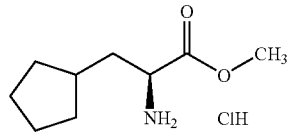

According to working procedure 2, the title compound is obtained from the N-protected amino acid (example 57A, 5.0 g, 18.43 mmol) with a crude yield of 3.9 g (quant.).

LC-MS (Method 30): $R_t$=2.02 min;

MS (ESIpos.): m/z (%)=172 (100) [M+H]$^+$.

$^1$H NMR (300 MHz, d$_6$) δ=0.98-1.18 (m, 2H), 1.40-1.67 (m, 4H) 1.68-1.85 (m, 4H in there 1.82 (d, J=6.6 Hz, 2H)), 1.92 (m, 1H), 3.75 (s, 3H), 3.90 (t, J=8.4 Hz, 1H), 8.63 (s, br, 3H).

Example 59A

Methyl N-(tert-butoxycarbonyl)-3-cyclopentyl-D-alaninate

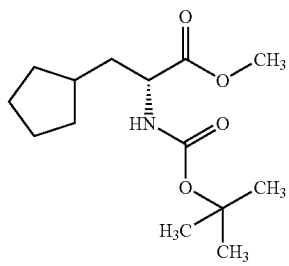

The acrylate (example 56A, 13.0 g, 48.27 mmol) and (+)-1,2-bis[(2R,5R)diethylphospholano]benzene(cyclooctadiene)rhodium(I) triflate (100.0 mg, 0.13 mmol) are, as described in the method of example 57A, used to prepare 12.6 g (96% of theory) of the title compound.

MS (DCI, $NH_3$): m/z (%)=289 (100) $[M+NH_4]^+$, 560 (15) $[2M+NH_4]^+$.

$^1$H NMR (300 MHz, $CDCl_3$) δ=1.00-1.21 (m, 2H), 1.45 (s, 9H), 1.48-1.93 (m, 9H), 3.73 (s, 3H), 4.28 (m, 1H), 4.95 (m, 1H).

Example 60A

N-(tert-Butoxycarbonyl)-3-cyclopentyl-D-alanine

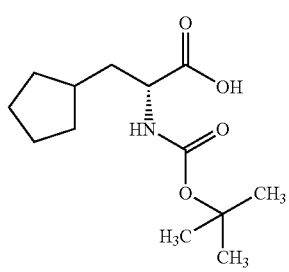

According to working procedure 4 example compound 59A (5.0 g, 18.43 mmol) is reacted to the N-protected amino acid within 2 h. 5.11 g (quant.) of the title compound are obtained.

$[α]^{20}_{Na}$=+7° (c=0.13 in $CH_2Cl_2$).
HPLC/UV-Vis (Method 2): $R_t$=2.33 min.
LC-MS (Method 7): $R_t$=2.26 min;
MS (ESIpos.): m/z (%)=158 (100) $[M-C_4H_8-CO_2+H]^+$;
MS (ESIneg): m/z (%)=256 (58) $[M-H]^-$.
$^1$H NMR (300 MHz, $d_6$-DMSO) δ=1.05 (m, 2H), 1.38 (s, 9H), 1.42-1.78 (m, 8H), 1.83 (m, 1H), 3.85 (m, 1H), 7.04 (d, J=8.2 Hz, 1H), 12.27 (s, br, 1H).

Example 61A

Methyl N-(tert-butoxycarbonyl)-3-cyclopentyl-D-alanyl-3-cyclopentyl-L-alaninate

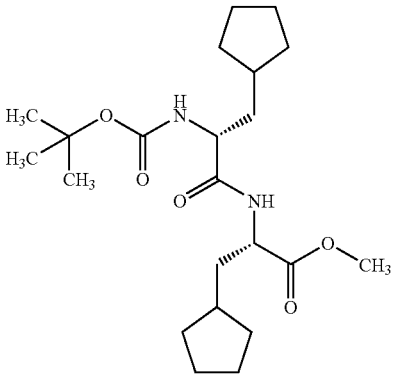

The peptidic amine (example 58A, 0.9 g, 4.27 mmol, 1.1 equivalents) is provided in dichloromethane (250 ml) under an argon protective gas atmosphere, the solution is cooled to −10° C. and HOBt (2.1 g, 15.54 mmol, 4 equivalents), NMM (1.3 ml, 1.2 g, 11.67 mmol, 3 equivalents), the peptidic acid (example 60A, 1.0 g, 3.89 mmol), EDC (1.5 g, 7.77 mmol, 2 equivalents) and once again NMM (0.8 ml, 0.8 g, 7.76 mmol, 2 equivalents) are successively added. The reaction is brought slowly to RT in a cooling bath converted completely overnight. For the workup, water is added to the reaction, the mixture is concentrated on a rotary evaporator (waterbath 35° C.), ethyl acetate and a saturated sodium hydrogen carbonate solution are added, and the separated aqueous phase is extracted twice with ethyl acetate, and the combined organic phases are subsequently washed successively with a saturated aqueous 5% citric acid solution, a saturated sodium hydrogen carbonate solution and a saturated sodium chloride solution. The organic phase is dried over sodium sulfate, filtered and concentrated. 1.64 g (quant.) of the title compound are obtained as crude product.

HPLC/UV-Vis (Method 2): $R_t$=2.97 min.
LC-MS (Method 7): $R_t$=2.94 min;
MS (ESIpos.): m/z (%)=411 (100) $[M+H]^+$, 311 (57) $[M-C_4H_8-CO_2+H]^+$.

Example 62A

N-(tert-Butoxycarbonyl)-3-cyclopentyl-D-alanyl-3-cyclopentyl-L-alanine

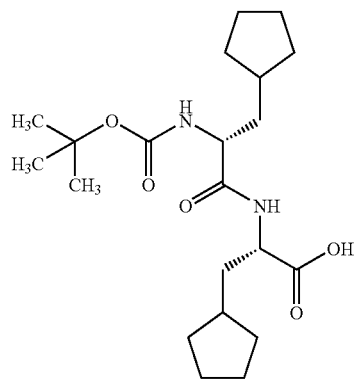

According to working procedure 4 the dipeptide (example 61A, 1.5 g, 3.65 mmol) is reacted to the dipeptidic carboxylic acid within 1 h. After the fine-purification (Method 13) of the freeze-dried crude product, the title compound is isolated with 923.4 mg (64% of theory).

HPLC/UV-Vis (Method 2): $R_t$=2.65 min.

LC-MS (Method 7): $R_t$=2.60 min;

MS (ESIpos.): m/z (%)=397 (100) $[M+H]^+$, 297 (60) $[M-C_4H_8-CO_2+H]^+$, 793 (46) $[2M+H]^+$;

MS (ESIneg): m/z (%)=395 (57) $[M-H]^-$, 791 (100) $[2M-H]^-$.

$^1$H NMR (400 MHz, $d_6$-DMSO) δ=1.05 (m, 4H) 1.38 (s, 9H), 1.43 (m, 4H), 1.55 (m, 6H), 1.61-1.86 (m, 8H), 3.96 (m, 1H), 4.16 (m, 1H), 6.75 (d, J=8.5 Hz, 1H), 7.96 (d, J=7.9 Hz, 1H) 12.55 (s, br, 1H).

HR-TOF-MS (Method 1): $C_{21}H_{38}N_2O_5$ calc. 397.2702, found 397.2697 $[M+H]^+$.

Example 63A $N^{2.1}$-(tert-Butoxycarbonyl)-[3-cyclopentyl-D-alanyl]-[3-cyclopentyl-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}-N^{3.3}$-lactam trifluoroacetate MS (ESIpos.): m/z (%)=1428 (35) $[M+H]^+$, 664 (100) $[M+2H]^{2+}$, MS (ESIneg): m/z (%)=1426 (100) $[M-H]^-$.

HR-TOF-MS (Method 1): $C_{67}H_{111}N_{16}O_{18}$ calc. 1427.8257, found 1427.8242 $[M+H]^+$.

Example 64A

N-[(Benzyloxy)carbonyl]-3-(tert-butyl)-D-alanyl-3-(pyridin-3-yl)-L-alanine methyl ester trifluoroacetate

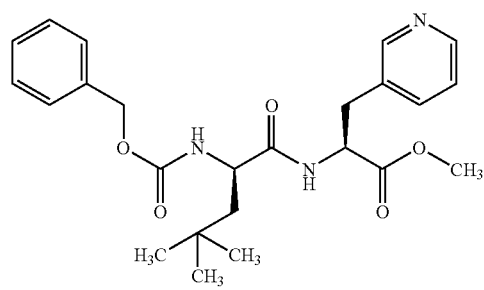

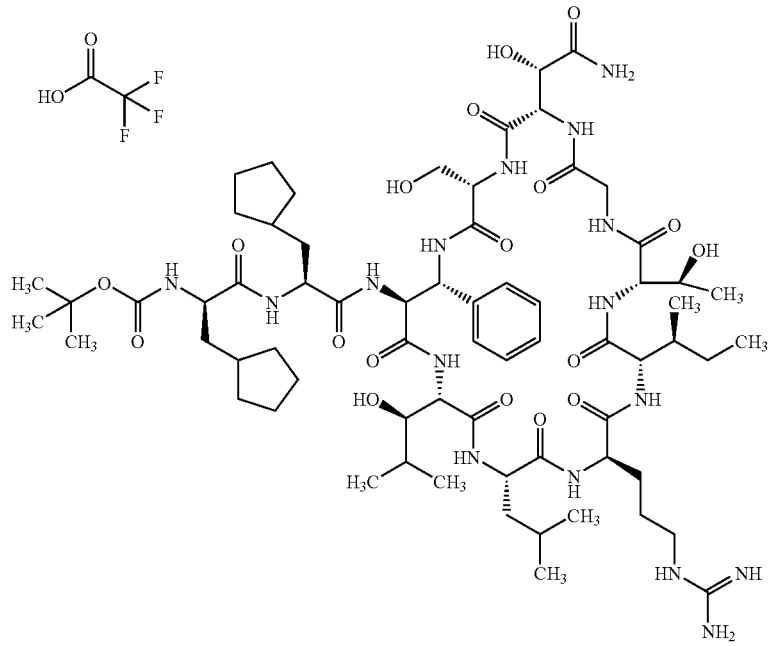

According to working procedure 5, the cyclopeptide (example 26A, 30.0 mg, 23.49 μmol) and the dipeptide acid (example 62A, 16.8 mg, 42.28 μmol, 1.8 equivalents), with the aid of NMM (13 μl, 117.43 μmol, 5 equivalents) and HATU (16.1 mg, 40.54 mmol, 1.8 equivalents), are reacted to the amide at −10° C. in DMF (2 ml) within 2.5 h. The title compound is obtained after chromatographing (Method 37) with a yield of 26.6 mg (67% of theory).

HPLC (Method 2): $R_t$=2.30 min.

LC-MS (Method 7): $R_t$=2.21 min;

-continued

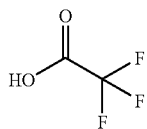

3-Pyridin-3-yl-L-alanine (800 mg, 3.16 mmol) and N-(benzyloxycarbonyl)-3-tert-butyl-D-alanine (1.47 g, 3.16 mmol, 1 equivalent) are dissolved at 0° C. in DMF (12 ml). 4-Methylmorpholine (1.74 ml, 15.8 mmol, 5 equivalents) and HATU (1.8 g, 4.74 mmol, 1.5 equivalents) are then added and the mixture is stirred at RT over about 3 h. The mixture is extracted with ethyl acetate (twice) against conc. sodium hydrogen carbonate, and the combined organic phases are washed with 1 M citric acid and again with conc. sodium hydrogen carbonate, dried over sodium sulfate, filtered and concentrated in vacuo. After chromatographic purification (Method 39), 1.1 g (63% of theory) of the title compound are obtained.

$[\alpha]^{19.9}{}_{Na}$=+6° (c=0.13 in methanol).
HPLC (Method 17): $R_t$=3.92 min.
HPLC (Method 23): $R_t$=4.06 min.
LC-MS (Method 7): $R_t$=2.03 min, MS (ESIpos.): m/z (%)=442 (100) $[M+H]^+$.
IR $\nu_{max}$ (NaCl, cm$^{-1}$): 3295, 2952, 2359, 1715, 1659, 1522, 1435, 1365, 1283, 1243, 1138, 1048, 1326.
HR-TOF-MS (Method 1): $C_{24}H_{32}N_3O_5$ $[M+H]^+$ calc. 442.2342, found 442.2342.

Example 65A

N-(Benzyloxycarbonyl)-3-(tert-butyl)-D-alanyl-3-(pyridin-3-yl)-L-alanine

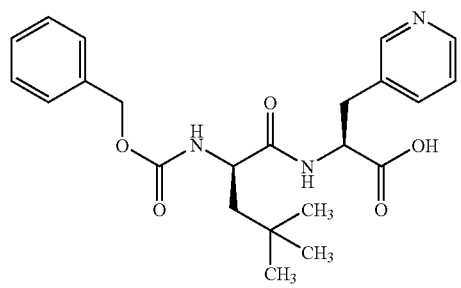

Example 64A (1.1 g, 1.98 mmol) is taken up in THF-water 3:1 (48 ml) and cooled to −20° C. Lithium hydroxide (119 mg, 2.5 mmol, 4.95 equivalents) is added and the mixture is stirred at RT for 12 h. The reaction is stopped by the addition of potassium dihydrogen phosphate (1.35 g) and concentrated in vacuo. After chromatographic purification (Method 14), 0.57 g (67% of theory) of the title compound are obtained as a solid.

$[\alpha]^{20}{}_{Na}$=+44° (c=0.15 in methanol).

HPLC (Method 17): $R_t$=3.73 min.

HPLC (Method 23): $R_t$=3.88 min.

LC-MS (Method 7): $R_t$=1.72 min,

MS (ESIpos.): m/z (%)=428 (100) $[M+H]^+$.

IR $\nu_{max}$ (NaCl, cm$^{-1}$): 3290, 2956, 1659, 1613, 1537, 1414, 1251, 1205, 1184, 1136, 1050, 1028.

HR-TOF-MS (Method 1): $C_{23}H_{29}N_3O_5$ $[M+H]^+$ calc. 428.2180, found 428.2169.

Example 66A $N^{2.1}$-(Benzyloxycarbonyl)-[3-(tert-butyl)-D-alanyl]-[3-(pyridin-3-yl)-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam bistrifluoroacetate

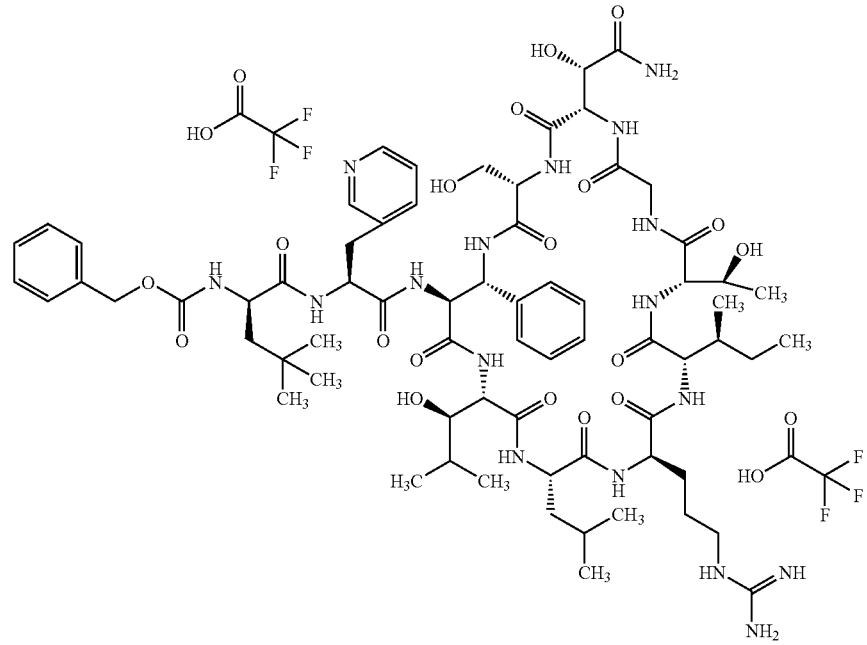

According to working procedure 5, the cyclopeptide (example 26A, 20.0 mg, 15.66 µmol) and the dipeptide acid (example 65A, 12.0 mg, 28.19 µmol, 1.8 equivalents), with the aid of NMM (9 µl, 78.3 µmol, 5 equivalents) and HATU (10.7 mg, 28.19 µmol, 1.8 equivalents) are reacted to the amide at −20° C. to −10° C. in DMF (6 ml) within 2.5 h. After chromatography (for example Method 36), 16.5 mg (61% of theory) of the title compound are obtained.

HPLC (Method 25): $R_t$=18.55 min.

LC-MS (Method 29): $R_t$=1.73 min;

MS (ESIpos.): m/z (%)=1458 (20) [M+H]$^+$, 730 (100) [M+2H]$^{2+}$,

MS (ESIneg): m/z (%)=1456 (27) [M−H]$^-$, 728 (100) [M−2H]$^{2-}$.

HR-TOF-MS (Method 1): $C_{69}H_{104}N_{17}O_{18}$ calc. 1458.7740, found 1458.7739 [M+H]$^+$.

Example 67A

Methyl 3-(tert-butyl)-L-alaninate trifluoroacetate

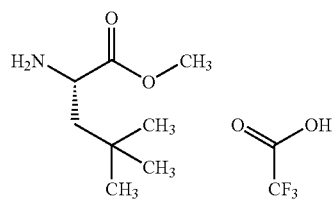

Trifluoroacetic acid/dichloromethane 3:1 (220 ml) is added to methyl N-(tert-butoxycarbonyl)-3-(tert-butyl)-L-alaninate (16 g, 61.70 mmol) [J. A. Bajgrowicz, et al., *Tetrahedron Lett.*, 1984, 2759-2762] and the mixture is stirred at RT for 1.5 h. The mixture is subsequently concentrated in vacuo and the residue is dried under HV. The yield is quantitative (16.5 g).

MS (DCI, NH$_3$): m/z=160 (100) [M+H]$^+$.

$^1$H NMR (300 MHz, d$_6$-DMSO): δ=0.92 (s, 9H), 1.59 (dd, J=4.7, 14.5 Hz, 1H), 1.80 (dd, J=7.6, 14.5 Hz, 1H), 3.75 (s, 3H), 3.95 (dd, J=4.7, 7.6 Hz, 1H), 8.5-8.3 (br. s, 3H).

Example 68A

Methyl N-(tert-butoxycarbonyl)-D-leucyl-3-(tert-butyl)-L-alaninate

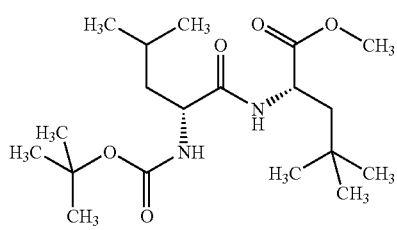

The peptidic amine (example 77A, 4.0 g, 14.68 mmol, 1.1 equivalents) is provided in dichloromethane (365 ml) under an argon protective gas atmosphere, and HOBt (7.2 g, 53.23 mmol, 4 equivalents), NMM (4.3 ml, 39.92 mmol, 3 equivalents), N-(tert-butoxycarbonyl)-D-leucine (3.1 g, 13.31 mmol, 1 equivalent) [T. Kato, N. Izumiya, *Bull. Chem. Soc. Jpn.*, 1966, 39, 2242-2249], EDC (5.1 g, 26.62 mmol, 2 equivalents) and further NMM (3 ml, 26.61 mmol, 2 equivalents) are successively added to the solution at −10° C., and the mixture is brought to complete conversion with stirring overnight. For the workup, the reaction solution is concentrated at 30° C. bath temperature on a rotary evaporator and then chromatographed by means of preparative HPLC (for example method 35). 5.5 g (80% of theory) of the title compound are obtained.

LC-MS (Method 7): $R_t$=2.72 min;

MS (ESIpos.): m/z (%)=373 (78) [M+H]$^+$, 273 (100) [M−C$_4$H$_8$−CO$_2$+H]$^+$.

Example 69A

N-(tert-Butoxycarbonyl)-D-leucyl-3-(tert-butyl)-L-alanine

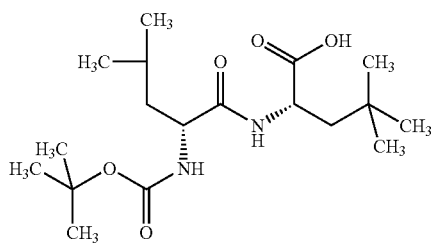

According to working procedure 4 example compound 68A (400 mg, 1.07 mmol) is reacted to the dipeptidic carboxylic acid within 1 h. For the workup, potassium dihydrogen phosphate (219.2 mg, 1.61 mmol, 1.5 equivalents) is added to the solution, the mixture is concentrated under cold conditions on a rotary evaporator and fine-purified by means of preparative HPLC (for example Method 35). The title compound is obtained as a lyophilizate (282.0 mg, 65% of theory). (For analytical data see WO2004099239).

Example 70A

N[2.1]-(tert-Butoxycarbonyl)-D-leucyl-[3-(tert-butyl)-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L- serine C[1.11]—N[3.3]-lactam fluoroacetate

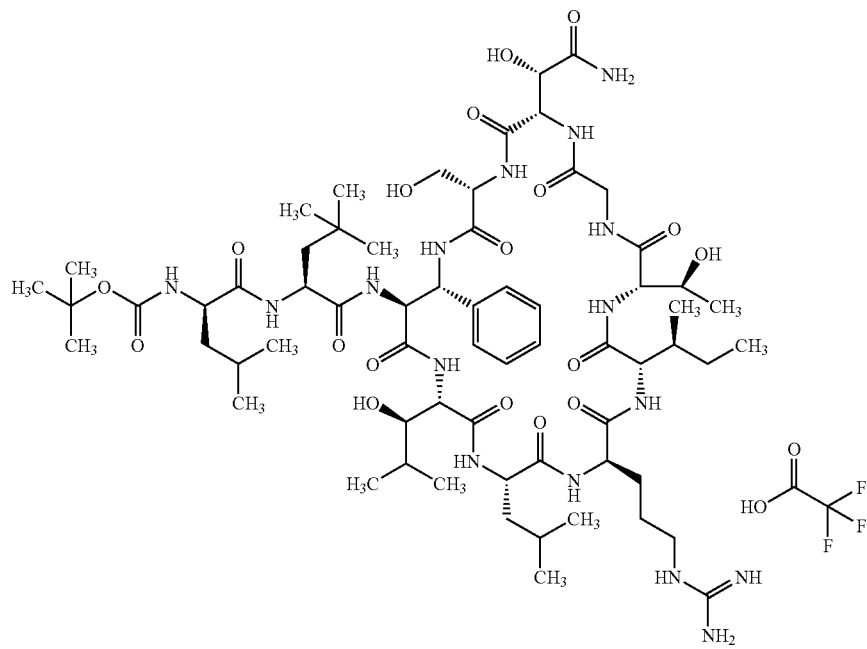

According to working procedure 5, the cyclopeptide (example 26A, 30.0 mg, 23.49 μmol) and the dipeptide acid (example 69A, 15.2 mg, 42.28 μmol, 1.8 equivalents), with the aid of NMM (13 μl, 117.45 μmol, 5 equivalents) and HATU (16.1 mg, 42.28 μmol, 1.8 equivalents), are reacted to the amide at RT in DMF (10 ml) overnight. The title compound is obtained after chromatographing (Method 36) with a yield of 34.0 mg (96% of theory).

HPLC (Method 2): $R_t$=2.25 min.
LC-MS (Method 7): $R_t$=2.18 min;
MS (ESIpos.): m/z (%)=1390 (77) [M+H]$^+$, 645 (100) [M–C$_4$H$_8$–CO$_2$+2 H]$^{2+}$,
MS (ESIneg): m/z (%)=1387 (73) [M–H]$^-$, 693 (100) [M–2H]$^{2-}$.
HR-TOF-MS (Method 1): C$_{64}$H$_{109}$N$_{16}$O$_{18}$ calc. 1389.8101, found 1389.8101 [M+H]$^+$.

Example 71A and Example 72A (2S)—N-(tert-Butoxycarbonyl)-3-(trimethylsilyl)-D-alanine (71A) and (2R)—N-(tert-butoxycarbonyl)-3-(trimethylsilyl)-L-alanine (72A)

The synthesis takes place according to M. Merget, et al., *J. Organomet. Chem.* 2001 628, 183-194. The separation of the enantiomers takes place by preparative HPLC on a chiral phase (Method 26). The isomers are assigned by HPLC comparison with an authentic sample of N-(tert-butoxycarbonyl)-L-3-trimethylsilylalanine (2R compound, Mercachem AMR 39.260).

Example 71A
N-(tert-Butoxycarbonyl)-3-trimethylsilyl-D-alanine

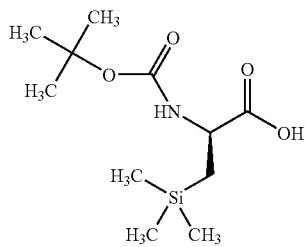

Chiral HPLC (Method 26): $R_f$=4.16 min, e.e.>99%. $[\alpha]_D^{20}$=+1.1 (c=0.83, methanol)

Example 72A

N-(tert-Butoxycarbonyl)-3-trimethylsilyl-L-alanine

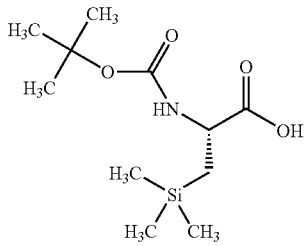

Chiral HPLC (Method 26): $R_f$=9.27 min, e.e.>99% $[\alpha]_D^{20}$=−1.6 (c=0.66, methanol)

Example 73A

3-Trimethylsilyl-L-alanine methyl ester hydrochloride

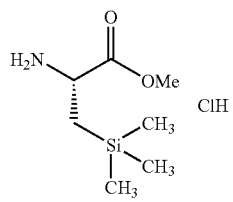

The compound from example 72A (300 mg) is dissolved in methanol (3 ml) and cooled to 0° C. Trimethylsilyl chloride (590 mg, 4.7 equivalents) is added dropwise within 30 min and the mixture is warmed to RT overnight. The volatile components are removed on a Rotavapor and subsequently under high vacuum. The target compound is obtained (224 mg, 92% of theory).

1H NMR (d6-DMSO, 300 MHz): δ=0.03 (s, 9H), 0.97-1.71 (m, 2H), 3.73 (s, 3H), 3.93 (dd, J=5.3, 10.9 Hz, 1H), 8.40 (br s, 3H).

Example 74A

N-Benzyloxycarbonyl-3-trimethylsilyl-L-alanine methyl ester

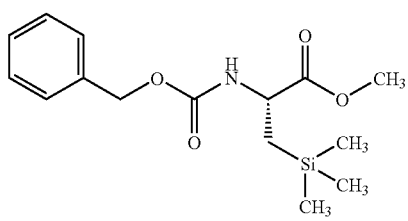

The compound from example 73A (2.0 g) is provided at 0° C. in THF (40 ml) under argon. Triethylamine (2.3 g, 2.4 equivalents) is added and then a solution of N-benzyloxycarbonyloxysuccinimide (2.83 g, 1.2 equivalents) in THF (20 ml) is added dropwise. The mixture is then stirred at RT overnight, concentrated by half, diluted with ethyl acetate, and washed twice with water and once with a saturated sodium chloride solution. The organic phase is dried over sodium sulfate and concentrated on a rotary evaporator. The residue is purified by means of preparative HPLC (Method 41). The target compound is obtained (2.32 g, 79% of theory).

HPLC (Method 18): $R_f$=4.96 min.

MS (DCI, NH$_3$): m/z=327 [M+NH$_4$]$^+$ (100), 310 (3) [M+H]$^+$.

Example 75A (2R)—N-Benzyloxycarbonyl-3-trimethylsilyl-L-alaninol

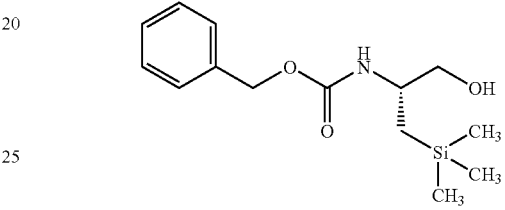

Lithium chloride (0.64 g, 15 mmol) and sodium borohydride (0.57 g, 15 mmol) and then ethanol (22 ml) are added to a solution of example 74A (2.32 g, 7.5 mmol) in THF (14 ml). The mixture is stirred at RT overnight. For the workup, the mixture is adjusted to pH 4 with a citric acid solution (10% in water) while cooling with ice water, then diluted with 200 ml of water and extracted three times with dichloromethane. The combined organic phases are dried over magnesium sulfate, filtered and concentrated in vacuo. The residue is separated by means of HPLC (Method 41) and the suitable fractions are concentrated in vacuo. The title compound is obtained as an oil (1.24 g, 59% of theory).

HPLC (Method 4): $R_f$=4.48 min.

MS (DCI, NH$_3$): m/z=299 [M+NH$_4$]$^+$ (100), 282 (13) [M+H]$^+$.

$^1$H NMR (CDCl$_3$, 300 MHz): δ=0.03 (s, 9H), 0.58-0.84 (m, 2H), 2.13 (br.s, 1H), 3.45 (br.m, 1H), 3.65 (br.m, 1H), 3.83 (br.m, 1H), 4.72 (br.m, 1H), 5.08 (s, 2H), 7.33 (m, 5H).

Example 76A (2R)—N-Benzyloxycarbonyl-3-trimethylsilyl-L-alaninal

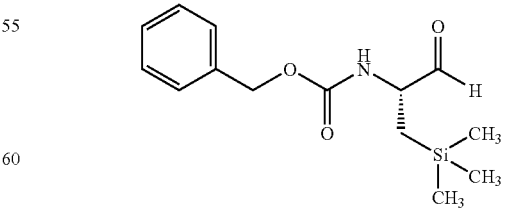

A solution of pyridine-SO$_3$ complex (2.04 g, 12.8 mmol) in anhydrous DMSO (12 ml) is added at 10° C. under argon to a solution of example 75A (0.36 g, 1.28 mmol) and N,N-diisopropylethylamine (1.65 g, 12.8 mmol) in 7 ml of DMSO. The cooling bath is removed and the mixture is stirred for another 20 min. 400 ml of ice-water are added and the solution is extracted three times with diethyl ether. The combined organic phases are washed twice with a citric acid solution (10% in water), once with water, once with a saturated bicarbonate solution and once with a saturated sodium chloride solution, dried over magnesium sulfate, filtered and concentrated on a rotary evaporator. The title compound is obtained as an oil (0.39 g, 93% of theory) and used further directly as the crude product.

MS (DCI, $NH_3$): m/z=297 $[M+NH_4]^+$ (100), 280 (25) $[M+H]^+$.

$^1$H NMR ($CDCl_3$, 300 MHz): δ=0.07 (s, 9H), 0.78 (dd, J=9.4, 14.0 Hz, 1H), 1.12 (dd, J=5.8, 14.0 Hz, 1H), 5.13 (s, 2H), 7.35 (m, 5H), 9.53 (s, 1H).

Example 77A 3-(tert-Butyl)-L-alanine methyl ester trifluoroacetate

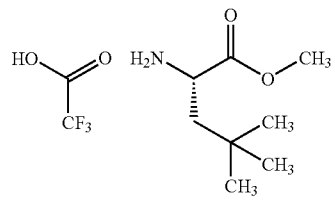

The (2S)—N-tert-butoxycarbonyl-3-tert-butyl-L-alanine methyl ester (529 mg, 2.04 mmol) is stirred at RT in TFA/dichloromethane 1:3 (3 ml), and the solution is concentrated on a rotary evaporator and dried under high vacuum. 540 mg (97% of theory) of product are obtained.

$^1$H NMR ($d_6$-DMSO, 300 MHz): δ=0.92 (s, 9H), 1.59 (dd, J=4.7, 14.4 Hz, 1H), 1.80 (dd, J=7.5, 14.4 Hz, 1H), 3.76 (s, 3H), 3.95 (dd, J=4.7, 7.5 Hz, 1H), 8.33 (br.s, 3H).

Example 78A

N-[(2R)-2-Benzyloxycarbonylamino-3-trimethylsilylpropyl]-3-(tert-butyl)-L-alanine methyl ester hydrotrifluoroacetate

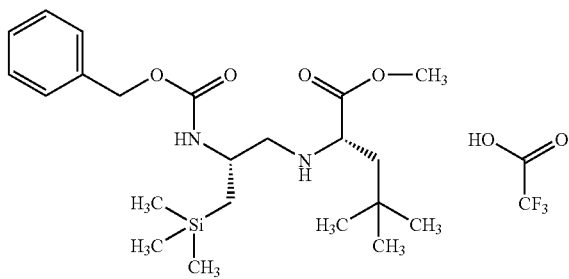

Under argon, example compound 77A (4.33 g, 15.9 mmol), example compound 76A (7.2 g, 20.6 mmol) and sodium acetate (1.3 g, 15.9 mmol) are provided in DMF (140 ml) at 0° C. Sodium cyanoborohydride (1.99 g, 31.7 mmol) is added and the mixture is stirred at 0° C. for 2 h. For the workup, the mixture is diluted with 1 l of ethyl acetate and washed twice with a 5% solution of sodium bicarbonate. The aqueous phases are reextracted with ethyl acetate. The combined organic phases are washed with a sat. sodium chloride solution, and dried over magnesium sulfate, filtered and concentrated. The residue is purified by preparative HPLC (Method 39). 6.02 g (71% of theory) of the title compound are obtained as crystals.

HPLC (Method 4): $R_t$=4.8 min.

ESI-MS (pos.): m/z=423 (100) $[M+H]^+$.

$^1$H NMR ($CDCl_3$, 300 MHz): δ=0.03 (s, 9H), 0.76 (dd, J=5.1, 14.7 Hz, 1H), 0.94 (s, 9H), 0.95 (dd, J=10.2, 14.7 Hz, 1H), 1.95-1.80 (m, 2H), 2.93 (dd, J=2.5, 12.5 Hz, 1H), 3.35 (dd, J=9.8, 11.3 Hz, 1H), 3.81 (s, 3H), 3.85 (dd, J=4.5, 7.9 Hz, 1H), 4.07-3.90 (m, 1H), 5.05 (d, J=11.5 Hz, 1H), 5.16 (d, J=11.5 Hz, 1H), 5.63 (d, J=0.9 Hz, 1H), 7.33 (s, 5H).

Example 79A

N-[(2R)-2-Benzyloxycarbonylamino-3-trimethylsilylpropyl]-3-(tert-butyl)-L-alanine hydrochloride

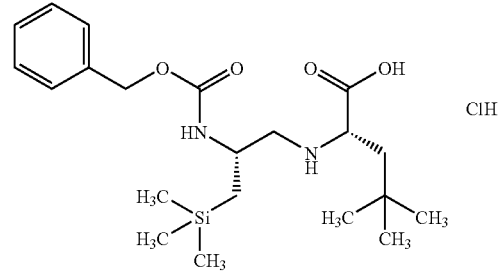

Example compound 78A (6.02 g, 11.2 mmol) is dissolved in methanol (225 ml) and a 1 N lithium hydroxide solution (101 ml) in water (9 equivalents) is added. At RT the reaction mixture is stirred at RT overnight (18 h), then acidified with 1 N hydrochloric acid and freed of methanol on a rotary evaporator. The remaining suspension is diluted with 200 ml of water and extracted three times with ethyl acetate. The combined organic phases are dried over sodium sulfate, filtered and concentrated. The residue is dried under high vacuum. 5.3 g (quantitative) of the title compound are obtained, which is reacted further without purification.

HPLC (Method 4): $R_t$=4.6 min.

MS (ESIpos): m/z (%)=409 (100) $[M+H]^+$,

MS (ESIneg): m/z (%)=407 (10) $[M-H]^-$.

$^1$H-NMR ($d_6$-DMSO, 400 MHz): δ=0.03 (s, 9H), 0.82 (m, 2H), 0.95 (s, 9H), 1.68 (br.d, J=14.5, 1H), 1.84 (dd, J=9.0, 14.5, 1H), 2.88 (m, 1H), 3.10 (m, 1H), 3.80-4.03 (m, 2H), 5.01 (d, J=12, 1H), 5.13 (d, J=12, 1H), 7.29 (d, J=9.0, 1H), 7.43-7.56 (m, 5H), 8.7-9.2 (br, 2H, $NH_2^+$).

Example 80A

N$^{2.1}$[(2R)-2-(Benzyloxycarbonylamino)-3-(trimethylsilyl)propyl]-[3-(tert-butyl)-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine C$^{1.10}$—N$^{3.2}$-lactam bisfluoroacetate

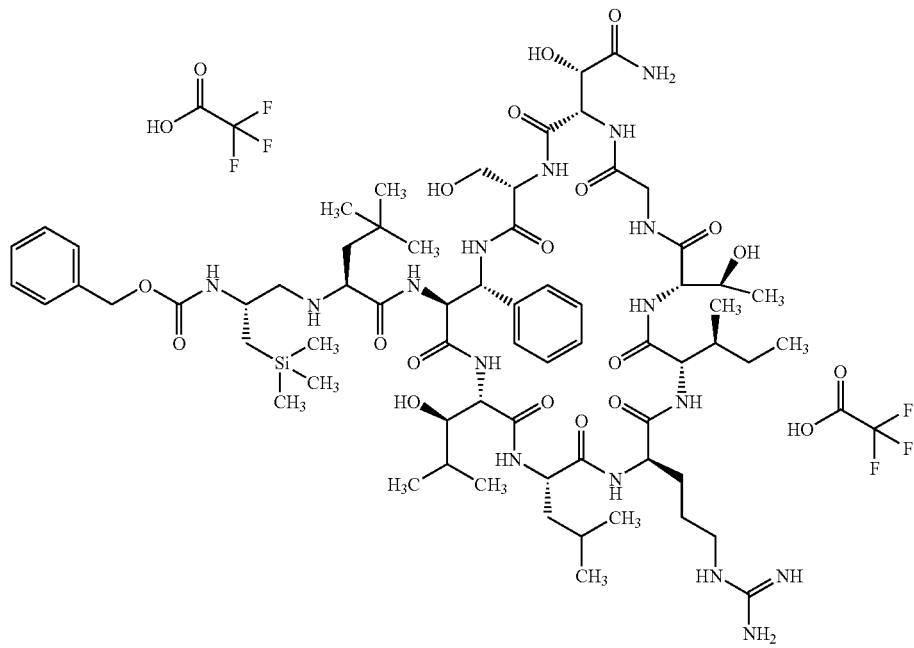

According to working procedure 5, the cyclopeptide (example 26A, 30.0 mg, 23.49 µmol) and the dipeptide acid (example 69A, 18.8 mg, 42.28 µmol, 1.8 equivalents), with the aid of NMM (13 µl, 117.45 µmol, 5 equivalents) and HATU (16.1 mg, 42.28 µmol, 1.8 equivalents), are converted to the amide at −20° C. to −10° C. in DMF (15 ml) within 2.5 h. The title compound is obtained after chromatography (Method 36) with a yield of 34.0 mg (96% of theory).

HPLC (Method 25): R$_t$=19.59 min.
LC-MS (Method 7): R$_t$=1.97 min; MS (ESIpos.): m/z (%)=720 (100) [M+2H]$^{2+}$.
HR-TOF-MS (Method 1): C$_{67}$H$_{111}$N$_{16}$O$_{17}$ calc. 1439.8077, found 1439.8036 [M+H]$^+$.

Example 81A (2S)—N-Benzyloxycarbonyl-3-tert-butyl-L-alaninal

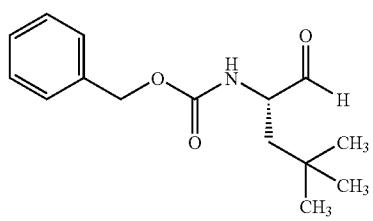

The compound is prepared in analogy to the synthesis sequence of example 75A and example 76A from Z-β-tert-butyl-alanine methyl ester.
MS (DCI, NH$_3$): m/z=281 [M+NH$_4$]$^+$ (100); 264 (20) [M+H]$^+$.
$^1$H NMR (CDCl$_3$, 300 MHz): δ=1.00 (s, 9H), 1.30 (dd, J=8.3, 14.7 Hz, 1H), 1.83 (dd, J=3.8, 14.6 Hz, 1H), 4.33 (dt, J=3.8, 8.7 Hz, 1H), 5.06 (m, 1H), 5.12 (s, 2H), 7.36 (m, 5H), 9.58 (s, 1H).

Example 82A

N-[(2S)-2-Benzyloxycarbonylamino-4,4-dimethylpentyl]-3-(tert-butyl)-L-alanine methyl ester trifluoroacetate

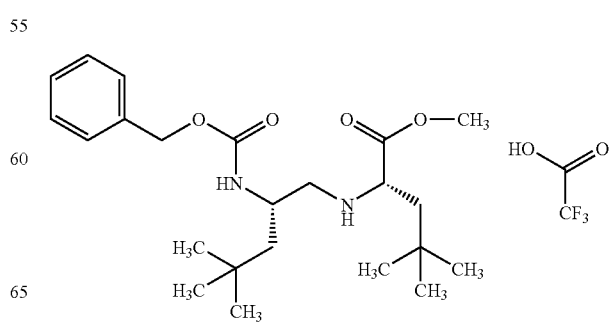

The compound is prepared in analogy to example 78A from example 81A and example 77A. Yield: 860 mg (36% of theory).

HPLC (Method 4): $R_t$=4.7 min.

MS (ESI pos): m/z=407 (100) [M+H]$^+$.

$^1$H NMR (CDCl$_3$, 300 MHz): δ=0.91 (s, 1H), 0.93 (s, 9H), 1.34 (br.d, J=15, 1H), 1.53 (dd, J=8.7, 14.7, 1H), 1.68-1.95 (m, 2H), 2.89 (dd, J=3.5, 12 Hz, 1H), 3.33 (dd, J=10.5, 12 Hz, 1H), 3.84 (m, 1H), 3.80 (s, 3H), 3.99 (m, 1H), 5.04 (d, J=12 Hz, 1H), 5.13 (d, J=12 Hz, 1H), 5.73 (br.d, J=8.5 Hz, 1H), 7.32 (m, 5H).

Example 83A

N-[(2S)-2-Benzyloxycarbonylamino-4,4-dimethyl-pentyl]-3-tert-butyl-L-alanine trifluoroacetate

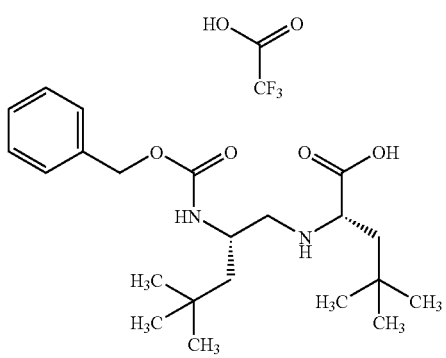

This compound is prepared in analogy to example 79A from example 83A (1.10 g, 2.11 mmol) and a 1 N lithium hydroxide solution (19 ml). Yield: 895 mg (83% of theory).

HPLC (Method 4): $R_t$=4.47 min.

MS (ESIpos.): m/z (%)=393 (100) [M+H]$^+$;

MS (ESIneg.): m/z (%)=391 (4) [M–H]$^-$.

$^1$H NMR (d$_6$-DMSO, 300 MHz): δ=0.89 (s, 9H), 0.93 (s, 9H), 1.30-1.45 (m, 2H), 1.64 (dd, J=2, 14 Hz, 1H), 1.81 (dd, J=9.7, 14 Hz, 1H), 2.88 (m, 1H), 2.98 (m, 1H), 3.85-3.99 (m, 2H), 4.99 (d, J=12.7 Hz, 1H), 5.12 (d, J=12.7 Hz, 1H), 7.07 (d, J=9.0 Hz, 1H), 7.27-7.40 (m, 5H).

$^{13}$C NMR (126 MHz, d$_6$-DMSO): δ=29.00 (3C), 29.38 (3C), 29.96 (2C), 42.22, 45.10, 45.64, 50.52, 56.97, 65.39, 127.56 (2C), 127.73, 128.23 (2C), 136.83, 155.47, 171.47.

HR-TOF-MS (Method 1): C$_{22}$H$_{37}$N$_2$O$_4$ [M+H]$^+$ found 393.2753, calc. 393.2748

Example 84A

N$^{2.1}$-[(2S)-2-(Benzyloxycarbonylamino)-3-(tert-butyl)propyl]-[3-(tert-butyl)-L-alanyl]-[(3R)-3-amino-L-phenylalanyl)]-[(3R)-3-hydroxy-L-leucyl]-L-leucyl-D-arginyl-L-iso-leucyl-L-allothreonyl-glycyl-[(3S)-3-hydroxy-L-asparaginyl]-L-serine C$^{1.10}$—N$^{3.2}$-lactam bistrifluoroacetate

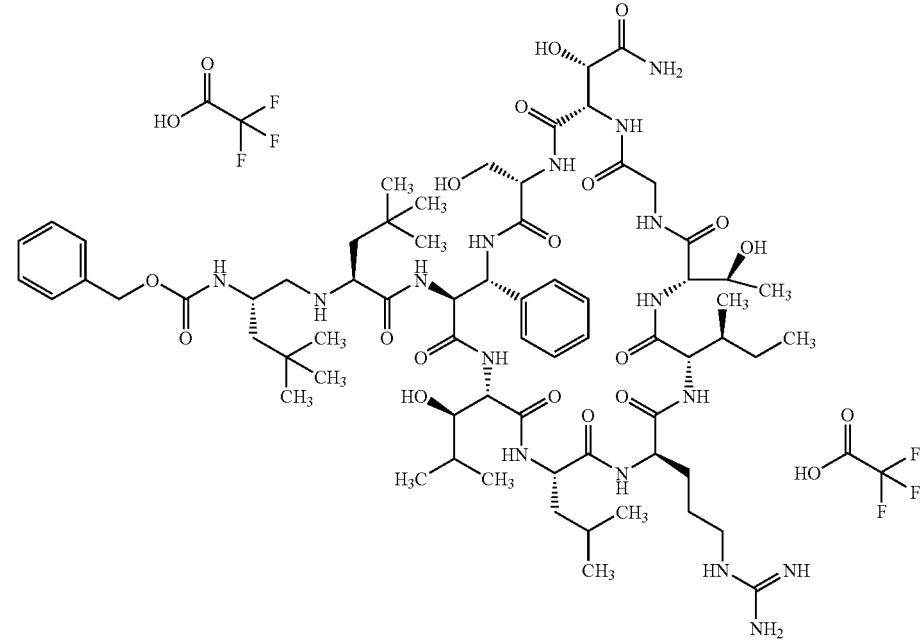

According to working procedure 5, the cyclopeptide (example 26A, 170.0 mg, 0.13 mmol), the dipeptide acid (example 83A, 121.4 mg, 0.24 mmol, 1.8 equivalents), NMM (73 µl, 0.67 µmol, 5 equivalents) and HATU (91.1 mg, 42.28 µmol, 1.8 equivalents) are reacted to the amide at −20° C. to −10° C. in DMF (6 ml) within 2.5 h. The title compound is chromatographed (for example Method 35) whereby 34.0 mg (96% of theory) of the title compound are obtained.

HPLC (Method 2): $R_t$=2.08 min.

LC-MS (Method 7): $R_t$=1.9 min;

MS (ESIpos.): m/z (%)=712.7 (100) $[M+2H]^{2+}$, 1424 (5) $[M+H]^+$;

MS (ESIneg.): m/z (%)=1422.7 (100) $[M-H]^-$.

HR-TOF-MS (Method 1): $C_{68}H_{111}N_{16}O_{17}$ $[M+H]^+$ found 1423.8318, calc. 1423.8313.

Example 85A $N^{2.1}$-[(2R)-2-(Benzyloxycarbonylamino)-3-(tert-butyl)propyl]-[3-(tert-butyl)-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.10}$—$N^{3.2}$-lactam bisfluoroacetate

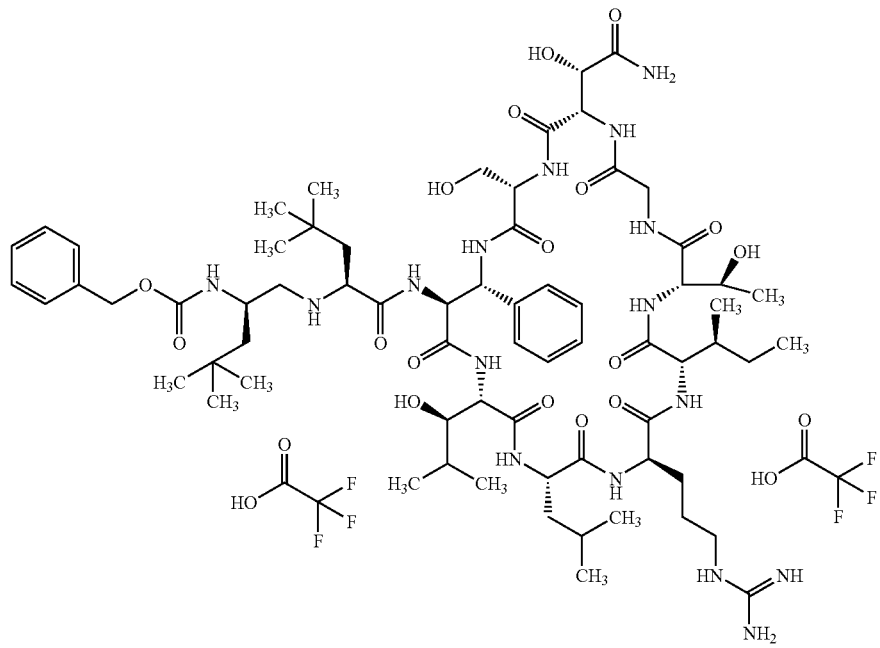

According to working procedure 5, the cyclopeptide (example 26A, 42.0 mg, 32.88 μmol), N-((2R)-2-{[(benzyloxy)carbonyl]amino}-4,4-dimethylpentyl)-3-(tert-butyl)-L-alanine trifluoroacetate (29.98 mg, 59.18 μmol, 1.8 equivalents), NMM (18 μl, 164.40 μmol, 5 equivalents) and HATU (22.5 mg, 59.18 μmol, 1.8 equivalents) are reacted to the amide at −20° C. to −10° C. in DMF (15 ml) within 2.5 h. The title compound is obtained after chromatography (Method 10) (37.5 mg, 69% of theory).

The dipeptide acid, N-((2R)-2-{[(benzyloxy)carbonyl]amino}-4,4-dimethylpentyl)-3-(tert-butyl)-L-alanine hydrotrifluoroacetate, can be prepared in analogy to the sequence of example 82A from compound 77A and N-benzyloxycarbonyl-3-(tert-butyl)-D-alaninal and subsequent hydrolysis (see example 83A).

HPLC (Method 2): $R_t$=2.13 min.

LC-MS (Method 7): $R_t$=1.98 min;

MS (ESIpos.): m/z (%)=712 (100) $[M+2H]^{2+}$,

MS (ESIneg.): m/z (%)=1422 (100) $[M-H]^-$, 710 (40) $[M-2H]^{2-}$.

HR-TOF-MS (Method 1): $C_{68}H_{111}N_{16}O_{17}$ $[M+H]^+$ found 1423.8282, calc. 1423.8308.

Example 86A

Methyl N-(tert-butoxycarbonyl)-3-(pyridin-3-yl)-L-alaninate

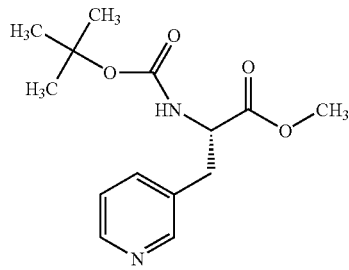

(2S)—N-(tert-Butoxycarbonyl)-3-(pyridin-3-yl)alanine (25.00 g, 93.88 mmol) is dissolved in 300 ml of dichloromethane under argon. Methanol (11.4 ml, 9.02 g, 281 mmol, 3 equivalents) and one grain of DMAP are added. The mixture is then cooled to 0° C. EDC (19.80 g, 103 mmol, 1.1 equivalents) is added. After 5 min, the ice bath is removed and the mixture is left to stir at RT over 1 h. The mixture is then concentrated in vacuo, and ethyl acetate is added to the residue and the mixture is extracted against a saturated sodium hydrogen carbonate solution. The aqueous phase is reextracted once with ethyl acetate, then the combined organic phases are washed with 0.5 M citric acid and then once again with a saturated sodium hydrogen carbonate solution. The organic phase is dried over sodium sulfate, filtered and concentrated in vacuo. An oil remains, which crystallizes during drying in an oil-pump vacuum. Yield: 23.60 g (90% of theory).

HPLC/UV-Vis (Method 17): $R_t$=3.28 min.

LC-MS (Method 7): $R_t$=1.21 min, MS (ESIpos.): m/z (%)=281 (100) $[M+H]^+$.

$^1$H NMR (400 MHz, $d_6$-DMSO) δ=1.30 (s, 9H), 2.86 (m, 1H), 3.04 (m, 1H), 3.63 (s, 3H), 4.22 (m, 1H), 7.28-7.39 (m, 2H), 7.69 (d, 1H), 8.43 (m, 2H).

Example 87A 3-(Pyridin-3-yl)-L-alanine methyl ester bistrifluoroacetate

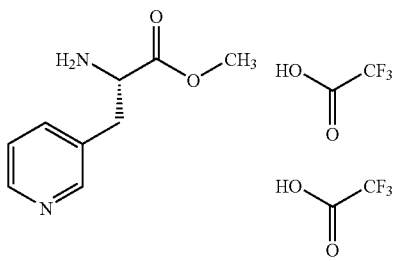

The compound from example 86A (11.8 g, 42.09 mmol) is dissolved in trifluoroacetic acid in dichloromethane (160 ml; 30% solution) and stirred at RT for 30 min. The mixture is then concentrated in vacuo. The residue is taken up in a little water and lyophilized. Toluene is then added to the lyophilizate and the mixture is concentrated in vacuo. Finally, the product is dried to constant weight in an oil-pump vacuum. Yield: 17.15 g (quant.).

HPLC/UV-Vis (Method 23): $R_t$=0.88 min.

LC-MS (Method 7): $R_t$=0.46 min,

MS (ESIpos.): m/z (%)=181 (100) $[M+H]^+$.

$^1$H NMR (400 MHz, $d_6$-DMSO) δ=2.79 (dd, 1H), 2.92 (dd, 1H), 3.60 (s, 3H), 3.63 (m, 1H), 7.30 (m, 1H), 7.62 (d, 1H), 8.41 (m, 2H).

Example 88A

Methyl N-(tert-butoxycarbonyl)-3-(trimethylsilyl)-D-alanyl-3-(pyridin-3-yl)-L-alaninate

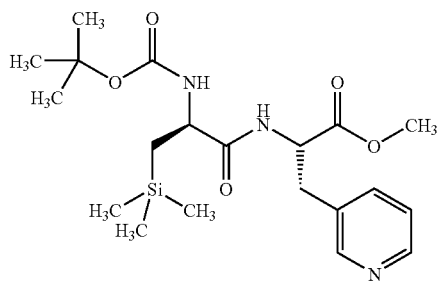

The compound from example 87A (10.31 g, 39.4 mmol) and the compound from example 71A (16.10 g, 39.4 mmol, 1 equivalent) are dissolved at 0° C. in DMF (186 ml). NMM (17.34 ml, 16.00 g, 4 equivalents) and HATU (22.49 g, 59.16 mmol, 1.5 equivalents) are then added. The mixture is stirred at RT for 2 hours. tert-Butyl methyl ether is added to the mixture and the mixture is washed with a saturated sodium carbonate solution. The aqueous phase is reextracted once with tert-butyl methyl ether, and the combined organic phases are then washed with 1 M aqueous citric acid and once again with a saturated sodium carbonate solution, dried over sodium sulfate, filtered and concentrated in vacuo. The mixture is filtered through silica gel (cyclohexane/ethyl acetate 2:1). Yield: 14.1 g (84% of theory).

HPLC/UV-Vis (Method 17): $R_f$=3.91 min.

LC-MS (Method 7): $R_t$=1.90 min,

MS (ESIpos.): m/z (%)=424 (100) [M+H]$^+$.

$^1$H NMR (400 MHz, $d_6$-DMSO) δ=−0.09 (s, 9H), 0.56-0.75 (m, 2H), 1.47 (s, 9H), 2.90 (dd, 1H), 3.09 (dd, 1H), 3.62 (s, 3H), 3.98 (m, 1H), 4.49 (m, 1H), 6.68 (d, 1H), 7.26 (dd, 1H), 7.61 (m, 1H), 8.20 (d, 1H), 8.40 (m, 2H).

Example 89A

N-(tert-Butoxycarbonyl)-3-(trimethylsilyl)-D-alanyl-3-(pyridin-3-yl)-L-alanine

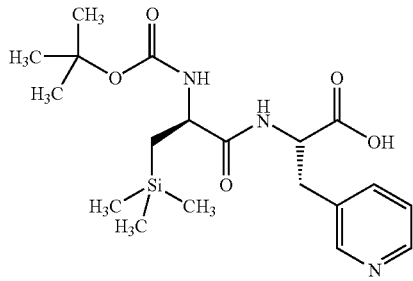

The compound from example 88A (7.4 g, 17.56 mmol) is taken up in THF-water (6:4), cooled to 0° C. and lithium hydroxide monohydrate (1.47 g, 35.13 mmol, 2 equivalents) is added. The mixture is stirred at 0° C. After one hour, a further equivalent (0.74 g) of lithium hydroxide monohydrate is added and the mixture is stirred for a further hour. The majority of the THF is distilled off in vacuo, the residue is washed with two portions of MTBE and then the aqueous phase is adjusted to pH 4 by the addition of citric acid. A solid precipitates. The mixture is extracted with three portions of ethyl acetate, whereby the solid dissolves. The combined organic phases are dried over sodium sulfate, filtered and concentrated. The crude product is purified by gel chromatography (Method 3, eluent: methanol). Yield: 6.67 g (93% of theory).

HPLC/UV-Vis (Method 17): $R_f$=3.73 min.

LC-MS (Method 7): $R_t$=1.68 min,

MS (ESIpos.): m/z (%)=410 (40) [M+H]$^+$.

$^1$H NMR (300 MHz, $d_6$-DMSO) δ=−0.090 (s, 9H), 0.56-0.75 (m, 2H), 1.35 (s, 9H), 2.90 (dd, 1H), 3.09 (dd, 1H), 3.98 (m, 1H), 4.41 (m, 1H), 6.70 (d, 1H), 7.26 (dd, 1H), 7.60 (m, 1H), 8.00 (d, 1H), 8.37 (m, 2H).

Example 90A

N-(tert-Benzyloxycarbonyl)-3-(trimethylsilyl)-D-alanyl-3-pyridin-3-yl-L-alanine

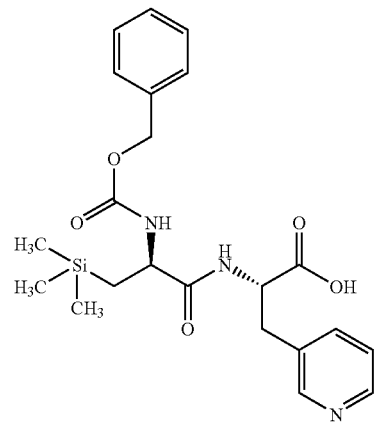

The compound from example 89A (500 mg, 1.22 mmol) is dissolved in 30% TFA in dichloromethane (20 ml) and stirred at RT for 30 min. The mixture is then concentrated, and the residue is taken up in water and lyophilized. The lyophilizate (600 mg of solid) is provided in THF (25 ml) under argon, then N-(benzyloxycarbonyloxy)succinimide (320 mg, 1.28 mmol, 1.15 equivalents) and finally 4-methylmorpholine (150 μl, 1.34 mmol, 1.2 equivalents) are added at 0° C. The mixture is allowed to warm to RT and stirred further overnight. The reaction is stopped by the addition of glacial acetic acid and concentrated in vacuo. The residue is taken up in ethyl acetate and shaken twice against 0.5 M of citric acid. The organic phase is dried over sodium sulfate, filtered and concentrated in vacuo. The residue is purified by chromatography (Method 34). Yield: 395 mg (0.71 mmol, 58% of theory).

HPLC (Method 17): $R_f$=3.79 min.

LC-MS (Method 7): $R_t$=1.84 min, MS (ESIpos.): m/z (%)=444.1 (100) [M+H]$^+$.

$^1$H NMR (400 MHz, $d_6$-DMSO) δ=−0.07 (s, 9H), 0.60-0.75 (m, 2H), 2.97-3.03 (m, 1H), 3.28 (m, 1H), 3.88 (m, 1H), 4.54 (m, 1H), 4.98 (d, J=12.7, 1H), 4.98 (d, J=12.7, 1H), 5.07 (d, J=12.7, 1H) 7.27-7.35 (m, 6H), 7.65 (m, 1H), 8.08 (d, J=7.04, 1H), 8.19 (d, J=8.8, 1H), 8.62 (s, 2H).

Example 91A

N$^{2.1}$-(Benzyloxycarbonyl)-[3-(trimethylsilyl)-D-alanyl]-[3-(pyrid-3-yl)-L-alanyl]-[(3R)-3-amino-L-phenylalanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-serine C$^{1.11}$—N$^{3.3}$-lactam bistrifluoroacetate HPLC/UV-Vis (Method 2): R$_t$=1.9 min, λ$_{max}$ (qualitative)= 210 nm (s), 255-270 (m).

LC-MS (Method 7): R$_t$=2.0 min;
MS (ESIpos.): m/z (%)=738 (100) [M−Boc+2H]$^{2+}$, 1475 (15) [M+H]$^+$;
MS (ESIneg.): m/z (%)=682 (100), 736 (80) [M−2H]$^{2-}$, 1473 (60) [M−H]$^-$.

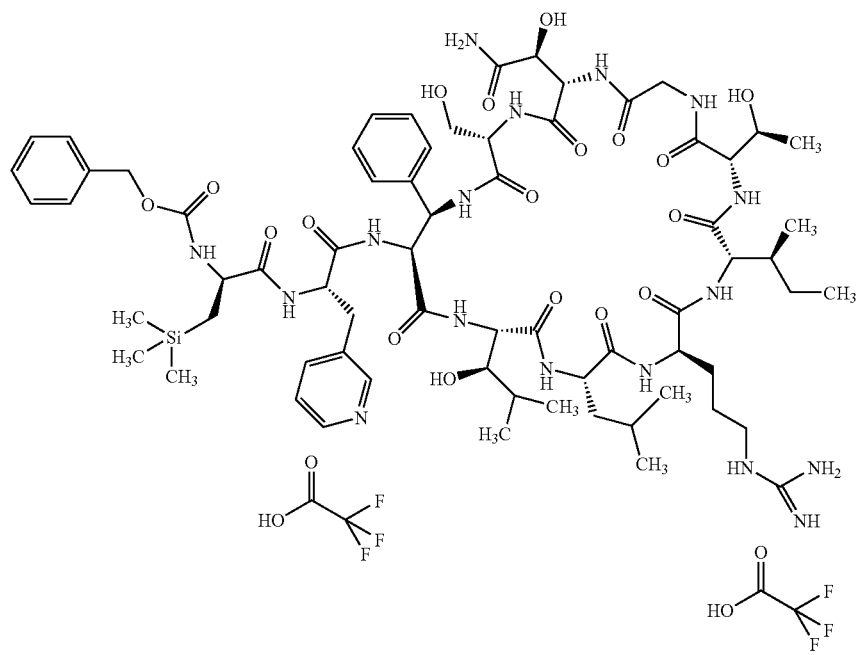

HATU (1.6 equivalents, 8.9 mg, 23 μmol) is first added under an argon protective gas atmosphere at −20° C. to a solution of the cyclopeptide (example 26A, 1.0 equivalent, 18.6 mg, 15 μmol), the dipeptide acid (example 90A, 1.5 equivalents, 9.7 mg, 22 μmol) and NMM (1.0 equivalent, 15 μmol) in dry DMF (200 μl). The reaction mixture is stirred (about 15 min) and NMM (2.5 equivalents, 38 μmol) is again added. The reaction mixture warms slowly (about 12 h) to RT and then shows complete conversion of the amine component (HPLC monitoring, Method 2). Solid potassium dihydrogen phosphate (10 equivalents, 500 μmol) is added to the reaction mixture and the mixture is then evaporated in vacuo and purified by chromatography (Method 21). 15.8 mg (63% of theory) of product are obtained.

Example 92A 3-tert-Butyl-D-alanyl-3-tert-butyl-L-alanine hydrochloride

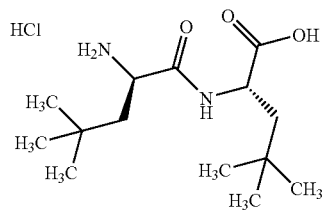

N-(tert-Butoxycarbonyl)-3-tert-butyl-D-alanyl-3-tert-butyl-L-alanine (4.5 g, 12.1 mmol, example 10A) is predis solved in dioxane (3 ml). At RT, a 4 N solution of hydrogen chloride in dioxane (30.2 mmol, 120 mmol, 10 equivalents) is added dropwise. The reaction mixture is stirred for 30 min, evaporated in vacuo and dried under high vacuum. The title compound is obtained as a solid (3.5 g, 99% of theory).

LC-MS (Method 7): $R_t$=1.52 min;
MS (ESIpos.): m/z (%)=273.6 (100) [M+H]$^+$;
MS (ESIneg): m/z (%)=271.5 (100) [M–H]$^-$.
$^1$H NMR (500 MHz, d$_6$-DMSO): δ=0.85 (s, 9H), 0.86 (s, 9H), 1.49 (dd, J=14.3, 1.6 Hz, 1H), 1.50 (d, J=13.8 Hz, 1H), 1.64 (dd, J=14.3, 4.0 Hz, 1H), 1.71 (dd, J=14.3, 6.9 Hz, 1H), 3.77 ("t", J=6.5 Hz, 1H), 4.14 (m, 1H), 8.27 (s, br, 3H), 8.94 (d, J=8.2 Hz, 1H), 12.58 (s, br, 1H).
$^{13}$C NMR (126 MHz, d$_6$-DMSO): δ=28.41 (3C), 29.50 (3C), 30.08, 30.38, 44.46, 44.80, 50.03, 50.30, 169.10, 173.98.
HR-TOF-MS (Method 1): C$_{14}$H$_{29}$N$_2$O$_3$ calc. 273.2173, found 273.2167 [M+H]$^+$.

Example 93A

N-(Benzyloxycarbonyl)-3-tert-butyl-D-alanyl-3-tert-butyl-L-alanine

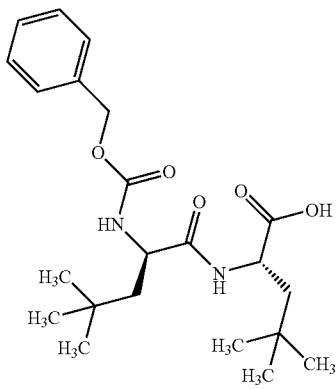

3-tert-Butyl-D-alanyl-3-tert-butyl-L-alanine (3.73 g, 12.1 mmol, example 92A) is dissolved in THF (170 ml) under an argon protective gas atmosphere. After the addition of water (170 ml), benzyloxycarbonyloxysuccinimide ester (4.52 g, 18.1 mmol, 1.5 equivalents) and N-methylmorpholine (4.28 g, 4.23 mmol, 3.5 equivalents) at 0° C., the mixture is stirred vigorously at RT until all starting material has been converted (several hours, HPLC monitoring, Method 2). The mixture is quenched with glacial acetic acid. The THF is drawn off in vacuo. The remaining aqueous phase is layered with ethyl acetate, adjusted to pH<3 with 4 N hydrochloric acid and then extracted several times with ethyl acetate. The organic phases are washed with brine, dried over sodium sulfate, filtered and concentrated. The resulting foam is stirred with acetonitrile, whereby a solid forms which is collected by filtration, then washed with a little acetonitrile. This process can be repeated several times more with the filtrate once it has been concentrated. The combined solids are dried under high vacuum whereby the title compound is obtained as a solid. The remaining mother liquor is concentrated and purified by means of preparative HPLC (Method 10). The title compound (combined solids and purification product from HPLC separation) is obtained as a solid (3.49 g, 71% of theory).

HPLC/UV-Vis (Method 2): $R_t$=2.6 min.
LC-MS (Method 8): $R_t$=2.46 min;
MS (ESIpos.): m/z (%)=363 (60), 407 (100) [M+H]$^+$.
MS (ESIneg): m/z (%)=297 (100), 405.5 (40) [M–H]$^-$.
$^1$H NMR (500 MHz, d$_6$-DMSO): δ=0.81 (s, 9H), 0.83 (s, 9H), 1.40-1.44 (m, 2H), 1.49 (dd, J=14.3, 9.7 Hz, 1H), 1.58 (dd, J=13.5, 1.4 Hz, 1H), 4.07 (m, 1H), 4.13 (m, 1H), 4.94 (d, J=12.3 Hz, 1H), 4.99 (d, J=12.5 Hz, 1H), 7.25-7.32 (m, 5H), 7.92 (d, J=8.5 Hz, 1H).
$^{13}$C NMR (126 MHz, d$_6$-DMSO): δ=29.49 (3C), 29.75 (3C), 30.41, 30.46, 44.52, 45.11, 49.55, 52.73, 65.49, 127.70 (2C), 127.91, 128.48 (2C), 137.31, 155.59, 172.52, 174.50.
HR-TOF-MS (Method 1): C$_{22}$H$_{34}$N$_2$O$_5$ calc. 407.2541, found 407.2531 [M+H]$^+$.

Example 94A

N$^2$-(Benzyloxycarbonyl-[3-tert-butyl-D-alanyl]-3-tert-butyl-L-alanyl)-[(3R)-3-tert-butylamino-L-phenylalanine]methyl ester

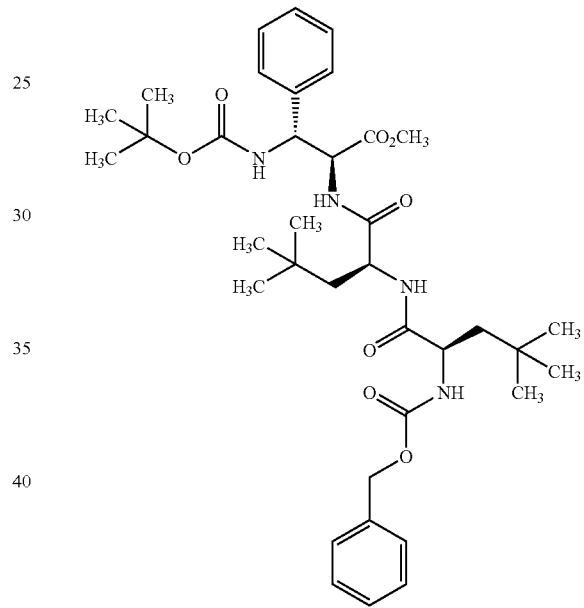

HOBt (4 equivalents, 5.51 g, 40.77 mmol), N-methylmorpholine (4 equivalents, 40.77 mmol), the N-benzyloxycarbonyl dipeptide (N-benzyloxycarbonyl)-3-tert-butyl-D-alanyl-3-tert-butyl-L-alanine, 1.1 equivalents, 4.56 g, 11.21 mmol, example 93A) and EDC (2 equivalents, 3.91 g, 20.38 mmol) are added successively at −30° C. to a solution of the racemic amino acid methyl ester (1.0 equivalent, 4.16 g, 10.19 mmol, example 14) in dichloromethane p.a. (100 ml). The reaction mixture warms slowly (about 12 h) to RT, whereby complete conversion of the amine component is observed by HPLC (Method 2). The reaction mixture is quenched with potassium dihydrogen phosphate (5.0 equivalents, 6.93 g, 50.96 mmol), concentrated in vacuo, taken up in ethyl acetate (about 400 ml) and then washed with 5% aqueous citric acid (twice), distilled water and a saturated sodium chloride solution. The mixture is dried over sodium sulfate and filtered. The crude product is subsequently filtered through silica gel. The solution is concentrated to dryness in vacuo and then dried further under high vacuum. 5.36 g (77% of theory) of the title compound are obtained as a diastereomer mixture with relative (2S*,3R*) stereochemistry on the aminophenylalanine. The diastereomers are separated from one another in a further chromatography step (Method 42). 2.87 g (41% of theory) of the title compound are obtained (de>99%, Method 28). This reaction can also be performed analogously with the enantiomerically pure amino acid methyl ester. Diastereomerically pure product is obtained directly.

HPLC/UV-Vis (Method 3): $R_t$=3.1 min.
HPLC/UV-Vis (Method 28): $R_t$=4.84 min.
LC-MS (Method 8): $R_t$=2.7 min;
MS (ESIpos.): m/z (%)=583.5 (100) [M+H–CO$_2$–C$_4$H$_8$]$^+$, 683.5 (60) [M+H]$^+$;
MS (ESIneg.): m/z (%)=681.6 (10) [M–H]$^-$, 727.6 (100) [M–H+HCO$_2$H]$^-$.
LC-MS (Method 7): $R_t$=3.1 min;
MS (ESIpos.): m/z (%)=583.5 (100) [M+H–CO$_2$–C$_4$H$_8$]$^+$, 683.5 (40) [M+H]$^+$;
MS (ESIneg.): m/z (%)=573 (100), 681.6 (5) [M–H]$^-$, 727.6 (40) [M–H+HCO$_2$H]$^-$.

Example 95A

N$^2$-(Benzyloxycarbonyl-[3-tert-butyl-D-alanyl]-3-tert-butyl-L-alanyl)-[(3R)-3-tert-butylamino-L-phenylalanine]

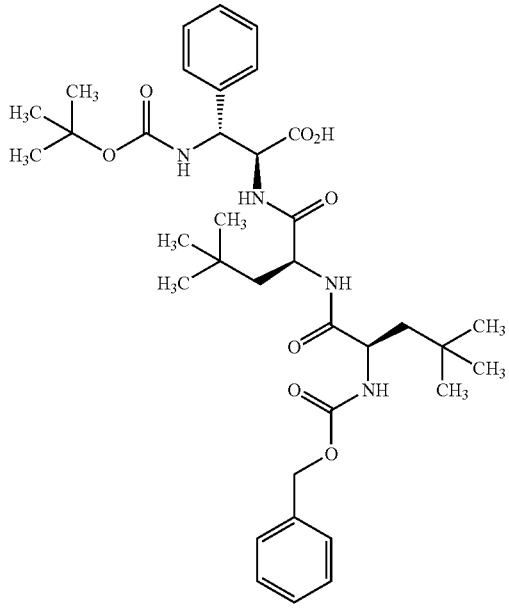

Under an argon protective gas atmosphere, a solution of the tripeptide methyl ester (example 94A, 1.00 g, 1.46 mmol) is provided in THF/water 2:1 (300 ml). At 0° C., a degassed 5% aqueous solution of lithium hydroxide (59.6 mg, 2.5 mmol, 1.7 equivalents) is slowly added dropwise with vigorous stirring. The mixture is stirred at 0° C. until the HPLC chromatogram (Method 2) indicates complete conversion (about 6 h). In the case of an excessively long reaction time, there is a risk of epimerization. Subsequently, acetic acid (0.4 ml) is added, the reaction mixture is concentrated in vacuo and layered with ethyl acetate (100 ml). The aqueous phase is now acidified with 5% citric acid (pH 2-3) and then extracted with ethyl acetate (50 ml, three times). The combined organic phases are washed with a saturated aqueous sodium chloride solution (20 ml, twice), dried over sodium sulfate, filtered, concentrated in vacuo and dried under high vacuum. The crude product is fine-purified by means of preparative HPLC (Method 38). 682 mg (56% of theory) of the title compound are obtained.

HPLC/UV-Vis (Method 2): $R_t$=2.9 min.
HPLC/UV-Vis (Method 25): $R_t$=24.6 min.
LC-MS (Method 7): $R_t$=2.9 min;
MS (ESIpos.): m/z (%)=569.2 (100), 669.3 (50) [M+H]$^+$, 1337.4 (40);
MS (ESIneg.): m/z (%)=667.2 (100) [M–H]$^-$, 1335.4 (80).
HR-TOF-MS (Method 1): C$_{36}$H$_{53}$N$_4$O$_8$ [M+H]$^+$ found 669.3881, calc. 669.3858.

Example 96A

N$^2$-(Benzyloxycarbonyl-[3-tert-butyl-D-alanyl]-3-tert-butyl-L-alanyl)-[(3R)-3-tert-butylamino-L-phenylalanine]2-(trimethylsilyl)ethyl ester

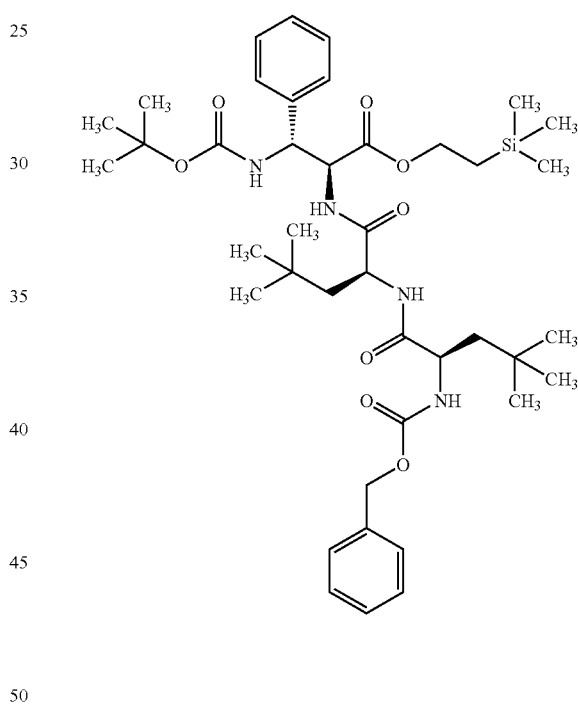

A mixture of the tripeptide acid (example 96A, 733 mg, 1.10 mmol), 2-(trimethyl-silyl)ethanol (1.30 g, 11.0 mmol, 10 equivalents) and 4 Å molecular sieve (about 100 mg) in dry dichloromethane p.a. (6.5 ml) is stirred under an argon protective gas atmosphere at RT for 30 min. Subsequently, DCC (452 mg, 2.20 mmol, 2 equivalents) and DMAP (134 mg, 1.10 mmol, 1 equivalent) are added at –30° C. The reaction mixture is allowed to thaw (about 12 h) and stirred at RT until the HPLC chromatogram (Method 2) indicates complete conversion (about 12 h). The reaction mixture is quenched with glacial acetic acid (125 µl), then evaporated at RT in vacuo, suspended in a little dichloromethane (6.5 ml), filtered through an ec RP18-HPLC cartridge (Macherey Nagel), concentrated again and then fine-purified by means of preparative HPLC (Method 35). 706 mg (84% of theory) of the title compound are obtained.

HPLC/UV-Vis (Method 2): $R_t$=3.4 min.

LC-MS (Method 7): $R_t$=3.4 min;

MS (ESIpos.): m/z (%)=669.5 (80), 769.6 (100) [M+2H]$^{2+}$, 1556 (30).

HR-TOF-MS (Method 1): $C_{41}H_{65}N_4O_8Si$ [M+H]$^+$ found 769.4548, calc. 769.4567.

Example 97A

N$^2$-(Benzyloxycarbonyl-[3-tert-butyl-D-alanyl]-3-tert-butyl-L-alanyl)-(3R)-3-amino-L-phenylalanine 2-(trimethylsilyl)ethyl ester trifluoroacetate

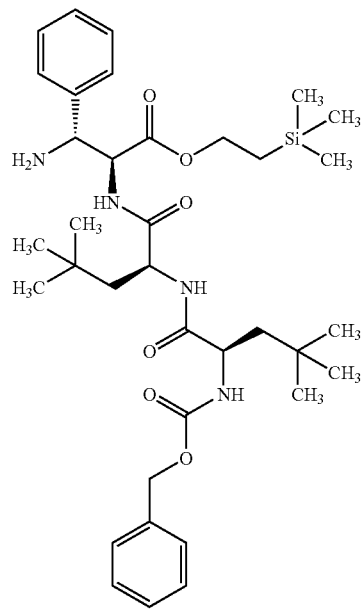

The N-(tert-butoxycarbonyl)-protected tripeptide (720 mg, 0.94 mmol, example 96A) is provided under an argon protective gas atmosphere. At RT and with vigorous stirring, 4 N hydrochloric acid in dioxane (40 ml) is added dropwise. The mixture is stirred until analytical HPLC (Method 2) indicates complete conversion (about 30 min). The reaction mixture is evaporated at RT in vacuo. The crude product is purified by means of preparative HPLC (Method 10) and lyophilized. The title compound is obtained as a lyophilizate (394 mg, 54% of theory).

HPLC/UV-Vis (Method 25): $R_t$=25.2 min.

HPLC/UV-Vis (Method 2): $R_t$=2.4 min.

LC-MS (Method 8): $R_t$=2.3 min;

MS (ESIpos.): m/z (%)=669.6 (100) [M+H]$^+$;

MS (ESIneg.): m/z (%)=703.6 (100) [M–H+HCO$_2$H]$^-$.

LC-MS (Method 7): $R_t$=2.6 min;

MS (ESIpos.): m/z (%)=669.4 (100) [M+H]$^+$.

Example 98A

N$^2$-(Benzyloxycarbonyl-[3-tert-butyl-D-alanyl]-3-tert-butyl-L-alanyl)-N$^3$-{tert-butoxycarbonyl-[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-L-phenylalanine 2-(trimethylsilyl)ethyl ester trifluoroacetate

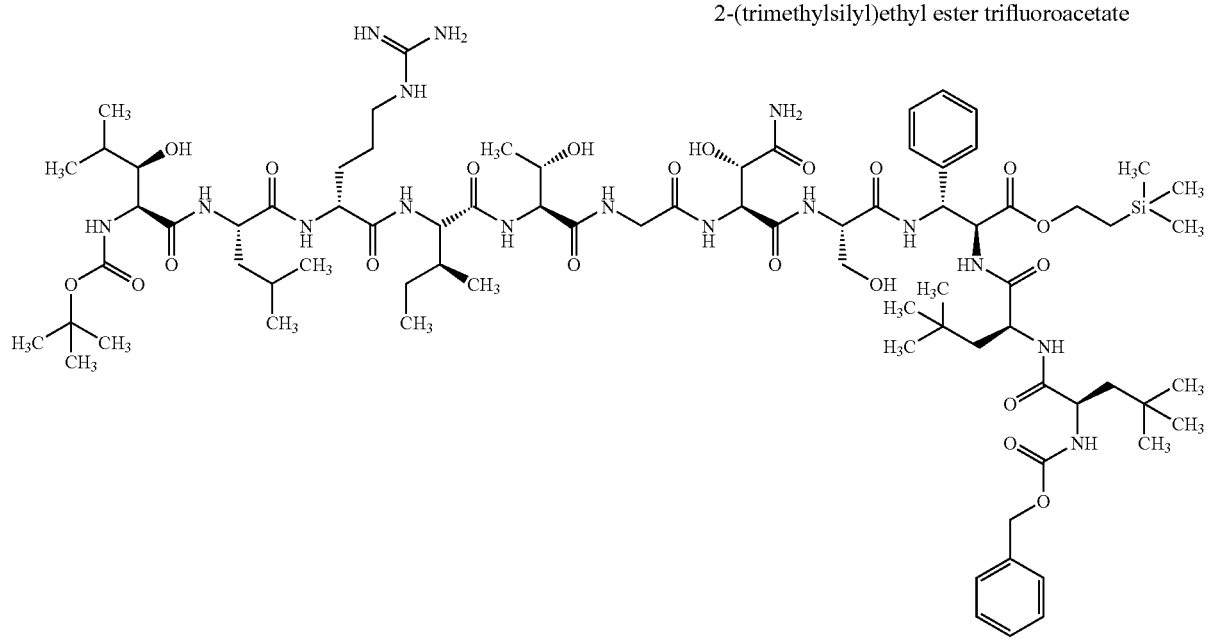

HATU (1.5 equivalents, 58.3 mg, 0.15 mmol) is first added at −15° C. under an argon protective gas atmosphere to a solution of the Boc-octapeptide (example 20A, 1.0 equivalent, 114.4 mg, 0.10 mmol), the tripeptide (example 97A, 1.0 equivalent, 80.0 mg, 0.10 mmol, example 97A) and of N-methylmorpholine (1.0 equivalent, 0.10 mmol) in dry DMF (3.0 ml). The reaction mixture is stirred (about 15 min) and NMM (1.0 equivalent, 0.10 mmol) is again added. The reaction mixture is warmed to 0° C. and HATU (2.5 equivalents, 0.25 mmol) is again added. The reaction mixture warms slowly (about 12 h) to RT and then shows complete conversion of the amine component (HPLC monitoring, method 3). Solid potassium dihydrogen phosphate (5 equivalents, 0.50 mmol) is added to the reaction mixture and the mixture is then evaporated under high vacuum and purified by chromatography (Method 21 or 13), followed by a subsequent salt exchange of the chromatography product by the addition of TFA (100 μmol, as a 0.05% solution in acetonitrile-water 1:1). 140.5 mg (78% of theory) of product are obtained.

HPLC/UV-Vis (Method 2): $R_t$=2.6 min.

HPLC/UV-Vis (Method 25): $R_t$=26.6 min.

LC-MS (Method 7): $R_t$=2.5 min;

MS (ESIpos.): m/z (%)=1656.8 (100) $[M+H]^+$;

MS (ESIneg.): m/z (%)=1655 (100) $[M-H]^-$.

HR-TOF-MS (Method 1): $C_{78}H_{131}N_{16}O_{21}Si$ $[M+H]^+$ found 1655.9467, calc. 1655.9439.

Example 99A $N^2$-(Benzyloxycarbonyl-[3-tert-butyl-D-alanyl]-3-tert-butyl-L-alanyl)-$N^3$-{tert-butoxycarbonyl-[(3R)-3-hydroxy-L-leucyl]-L-leucyl-D-arginyl-L-isoleucyl-L-allothreonyl-glycyl-[(3S)-3-hydroxy-L-asparaginyl]-L- seryl}-(3R)-3-amino-L-phenylalanine trifluoroacetate

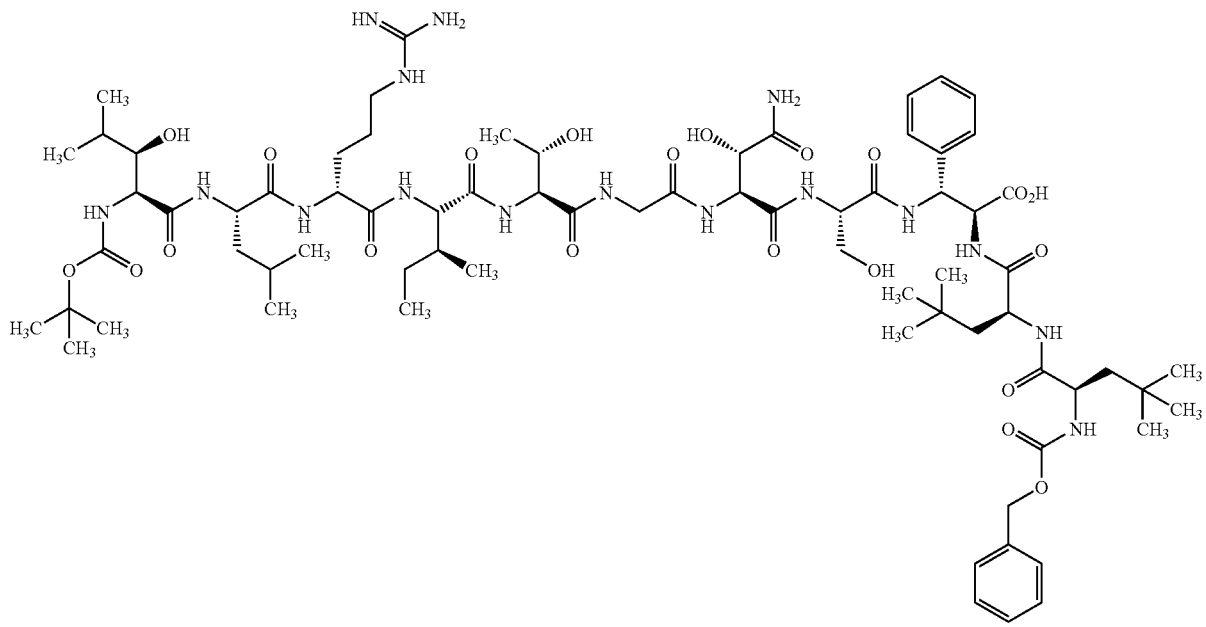

4 Å molecular sieve is added to a solution of the TMSE ester (460 mg, 0.260 mmol, example 98A) in dry THF (8 ml) and the mixture is stirred at RT under an argon protective gas atmosphere (15 min). Subsequently a 1 N solution of tetrabutylammonium fluoride in THF (4.16 ml, 4.16 mmol, 16 equivalents) is added over a period of 2 h in two portions to the dried solution. The mixture is stirred until complete conversion is observed (HPLC, method 2). The reaction mixture is quenched with glacial acetic acid (298 μl, 5.198 mmol, 20 equivalents), concentrated in vacuo and purified directly by means of preparative HPLC (Method 21). After lyophilization, the product is obtained as a lyophilizate (375 mg, 86% of theory).

HPLC/UV-Vis (Method 2): $R_t$=2.4 min.

LC-MS (Method 7): $R_t$=2.3 min;

MS (ESIpos.): m/z (%)=728.8 (100) $[M+2H-CO_2-C_4H_8]^{2+}$, 778.8 (30) $[M+2H]^{2+}$, 1556.9 (40) $[M+H]^+$;

MS (ESIneg.): m/z (%)=1554 (100) $[M-H]^-$.

HR-TOF-MS (Method 1): $C_{73}H_{119}N_{16}O_{21}$ $[M+H]^+$ found 1555.8737, calc. 1555.8731.

Example 100A $N^2$-(Benzyloxycarbonyl-[3-tert-butyl-D-alanyl]-3-tert-butyl-L-alanyl)-$N^3$-{(3R)-3-hydroxy-L-leucyl-L-leucyl-D-arginyl-L-isoleucyl-L-allothreonyl-glycyl-[(3S)-3-hydroxy-L-asparaginyl]-L-seryl}-(3R)-3-amino-L-phenylalanine bistrifluoroacetate

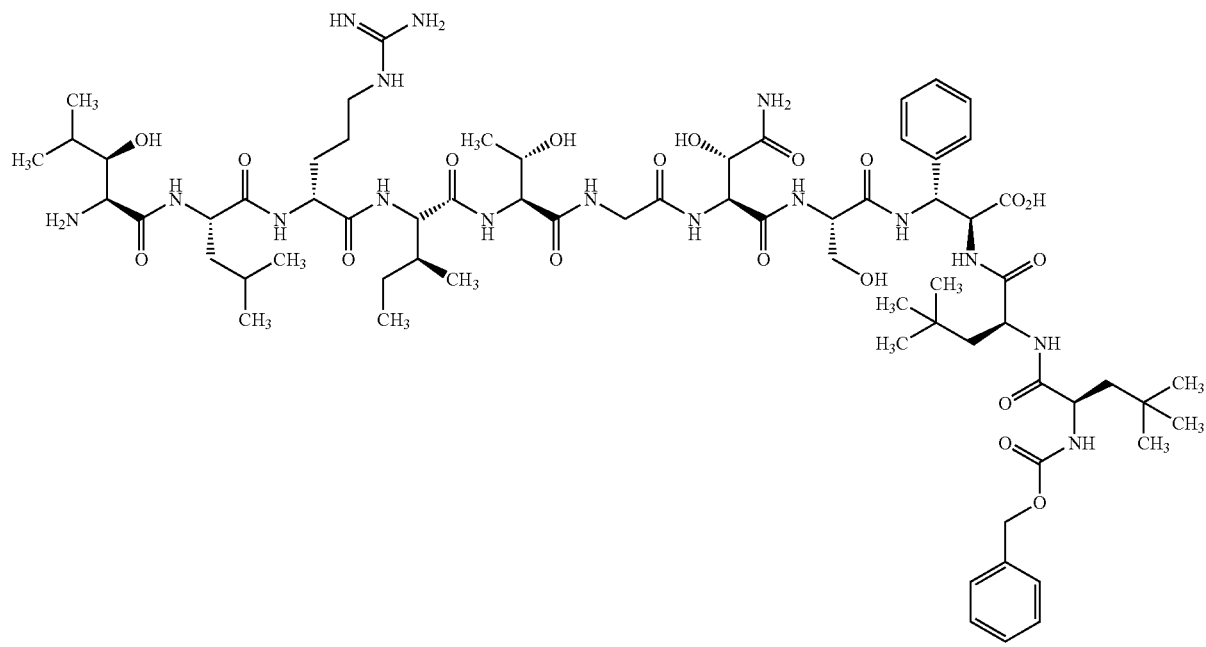

The N-(tert-butoxycarbonyl)-protected compound (100 mg, 0.06 mmol, example 99A) is provided under an argon protective gas atmosphere. At RT and with vigorous stirring, 4 N hydrochloric acid in dioxane (15 ml) is added dropwise. The mixture is stirred until analytical HPLC (Method 2) indicates complete conversion (about 30 min). The reaction mixture is evaporated in vacuo at RT. The crude product is purified by means of preparative HPLC (Method 35) and lyophilized. The title compound is obtained as a lyophilizate (85.5 mg, 85% of theory).

HPLC/UV-Vis (Method 2): $R_t$=1.9 min.
HPLC/UV-Vis (Method 25): $R_t$=18.4 min, $\lambda_{max}$ (qualitative)=210 nm (s), 255-270 (w).
LC-MS (Method 7): $R_t$=1.8 min;
MS (ESIpos.): m/z (%)=728.7 (100) $[M+2H]^{2+}$;
MS (ESIneg.): m/z (%)=1454 (100) $[M-H]^-$.
HR-TOF-MS (Method 1): $C_{68}H_{111}N_{16}O_{19}$ $[M+H]^+$ found 1455.8192, calc. 1455.8206.

Example 101A $N^2$-(Benzyloxycarbonyl)-$N^3$-{[(3R)-3-hydroxy-L-leucyl]-L-leucyl-D-arginyl-L-isoleucyl-L-allothreonyl-glycyl-[(3S)-3-hydroxy-L-asparaginyl]-L-seryl}-(3R)-3-amino-L-phenylalanine trifluoroacetate The N-(tert-butoxycarbonyl)-protected nonapeptide (example 22A, 1200 mg, 0.848 mmol) is provided in dioxane (10 ml) under an argon protective gas atmosphere. At RT and with vigorous stirring, 4 N hydrochloric acid in dioxane (230 ml) is added. The mixture is stirred until the analytical HPLC (Method 2) indicates complete conversion (about 1 h). The reaction mixture is concentrated on a rotary evaporator, then the residue is mixed with water at RT and then evaporated in vacuo. The crude product is purified by means of preparative HPLC (Method 11) and lyophilized. The title compound is obtained as a colorless solid (918 mg, 95% purity, 83% of theory).

HPLC/UV-Vis (Method 2): $R_t$=1.6 min.
HPLC/UV-Vis (Method 25): $R_t$=14.3 min.
LC-MS (Method 7): $R_t$=1.4 min;
MS (ESIpos.): m/z (%)=601.6 (100) $[M+2H]^{2+}$, 1201.7 (20) $[M+H]^+$;
MS (ESIneg.): m/z (%)=1199.8 (100) $[M-H]^-$.

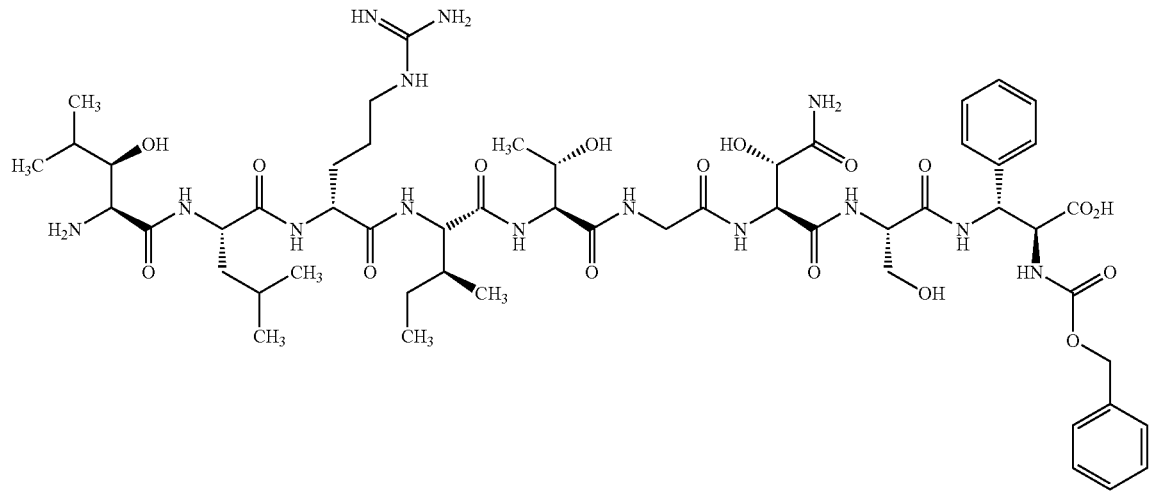

Example 102A $N^{2.1}$-(Benzyloxycarbonyl)-[3-tert-butyl-D-alanyl]-[3-tert-butyl-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam trifluoroacetate

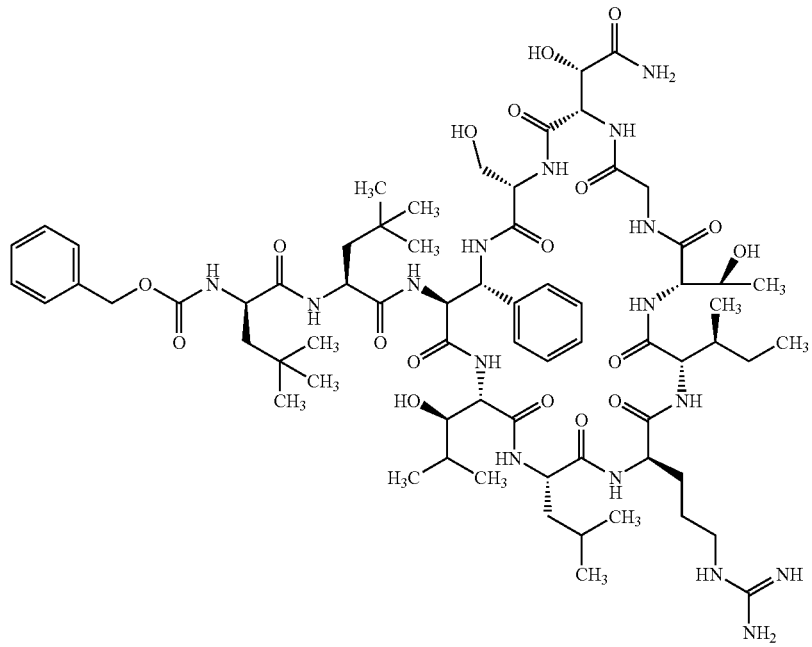

HATU (1.6 equivalents, 9.4 mg, 25 μmol) is first added at 0° C. under an argon protective gas atmosphere to a solution of the cyclopeptide (example 26A, 1.0 equivalent, 16.1 mg, 15 μmol), the dipeptide acid N-(benzyloxycarbonyl)-3-tert-butyl-D-alanyl-3-tert-butyl-L-alanine (9.4 mg, 23 μmol, 1.5 equivalents, example 93A) and N-methylmorpholine (1.0 equivalent, 15 μmol) in dry DMF (250 μl). The reaction mixture is stirred (about 15 min) and N-methylmorpholine (3.5 equivalents, 54 μmol) is again added. The reaction mixture warms slowly (about 12 h) to RT and then shows complete conversion of the amine component (HPLC monitoring, Method 3). Solid potassium dihydrogen phosphate (10 equivalents, 150 μmol) is added to the reaction mixture and the mixture is then evaporated under high vacuum and purified by chromatography (Method 10). 17.7 mg (74% of theory) of product are obtained. phenylalanine bistrifluoroacetate, example 100A, 70 mg, 42 μmol) in DMF (30 ml) and NMM (32 μl, 6 equivalents). The reaction mixture is stirred until complete conversion (12 h, HPLC monitoring). Subsequently, the reaction mixture is quenched with potassium dihydrogen phosphate (10 equivalents, 56.6 mg), concen- Alternative preparation method: At 0° C., HATU (47 mg, 125 μmol, 3 equivalents) is added to a solution of the free undecapeptide ($N^2$-(benzyloxycarbonyl-[3-tert-butyl-D-alanyl]-3-tert-butyl-L-alanyl)-$N^3$-{(3R)-3-hydroxy-L-leucyl-L-leucyl-D-arginyl-L-isoleucyl-L-allothreonyl-glycyl-[(3S)-3-hydroxy-L-asparaginyl]-L-seryl}-(3R)-3-amino-L-trated in vacuo and purified directly by means of preparative HPLC (Method 36). The product is obtained as a solid (74.4 mg, 73% of theory).

HPLC/UV-Vis (Method 2): $R_t$=2.3 min.

HPLC/UV-Vis (Method 25): $R_t$=24.0 min, $\lambda_{max}$ (qualitative)=210 nm (s), 255-270 (w).

$^1$H NMR (500 MHz, $d_5$-pyridine) δ 0.98-1.21 (m, 39H, 12 CH$_3$), 1.36 (m, 1H), 1.52 (s, br, 1H), 1.60 (d, J=4.1 Hz, 3H, CH$_3$), 1.89 (m, 1H), 1.96-2.03 (m, 2H), 2.09-2.35 (m, 5H), 2.47 ("d", J=15.3 Hz, 1H), 3.15 (s, br, 2H), 3.87 ("d", J=14.2 Hz, 1H), 4.04 ("d", J=9.5 Hz, 1H), 4.17 (s, br, 1H), 4.37-4.55 (m, 4H), 4.66 (s, br, 1H), 4.74 (q, J=5.2 Hz, 1H), 4.83 ("t", J=9.3 Hz, 1H), 4.91 (s, br, 1H), 5.20 (s, 1H), 5.36-5.42 (m, 2H), 5.62 (d, J=12.1 Hz, 1H), 5.70 (d, J=12.5 Hz, 1H), 5.99-6.06 (m, 2H), 6.73 (s, br, 2H), 7.24 ("t", J=7.6 Hz, 1H), 7.28 (d, J=6.8 Hz, 1H), 7.34 ("t", J=7.6 Hz, 2H), 7.40 (m, 1H), 7.46 ("t", J=7.2 Hz, 2H), 7.57 (m, 2H), 7.62 (s, br, 1H), 7.68 (s, br, 1H), 7.82 (s, br, 1H), 7.97 ("d", J=6.5 Hz, 2H), 8.19 (s, br, 1H), 8.24-8.29 (m, 2H), 8.35 (s, 1H), 8.52 (s, 1H), 8.57 (m, 1H), 8.63 (m, 1H), 8.85 (s, br, 1H), 9.05 (s, 1H), 9.75 (s, 1H), 11.30 (s, br, 1H). For 8 protons, no signals can be assigned.

LC-MS (Method 7): $R_t$=2.1 min; MS (ESIpos.): m/z (%)=719.8 (100) [M+2H]$^{2+}$, 1437.9 (30) [M+H]$^+$;

MS (ESIneg.): m/z (%)=663.7 (100), 1435.9 (100) [M−H]$^−$.

HR-TOF-MS (Method 1): $C_{68}H_{109}N_{16}O_{18}$ [M+H]$^+$ found 1437.8135, calc. 1437.8101.

Example 103A

D-Leucyl-N¹-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-isopropyl-2,5,8,11,14,17,20,23,26-nonaoxo-28-phenyl-1-oxa-4,7,10,13,16,19,22,25-octaazacyclooctacosan-27-yl}-L-leucinamide bistrifluoroacetate

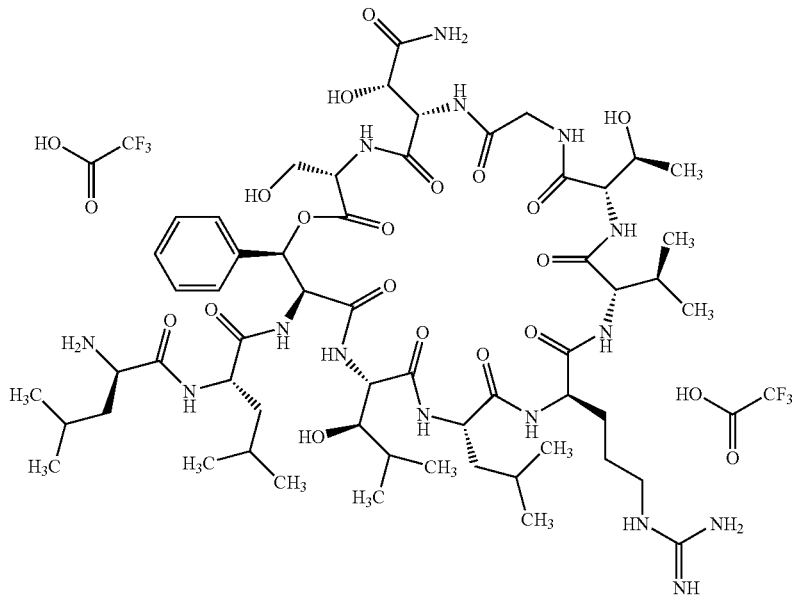

For the synthesis of katanosin A, see WO 04/099239 example 2A.

EXEMPLARY EMBODIMENTS

Example 1

[3-tert-Butyl-D-alanyl]-[3-tert-butyl-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine C$^{1.11}$—N$^{3.3}$-lactam bistrifluoroacetate

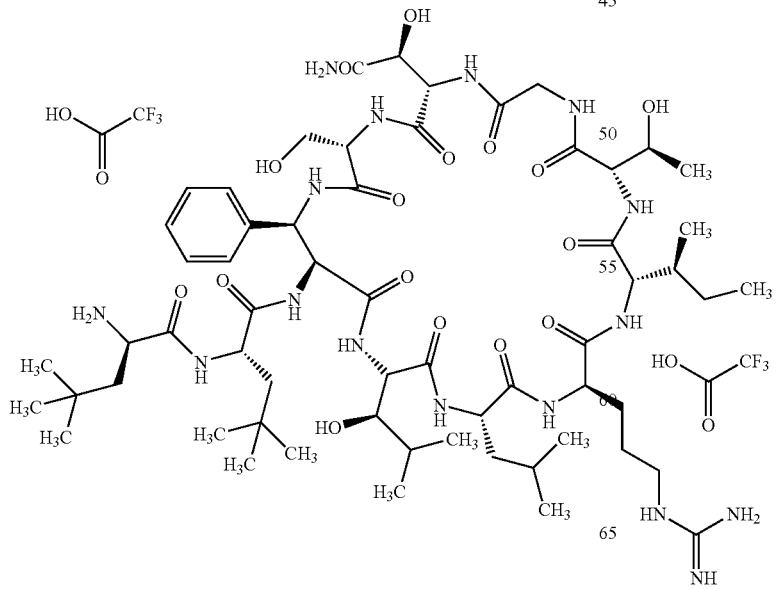

The N-(tert-butoxycarbonyl)cyclopeptide (example 27A, 10 mg, 10 µmol) is reacted according to working procedure 1. After chromatographic purification by means of preparative HPLC (Method 10), 6.5 mg of product (64% of theory) are obtained by freeze-drying.

In an alternative process, the title compound is prepared from the Cbz-protected cyclopeptide (example 102A) according to working procedure 3.

The structure is confirmed by a single-crystal X-ray structural analysis.

Example 2

D-Leucyl-L-leucyl-[(3R)-3-amino-L-phenylalanyl]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam bistrifluoroacetate

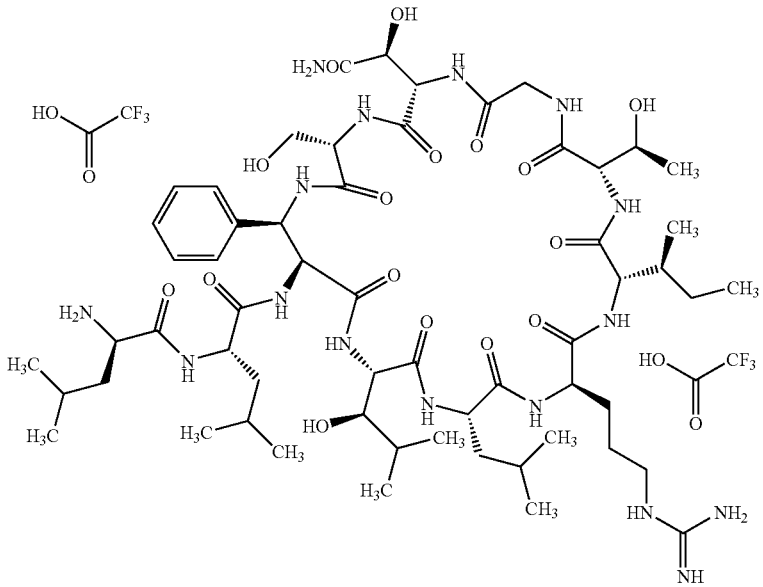

HPLC/UV-Vis (Method 3): $R_t$=1.9 min, $\lambda_{max}$ (qualitative)=210 nm (s), 265 (m).

LC-MS (Method 5): $R_t$=4.51 min;

MS (ESIpos.): m/z (%)=652.8 (100) $[M+2H]^{2+}$, 1304.9 (10) $[M+H]^+$.

MS (ESIneg.): m/z (%)=650.7 (10), 1301.9 (10) $[M-H]^-$, 1347.9 $[M-H+HCO_2H]^-$.

$^1$H NMR (500 MHz, $d_5$-pyridine) δ=0.82 (3H), 0.95 (3H), 0.99 (3H), 1.05 (9H), 1.07 (3H), 1.11 (9H), 1.12 (3H), 1.18 (3H), 1.32, 1.46, 1.61 (3H), 1.93, 1.97, 2.02, 2.03, 2.13 (2H), 2.19 (2H), 2.27, 2.32, 2.35, 2.35, 2.35, 3.18 (2H), 3.94, 4.02, 4.15, 4.31, 4.36, 4.37, 4.47, 4.50, 4.58, 4.59, 4.75, 4.99, 5.17, 5.33, 5.38, 6.00, 6.00, 6.40, 7.21 (2H), 7.45 (2H), 7.64, 7.72, 7.73, 7.92, 8.02, 8.17, 8.23, 8.30, 8.50, 8.55, 8.85, 9.09, 11.29. No unambiguous $^1$H signals are found for: tBuAla$^1$NH$_2$, tBuAla$^2$NH, HyLeu$^4$NH, HyLeu$^4$OH, Arg$^6$N$^ε$H, Arg$^6$N$^ε$H$_2$, alloThr$^8$OH, HyAsn$^{10}$OH, Ser$^{11}$OH.

$^{13}$C NMR (126 MHz, $d_5$-pyridine) δ=10.40, 16.00, 19.20, 19.20, 20.70, 21.30, 23.90, 24.70, 26.20, 26.50, 28.60, 29.40 (3C), 29.80 (3C), 30.90, 36.00, 41.10, 41.30, 44.00, 44.23, 44.60, 47.00, 47.20, 51.50, 52.80, 54.30, 55.50, 55.60, 56.60, 57.70, 58.40, 60.30, 60.60, 62.60, 63.00, 70.20, 71.90, 75.20, 128.20 (2C), 128.30, 129.10 (2C), 137.70, 158.23, 169.38, 171.04, 172.23, 172.43 (2C), 173.12, 174.04, 174.29, 174.66, 174.84, 175.41, 176.64.

HR-TOF-MS (Method 1): $C_{60}H_{103}N_{16}O_{16}$ $[M+H]^+$ found 1303.7719, calc. 1303.7733.

Under an argon protective gas atmosphere, the Cbz-protected cyclopeptide (example 28A, 800 µg, 0.5 µmol) is dissolved in methanol (1 ml) and 1 N aqueous hydrochloric acid (50 µl) and 10 percent palladium carbon (1 mg) are then added. The mixture is hydrogenated at RT and under atmospheric pressure until (about 1 h) analytical HPLC (Method 2) indicates complete conversion. The reaction mixture is filtered (syringe filter Biotage, PTFE), concentrated in vacuo and dried under high vacuum. The crude product is purified by means of preparative HPLC (Method 10). 600 µg (76% of theory) of a solid are obtained as product.

$[α]^{20}_{Na}$=−66.0° (c=0.24 in methanol).

HPLC/UV-Vis (Method 3): $R_t$=1.7 min, $\lambda_{max}$ (qualitative)=210 nm (s), 265 (m).

LC-MS (Method 5): $R_t$=4.3 min;

MS (ESIpos.): m/z (%)=638.7 (100) $[M+2H]^{2+}$.

MS (ESIneg.): m/z (%)=1274 (100) $[M-H]^-$.

$^1$H NMR (500 MHz, $d_5$-pyridine) δ=0.72 (3H), 0.77 (3H), 0.89 (3H), 0.96 (3H), 0.99 (3H), 1.02 (3H), 1.02 (3H), 1.08 (3H), 1.09 (3H), 1.22 (3H), 1.29, 1.44, 1.58 (3H), 1.75, 1.99, 2.00, 2.09 (2H), 2.10, 2.14 (2H), 2.17, 2.21 (2H), 2.21, 2.29, 2.29, 2.39, 2.39, 3.18, 3.33, 4.00, 4.10, 4.21, 4.35, 4.35, 4.48, 4.53, 4.61, 4.71, 4.80, 5.06, 5.17, 5.35, 5.36, 6.04, 6.05, 6.63, 7.25 (2H), 7.50 (2H), 7.67, 7.70, 7.88, 8.07, 8.11, 8.24, 8.24, 8.26, 8.47, 8.54, 8.95, 9.23, 9.31, 11.26. No unambiguous $^1$H signals are found for: Leu$^1$NH$_2$, Leu$^2$NH, HyLeu$^4$OH, Arg$^6$N$^ε$H, Arg$^6$N$^ε$H$_2$, alloThr$^8$OH, HyAsn$^{10}$OH, Ser$^{11}$OH.

$^{13}$C NMR (126 MHz, $d_5$-pyridine) δ=16.27, 19.17, 19.90, 20.49, 20.87, 21.11, 21.70, 22.63, 23.40, 24.19, 24.81, 25.23, 25.23, 26.06, 26.61, 21.70, 28.97, 31.04, 36.52, 40.00, 41.31, 41.94, 42.40, 45.43, 52.60, 53.26, 53.72, 56.09, 56.62, 57.94, 58.53, 58.75, 60.83, 60.83, 62.61, 63.47, 70.50, 72.11, 75.39, 128.09 (2C), 128.19, 128.99 (2C), 138.52, 158.12, 169.39, 170.44, 172.25, 172.46, 173.13, 173.58, 174.16, 174.32, 174.59, 174.59, 174.69, 176.64.

MALDI-MS: m/z (%)=1275 (100) [M+H]$^+$, 1297 (5) [M+Na]$^+$, 1313 (5) [M+K]$^+$.

MALDI-MS/MS@1275: m/z (%)=86 (100), 199 (50), 1049 (20).

HR-TOF-MS (Method 1): $C_{58}H_{99}N_{16}O_{16}$ [M+H]$^+$ found 1275.7424, calc. 1275.7420.

The structure is confirmed by single-crystal X-ray structural analysis.

An amino acid analysis (Method 9) is carried out (table A).

TABLE A

| | 1 mg/ml dissolved in 20% methanol | | |
|---|---|---|---|
| AA- | factorized amino acids nmol/20 | theroret. numbers of lysobaticn | percent without TR |
| Hy-AS | | 1 | |
| allo-SE | 0.8 | 1 | 10.62 |
| GL | 1.0 | 1 | 12.46 |
| GLY | 1.2 | 1 | 15.76 |
| AL | | | |
| VA | | | |
| ME | | | |
| ILE *reference | 1.0 | 1 | 12.40 |
| LEU | 2.9 | 3 | 36.50 |
| TY | | | |

TABLE A-continued

| | 1 mg/ml dissolved in 20% methanol | | |
|---|---|---|---|
| AA- | factorized amino acids nmol/20 | theroret. numbers of lysobaticn | percent without TR |
| β-Amino-Hl | | 1 | |
| Hy-LY | | 1 | |
| AR | 0.9 | 1 | 12.26 |
| PR | | | |
| TR | | | |
| Total | | 1 | |
| Hy-βNH2Ph | n.d. no standard not stainable in the AA | | |
| Hy- | n.d. no standard | | |

Hy-Asn, Hy-Leu were not quantifiable, since no standard present.
Hy-Asn is very probably present as Hy-Asp.

Example 3

[3-(Trimethylsilyl)-D-alanyl]-[3-(pyrid-3-yl)-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam tristrifluoroacetate

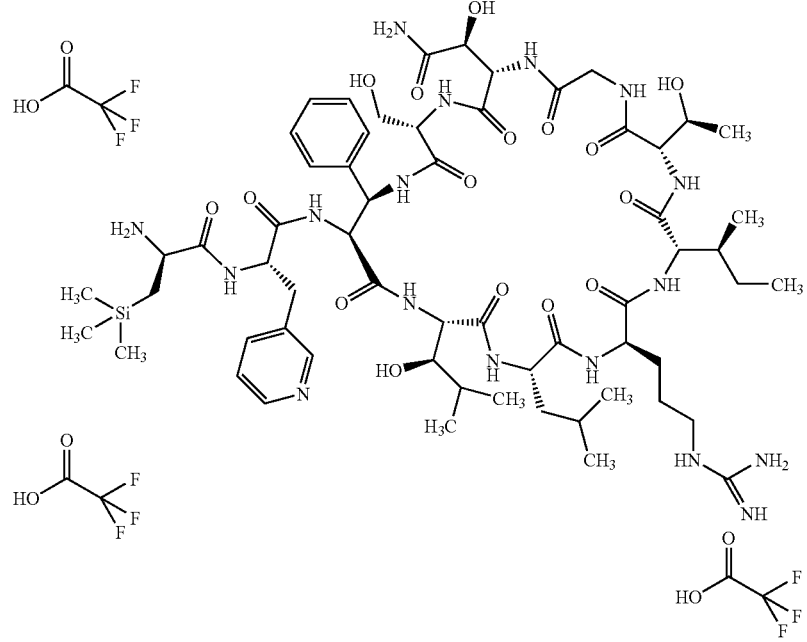

The Cbz-protected cyclopeptide (example 91A, 19.9 mg, 12 mmol) is reacted according to working procedure 3. After chromatographic purification by means of preparative HPLC (Method 21), 14.7 mg (99% of theory) of product are obtained by freeze-drying.

HPLC/UV-Vis (Method 2): $R_t$=1.4 min, $\lambda_{max}$ (qualitative) 210 nm (s), 265 (m).

LC-MS (Method 5): $R_t$=1.50 min;

MS (ESIpos.): m/z (%)=671.0 (100) [M+2H]$^{2+}$, 1340.4 (10) [M+H]$^+$;

MS (ESIneg.): m/z (%)=668.8 (100), 1338.4 (10) [M−H]$^-$.

HR-TOF-MS (Method 1): $C_{60}H_{97}N_{17}O_{16}Si$ [M+H]$^+$ found 1340.7117, calc. 1340.7142.

The structure is confirmed by single-crystal X-ray structural analysis.

Example 4

[3-(tert-Butyl)-D-alanyl]-[3-(pyrid-3-yl)-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam tristrifluoroacetate

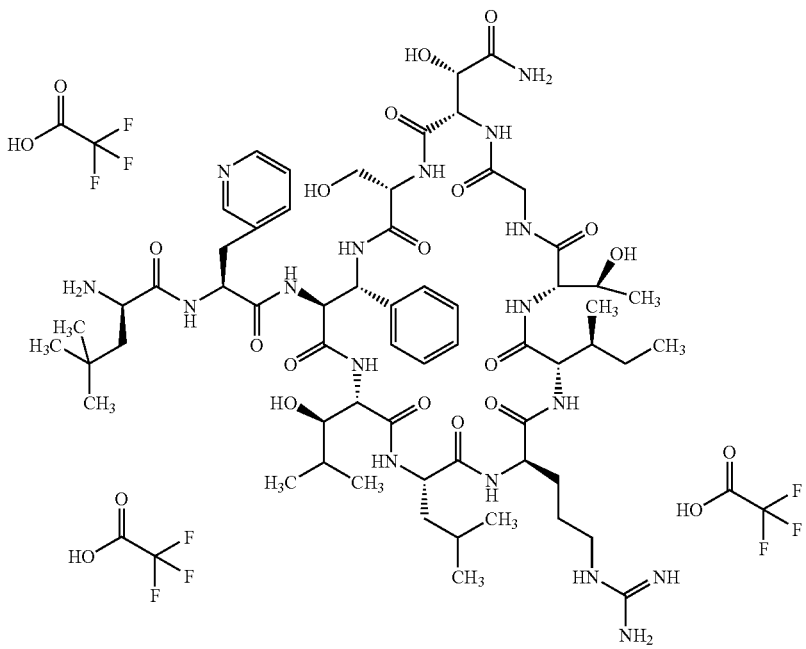

The Cbz-protected cyclopeptide (example 66A, 15.0 mg, 8.89 µmol) is reacted according to working procedure 3. After chromatographic purification by means of preparative HPLC (Method 38), 11.7 mg (79% of theory) of product are obtained by freeze-drying.

HPLC/UV-Vis (Method 2): $R_t$=1.51 min.

LC-MS (Method 7): $R_t$=1.36 mm;

MS (ESIpos.): m/z (%)=1326 (10) [M+H]$^+$, 663 (100) [M+2H]$^{2+}$,
MS (ESIneg.): m/z (%)=1324 (28) [M−H]$^+$, 662 (100) [M−2H]$^{2-}$.
HR-TOF-MS (Method 1): $C_{61}H_{98}N_{17}O_{16}$ [M+H]$^+$ found 1324.7352, calc. 1324.7372.

Example 5

N$^{2.1}$-[(2S)-2-Amino-3-(tert-butyl)propyl]-[3-(tert-butyl)-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine C$^{1.10}$—N$^{3.2}$-lactam tristrifluoroacetate

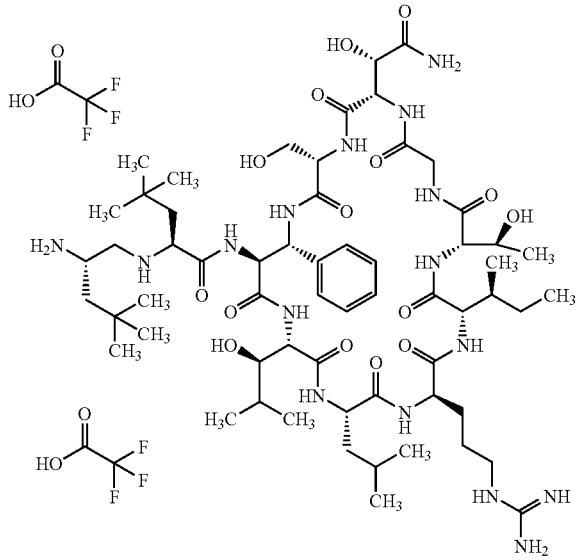

The Cbz-protected cyclopeptide (example 84A, 169.0 mg, 0.11 mmol) is reacted in analogy to working procedure 3. After fine-purification by means of preparative RP-HPLC (for example method 35), the product is isolated with a yield of 140.0 mg (84% of theory).

HPLC/UV-Vis (Method 25): R$_t$=15.01 mm.

LC-MS (Method 7): R$_t$=1.54 mm;

MS (ESIpos.): m/z (%)=645 (100) [M+2H]$^{2+}$,

MS (ESIneg.): m/z (%)=1288 (100) [M−H]$^-$, 643.8 (16) [M−2H]$^{2-}$.

HR-TOF-MS (Method 1): C$_{60}$H$_{105}$N$_{16}$O$_{15}$ [M+H]$^+$ found 1289.7950, calc. 1289.7940.

Example 6

[3-(tert-Butyl)-D-alanyl]-[3-(6-methylpyrid-2-yl)-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L- serine C$^{1.11}$—N$^{3.3}$-lactam tristrifluoroacetate

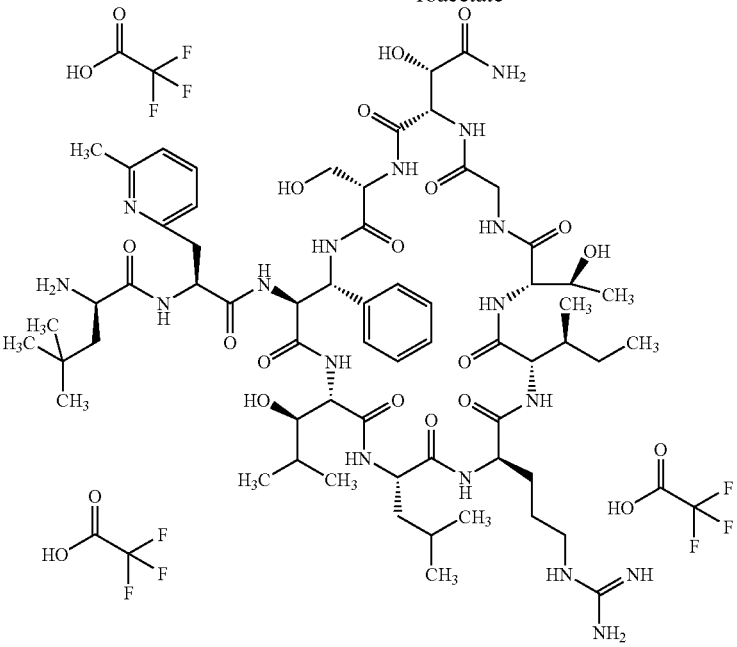

The tert-butoxycarbonyl-protected cyclopeptide (example 44A, 142.0 mg, 85.20 µmol) is reacted in analogy to working procedure 1. After fine-purification by means of preparative RP-HPLC (Method 39), the product is isolated with a yield of 118.0 mg (82% of theory).

HPLC/UV-Vis (Method 25): $R_t$=12.88 min.

LC-MS (Method 7): $R_t$=1.58 min;

MS (ESIpos.): m/z (%)=1339 (5) [M+H]$^+$, 670 (100) [M+2H]$^{2+}$,

MS (ESIneg.): m/z (%)=1337 (100) [M−H]$^-$, 668 (6) [M−2H]$^{2-}$.

HR-TOF-MS (Method 1): $C_{62}H_{101}N_{17}O_{16}$ [M+H]$^+$ found 1338.7507, calc. 1338.7529.

Example 7

[3-(tert-Butyl)-D-alanyl]-[3-(6-trifluormethylpyrid-3-yl)-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam bistrifluoroacetate

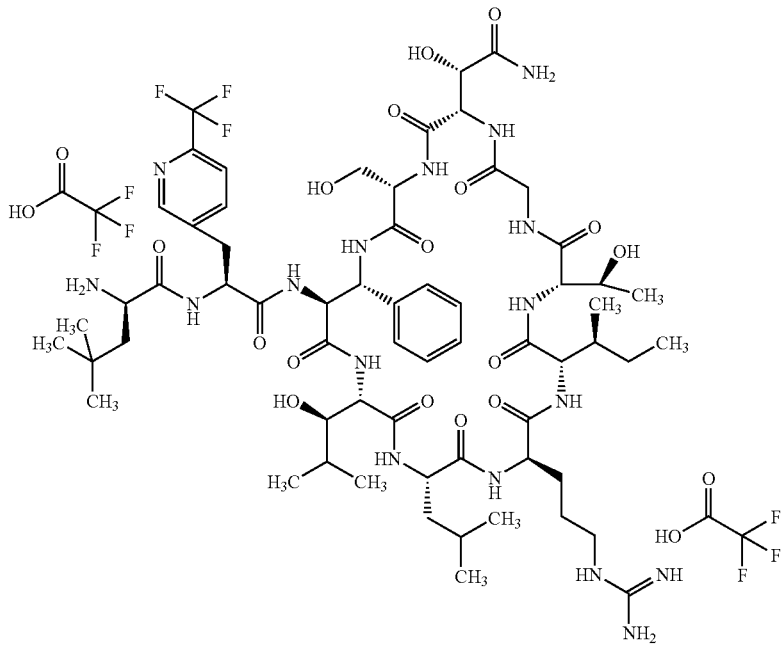

The tert-butoxycarbonyl-protected cyclopeptide (example 55A, 180.0 mg, 0.11 mmol) is reacted in analogy to working procedure 1. After fine-purification by means of preparative RP-HPLC (Method 39), the product is isolated with a yield of 182.0 mg (97% of theory).

HPLC/UV-Vis (Method 2): $R_t$=1.71 min.

LC-MS (Method 29): $R_t$=1.30 min;

MS (ESIpos.): m/z (%)=1392 (10) [M+H]$^+$, 697 (100) [M+2H]$^{2+}$,

MS (ESIneg.): m/z (%)=1391 (20) [M+H]$^-$, 695 (100) [M−2H]$^{2-}$.

HR-TOF-MS (Method 1): $C_{62}H_{97}N_{17}O_{16}F_3$ [M+H]$^+$ found 1392.7267, calc. 1392.7260.

Example 8

$N^{2.1}$-[(2R)-2-Amino-3-(trimethylsilyl)propyl]-[3-(tert-butyl)-L-alanyl]-[(3R)-3-amino-L-phenyl-alanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.10}$—$N^{3.2}$-lactam tristrifluoroacetate

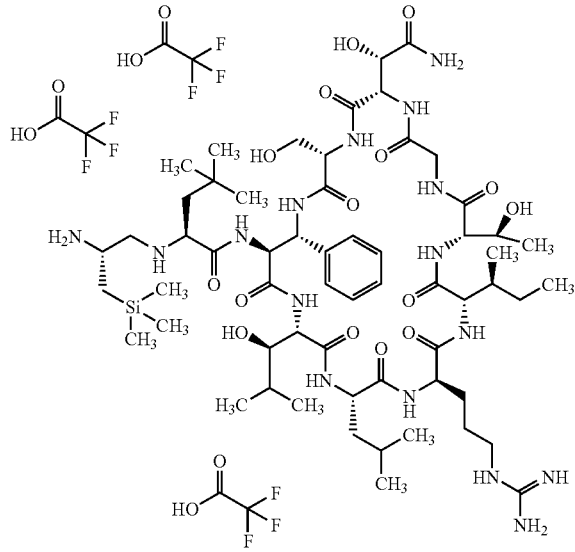

The benzyloxycarbonyl-protected cyclopeptide (example 80A, 32 mg, 19.19 μmol) is reacted in analogy to working procedure 3. After fine-purification by means of preparative RP-HPLC (Method 39), the product is isolated with a yield of 21.3 mg (67% of theory).

HPLC/UV-Vis (Method 25): $R_t$=15.60 min.

LC-MS (Method 7): $R_t$=1.74 min;

MS (ESIpos.): m/z (%)=653 (100) $[M+2H]^{2+}$,

MS (ESIneg.): m/z (%)=1304 (100) $[M-H]^-$, 651 (95) $[M-2H]^{2-}$.

HR-TOF-MS (Method 1): $C_{59}H_{105}N_{16}O_{15}Si$ $[M+H]^-$ found 1305.7667, calc. 1305.7710.

Example 9

D-Leucyl-[3-tert-butyl-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam bistrifluoroacetate

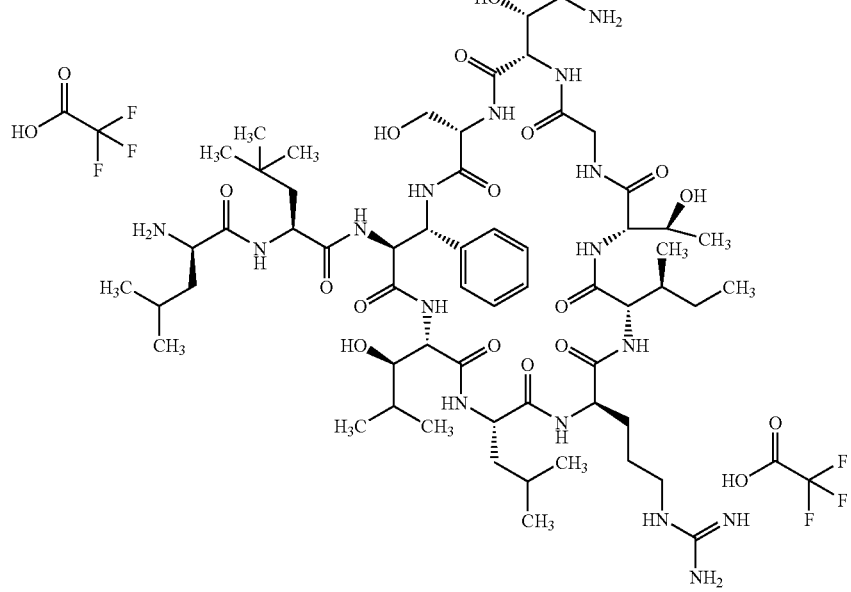

The benzyloxycarbonyl-protected cyclopeptide (example 70A, 32.0 mg, 21.28 μmol) is reacted in analogy to working procedure 3. After fine-purification by means of preparative RP-HPLC (Method 35), the product is isolated with a yield of 22.7 mg (70% of theory).

HPLC/UV-Vis (Method 25): $R_t$=14.00 min.

LC-MS (Method 7): $R_t$=1.63 min;

MS (ESIpos.): m/z (%)=1289 (4) [M+H]⁻, 645 (100) [M+2H]²⁺,

MS (ESIneg.): m/z (%)=1287 (100) [M−H]⁻.

HR-TOF-MS (Method 1): $C_{59}H_{101}N_{16}O_{16}$ [M+H]⁺ found 1289.7583, calc. 1289.7576.

Example 10

[3-tert-Butyl-D-alanyl]-[3-(pyrid-2-yl)-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam tristrifluoroacetate

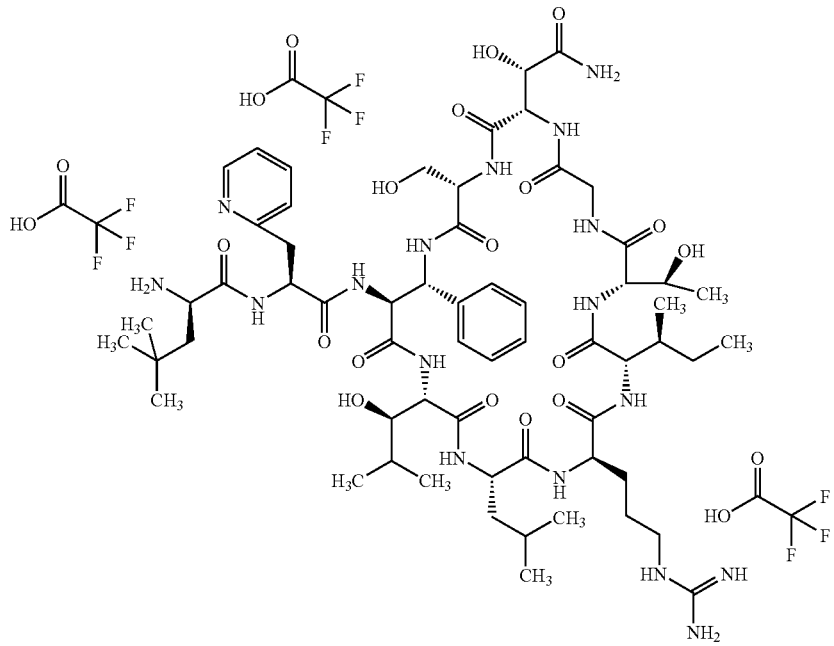

The tert-butoxycarbonyl-protected cyclopeptide (example 45A, 105.0 mg, 63.53 μmol) is reacted in analogy to working procedure 1. After fine-purification by means of preparative RP-HPLC (Method 35), the product is isolated with a yield of 84.4 mg (80% of theory).

HPLC/UV-Vis (Method 25): $R_t$=14.16 min.

LC-MS (Method 7): $R_t$=1.30 min;

MS (ESIpos.): m/z (%)=1325 (15) [M+H]$^+$, 663 (100) [M+2H]$^{2+}$,

MS (ESIneg.): m/z (%)=1323 (100) [M−H]$^-$.

HR-TOF-MS (Method 1): $C_{61}H_{98}N_{17}O_{16}$ [M+H]$^+$ found 1324.7351, calc. 1324.7372.

Example 11

[3-tert-Butyl-D-alanyl]-L-leucyl-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam tristrifluoroacetate

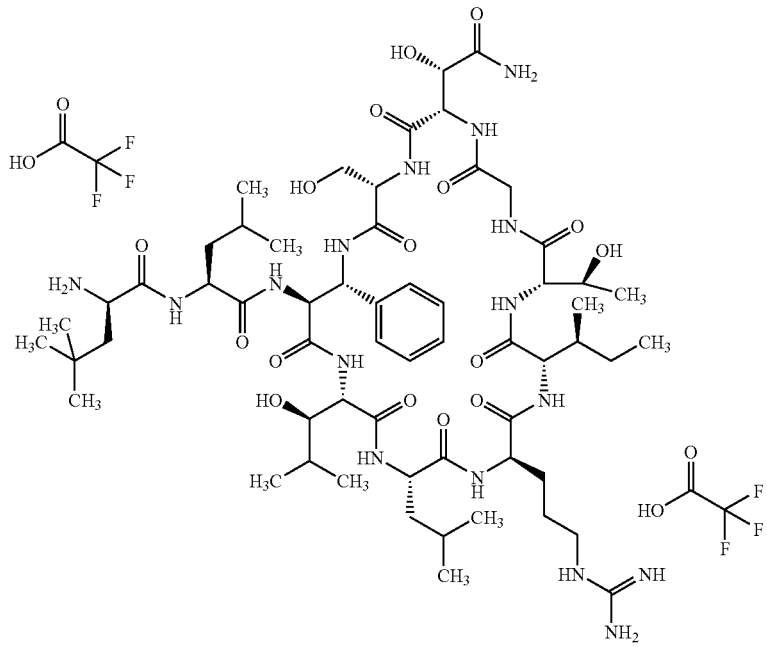

The tert-butoxycarbonyl-protected cyclopeptide (example 50A, 131.0 mg, 85.19 μmol) is reacted in analogy to working procedure 1. After fine-purification by means of preparative RP-HPLC (Method 35), the product is isolated with a yield of 49.5 mg (38% of theory).

HPLC/UV-Vis (Method 25): $R_t$=14.56 min.

LC-MS (Method 7): $R_t$=1.58 min;

MS (ESIpos.): m/z (%)=1290 (5) [M+H]$^+$, 645 (100) [M+2H]$^{2+}$,

MS (ESIneg.): m/z (%)=1288 (100) [M−H]$^-$, 643 (100) [M−2H]$^{2-}$.

HR-TOF-MS (Method 1): $C_{59}H_{101}N_{16}O_{16}$ [M+H]$^+$ found 1289.7567, calc. 1289.7576.

Example 12

[3-cyclo-Pentyl-D-alanyl]-[3-cyclo-pentyl-L-alanyl]-[(3R)-3-amino-L-phenylalanyl)]-[(3R)-3-hydroxy-L-leucyl]-L-leucyl-D-arginyl-L-isoleucyl-L-allothreonyl-glycyl-[(3S)-3-hydroxy-L-asparaginyl]-L-serine $C^{1.11}$—$N^{3.3}$-lactam bistrifluoroacetate

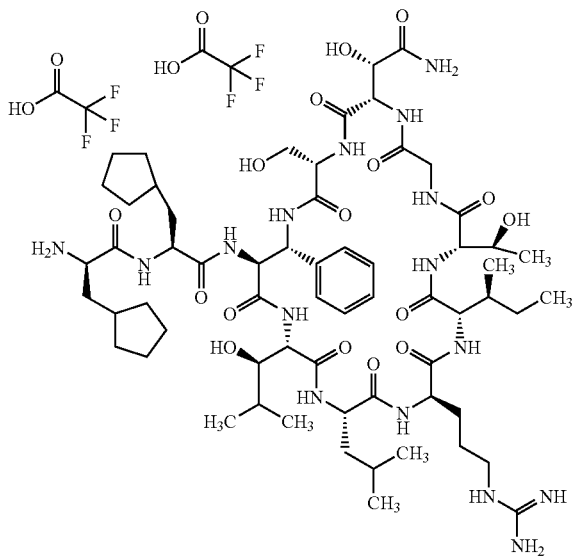

The tert-butoxycarbonyl-protected cyclopeptide (example 63A, 25.0 mg, 15 μmol) is reacted in analogy to working procedure 1. After fine-purification by means of preparative RP-HPLC (Method 35), the product is isolated with a yield of 24.5 mg (quant.).

HPLC/UV-Vis (Method 25): $R_t$=17.2 min.

LC-MS (Method 7): $R_t$=1.66 min;

MS (ESIpos.): m/z (%)=664.8 (100) [M+2H]$^{2+}$, 1328 (10) [M+H]$^+$,

MS (ESIneg.): m/z (%)=1326 (100) [M−H]$^-$.

HR-TOF-MS (Method 1): $C_{62}H_{103}N_{16}O_{16}$ [M+H]$_+$ found 1327.7761, calc. 1327.7733.

B. EVALUATION OF THE PHYSIOLOGICAL ACTIVITY

The in vitro activity of the compounds of the invention can be shown in the following assays:

Determination of the Minimum Inhibitory Concentration (MIC):

The MIC is determined in the liquid dilution test in accordance with the NCCLS guidelines. Overnight cultures of *Staphylococcus aureus* 133, *Entercococcus faecalis* 27159, *E. faecium* and *Streptococcus pneumoniae* G9a are incubated with the described test substances in a 1:2 dilution series. The MIC determination is carried out with a cell count of 10$^5$ microorganisms per ml in Isosensitest medium (Difco, Irvine/USA), with the exception of *S. pneumoniae* which is tested in BHI broth (Difco, Irvine/USA) with 10% bovine serum at a cell count of 10$^6$ microorganisms per ml. The cultures are incubated at 37° C. for 18-24 hours, *S. pneumoniae* in the presence of 10% $CO_2$.

The lowest substance concentration in each case at which visible bacterial growth occurs any more is defined as the MIC. The MIC values are reported in μg/ml.

Representative in-vitro activity data for the compounds of the invention are shown in Table B:

TABLE B

| Example no. | MIC S. aureus 133 [μg/ml] | MIC S. pneumoniae G9a [μg/ml] | MIC E. faecium L4001 [μg/ml] | MIC E. faecalis ICB 27159 [μg/ml] |
|---|---|---|---|---|
| 1 | 0.5 | 0.063 | 0.25 | 0.25 |
| 3 | 0.125 | 0.25 | — | 2 |
| 6 | 0.25 | 0.25 | — | 0.5 |
| 7 | 0.125 | 0.125 | — | 0.25 |
| 9 | 0.25 | 0.125 | — | 0.5 |
| 1A | 0.5 | 0.063 | 0.5 | 0.5 |

The suitability of the compounds of the invention for the treatment of bacterial infections can be shown in the following animal model:

Systematic infection with *Staphylococcus aureus* 133:

Cell of *S. aureus* 133 are cultured overnight in BHI broth (Oxoid, N.Y./USA). The overnight culture is diluted 1:100 in fresh BHI broth and incubated for 3 hours. The cells which are then in the logarithmic growth phase are centrifuged off and washed twice with buffered, physiological saline. A cell suspension in saline is then adjusted photometrically to an extinction of 50 units. After a dilution step (1:15), this suspension is mixed 1:1 with a 10% mucin solution. 0.25 ml/20 g mouse of this infection solution is administered intraperitoneally (corresponding to 1×10$^6$ microorganisms/mouse). The therapy takes place intraperitoneally or intravenously 30 minutes after infection. Female CFW1 mice are used for the infection experiment. The survival of the animals is recorded over a period of 6 days.

The properties of the compounds of the invention with respect to the renal tolerability can be shown in the following animal model:

Mouse Model for the Determination of Nephrotoxic Effects:

Nephrotoxic side effects of the nonadepsipeptides are analyzed by histopathological examinations of the kidneys in mice after multiple administration of a particular dose. For this, 5-6 animals are treated daily either intravenously (i.v.) or intraperitoneally (i.p.) with substances which are dissolved in an aqueous solution or with addition of Solutol. Nephrotoxic effects are determined by light-microscopical assessment of hematoxilin and eosin (H&E) stained paraffin sections of the kidneys. A 'periodic acid Schiff' (PAS) reaction is optionally carried out for a better visualization of glycoproteins. Nephrotoxic effects are defined semiquantitatively for each animal as the degrees of severity of the tubular basophilia and degeneration/regeneration occurring (degrees of severity: 0=no effect; 1=minimal effect; 2=slight effect; 3=moderate effect; 4=severe lesions). The average degree of severity of the tubular degeneration/regeneration and the incidence (number of animals concerned) is calculated per animal group or derivative. Kidney changes going beyond this such as tubular dilatation and necrosis as well as the accumulation of necrotic materials are likewise listed.

C. EXEMPLARY EMBODIMENTS OF PHARMACEUTICAL COMPOSITIONS

The compounds of the invention can be converted into pharmaceutical preparations in the following ways:

Tablet:

Composition:

100 mg of the compound of Example 1, 50 mg of lactose (monohydrate), 50 mg of maize starch (native), 10 mg of polyvinylpyrolidone (PVP 25) (BASF, Ludwigshafen, Germany) and 2 mg of magnesium stearate.

Tablet weight 212 mg. Diameter 8 mm, radius of curvature 12 mm.

Preparation:

The mixture of active compound, lactose and starch is granulated with a 5% solution (m/m) of the PVP in water. The granules are dried and then mixed with the magnesium stearate for 5 min. This mixture is compressed using a conventional tablet press (for format of the tablet see above). A guideline for the compressive force used for the compression is 15 kN.

Suspension Which Can Be Administered Orally:

Composition:

1000 mg of the compound of Example 1, 1000 mg of ethanol (96%), 400 mg of Rhodigel (xanthan gum from FMC, Pennsylvania, USA) and 99 g of water.

10 ml of oral suspension correspond to a single dose of 100 mg of the compound of the invention.

Preparation:

The Rhodigel is suspended in ethanol, and the active compound is added to the suspension. The water is added while stirring. The mixture is stirred for about 6 h until the swelling of the Rhodigel is complete.

Solution Which Can Be Administered Intravenously:

Composition:

100-200 mg of the compound of Example 1, 15 g of polyethylene glycol 400 and 250 g of water for injection.

Preparation:

The compound of Example 1 is dissolved together with polyethylene glycol 400 in the water with stirring. The solution is sterilized by filtration (pore diameter 0.22 μm) and dispensed under aseptic conditions into heat-sterilized infusion bottles. The latter are closed with infusion stoppers and crimped caps.

What is claimed is:

1. A compound of formula

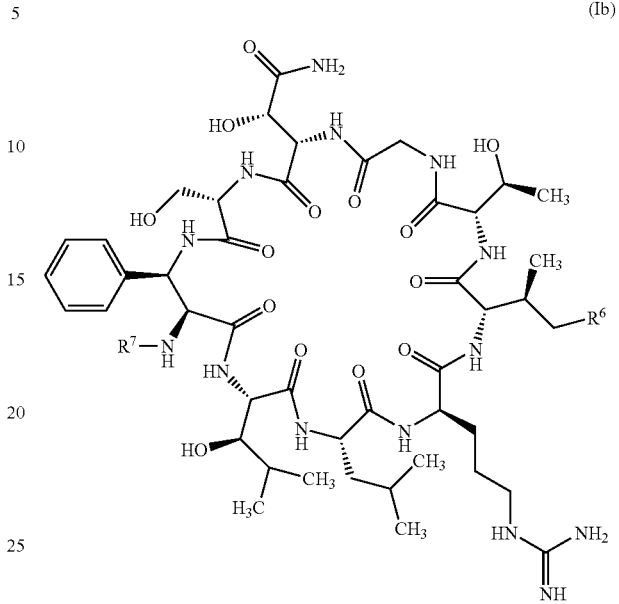

(Ib)

in which $R^6$ represents hydrogen or methyl, $R^7$ represents a group of the formula

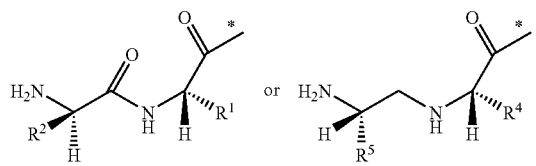

whereby

* is the linkage site to the amine, $R^1$ represents $C_1$-$C_6$-alkyl, $C_2$-$C_6$-alkenyl, $C_3$-$C_6$-cycloalkyl or $C_6$-$C_{10}$-aryl, whereby alkyl, alkenyl, cycloalkyl and aryl are optionally substituted with 0, 1, 2 or 3 substituents selected independently of one another from the group consisting of halogen, hydroxy, amino, cyano, trimethylsilyl, $C_1$-$C_6$-alkyl, $C_1$-$C_6$-alkoxy, benzyloxy, $C_3$-$C_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-arylcarbonyl and benzyloxycarbonylamino, wherein cycloalkyl, aryl, heterocyclyl and heteroaryl for their part are optionally substituted by 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, $R^2$ represents $C_1$-$C_6$-alkyl, $C_2$-$C_6$-alkenyl, $C_3$-$C_6$-cycloalkyl or $C_6$-$C_{10}$-aryl, whereby alkyl, alkenyl, cycloalkyl and aryl are optionally substituted with 0, 1, 2 or 3 substituents selected independently of one another from the group consisting of halogen, hydroxy, amino, cyano, trimethylsilyl, $C_1$-$C_6$-alkyl, $C_1$-$C_6$-alkoxy, benzyloxy, $C_3$-$C_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-arylcarbonyl and benzyloxycarbonylamino, wherein cycloalkyl, aryl, heterocyclyl and heteroaryl for their part are optionally substituted with 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, $R^4$ represents $C_1$-$C_6$-alkyl, $C_2$-$C_6$-alkenyl, $C_3$-$C_6$-cycloalkyl or $C_6$-$C_{10}$-aryl, whereby alkyl, alkenyl, cycloalkyl and aryl are optionally substituted with 0, 1, 2 or 3 substituents selected independently of one another from the group consisting of halogen, hydroxy, amino, cyano, trimethylsilyl, $C_1$-$C_6$-alkyl, $C_1$-$C_6$-alkoxy, benzyloxy, $C_3$-$C_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-arylcarbonyl and benzyloxycarbonylamino, wherein cycloalkyl, aryl, heterocyclyl and heteroaryl for their part are optionally substituted with 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, $R^5$ represents $C_1$-$C_6$-alkyl, $C_2$-$C_6$-alkenyl, $C_3$-$C_6$-cycloalkyl or $C_6$-$C_{10}$-aryl, whereby alkyl, alkenyl, cycloalkyl and aryl are optionally substituted with 0, 1, 2 or 3 substituents selected independently of one another from the group consisting of halogen, hydroxy, amino, cyano, trimethylsilyl, $C_1$-$C_6$-alkyl, $C_1$-$C_6$-alkoxy, benzyloxy, $C_3$-$C_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-arylcarbonyl and benzyloxycarbonylamino, wherein cycloalkyl, aryl, heterocyclyl and heteroaryl for their part are optionally substituted with 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, or one of its salts.

2. The compound of claim 1, whereby $R^6$ represents methyl, $R^7$ represents a group of formula

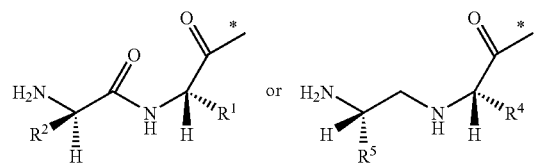

whereby

* is the linkage site to the amine, $R^1$ represents 2-methylprop-1-yl, 2,2-dimethylprop-1-yl, 2,2-dimethylbut-1-yl, tri-methylsilylmethyl, 1-hydroxy-2-methylprop-1-yl, 1-hydroxy-2,2-dimethylprop-1-yl, 1-hydroxy-2,2-dimethylbut-1-yl, 1-hydroxy-2-ethyl-2-methylbut-1-yl, 1-hydroxy-2,2-diethylbut-1-yl, phenylmethyl, 1-hydroxy-1-phenylmethyl, 2-pyridylmethyl or 3-pyridylmethyl, whereby 2-pyridylmethyl or 3-pyridylmethyl is optionally substituted with 0, 1, 2 or 3 substituents selected independently of one another from the group consisting of hydroxy, amino, trifluoromethyl, methyl, methoxy and morpholinyl, $R^2$ represents 2-methylprop-1-yl, 2,2-dimethylprop-1-yl, 2,2-dimethylbut-1-yl, tri-methylsilylmethyl, 1-hydroxy-2-methylprop-1-yl, 1-hydroxy-2,2-dimethylprop-1-yl, 1-hydroxy-2,2-dimethylbut-1-yl, 1-hydroxy-2-ethyl-2-methylbut-1-yl, 1-hydroxy-2,2-diethylbut-1-yl, phenylmethyl, 1-hydroxy-1-phenylmethyl, 2-pyridylmethyl or 3-pyridylmethyl, whereby 2-pyridylmethyl or 3-pyridylmethyl is optionally substituted with 0, 1, 2 or 3 substituents selected independently of one another from the group consisting of hydroxy, amino, trifluoromethyl, methyl, methoxy and morpholinyl, $R^4$ represents 2-methylprop-1-yl, 2,2-dimethylprop-1-yl, 2,2-dimethylbut-1-yl, trimethylsilylmethyl, 1-hydroxy-2-methylprop-1-yl, 1-hydroxy-2,2-dimethylprop-1-yl, 1-hydroxy-2,2-dimethyl-but-1-yl, 1-hydroxy-2-ethyl-2-methylbut-1-yl, 1-hydroxy-2,2-diethylbut-1-yl, phenylmethyl, 1-hydroxy-1-phenylmethyl, 2-pyridylmethyl or 3-pyridylmethyl, whereby 2-pyridylmethyl or 3-pyridylmethyl is optionally substituted with 0, 1, 2 or 3 substituents selected independently of one another from the group consisting of hydroxy, amino, trifluoromethyl, methyl, methoxy and morpholinyl, $R^5$ represents 2-methylprop-1-yl, 2,2-dimethylprop-1-yl, 2,2-dimethylbut-1-yl, trimethylsilylmethyl, 1-hydroxy-2-methylprop-1-yl, 1-hydroxy-2,2-dimethylprop-1-yl, 1-hydroxy-2,2-dimethylbut-1-yl, 1-hydroxy-2-ethyl-2-methylbut-1-yl, 1-hydroxy-2,2-diethylbut-1-yl, phenylmethyl, 1-hydroxy-1-phenylmethyl, 2-pyridylmethyl or 3-pyridylmethyl, whereby 2-pyridylmethyl or 3-pyridylmethyl is optionally substituted with 0, 1, 2 or 3 substituents selected independently of one another from the group consisting of hydroxy, amino, trifluoromethyl, methyl, methoxy and morpholinyl, or one of its salts.

3. The compound of claim 1, whereby
R⁶ represents methyl,
R⁷ represents a group of formula

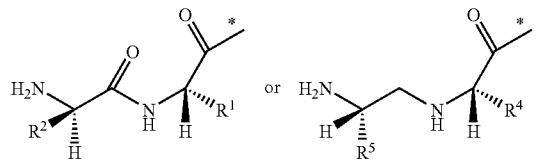

whereby
* is the linkage site to the amine,
R¹ represents 2-methylprop-1-yl, 2,2-dimethylprop-1-yl, trimethylsilylmethyl or 3-pyridylmethyl,
  whereby 3-pyridylmethyl is optionally substituted with 0, 1 or 2 substituents selected independently of one another from the group consisting of hydroxy, amino, trifluoromethyl, methyl, methoxy and morpholinyl,
R² represents 2-methylprop-1-yl, 2,2-dimethylprop-1-yl, trimethylsilylmethyl or 3-pyridylmethyl,
  whereby 3-pyridylmethyl is optionally substituted with 0, 1 or 2 substituents selected independently of one another from the group consisting of hydroxy, amino, trifluoromethyl, methyl, methoxy and morpholinyl,
R⁴ represents 2-methylprop-1-yl, 2,2-dimethylprop-1-yl, trimethylsilylmethyl or 3-pyridylmethyl,
  whereby 3-pyridylmethyl is optionally substituted with 0, 1 or 2 substituents selected independently of one another from the group consisting of hydroxy, amino, trifluoromethyl, methyl, methoxy and morpholinyl,
R⁵ represents 2-methylprop-1-yl, 2,2-dimethylprop-1-yl, trimethylsilylmethyl or 3-pyridylmethyl,
  whereby 3-pyridylmethyl is optionally substituted with 0, 1 or 2 substituents selected independently of one another from the group consisting of hydroxy, amino, trifluoromethyl, methyl, methoxy and morpholinyl,
or one of its salts.

4. A method for preparing a compound of formula (Ib) of claim 1, whereby
[A] a compound of formula

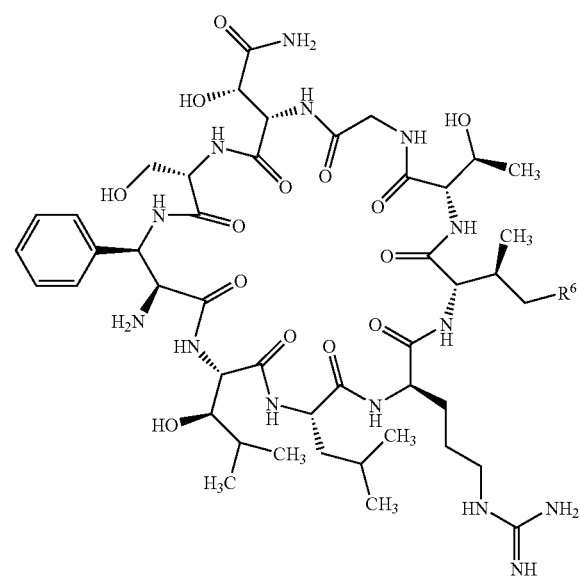

(II)

in which
R⁶ has the meaning indicated in claim 1
is reacted first with a compound of formula

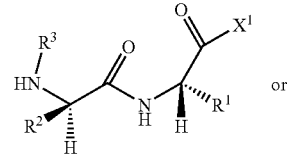

(III)

or

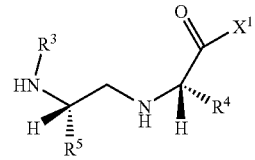

(VI)

in which
R¹, R², R⁴ and R⁵ have the meaning indicated in claim 1,
R³ represents tert-butoxycarbonyl or benzyloxycarbonyl, and
X¹ represents halogen, preferably bromine, chlorine or fluorine, or hydroxy,
and then with an acid and/or by hydrogenolysis,
or
[B] a compound of formula

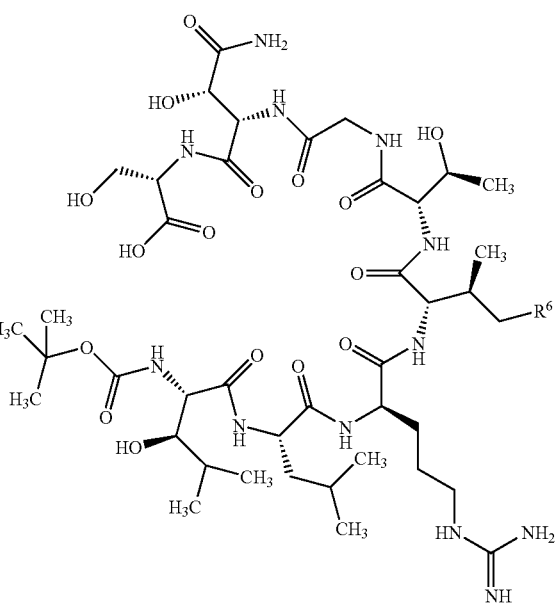

(IV)

in which
R⁶ has the meaning indicated in claim 1
is reacted first with a compound of formula

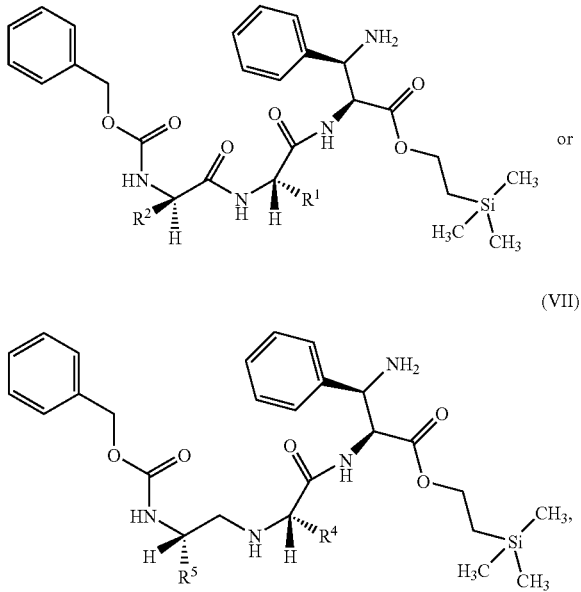

in which
R¹, R², R⁴ and R⁵ have the meaning indicated in claim 1,
and then, in a 4-stage synthesis, a) with a fluoride reagent,
b) with an acid,
c) with a dehydrating reagent, where appropriate in the presence of a base, and
d) by hydrogenolysis.

5. A method for the production of a medicament comprising mixing a compound of claim 1 with at least one inert, nontoxic, pharmaceutically acceptable excipient.

6. A medicament comprising a compound of claim 1 in combination with an inert, nontoxic, pharmaceutically acceptable excipient.

7. A method for treating bacterial infections in humans and animals comprising administering an antibacterially effective amount of at least one compound of claim 1 to a human or animal in need thereof.

8. A method for treating bacterial infections in humans and animals comprising administering an antibacterially effective amount of a medicament of claim 6 to a human or animal in need thereof.

* * * * *